(12) United States Patent
Dhallan

(10) Patent No.: US 7,208,274 B2
(45) Date of Patent: Apr. 24, 2007

(54) RAPID ANALYSIS OF VARIATIONS IN A GENOME

(75) Inventor: Ravinder S. Dhallan, Bethesda, MD (US)

(73) Assignee: Ravgen, Inc., Columbia, MD (US)

( * ) Notice: Subject to any disclaimer, the term of this patent is extended or adjusted under 35 U.S.C. 154(b) by 487 days.

(21) Appl. No.: 10/376,770

(22) Filed: Feb. 28, 2003

(65) Prior Publication Data

US 2004/0106102 A1 Jun. 3, 2004

Related U.S. Application Data

(63) Continuation-in-part of application No. 10/093,618, filed on Mar. 11, 2002, now Pat. No. 6,977,162.

(60) Provisional application No. 60/378,354, filed on May 8, 2002, provisional application No. 60/360,232, filed on Mar. 1, 2002.

(51) Int. Cl.
C12Q 1/68 (2006.01)
C07H 21/02 (2006.01)
C07H 21/04 (2006.01)

(52) U.S. Cl. .......................... 435/6; 536/23.1; 536/24.3

(58) Field of Classification Search .................... 435/6; 536/23.1, 24.3
See application file for complete search history.

(56) References Cited

U.S. PATENT DOCUMENTS

| | | | |
|---|---|---|---|
| 4,521,509 A | 6/1985 | Benkovic et al. | |
| 4,683,195 A | 7/1987 | Mullis et al. | |
| 4,683,202 A | 7/1987 | Mullis | |
| 4,800,159 A | 1/1989 | Mullis et al. | |
| 4,889,818 A | 12/1989 | Gelfand et al. | |
| 4,965,188 A | 10/1990 | Mullis et al. | |
| 4,994,372 A * | 2/1991 | Tabor et al. | 435/6 |
| 5,023,171 A | 6/1991 | Ho et al. | |
| 5,066,584 A | 11/1991 | Gyllensten et al. | |
| 5,075,216 A | 12/1991 | Innis et al. | |
| 5,079,352 A | 1/1992 | Gelfand et al. | |
| 5,091,310 A | 2/1992 | Innis | |
| 5,104,792 A | 4/1992 | Silver et al. | |
| 5,326,857 A | 7/1994 | Yamamoto et al. | |
| 5,432,054 A | 7/1995 | Saunders et al. | |
| 5,501,963 A | 3/1996 | Burckhardt | |
| 5,538,848 A | 7/1996 | Livak et al. | |
| 5,538,871 A | 7/1996 | Nuovo et al. | |
| 5,545,552 A | 8/1996 | Mathur | |
| 5,565,339 A | 10/1996 | Bloch et al. | |
| 5,582,989 A | 12/1996 | Caskey et al. | |
| 5,618,664 A | 4/1997 | Kiessling | |
| 5,631,147 A | 5/1997 | Lohman et al. | |
| 5,639,611 A | 6/1997 | Wallace et al. | |
| 5,641,628 A | 6/1997 | Bianchi | |
| 5,648,222 A | 7/1997 | Tse et al. | |
| 5,693,469 A | 12/1997 | Hogan | |
| 5,723,591 A | 3/1998 | Livak et al. | |
| 5,744,301 A | 4/1998 | Birkenbach et al. | |
| 5,759,772 A | 6/1998 | Kirkpatrick et al. | |
| 5,817,797 A | 10/1998 | Mitchell et al. | |
| 5,831,065 A | 11/1998 | Brenner | |
| 5,858,671 A | 1/1999 | Jones | |
| 5,882,857 A * | 3/1999 | Western et al. | 435/6 |
| 5,965,363 A | 10/1999 | Monforte et al. | |
| 5,998,141 A | 12/1999 | Acton | |
| 6,004,744 A * | 12/1999 | Goelet et al. | 435/5 |
| 6,017,699 A | 1/2000 | Jordan | |
| 6,090,553 A | 7/2000 | Matson | |
| 6,100,029 A | 8/2000 | Lapidus et al. | |
| 6,110,709 A | 8/2000 | Ausubel et al. | |
| 6,124,120 A | 9/2000 | Lizardi | |
| 6,180,372 B1 | 1/2001 | Franzen | |
| 6,197,563 B1 | 3/2001 | Erlich et al. | |
| 6,203,989 B1 | 3/2001 | Goldberg et al. | |
| 6,214,558 B1 | 4/2001 | Shuber et al. | |
| 6,221,600 B1 | 4/2001 | MacLeod et al. | |
| 6,225,061 B1 | 5/2001 | Becker et al. | |
| 6,251,639 B1 | 6/2001 | Kurn | |
| 6,258,540 B1 | 7/2001 | Lo et al. | |
| 6,268,146 B1 | 7/2001 | Shultz et al. | |
| 6,387,621 B1 | 5/2002 | Wittwer | |
| 6,475,736 B1 | 11/2002 | Stanton, Jr. | |
| 6,506,561 B1 | 1/2003 | Cheval et al. | |

(Continued)

FOREIGN PATENT DOCUMENTS

EP 0 994 963 4/2000

(Continued)

OTHER PUBLICATIONS

Foreman, K. E. et al. (Jun. 1997). "In Situ Polymerase Chain Reaction-Based Localization Studies Support Role of Human Herpesvirus-8 as the Cause of Two AIDS-related Neoplasms: Kaposi's Sarcoma and Body Cavity Lymphoma," *J. Clinical Inves*. 99(12):2971-2978.

(Continued)

*Primary Examiner*—Ethan Whisenant
(74) *Attorney, Agent, or Firm*—Morrison & Foerster LLP

(57) ABSTRACT

The invention provides a method useful for determining the sequence of large numbers of loci of interest on a single or multiple chromosomes. The method utilizes an oligonucleotide primer that contains a recognition site for a restriction enzyme such that digestion with the restriction enzyme generates a 5' overhang containing the locus of interest. The 5' overhang is used as a template to incorporate nucleotides, which can be detected. The method is especially amenable to the analysis of large numbers of sequences, such as single nucleotide polymorphisms, from one sample of nucleic acid.

51 Claims, 23 Drawing Sheets

U.S. PATENT DOCUMENTS

| | | | |
|---|---|---|---|
| 6,613,517 | B2 | 9/2003 | Michelotti |
| 6,730,517 | B1* | 5/2004 | Koster et al. ............... 436/47 |
| 2001/0051341 | A1 | 12/2001 | Lo et al. |
| 2002/0045176 | A1 | 4/2002 | Lo et al. |
| 2003/0044388 | A1 | 3/2003 | Dennis et al. |
| 2003/0044791 | A1* | 3/2003 | Flemington ............... 435/6 |
| 2003/0054386 | A1 | 3/2003 | Antonarakis et al. |
| 2003/0082576 | A1 | 5/2003 | Jones et al. |
| 2003/0099964 | A1 | 5/2003 | Patil et al. |
| 2003/0180746 | A1* | 9/2003 | Kmiec et al. ............... 435/6 |
| 2003/0186239 | A1 | 10/2003 | Dhallan |
| 2003/0232348 | A1 | 12/2003 | Jones et al. |
| 2003/0235834 | A1* | 12/2003 | Dunlop et al. ............... 435/6 |
| 2004/0137470 | A1 | 7/2004 | Dhallan |
| 2004/0185495 | A1 | 9/2004 | Schueler et al. |
| 2005/0037388 | A1 | 2/2005 | Antonarakis et al. |

FOREIGN PATENT DOCUMENTS

| | | |
|---|---|---|
| GB | 2 299 166 | 9/1996 |
| WO | WO 91/08304 | 6/1991 |
| WO | WO 95/06137 | 3/1995 |
| WO | WO-98/12355 A | 3/1998 |
| WO | WO 98/39474 | 9/1998 |
| WO | WO 02/04672 | 1/2002 |
| WO | WO 02/083839 | 10/2002 |
| WO | WO 03/074723 | 9/2003 |
| WO | WO 03/74740 | 9/2003 |
| WO | WO 03/106642 | 12/2003 |
| WO | WO 2004/078994 | 9/2004 |
| WO | WO 2004/079011 | 9/2004 |

OTHER PUBLICATIONS

International Search Report mailed on Jun. 14, 2005 for PCT patent Application No. PCT/US04/06337 filed Mar. 1, 2004, 5 pages.

Kawasaki, E. S. (1990). "Sample Preparation From Blood, Cells and Other Fluids," Chapter 18 In *PCR Protocols: A Guide to Methods and Applications*. Innis, M. A. et al., eds., Academic Press, Inc, pp. 146-152.

Lee, M. S. et al. (Jun. 1989). "Detection of Two Alternative bcr/abl mRNA Junctions and Minimal Residual Disease in Philadelphia Chromosome Positive Chronic Myelogenous Leukemia by Polymerase Chain Reaction, " *Blood* 73(8):2165-2170.

Written Opinion mailed on Jun. 14, 2005 for PCT patent application No. PCT/US04/06337 filed Mar. 1, 2004, 6 pages.

Witten Opinion mailed on May 23, 2005 for PCT patent application No. PCT/US03/06198 filed Feb. 28, 2003, 8 pages.

Written Opinion mailed on Mar. 10, 2005 for PCT patent application No. PCT/US03/06376 filed on Feb. 28, 2003, 3 pages.

U.S. Appl. No. 10/093,618, filed Mar. 11, 2002, Dhallan.

Ahlquist, D. A. et al. (2000). "Colorectal Cancer Screening by Detection of Altered Human DNA in Stool: Feasibility of A Multitarget Assay Panel," *Gastroenterology* 119:1219-1227.

Bianchi, D. W. et al. (1990). "Isolation of Fetal DNA From Nucleated Erythrocytes in Maternal Blood,"*Proc. Nalt. Acad. Sci USA* 87:3279-3283.

Bianchi, D. W. et al. (1996). "Male Fetal Progenitor Cells Persist in Maternal blood for as Longas 27 Years Postpartum," Proc. Natl. Acad. Sci. USA 93:705-708.

Bianchi, D. W. et al. (1997). "PCR Quantitation of Fetal Cells in Maternal Blood in Normal and Aneuploid Pregnancies," *Am. J. Hum. Genet.* 61:822-829.

Blanchard, A.P. and L. Hood (1996). "Sequence to Array: Probing the Genome's Secrets," *Nature Biotechnology*149:1649.

Brenner, S. et al. (2000). "Gene Expression Analysis by Massively Parallel Signature Sequencing (MPSS) on Microbead Arrays," *Nature Biotechnology* 18:630-634.

Broude, N. et al. (2001). "High-Level Multiplex DNA Amplification," *Antisense & Nucleic Acid Drug Development* 11:327-332.

Brown, E. L. et al. (1979). "Chemical Synthesis and Cloning of a Tyrosine tRNA Gene," *Methods in Enzymology* 68:109-151.

Bruch, J. F. et al., (1991). "Trophoblast-Like Cells Sorted From Peripheral Maternal BloodUsing Flow Cytometry: A Multiparametric Study Involving Transmission Electro Microsopy and Fetal DNA Amplification," *Prenatal Disgnosis* 11:787-798.

Cairns, P. et al. (2001). "Molecular Detection of Prostate Cancer in Urine by GSTP1 Hypermethylation," *Clin. Can. Res.* 7:2727-2730.

Center for Medical Genetics. (1998-2003). Human Insertion/Deletion Polymorphisms http://research. marshfieldclinicorg/genetics/. Last visited on Apr. 14, 2003. 3 pages Chen, J. et al. (2000). "A Microsphere-Based Assay for Multiplexed Single Nucleotide Polymorphism Analysis Using Single Base Chain Extension," *Genome Research* 10:549-557.

Chicurel, M. (2001). "Faster, Better, Cheaper Genotyping," *Nature* 412:580-582.

Collins, F. S. and Mansoura, M. K. (2001). "The Human Genome Project: Revealing the Shared Inheritance of All Humankind," 7th *Biennial Symposium on Minorities, the Medically Underserved and Cancer* 91(1):221-225.

Cooper, D. N. and Krawczak, M. eds.(1993). "Human Gene Mutation," In *Duchenne Muscular Dystrophy, Alzheimer's Disease, Cystic Fibrosis, and Huntington's Disease*. BIOS Scientific Publishers Limited. (Table of Contents only).

Cutler, D. J. et al. (2001). "High-Throughput Variation Detection and Genotyping Using Microarrays," *Genome Research* 11:1913-1925.

Drábek, J. (2001). "A Commented Dictionary of Techniques for Genotyping," *Electrophoresis* 22:1024-1045.

Durant, J. et al. (1999). "Drug-Resistance Genotyping in HIV-1 Therapy," *The Lancet* 354:1120-1122.

Durant, J. et al. (1999). "Drug-Resistance Genotyping in HIV-1 Therapy: The Virad APT Randomised Controlled Trial," *The Lancet* 353:2195-2199.

Egholm, M. et al. (1992). "Peptide Nucleic Acids (PNA). Oligonucleotide Analogues with an Achiral Peptide Backbone," *J. Am. Chem. Soc.* 114(5):1895-1897.

El-Naggar, A. K. et al. (2001). "Genetic Heterogeneity in Saliva from Patients with ORal Squamos Carcinomas: Implications in Molecular Diagnosis and Screening," *J. Mol. Diag.* 3(4):164-170.

Erlich, H. A. ed. (1989). *PCR Technology: Principals and Applications of DNA Amplification*, Stockton Press. pp. ix-x. (Table of Contents only).

Field, F. et al. (1999). "Genetic Alterations in Bronchial Lavage as a Potential Marker for Individuals with a High Risk of Developing Lung Cancer," *Cancer Research* 59:2690-2695.

Ganshert-Ahert, D. et al. (1992). "Magnetic Cell Sorting and Transferrin Receptor as Potential Means of Prenatal Diagnosis form Materanl Blood," *Am. J. Obstet. Gynecol.* 166:1350-1355.

Gerhold, D. et al. (1999). "DNA Chips: Promising Toys have Become Powerful Tools," *TIBS* 24:168-173.

Green, A. et al. (1990). "Direct Single Stranded Sequencing from Agarose of Polymerase Chain Reaction Products," *Nucleic Acids Res.* 18(20):6163-6164.

Grösch, S. et al. (2001). "A Rapid Screening Method for a Single Nucleotide Polymorphism (SNP) in the Human MOR Gene," *Br. J. Clin Pharmacol* 52:711-714.

Hedenfalk, I.et al. (2001). "Gene-Expression Profiles in Hereditary Breast Cancer," *New Engl. Jnl. Med.* 344(8):539-548.

Herzenberg , L. A. et al. (1979). "Fetal Cells in the Blood of Pregnant Women: Detection ad Engrichment by Fluroescence-Activated Cell Sorting," *Proc. Natl. Acad. Sci. USA* 76:1453-1455.

Hogervorst, F.B.L. et al. (1995). "Rapid Detection of BRCA1 Mutations by the Protein Truncation Test," *Nature Genetics* 10:208-212.

HSU, T. M. et al. (2001). "Genotyping Single-Nucleotide Polymorphisms by the Invader Assay with Dual-Color Fluorescence Polarization Detection," *Clinical Chemistry* 47(8):1373-1377.

Huber, M. et al. (2001). "Detection of Single Base Alterations in Genomic DNA by Solid Phase Polymerase Chain Reaction on Oligonucleotide Microarrays," *Analytical Biochemistry* 299:34-30.

Human Gene Mutation Database (HGMD). (2003). http:archive. uwcm.ac.uk/uwcm/mg/hgmd0.html. Last visited on Oct. 2, 2003. 3 pages total.

Innis, M. A. ed., (1990). *PCR Protocols: A Guide to Methods and Applications*. Academic Press, Inc. pp. v-x. (Table of Contents only).

James, P. et al. (1994). "Protein Identification in DNA Databases by Peptide Mass Fingerprinting," *Protein Science* 3:1347-1350.

Kandpal, R.P. et al. (1990). "Selective Enrichment of a Large Size Genomic DNA Fragment by Affinity Capture: An Approach for Genome Mapping," *Nucleic Acids Res.* 18(7):1789-1795.

Kaneoka, H. et al. (1991). "Solid-Phase Direct DNA Sequencing of Allele-Specific Polymerase Chain Reaction-Amplified HLA-DR Genes," *Biotechniques* 10(1):30, 32 and 34 only.

Kinzler, K. W. et al. (1991). "Indentification of FAP Locus Genes from Chromosome 5q21," *Science* 253:661-665.

Kwok, P-Y. (2001). "Methods for Genotyping Single Nucleotide Polymorphisms," *Annual Review of Genomics and Human. Genetics* 2:235-258.

Lander, E. S. et al. (2001). "Initial Sequencing and Analysis of the Human Genome," *Nature* 409:860-921.

Li, J. et al. (1999). "Single Nucleotide Polymorphism Determination using Primer Extension and Time-of-Flight Mass Spectrometry," *Electrophoresis* 20:1258-1265.

Liloglou,T. et al. (2001). "Cancer-Specific Genomic Instablilty in Bronchial Lavage: A Molecular Tool for Lung Cancer Detection," *Cancer Research* 61:1624-1628.

Lockhart, D. J. and Winzeler, E. A. ( 2000). "Genomics, Gene Expression and DNA Arrays," *Nature* 405:827-836.

Lo, Y-M. D. et al. (1989). "Prenatal Sex Determination by DNA Amplification From Maternal Peripheral Blood," *The Lancet* 2:1363-1365.

Lo, Y.M.D. et al. (1996). "Two-Way Cell Traffic Between Mother and Fetus: Biologic and Clinical Implications," *Blood* 88:4390-4395.

Lo, Y.M.D. et al. (1997). "Presence of Fetal DNA in Maternal Plasma and Serum," *Lancet* 350:485-487.

Lo, Y.M.D. et al. (1998). "Quantitative Anaylysis of Fetal DNA in Maternal Plasma and Serum: Implications for Noninvasive Prenatal Diagnosis," *Am. J. Hum. Genet.* 62:768-775.

Mao, L. et al. (1996). "Molecular Detection of Primary Bladder Cancer by Microsatellite Analysis," *Science* 271:659-662.

Maxam, A. M. and Gilbert, W. (1977). "A New Method for Sequencing DNA," *Proc. Natl. Acad. Sci.* 74(2):560-564.

McPherson, M. J. et al. eds., (1991). *PCR: A Practical Approach*, IRL Press at Oxford University Press. Total pp. 6. (Table of Contents).

Munoz, N. et al. (2003). "Epidemiologic Classification of Human Papillomavirus Types Associated with Cervical Cancer," *New England Jnl. Med.* 348:518-527.

Mueller et al. (1990). "Isolation of Fetal Trophoblast Cells From Peripheral Blood of Pregnant Women," *Lancet* 336:197-200.

Narang, S. A. et al. (1979). "Improved Phosphotriester Method for the Synthesis of Gene Fragments," *Methods in Enzymology* 68:90-98.

Newman, L. (2002). "Ductal Lavage for Breast Cancer Risk Assessment," *Cancer Control* 9(6):473-479.

Nielsen, P.E. et al. (1991). "Sequence-Selective Recognition of DNA by Strand Displacement with a Thymine-Substituited Polyamide," *Science* 254:1497-1500.

Orban, T. et al. (2000). "Sequence Alterations Can Mask Eash Other's Presence during Screening with SSCP or Heterodulplex Analysis: BRCA Genes as Examples," *BioTechniques* 29(1):94-98.

Pertl, B. MD, and Bianchi, D. W. MD, (2001). "Fetal DNA in Maternal Plasma: Emerging Clinical Applications," *Obstetrics and Gynecology* 98(3):483:490.

Poch, M. T. et al. (1997). "*Sth*132I, A Novel Class-IIS Restriction Endonuclease of *Streptococcus thermophilus* ST132," *Gene* 195:201-206.

Riordan, J. R. et al. (1989). "Identification of the Cystic Fibrosis Gene: Cloning and Characterization of Complementary DNA," *Science* 245 (4922):1066-1073.

Roest, P.A.M. et al. (1993). "Protein Truncation Test (PTT) for Rapid Detection of Translation-Terminating Mutations," *Human Molecular Genetics* 2(10):1719-1721.

Rommens, J. M. et al. (1989). "Identification of the Cystic Fibrosis Gene: Chromosome Walking and Jumping," *Science* 245:1059-1065.

Ryan, B. M. et al. (2003). "A Prospective Study of Circulationg Mutant *KRAS2* in the Serum of Patients with Colorectal Neoplasia: Strong Prognostic Indicator in Postoperative Follow Up," *Gut.* 52:101-108.

Sambrook, J. and Russell, D. W. eds., (2001). *Molecular Cloning Laboratory Manual*. vol. 2 Third Edition, Cold Spring Harbor Laboratory Press. pp. v-xx. (Table of Contents only).

Sanger, F. et al. (1977). "DNA Sequencing with Chain-Terminating Inhibitors," *PNAS USA* 74(12):5463-5467.

Shah, J. S. et al. (1995). "Q-Beta Replicase-Amplified Assay for Detection of *Mycobacterium tuberculosis* Directly from Clinical Specimens," *Journal of Clinical Microbiology*. 33(6):1435-1441.

Shapero, M. H. et al. (2001). "SNP Genotyping by Multiplexed Solid-Phase Amplification and Fluorescent Minisequencing," *Genome Research* 11:1926-1934.

Shi, M. M. (2001). "Enabling Large-Scale Pharmacogenetic Studies by High-Throughput Mutation Detection and Genotyping Technologies," *Clinical Chemistry* 47(2):164-172.

Sibson, D. R. et al. (2001). "Molecular Indexing of Human Genomic DNA," *Nucleic Acids Research* 29(19):1-10.

Small, K. M. et al. (2002). "Synergistic Polymorphisms of $\beta_1$- and $\alpha_{2c}$-Adrenergic Receptors and The Risk of Congestive Heart Failure," *New Eng. Jnl Med*. 347(15):1135-1142.

SNP Report for TSC 0034767. (Jan. 2000). http://snp.cshl.org/snpsearch.shtml. Last visited on Aug. 12, 2003. 2 pages.

SNP Report for TSC 0087315. (Aug. 2000). http://snp.cshl.org/snpsearch.shtml. Last visited on Apr. 14, 2003. 2 pages.

SNP Report for TSC 0095512. (Aug. 2000). http://snp.cshl.org/snpsearch.shtml. Last visited on Apr. 14, 2003. 2 pages.

SNP Report for TSC 0115603. (Mar. 2000). http://snp.cshl.org/snpsearch.shtml. Last visited on Aug. 12, 2003. 2 pages.

SNP Report for TSC 0195492. (Jun. 2000). http://snp.cshl.org/snpsearch.shtml. Last visited on Aug. 12, 2003. 2 pages.

SNP Report for TSC 0197279. (Jun. 2000). http://snp.cshl.org/snpsearch.shtml. Last visited on Aug. 12, 2003. 2 pages.

SNP Report for TSC 0198557. (Jun. 2000). http://snp.cshl.org/snpsearch.shtml. Last visited on Aug. 12, 2003. 2 pages.

SNP Report for TSC 0214366. (Jun. 2000). http://snp.cshl.org/snpsearch.shtml. Last visited on Aug. 12, 2003. 2 pages.

SNP Report for TSC 0264580. (Aug. 2000). http://snp.cshl.org/snpsearch.shtml. Last visited on Apr. 14, 2003. 2 pages.

SNP Report for TSC 0413944. (Aug. 2000). http://snp.cshl.org/snpsearch.shtml. Last visited on Apr. 14, 2003. 2 pages.

SNP Report for TSC 0597888. (Jun. 2000). http://snp.cshl.org/snpsearch.shtml. Last visited on Aug. 12, 2003. 2 pages.

SNP Report for TSC 0813773. (Oct. 2000). http://snp.cshl.org/snpsearch.shtml. Last visited on Aug. 12, 2003. 2 pages.

SNP Report for TSC 0837969. (Dec. 2000). http://snp.cshl.org/snpsearch.shtml. Last visited on Aug. 12, 2003. 2 pages.

SNP Report for TSC 1130902. (May 2001). http://snp.cshl.org/snpsearch.shtml. Last visited on Aug. 12, 2003. 2 pages.

SNP Report TSC 0309610. (Jul. 2000). http://snp.cshl.org/snpsearch.shtml. Last visited on Sep. 10, 2003.

SNP Report TSC 0607185 (Oct. 2000). http://snp.cshl.org/snpsearch.shtml. Last visited on Sep. 11, 2003. 2 pages.

SNP TSC 0200347. (Jun. 2000). http://snp.cshl.org/snpsearch.shtml. Last visited on Sep. 10, 2003. 2 pages.

Spafford, M. F. et al. (2001). "Detection of Head and Neck Squamos Cell Carcinoma Among Exfoliated Oral Mucosal Cells by Microsatellite Analysis," *Clinical Cancer Research* 7:607-612.

Subramanian, G. et al. (2001) "Implications of the Human Genome for Understanding Human Biology and Medicine," *JAMA* 286(18):2296-2307.

Syvänen, A-C. (1999). "From Gels to Chips: "Minisequencing" Primer Extension for Analysis of Point Mutations and Single Nucleotide Polymorphisms," *Human Mutation* 13:1-10.

Szybalski, W. et al. (1991). "Class-IIS Restriction Enzymes—A Review," *Gene* 100:13-16.

Taton, T.A. et al. (2000). "Scanometric DNA Array Detection with Nanoparticle Probes," *Science* 289:1757-1760.

Tockman, M. MD, PhD. (2000). "Advances in Sputum Analysis for Screening and Early Detection of Lung Cancer," *Cancer Control* 7(1):19-24.

Traverso, G. et al. (2002). "Detection of *APC* Mutations in Fecal DNA from Patients With Colorectal Tumors," *New England Journal of Medicine* 346(5):311-320.

Tsao, J. and Shibata, D. (1994). "Further Evident That One of the Earliest Alterations in Colorectal Carcinogenesis Involves APC," *Am. J. Pathol.* 145(3):531-534.

Tsongalis, G. J. et al. (2001). "READIT: A Novel Technology Used in the Interrogation of Nucleic Acid Sequences for Single-Nucleotide Polymorphisms," *Experimental and Molecular Pathology* 71:222-225.

Utting, M. et al. (2002). "Micorsatellite Analysis of Free Tumor DNA in Urine, Serum, and Plasma of Patients: A Minimally Invasive Method for the Detection of Bladder Cancer," *Clinical Cancer Res.* 8:35-40.

van der Luijt, R. et al. (1994). "Rapid Detection of Translation-Terminating Mutations at the Ademomatous Polyposis Coli (APC) Gene by Direct Protein Truncation Test," *Genomics* 20:1-4.

van Rhijin, Bas, W. G. et al. (2003). "Combined Microsatellite and *FGFR3* Mutation analysis Enables a Highly Sensitive Detection of Urothelial Cell Carcinoma in Voided Urine," *Clinical Cancer Res.* 9:257-263.

Venter, J.C. et al. (2001). "The Sequence of the Human Genome," *Science* 291:1304-1351. (Erratum attached, 1 page Jun. 2001).

Walknowska, J. et al. (1969). "Practical and Theoretical Implicationsof Fetal/Maternal Lymphocyte Transfer," *The Lancet* 1:1119-1122.

Wallace, R.W. (1997). "DNA on a Chip: Serving Up the Genome for Diagnostics and Research," *Molecular Medicine Today* 3:384-389.

Wang, D. G. et al. (1998). "Large-Scale Identification, Mapping, and Genotyping of Single-Nucleotide Polymorphisms in the Human Genome," *Science* 280:1077-1082.

Waterston, R.H. and McPherson, J.D. (2001). "A Map of Human Genome Sequence Variation Containing 1.42 Million Single Nucleotide Polymorphisms," *Nature* 409:928-933.

Welsh K. and Bunce, M. (1999). "Molecular Typing for the MHC and PCR-SSP," *Reviews in Immunogenetics* 1:157-176.

Westin, L. et al. (2000). "Anchored Multiplex Amplification on a Microelectronic Chip Array," *Nature Biotechnology* 18:199-204.

Wilson, K. S. et al. (2002). "Differential Gene Expression Patterns in HER2/*neu*-Positive and—Negative Breast Cancer Cell Lines and Tissues," *Am. J. Pathol.* 161 (4):1171-1185.

Xie, D. et al. (2000). "Population-Based, Case-Control Study of HER2 Genetic Polymorphism and Breast Cancer Risk," *J. Natl. Cancer Institute* 92(5):412-417.

Zhou, G-H. et al. (2001). "Quantitative Detection of Single Nucleotide Polymorphisms for a Pooled Sample by a Bioluminometric Assay Coupled with Modified Primer Extension Reactions (BAMPER)," *Nucleic Acids Research* 29(19):1-11.

Saito, H. et al. (Sep. 30, 2000). "Prenatal DNA Diagnosis of a Single-Gene Disorder from Maternal Plasma," *The Lancet* 356:1170.

U.S. Appl. No. 60/360,232, filed Mar. 1, 2002, Dhallan.

U.S. Appl. No. 60/378,354, filed May 8, 2002, Dhallan.

Amicucci, P. et al. (2000). "Prenatal Diagnosis of Myotonic Dystrophy Using Fetal DNA Obtained from Maternal Plasma," *Clinical Chemistry* 46(2):301-302.

Angert, R.M. et al. (Jan. 2003). "Fetal Cell-Free Plasma DNA Concentrations in Maternal Blood Are Stable 24 Hours after Collection: Analysis of First- and Third-Trimester Samples," *Clinical Chemistry* 49(1):195-198.

Anker, P. et al. eds. (Apr. 2000). "Circulating Nucleic Acids in Plasma or Serum," Table of Contents from the *First International Symposium on Circulating Nucleic Acids in Plasma/Serum: Implication in Cancer Diagnosis, Prognosis, or Follow-up and in Prenatal Diagnosis*, Apr. 18-20, 1999 in Menthon Saint-Bernard, France, located at <http://www.unige.ch/LABPV/symposium/cnaps/cnaps_book.html> last visited on Mar. 27, 2001, four pages.

Anonymous. (Dec. 16, 1996). "Birth Defects: Maternal Blood Gets Put to the Test," *Physician's Weekly Clinical Updates* located at: <http://www.physweekly.com/archive/96/12_16_19/cu4.html> last visited on Mar. 27, 2001, one page.

Anonymous. (Dec. 17, 1998). "Strategies for the Rapid Prenatal Detection of Down's Syndrome," *CMGS* located at <http://www.ich.ucl/ac/uk/cmgs/downs98.html> last visited on Mar. 27, 2001, four pages.

Anonymous. (Feb. 5, 2001). "Methods of Ultrasensitive Bioanalysis: DNA Sequencing and Indexing" *Union Bay Ultrasensitive Bioanalysis Team* located at <http://faculty.washington.edu/dovichi/research/application/DNA/DNASequencing.html> last visited Apr. 16, 2001, four pages.

Anonymous. (2001). "Molecular Indexing (MI) Home Page," *Helix Research Institute* located at <http://www.hri.co.jp/MI> last visited Apr. 16, 2001, four pages.

Barnett, E.V. (Jun. 1968). "Detection of Nuclear Antigens (DNA) in Normal and Pathologic Human Fluids by Quantitative Complement Fixation," *Arthritis and Rheumatism* 11(3):407-417.

Bauer, M. et al. (Jan. 2002). "Detection of Maternal Deoxyribonucleic Acid in Umbilical Cord Plasma by Using Fluorescent Polymerase Chain Reaction Amplification of Short Tandem Repeat Sequences," *Am. J. Obstet. Gynecol.* 186:117-120.

Beer, A.E. et al. (Sep. 7, 1994). "The Biological Basis of Passage of Fetal Celular Material into the Maternal Circulation," *Annals New York Academy of Sciences* 731:21-35.

Bennett, P.R. et al. (Aug. 26, 1993). "Prenatal Determination of Fetal RhD Type of DNA Amplification," *The New England Journal of Medicine* 329(9):607-610.

Bianchi, D.W. (Dec. 1995). "Prenatal Diagnosis by Analysis of Fetal Cells in Maternal Blood," *The Journal of Pediatrics* 127(6):847-856.

Bianchi, D.W. (1998). "Current Knowledge About Fetal Blood Cells in the Maternal Circulation," *J. Perinat. Med.* 26:175-185.

Bianchi, D.W. (1998). "Fetal DNA in Maternal Plasma: The Plot Thickens and the Placental Barrier Thins," *Am. J. Hum. Genet.* 62:763-764.

Bianchi, D.W. (2000). "A Guest Editorial: State of Fetal Cells in Maternal Blood: Diagnosis or Dilemma," *Obstetrical and Gynecological Survey* 55(11):665-667.

Bianchi, D.W. (Sep. 2000). "Fetal Cells in the Mother: From Genetic Diagnosis to Diseases Associated with Fetal Cell Microchimerism," *European Journal of Obstetrics & Gynecology and Reproductive Biology* 92:103-108.

Bianchi, D.W. (May 2002). "Prenatal Exclusion of Recessively Inherited Disorders: Should Maternal Plasma Analysis Precede Invasive Techniques?" *Clinical Chemistry* 48(5):689-670.

Bianchi, D.W. et al. (2001). "Longitudinal Fetal DNA Quantitation Studies in Maternal Cells and Plasma over a 24 Hour Period," Program Nr: 2377 located at <http://www.faseb.org/genetics/ashg00/f2377.html> last visited on Mar. 27, 2001, one page.

Bianchi, D.W. et al. (May 12-13, 2001). "Thoughts on the Origin of Fetal DNA in the Pregnant Woman," Abstract 3.4 *In* Chapter 3 "Clinical Applications of Fetal DNA in Maternal Plasma," *In Abstracts, 12th Fetal Cell Workshop, Fetal Diagn. Ther.* 16:450.

Bianchi, D.W. et al. (Jul. 2002). "Fetal Gender and Aneuploidy Detection Using Fetal Cells in Maternal Blood: Analysis of NIFTY I Data," *Prenatal Diagnosis* 22:609-615.

Brambati, B. (Sep. 7, 1994). "Prenatal Diagnosis by Isolating and Analyzing Fetal Nucleated Red Cells: Dream or Reality?" *Annals New York Academy of Sciences* 731:248-252.

Byrne, B.M. et al. (Jul. 1, 2003). "Fetal DNA Quantitation in Peripheral Blood Is Not Useful as a Marker of Disease Severity in Women with Preeclampsia," *Hypertens Pregnancy* 22(2):157-164.

Camaschella, C. et al. (Jun. 1, 1990). "Prenatal Diagnosis of Fetal Hemoglobin Lepore-Boston Disease on Maternal Peripheral Blood," *Blood* 75(11):2102-2106.

Chen, X.Q. et al. (Sep. 1996). "Microsatellite Alterations in Plasma DNA of Small Cell Lung Cancer Patients," *Nature Medicine* 2(9):1033-1035.

Cohen, J. (Oct. 2002). "Fetal Fortunes," *Technology Review* 54-61.

Cox, R.A. et al. (Feb. 1977). "DNA Concentrations in Serum Mand Plasma," *Clinical Chemistry* 23(2):297.

Cunningham, J. et al. (Oct. 1999). "Non-Invasive RNA-Based Determination of Fetal Rhesus D Type: A Prospective Study Based on 96 Pregnancies," *British J. of Ob-Gyn* 106:1023-1028.

Davis, G.L. et al. (Jan.-Feb. 1973). "Detection of Circulating DNA by Counterimmuno-electrophoresis (CIE)," *Arthritis and Rheumatism* 16(1):52-58.

Dhallan, R. et al. (Mar. 3, 2004). "Methods to Increase the Percentage of Free Fetal DNA Recovered From the Maternal Circulation," *JAMA* 291(9):1114-1119.

Ding, C. et al. (Jul. 20, 2004). "MS Analysis of Single-Nucleotide Differences in Circulating Nucleic Acids: Application to Noninvasive Prenatal Diagnosis," *PNAS* 101(29):10762-10767.

Douglas, G.W. et al. (Nov. 1959). "Trophoblast in the Circulating Blood During Pregnancy," *American Journal of Obstetrics and Gynecology* 78(5):960-973.

Emanuel, S.L. et al. (1993). "Amplification of Specific Gene Products from Human Serum," *GATA* 10(6):144-146.

Farnia, A. et al. (1998). "Fetal Cells in Maternal Blood as a Second Non-Invasive Step for Fetal Down Syndrome Screening," *Prenat. Diagn.* 18:983-986.

Fournié, G.J. et al. (1993). "Plasma DNA as Cell Death Marker in Elderly Patients," *Gerontology* 39:215-221.

Fowke, K.R. et al. (1995). "Genetic Analysis of Human DNA Recovered From Minute Amounts of Serum or Plasma," *Journal of Immunological Methods* 180:45-51.

Hahn, S. et al. (May 12-13, 2001). "An Examination of Fetal Cells, Free Fetal DNA and Fetal Cell Culture: The Basel Experience," Abstract 3.2 *In* Chapter 3 "Clinical Applications of Fetal DNA in Maternal Plasma," *In Abstracts, 12th Fetal Cell Workshop, Fetal Diagn. Ther.* 16:449.

Hahn, S. et al. (Sep. 2002). "Prenatal Diagnosis Using Fetal Cells and Cell-Free Fetal DNA in Maternal Blood: What is Currently Feasible?" *Clinical Obstetrics and Gynecology* 45(3):649-656.

Heinemann, J.A. et al. (Apr. 2000). "New Hypotheses on the Material Nature of Horizontally Mobile Genes," *Annals New York Academy of Sciences* 906:169-186.

Holzgreve, W. et al. (2000). "Fetal Cells in Cervical Mucus and Maternal Blood," *Bailliere's Clinical Obstetrics and Gynaecology* 14(4):709-722.

Holzgreve, W. et al. (Jun. 2001). "Prenatal Diagnosis Using Fetal Cells and Free Fetal DNA in Maternal Blood," *Clinical Perinatology* 28(2):353-365.

Human Gene Mutation Database (HGMD). (Date Unknown). Located at <http:archive.uwcm.ac.uk/uwcm/mg/hgmd0.html> last visited on Sep. 20, 2004. 3 pages total.

International Search Report mailed on Jul. 17, 2003, for PCT Patent Application No. PCT/US03/06376 filed on Feb. 28, 2003, 4 pages.

International Search Report mailed on Sep. 2, 2003, for PCT patent application No. PCT/US03/06198 filed on Feb. 28, 2003, 9 pages.

International Search Report mailed on Jul. 20, 2004 for PCT patent application No. PCT/US03/27308 filed Aug. 29, 2003, 8 pages.

Kamm, R.C. et al. (1972). "Nucleic Acid Concentrations in Normal Human Plasma," *Clinical Chemistry* 18(6):519-522.

Kamm, R.C. et al. (1975). "Plasma Deoxyribonucleic Acid Concentrations of Women in Labor and Umbilical Cords," *American Journal of Obstetrics and Gynecology* 121(1):29-31.

Kang, A. et al. (1999). "Fetal Cells in Maternal Blood: Their Role in Non-Invasive Prenatal Diagnosis and in the Etiology of Certain Diseases," ("Fetale Zellen im mütterlichen Blut—ihre Bedeutung für eine nicht-invasive pränatale Diagnostik und bei der Ätiologic bestimmter Erkrankungen,") *Schweiz Med. Wochenschr* 129:1470-1743. English Translation and original language article.

Kuo, P-L. (1999). "Fetal Cell Isolation From Maternal Blood—Clinical and Biological Implications," *Adv. Obstet. Perinatol.* 10(1):15-24.

Kwak, J.Y.H. et al. (Sep. 7, 1994). "Biological Basis of Fetoplacental Antigenic Determinants in the Induction of the Antiphospholipid Antibody Syndrome and Recurrent Pregnancy Loss," *Annals New York Academy of Sciences* 731:242-245.

Lagona, F. et al. (Apr. 2000). "Fetal DNA Analysis from Maternal Plasma and Nucleated Blood Cells," *Annals New York Academy of Sciences* 906:156-160.

Lee, T. et al. (Nov. 2002). "Down Syndrome and Cell-Free Fetal DNA in Archived Maternal Serum," *Am. J. Obstet. Gynecol.* 187:1217-1221.

Leon, S.A. et al. (1977). "Free DNA in the Serum of Rheumatoid Arthritis Patients," *Journal of Rheumatology* 4(2):139-143.

Lo, Y.M.D. (Sep. 7, 1994). "An Improved PCR-Based System for Prenatal Sex Determination from Maternal Peripheral Blood," *Annals New York Academy of Sciences* 731:214-216.

Lo, Y.M.D. et al. (Sep. 7, 1994). "Strategies for the Detection of Autosomal Fetal DNA Sequence from Maternal Peripheral Blood," *Annals New York Academy of Sciences* 731:204-213.

Lo, Y.M.D. (Sep. 7, 1994). "Prenatal Determination of Fetal Rhesus D Status by DNA Amplification of Peripheral Blood of Rhesus-Negative Mothers," *Annals New York Academy of Sciences*, 731:229-236.

Lo, Y.M.D. (Dec. 1994) "Non-Invasive Prenatal Diagnosis Using Fetal Cells in Maternal Blood," *Journal of Clinical Pathology* 47(12):1060-1065.

Lo, Y.M.D. (1999). "Fetal RhD Genotyping From Maternal Plasma," *Annals of Medicine* 31(5):308-312.

Lo, Y.M.D. (1999). "Rapid Clearance of Fetal DNA from Maternal Plasma," *Am. J. Hum. Genet.* 64:218-224.

Lo, Y.M.D. (Apr. 2000). "Fetal DNA in Maternal Plasma," *Annals of New York Academy of Sciences* 906:141-147.

Lo, Y.M.D. (Dec. 2000). "Fetal DNA in Maternal Plasma: Biology and Diagnostic Applications," *Clinical Chemistry* 46(12):1903-1906.

Lo, Y.M.D. (May 12-13, 2001). "Fetal DNA in Maternal Plasma," Abstract 3.1 *In* Chapter 3 "Clinical Applications of Fetal DNA in Maternal Plasma," *In Abstracts, 12th Fetal Cell Workshop, Fetal Diagn. Ther.*, 16:448-449.

Lo, Y.M.D. (Jun. 2001). "Fetal DNA in Maternal Plasma: Application to Non-Invasive Blood Group Genotyping of the Fetus," *Transfus. Clin. Biol.* 8(3):306-310.

Lo, Y.M.D. (Jan. 2003). "Fetal DNA in Maternal Plasma/Serum: The First 5 Years," *Pediatric Research* 53(1):16-17.

Lo, Y.M.D. et al. (Jun. 16, 1990). "Detection of Single-Copy Fetal DNA Sequence From Maternal Blood," *The Lancet* 335:1463-1464.

Lo, Y.M.D. et al. (1994). "Detection of Fetal RhD Sequence From Peripheral Blood of Sensitized RhD-Negative Women," *British Journal of Hematology* 87:658-660.

Lo, Y.M.D. et al. (1999). "Increased Fetal DNA Concentrations in the Plasma of Pregnant Women Carrying Fetuses with Trisomy 21," *Clinical Chemistry* 45(10):1747-1751.

Longo, M.C. et al. (1990). "Use of Uracil DNA Glycosylase to Control Carry-Over Contamination in Polymerase Chain Reactions," *Gene* 93:125-128.

Martin, M. et al. (Feb. 1992). "A Method for Using Serum or Plasma as a Source of DNA for HLA Typing," *Human Immunology* 33(2):108-113.

Miller, D. ed. (Aug. 16, 1996). "Notes on Fifth Fetal Cell Workshop," Amsterdam, May 3, 1996, published and located at <http://iubio.bio.indiana.edu> last visited on Mar. 27, 2001, four pages.

Mulcahy, H.E. et al. (Sep. 7, 1996). "Cancer and Mutant DNA in Blood Plasma," *The Lancet* 348(9028):628.

Muller, F. et al. (Mar. 2000). "Parental Origin of the Extra Chromosome in Prenatally Diagnosed Fetal Trisomy 21," *Hum. Genet.* 106:340-344.

Nawroz, H. et al. (Sep. 1996). "Microsatelite Alterations in Serum DNA of Head and Neck Cancer Patients," *Nature Medicine* 2(9):1035-1037.

Oliphant, A. et al. (Jun. 2002). "BeadArray™ Technology: Enabling An Accurate, Cost-Effective Approach to High-Throughput Genotyping," *Biotechniques* 32(Suppl):S56-S61.

Pertl, B. et al. (May 14, 1994). "Rapid Molecular Method for Prenatal Detection of Down's Syndrome," *The Lancet* 343:1197-1198.

Pertl, B. et al. (Oct. 1999). "First Trimester Prenatal Diagnosis: Fetal Cells in the Maternal Circulation," *Seminars in Perinatology* 23(5):393-402.

Pertl, B. et al. (Jan. 6, 2000). "Detection of Male and Female Fetal DNA in Maternal Plasma by Multiplex Fluorescent Polymerase Chain Reaction Amplification of Short Tandem Repeats," *Hum. Genet.* 106:45-49.

Pertl, B. et al. (Mar. 27, 2001). "Detection of Male and Female Fetal DNA in Maternal Plasma by Multiplex Fluorescent Polymerase Chain Reaction Amplification of Short Tandem Repeats," located at <http://link.springer.de/link/service/journals/00439/contents/99/00166/s004399900166ch002.html> last visited on Mar. 27, 2001, one page.

Pertl, B. et al. (Mar. 27, 2001). "Detection of Male and Female Fetal DNA in Maternal Plasma by Multiplex Fluorescent Polymerase Chain Reaction Amplification of Short Tandem Repeats (STRs)," Program Nr: 410 located at <http://www.faseb.org.genetics/ashg99/f410.html> last visited Mar. 27, 2001, one page.

Poon, L.L.M. (2000). "Presence of Fetal RNA in Maternal Plasma," *Clin. Chem.* 46(11):1832-1834.

Poon, L.L.M. et al. (Nov. 25, 2000). "Prenatal Detection of Fetal Down's Syndrome from Maternal Plasma," *The Lancet* 356:1819-1820.

Poon, L.L.M. et al. (Nov. 2001). "Circulating Fetal DNA in Maternal Plasma," *Clinica Chimmica Acta* 313:151-155.

Promega, Inc. (Dec. 1999). "Wizard® DNA Clean-Up System," *Promega Corp. Technical Bulletin* TB141:1-4.

Ramster, B. (Jul. 2, 2001). "IVF Screening for Down's Syndrome Flawed, Say Experts," BioMedNet located at <http://news.bmn,com/news/story?day=010703&story> last visited Jul. 3, 2001, one page.

Raptis, L. et al. (Dec. 1980). "Quantitation and Characterization of Plasma DNA in Normals and Patients with Systemic Lupis Erythematosus," *Journal of Clinical Investigation* 66:1391-1399.

Samura, O. et al. (Jul. 2000). "Female Fetal Cells in Maternal Blood: Use of DNA Polymorphisms to Prove Origin," *Hum. Genet.* 107:28-32.

Samura, O. et al. (Sep. 2001). "Diagnosis of Trisomy 21 in Fetal Nucleated Erythrocytes from Maternal Blood by Use of Short Tandem Repeat Sequences," *Clinical Chemistry* 47(9):1622-1626.

Shapiro, B. et al. (1983). "Determination of Circulating DNA Levels in Patients with Benign or Malignant Gastrointestinal Disease," *Cancer* 51:2116-2120.

Sidransky, D. (Apr. 2000). "Circulating DNA: What We Know and What We Need to Learn," *In* Circulating Nucleic Acids in Plasma or Serum, *Annals New York Academy of Sciences* 906:1-4.

Simpson, J.L. et al. (1994). "Isolating Fetal Cells in Maternal Circulation for Prenatal Diagnosis," *Prenatal Diagnosis* 14:1229-1242.

Simpson, J.L. et al. (Sep. 7, 1994). "Fetal Cells in Maternal Blood. Overview and Historical Perspective," *Annals New York Academy of Sciences* 731:1-8.

Simpson, J.L. et al. (Mar. 3, 2004). "Cell-Free Fetal DNA in Maternal Blood," *JAMA* 291(9):1135-1137.

Smid, M. et al. (1999). "Evaluation of Different Approaches for Fetal DNA Analysis from Maternal Plasma and Nucleated Blood Cells," *Clinical Chemistry* 45(8):1570-1572.

Smid, M. et al. (2001). "Quantitative Analysis of Fetal DNA in Maternal Plasma in Pregnancies Affected by Insulin-Dependent Diabetes mellitus (IDDM)," Abstract 3.3 *In* Chapter 3 "Clinical Applications of Fetal DNA in Maternal Plasma," *In Abstracts, 12th Fetal Cell Workshop, Fetal Diagn. Ther.*, 16:449-450.

SNP Entry Report for HC21S00007. (Date Unknown). located at <http//:csnp.unige.ch/cgi-bin/csnp_fetch?entry=HC21S00007> last visited on Sep. 27, 2004, one page.

SNP Entry Report for HC21S00027. (Date Unknown). located at <http//:csnp.unige.ch/cgi-bin/csnp_fetch?db+csnp&format=html &entry=HC21S00027> last visited on Sep. 27, 2004, one page.

SNP Entry Report for HC21S00131. (Date Unknown). located at <http//:csnp.unige.ch/cgi-bin/csnp_fetch?db+csnp&format=html &entry=HC21S00131> last visited on Sep. 27, 2004, one page.

SNP Entry Report for HC21S00340. (Date Unknown). located at <http//:csnp.unige.ch/cgi-bin/csnp_fetch?entry=HC21S00340> last visited on Sep. 27, 2004, 2 pages.

SNP Report for TSC 0200347. (Aug. 2000). http://snp.cshl.org/snpsearch.shtml. Last visited on Sep. 10, 2003, 2 pages.

SNP Report for TSC 0214366. (Oct. 2000). http://snp.cshl.org/snpsearch.shtml. Last visited on Aug. 12, 2003, 2 pages.

SNP Report for TSC 0214366. (Oct. 2000). (http://snp.cshl.org/snpsearch.shtml. Last visited on Dec. 30, 2003, 2 pages.

SNP Report for TSC 0309610. (Aug. 2000). http://snp.cshl.org/snpsearch.shtml. Last visited on Sep. 10, 2003, 2 pages.

SNP Report for TSC 0607185. (Oct. 2000). http://snp.cshl.org/snpsearch.shtml. Last visited on Sep. 11, 2003, 2 pages.

SNP Report for TSC 0813773. (Oct. 2000). http://snp.cshl.org/snpsearch.shtml. Last visited on Aug. 12, 2003, 2 pages.

SNP Report for TSC 0837969. (Dec. 2000). http://snp.cshl.org/snpsearch.shtml. Last visited on Aug. 12, 2003, 2 pages.

SNP Report for TSC 1130902. (May 2001). http://snp.cshl.org/snpsearch.shtml. Last visited on Aug. 12, 2003, 2 pages.

Steele, C.D. et al. (Dec. 1996). "Prenatal Diagnosis Using Fetal Cells Isolated From Maternal Peripheral Blood: A Review," *Clinical Obstetrics and Gynecology* 39(4):801-813.

Stroun, M. et al. (Apr. 2000). "The Origin and Mechanism of Circulating DNA," *Annals New York Academy of Sciences* 906:161-168.

Tan, E.M. et al. (1966). "Deoxyribonucleic Acid (DNA) and Antibodies to DNA in the Serum of Patients with Systemic Lupis Erythematosus," *Journal of Clinical Investigation* 45(11):1732-1740.

Tang, N.L.S. et al. (1999). "Detection of Fetal-Derived Paternally Inherited X-Chromosome Polymorphisms in Maternal Plasma," *Clinical Chemistry* 45(11):2033-2035.

Thomas, M.R. et al. (Sep. 7, 1994). "The Time of Appearance, and Quantitation, of Fetal DNA in the Maternal Circulation," *Annals New York Academy of Sciences* 731:217-225.

Ugozzoli, L. et al. (1992). "Detection of Specific Alleles by Using Allele-Specific Primer Extension Followed by Capture on Solid Support," *GATA* 9(4):107-112.

Uitto, J. et al. (Aug. 2003). "Probing the Fetal Genome: Progress in Non-Invasive Prenatal Diagnosis," *Trends in Molecular Medicine* 9(8):239-243.

van Wijk, I.J. et al. (2000). "Detection of Apoptotic Fetal Cells in Plasma of Pregnant Women," *Clinical Chemistry* 46(5):729-731.

Velculescu, V.E. et al. (Oct. 2000). "Analysing Uncharted Transcriptomes with SAGE," *TIG* 16(10): 423-425.

Verma, L. et al. (Jul. 4, 1998). "Rapid and Simple Prenatal DNA Diagnosis of Down's Syndrome," *The Lancet* 352:9-11.

Wataganara, T. et al. (Jan. 2003). "Maternal Serum Cell-Free Fetal DNA Levels are Increased in Cases of Trisomy 13 but not Trisomy 18," *Hum. Genet.* 112(1):204-208.

Yamamoto et al. (Mar. 1994). "Anti-ssDNA and dsDNA Antibodies in Preeclampsia," *Asia Oceania J. Obstet Gynaecol.* 20(1):93-99.

Zhang, L. et al. (Jul. 1992). "Whole Genome Amplification From a Single Cell: Implications for Genetic Analysis," *Proc. Nat. Acad. Sci.* 89:5847-5851.

Zhen, D.K. et al. (1998). "Poly-Fish: A Technique of Repeated Hybridizations That Improves Cytogenetic Analysis of Fetal Cells in Maternal Blood," *Prenat. Diagn.* 18:1181-1185.

Zhong, X.Y. et al. (2000). "Fetal DNA in Maternal Plasma is Elevated in Pregnancies with Aneuploid Fetuses," *Prenatal Diagnosis* 20:795-798.

Stratagene Corporation. (1988). "Gene Characterization Kits," *The Stratagene Catalog*, p. 39.

Supplementary European Search Report mailed on Jul. 4, 2006 for EP Application No. 03 74 3737.3, three pages.

\* cited by examiner

FIG. 1B
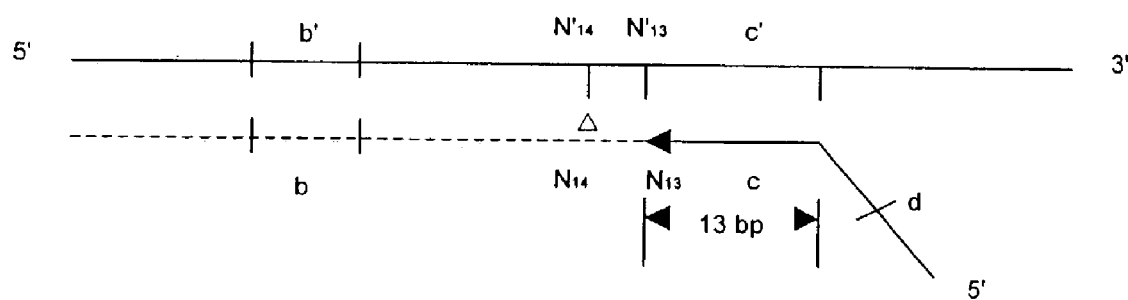
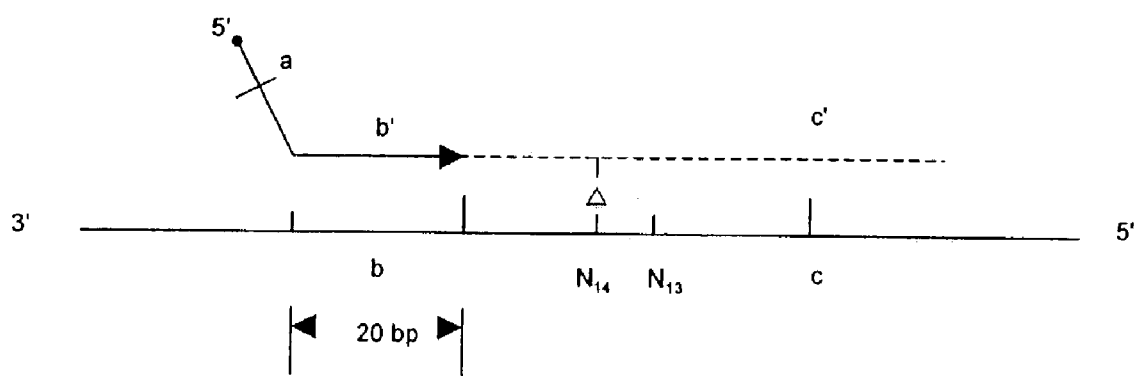

FIG. 1C
First Primer
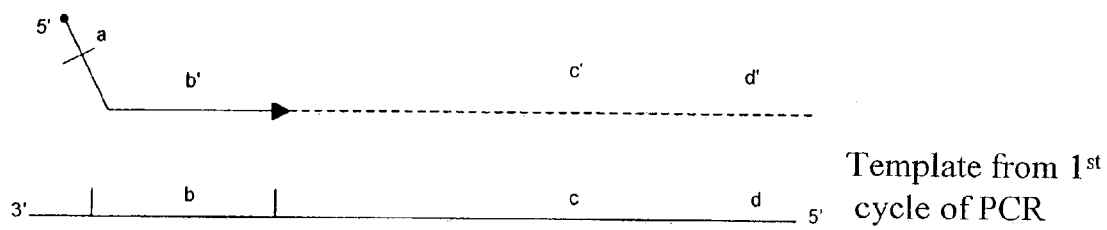
Template from 1st cycle of PCR
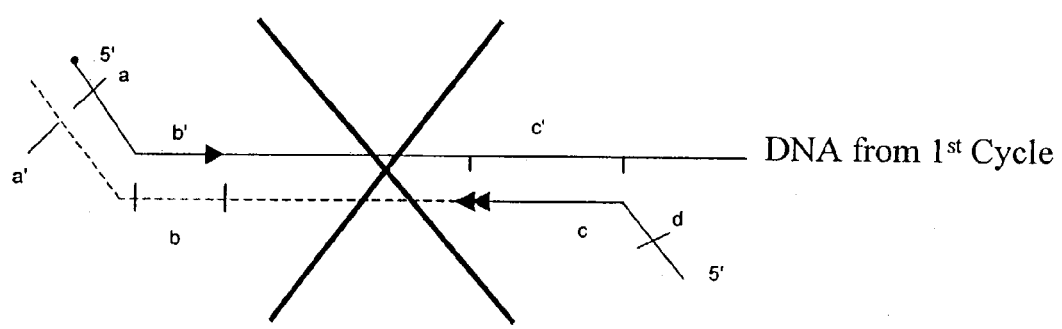
DNA from 1st Cycle Template from 2nd cycle of PCR Second Primer Template from 3rd cycle of PCR Second Primer

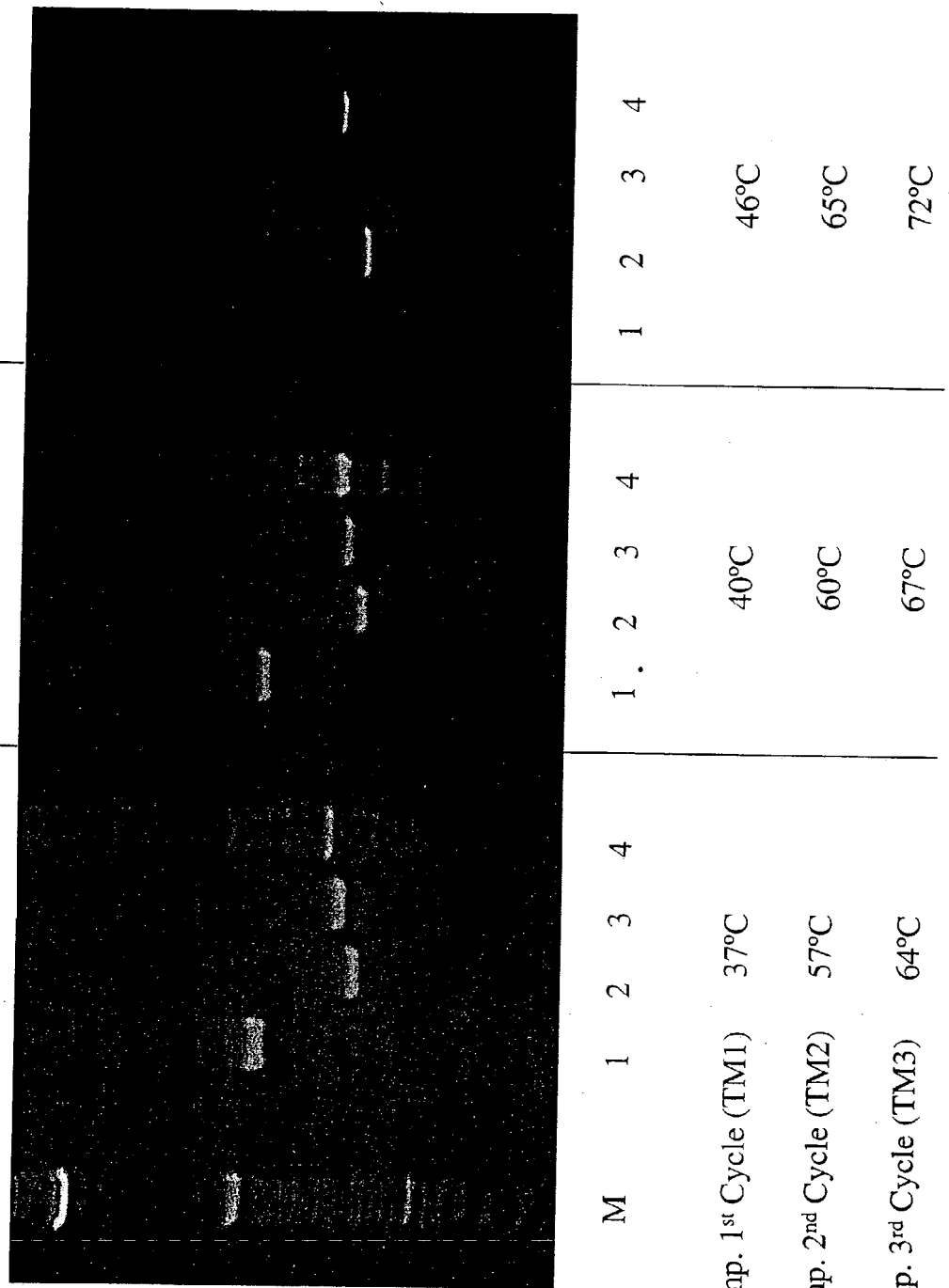

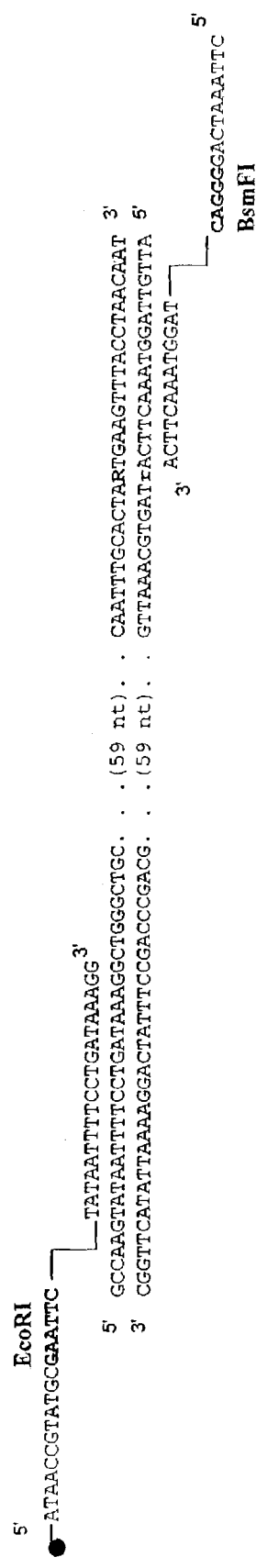
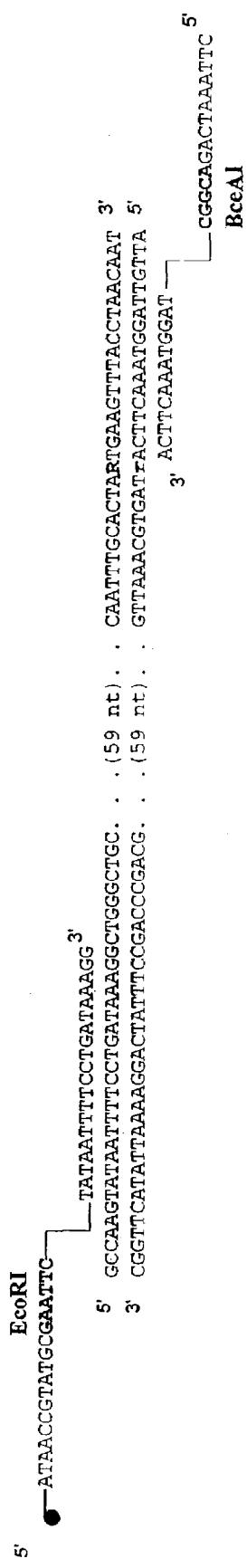
FIG. 4A
FIG. 4B

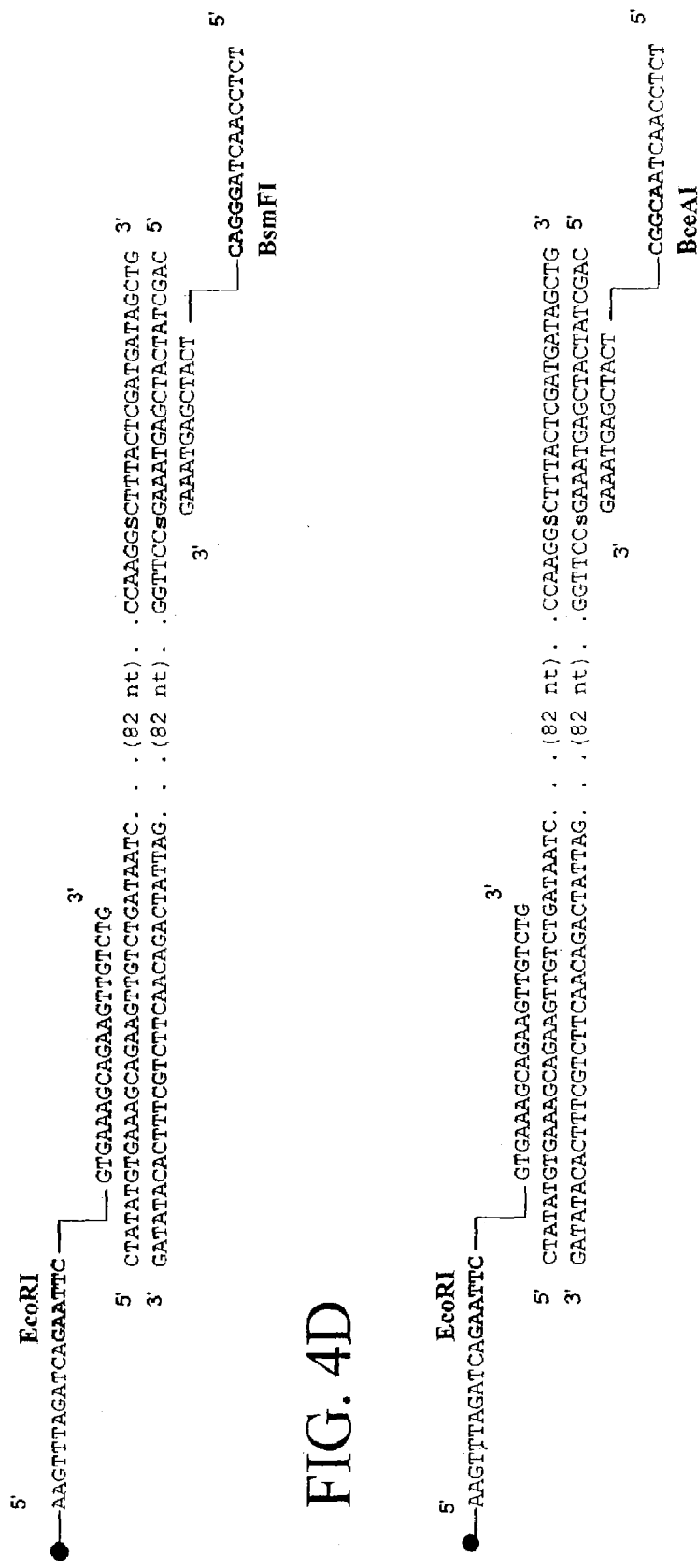

FIG. 5A

```
        EcoRI
5' ―●―ATAACCGTATGCGAATTCTATAATTTCCTGATAAAGGCTG...(59 nt)...CAATTTGCACTARTGAAGTTACCTAGTCCCCAGATTAAG 3'
    3'  TATTGGCATACGCTTAAGATATTAAAAGGACTATTTCCGAC...(59 nt)...GTTAAACGTGATIACTTCAAATGGATCAGGGGACTAAATTC 5'
                                                                            BsmFI
```

FIG. 5B

```
        EcoRI
5' ―――ATAACCGTATGCGAATTCTATAATTTCCTGATAAAGGCTG...(59 nt)...CAATTTGCACTARTGAAGTTACCTAGCCGTCAGATTAAG 3'
    3'  TATTGGCATACGCTTAAGATATTAAAAGGACTATTTCCGAC...(59 nt)...GTTAAACGTGATIACTTCAAATGGATCGGCAGACTAAATTC 5'
                                                                            BceAI
```

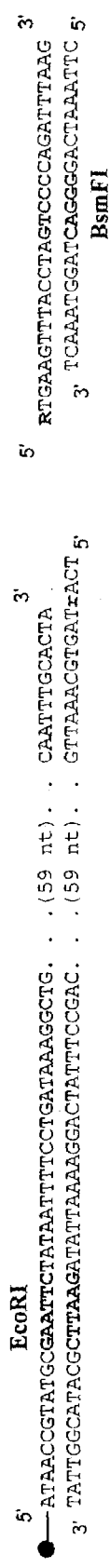
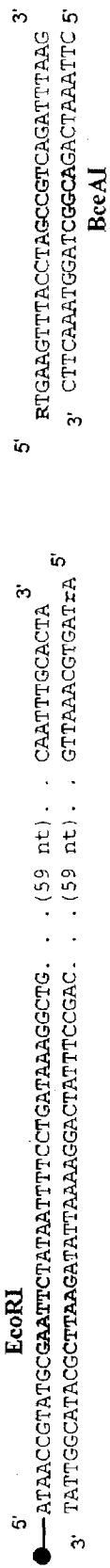
FIG. 6A
FIG. 6B

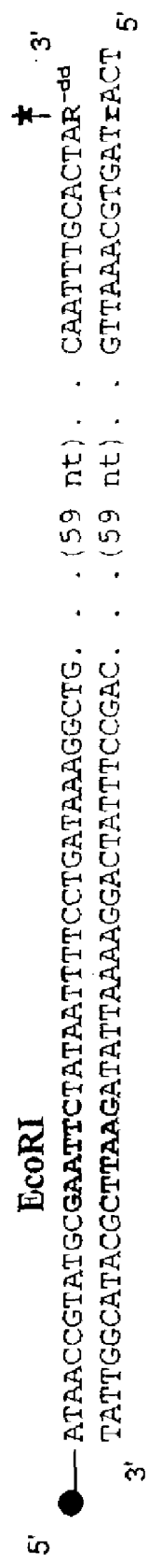
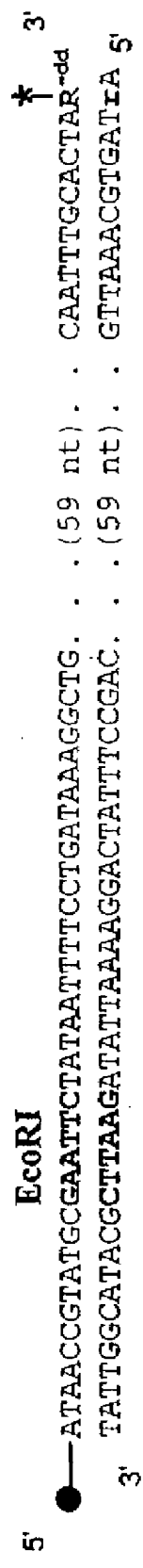
FIG. 7A
FIG. 7B

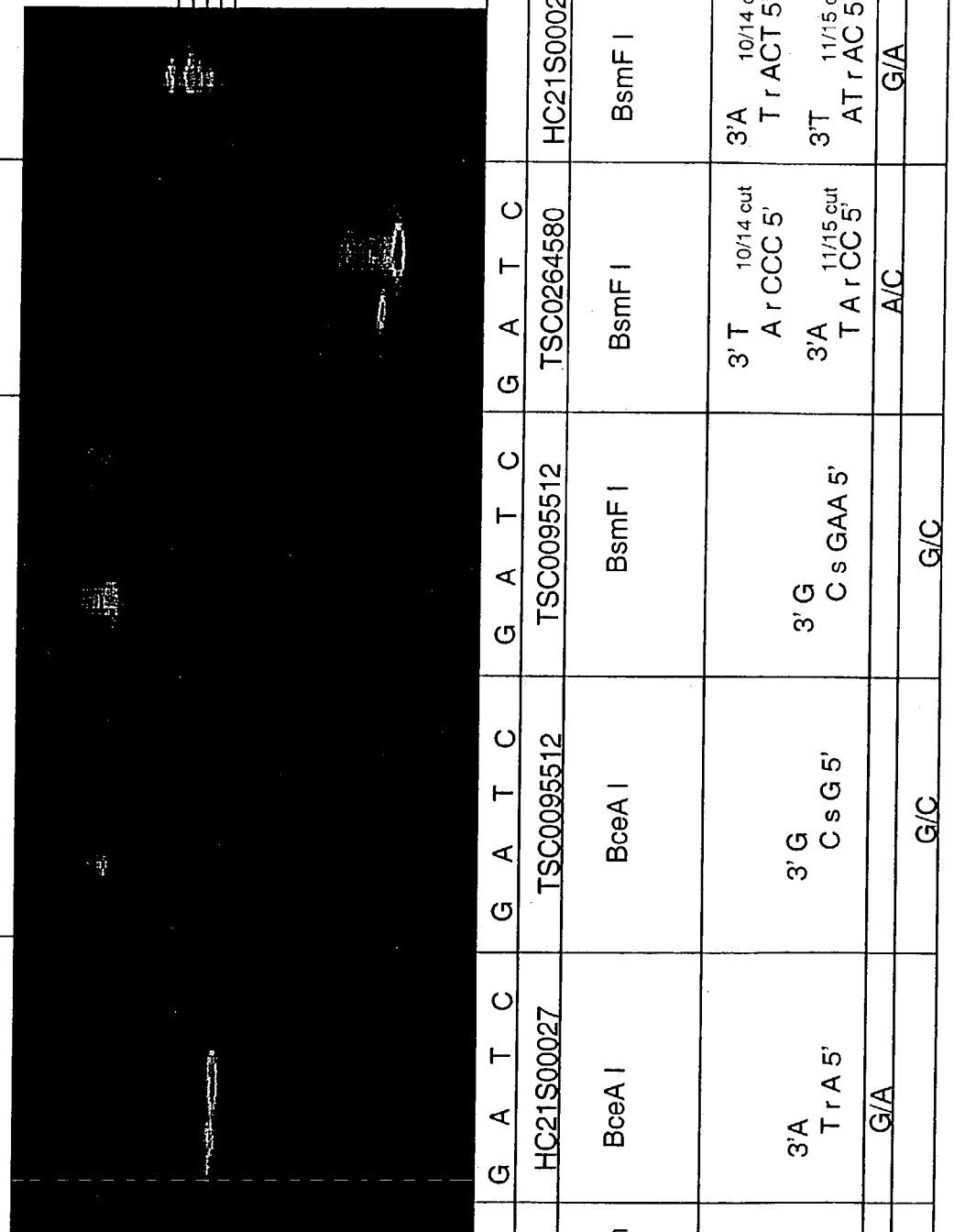

SEQUENCE LISTING

<160> NUMBER OF SEQ ID NOS: 262

<210> SEQ ID NO 1
<211> LENGTH: 15
<212> TYPE: DNA

```
<213> ORGANISM: Unknown
<220> FEATURE:
<221> NAME/KEY: misc_feature
<222> LOCATION: (6)...(15)
<223> OTHER INFORMATION: n = A,T,C or G
<220> FEATURE:
<223> OTHER INFORMATION: Restriction site

<400> SEQUENCE: 1
gggacnnnnn nnnnn                                                    15

<210> SEQ ID NO 2
<211> LENGTH: 19
<212> TYPE: DNA
<213> ORGANISM: Unknown
<220> FEATURE:
<221> NAME/KEY: misc_feature
<222> LOCATION: (1)...(14)
<223> OTHER INFORMATION: n = A,T,C or G
<220> FEATURE:
<223> OTHER INFORMATION: Restriction site

<400> SEQUENCE: 2
nnnnnnnnnn nnnngtccc                                                19

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
ggaaattcca tgatgcgtgg g                                             21

<210> SEQ ID NO 4
<211> LENGTH: 23
<212> TYPE: DNA
<213> ORGANISM: Homo sapiens
<220> FEATURE:
<221> NAME/KEY: misc_feature
<222> LOCATION: (19)...(21)
<223> OTHER INFORMATION: n = A,T,C or G

<400> SEQUENCE: 4
ggaaattcca tgatgcgtnn nac                                           23

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
ggaaattcca tgatgcgtac c                                             21

<210> SEQ ID NO 6
<211> LENGTH: 25
<212> TYPE: DNA
<213> ORGANISM: Homo sapiens
<220> FEATURE:
<221> NAME/KEY: misc_feature
<222> LOCATION: (22)...(23)
<223> OTHER INFORMATION: n = A,T,C or G

<400> SEQUENCE: 6
ggaaattcca tgatgcgtac cnngg                                         25
```

<210> SEQ ID NO 7
<211> LENGTH: 11
<212> TYPE: DNA
<213> ORGANISM: Unknown
<220> FEATURE:
<221> NAME/KEY: misc_feature
<222> LOCATION: (4)...(8)
<223> OTHER INFORMATION: n = A,T,C or G
<220> FEATURE:
<223> OTHER INFORMATION: Restriction site

<400> SEQUENCE: 7
cctnnnnnag g                                                                11

<210> SEQ ID NO 8
<211> LENGTH: 25
<212> TYPE: DNA
<213> ORGANISM: Homo sapiens
<220> FEATURE:
<221> NAME/KEY: misc_feature
<222> LOCATION: (20)...(23)
<223> OTHER INFORMATION: n = A,T,C or G

<400> SEQUENCE: 8
ggaaattcca tgatgcgtan nnngg                                                 25

<210> SEQ ID NO 9
<211> LENGTH: 38
<212> TYPE: DNA
<213> ORGANISM: Artificial Sequence
<220> FEATURE:
<223> OTHER INFORMATION: Primer

<400> SEQUENCE: 9
tagaatagca ctgaattcag gaatacaatc attgtcac                                   38

<210> SEQ ID NO 10
<211> LENGTH: 28
<212> TYPE: DNA
<213> ORGANISM: Artificial Sequence
<220> FEATURE:
<223> OTHER INFORMATION: Primer

<400> SEQUENCE: 10
atcacgataa acggccaaac tcaggtta                                              28

<210> SEQ ID NO 11
<211> LENGTH: 38
<212> TYPE: DNA
<213> ORGANISM: Artificial Sequence
<220> FEATURE:
<223> OTHER INFORMATION: Primer

<400> SEQUENCE: 11
aagtttagat cagaattcgt gaaagcagaa gttgtctg                                   38

<210> SEQ ID NO 12
<211> LENGTH: 28
<212> TYPE: DNA
<213> ORGANISM: Artificial Sequence
<220> FEATURE:
<223> OTHER INFORMATION: Primer

<400> SEQUENCE: 12
tctccaacta acggctcatc gagtaaag                                              28

<210> SEQ ID NO 13
<211> LENGTH: 38
<212> TYPE: DNA
<213> ORGANISM: Artificial Sequence
<220> FEATURE:
<223> OTHER INFORMATION: Primer

<400> SEQUENCE: 13
atgactagct atgaattcgt tcaaggtaga aaatggaa				38

<210> SEQ ID NO 14
<211> LENGTH: 28
<212> TYPE: DNA
<213> ORGANISM: Artificial Sequence
<220> FEATURE:
<223> OTHER INFORMATION: Primer

<400> SEQUENCE: 14
gagaattaga acggcccaaa tcccactc						28

<210> SEQ ID NO 15
<211> LENGTH: 37
<212> TYPE: DNA
<213> ORGANISM: Artificial Sequence
<220> FEATURE:
<223> OTHER INFORMATION: Primer

<400> SEQUENCE: 15
ttacaatgca tgaattcatc ttggtctctc aaagtgc				37

<210> SEQ ID NO 16
<211> LENGTH: 28
<212> TYPE: DNA
<213> ORGANISM: Artificial Sequence
<220> FEATURE:
<223> OTHER INFORMATION: Primer

<400> SEQUENCE: 16
tggaccataa acggccaaaa actgtaag						28

<210> SEQ ID NO 17
<211> LENGTH: 38
<212> TYPE: DNA
<213> ORGANISM: Artificial Sequence
<220> FEATURE:
<223> OTHER INFORMATION: Primer

<400> SEQUENCE: 17
ataaccgtat gcgaattcta taattttcct gataaagg				38

<210> SEQ ID NO 18
<211> LENGTH: 28
<212> TYPE: DNA
<213> ORGANISM: Artificial Sequence
<220> FEATURE:
<223> OTHER INFORMATION: Primer

<400> SEQUENCE: 18
cttaaatcag gggactaggt aaacttca						28

<210> SEQ ID NO 19
<211> LENGTH: 28
<212> TYPE: DNA
<213> ORGANISM: Artificial Sequence
<220> FEATURE:
<223> OTHER INFORMATION: Primer

<400> SEQUENCE: 19
cttaaatcag acggctaggt aaacttca                                28

<210> SEQ ID NO 20
<211> LENGTH: 28
<212> TYPE: DNA
<213> ORGANISM: Artificial Sequence
<220> FEATURE:
<223> OTHER INFORMATION: Primer

<400> SEQUENCE: 20
tctccaacta gggactcatc gagtaaag                                28

<210> SEQ ID NO 21
<211> LENGTH: 37
<212> TYPE: DNA
<213> ORGANISM: Artificial Sequence
<220> FEATURE:
<223> OTHER INFORMATION: Primer

<400> SEQUENCE: 21
aacgccgggc gagaattcag tttttcaact tgcaagg                      37

<210> SEQ ID NO 22
<211> LENGTH: 28
<212> TYPE: DNA
<213> ORGANISM: Artificial Sequence
<220> FEATURE:
<223> OTHER INFORMATION: Primer

<400> SEQUENCE: 22
ctacacatat ctgggacgtt ggccatcc                                28

<210> SEQ ID NO 23
<211> LENGTH: 38
<212> TYPE: DNA
<213> ORGANISM: Artificial Sequence
<220> FEATURE:
<223> OTHER INFORMATION: Primer

<400> SEQUENCE: 23 tacctttga tcgaattcaa ggccaaaaat attaagtt                      38

<210> SEQ ID NO 24
<211> LENGTH: 28
<212> TYPE: DNA
<213> ORGANISM: Artificial Sequence
<220> FEATURE:
<223> OTHER INFORMATION: Primer

<400> SEQUENCE: 24
tcgaacttta acggccttag agtagaga                                28

<210> SEQ ID NO 25
<211> LENGTH: 38
<212> TYPE: DNA
<213> ORGANISM: Artificial Sequence
<220> FEATURE:
<223> OTHER INFORMATION: Primer

<400> SEQUENCE: 25
cgatttcgat aagaattcaa aagcagttct tagttcag                     38

<210> SEQ ID NO 26

```
<211> LENGTH: 28
<212> TYPE: DNA
<213> ORGANISM: Artificial Sequence
<220> FEATURE:
<223> OTHER INFORMATION: Primer

<400> SEQUENCE: 26
tgcgaatctt acggctgcat cacattca                                28

<210> SEQ ID NO 27
<211> LENGTH: 23
<212> TYPE: DNA
<213> ORGANISM: Homo sapiens
<220> FEATURE:
<221> NAME/KEY: misc_feature
<222> LOCATION: (3)...(5)
<223> OTHER INFORMATION: n = A,T,C or G

<400> SEQUENCE: 27
gtnnnacgca tcatggaatt tcc                                     23

<210> SEQ ID NO 28
<211> LENGTH: 25
<212> TYPE: DNA
<213> ORGANISM: Homo sapiens
<220> FEATURE:
<221> NAME/KEY: misc_feature
<222> LOCATION: (3)...(4)
<223> OTHER INFORMATION: n = A,T,C or G

<400> SEQUENCE: 28
ccnnggtacg catcatggaa tttcc                                   25

<210> SEQ ID NO 29
<211> LENGTH: 25
<212> TYPE: DNA
<213> ORGANISM: Homo sapiens
<220> FEATURE:
<221> NAME/KEY: misc_feature
<222> LOCATION: (3)...(6)
<223> OTHER INFORMATION: n = A,T,C or G

<400> SEQUENCE: 29
ccnnnntacg catcatggaa tttcc                                   25

<210> SEQ ID NO 30
<211> LENGTH: 38
<212> TYPE: DNA
<213> ORGANISM: Artificial Sequence
<220> FEATURE:
<223> OTHER INFORMATION: Primer

<400> SEQUENCE: 30
gggctagtct ccgaattcca cctatcctac caaatgtc                     38

<210> SEQ ID NO 31
<211> LENGTH: 29
<212> TYPE: DNA
<213> ORGANISM: Artificial Sequence
<220> FEATURE:
<223> OTHER INFORMATION: Primer

<400> SEQUENCE: 31
tagctgtagt tagggactgt tctgagcac                               29

<210> SEQ ID NO 32
<211> LENGTH: 38
```

<212> TYPE: DNA
<213> ORGANISM: Artificial Sequence
<220> FEATURE:
<223> OTHER INFORMATION: Primer

<400> SEQUENCE: 32
cgaatgcaag gcgaattcgt tagtaataac acagtgca                                38

<210> SEQ ID NO 33
<211> LENGTH: 29
<212> TYPE: DNA
<213> ORGANISM: Artificial Sequence
<220> FEATURE:
<223> OTHER INFORMATION: Primer

<400> SEQUENCE: 33
aagactggat ccgggaccat gtagaatac                                          29

<210> SEQ ID NO 34
<211> LENGTH: 38
<212> TYPE: DNA
<213> ORGANISM: Artificial Sequence
<220> FEATURE:
<223> OTHER INFORMATION: Primer

<400> SEQUENCE: 34
tctaaccatt gcgaattcag ggcaaggggg gtgagatc                                38

<210> SEQ ID NO 35
<211> LENGTH: 29
<212> TYPE: DNA
<213> ORGANISM: Artificial Sequence
<220> FEATURE:
<223> OTHER INFORMATION: Primer

<400> SEQUENCE: 35
tgacttggat ccgggacaac gactcatcc                                          29

<210> SEQ ID NO 36
<211> LENGTH: 38
<212> TYPE: DNA
<213> ORGANISM: Artificial Sequence
<220> FEATURE:
<223> OTHER INFORMATION: Primer

<400> SEQUENCE: 36
acccaggcgc cagaattctt tagataaagc tgaaggga                                38

<210> SEQ ID NO 37
<211> LENGTH: 29
<212> TYPE: DNA
<213> ORGANISM: Artificial Sequence
<220> FEATURE:
<223> OTHER INFORMATION: Primer

<400> SEQUENCE: 37
gttacgggat ccgggactcc atattgatc                                          29

<210> SEQ ID NO 38
<211> LENGTH: 38
<212> TYPE: DNA
<213> ORGANISM: Artificial Sequence
<220> FEATURE:
<223> OTHER INFORMATION: Primer

<400> SEQUENCE: 38
cgttggcttg aggaattcga ccaaaagagc caagagaa                        38

<210> SEQ ID NO 39
<211> LENGTH: 29
<212> TYPE: DNA
<213> ORGANISM: Artificial Sequence
<220> FEATURE:
<223> OTHER INFORMATION: Primer

<400> SEQUENCE: 39
aaaaagggat ccgggacctt gactaggac                                 29

<210> SEQ ID NO 40
<211> LENGTH: 38
<212> TYPE: DNA
<213> ORGANISM: Artificial Sequence
<220> FEATURE:
<223> OTHER INFORMATION: Primer

<400> SEQUENCE: 40
acttgattcc gtgaattcgt tatcaataaa tcttacat                       38

<210> SEQ ID NO 41
<211> LENGTH: 29
<212> TYPE: DNA
<213> ORGANISM: Artificial Sequence
<220> FEATURE:
<223> OTHER INFORMATION: Primer

<400> SEQUENCE: 41
caagttggat ccgggaccca gggctaacc                                 29

<210> SEQ ID NO 42
<211> LENGTH: 38
<212> TYPE: DNA
<213> ORGANISM: Artificial Sequence
<220> FEATURE:
<223> OTHER INFORMATION: Primer

<400> SEQUENCE: 42
gtgcaaaggc ctgaattccc aggcacaaag ctgttgaa                       38

<210> SEQ ID NO 43
<211> LENGTH: 29
<212> TYPE: DNA
<213> ORGANISM: Artificial Sequence
<220> FEATURE:
<223> OTHER INFORMATION: Primer

<400> SEQUENCE: 43
tgaagcgaac tagggactca ggtggactt                                 29

<210> SEQ ID NO 44
<211> LENGTH: 38
<212> TYPE: DNA
<213> ORGANISM: Artificial Sequence
<220> FEATURE:
<223> OTHER INFORMATION: Primer

<400> SEQUENCE: 44
gattccgtaa acgaattcag ttcattatca tctttgtc                       38

<210> SEQ ID NO 45
<211> LENGTH: 29
<212> TYPE: DNA
<213> ORGANISM: Artificial Sequence

```
<220> FEATURE:
<223> OTHER INFORMATION: Primer

<400> SEQUENCE: 45
ccattgttaa gcgggacttc tgctatttg                                              29

<210> SEQ ID NO 46
<211> LENGTH: 17
<212> TYPE: DNA
<213> ORGANISM: Homo sapiens

<400> SEQUENCE: 46
cccaaaagtc cacctga                                                           17

<210> SEQ ID NO 47
<211> LENGTH: 17
<212> TYPE: DNA
<213> ORGANISM: Homo sapiens

<400> SEQUENCE: 47
tcaggtggac ttttggg                                                           17

<210> SEQ ID NO 48
<211> LENGTH: 18
<212> TYPE: DNA
<213> ORGANISM: Homo sapiens

<400> SEQUENCE: 48
accctgcaaa tagcagaa                                                          18

<210> SEQ ID NO 49
<211> LENGTH: 18
<212> TYPE: DNA
<213> ORGANISM: Homo sapiens

<400> SEQUENCE: 49
ttctgctatt tgcagggt                                                          18

<210> SEQ ID NO 50
<211> LENGTH: 17
<212> TYPE: DNA
<213> ORGANISM: Homo sapiens

<400> SEQUENCE: 50
acccgcaaat agcagaa                                                           17

<210> SEQ ID NO 51
<211> LENGTH: 17
<212> TYPE: DNA
<213> ORGANISM: Homo sapiens

<400> SEQUENCE: 51
ttctgctatt tgcgggt                                                           17

<210> SEQ ID NO 52
<211> LENGTH: 17
<212> TYPE: DNA
<213> ORGANISM: Homo sapiens
<220> FEATURE:
<221> NAME/KEY: misc_feature
<222> LOCATION: 4, 5, 6, 7
<223> OTHER INFORMATION: These nucleotides may be absent

<400> SEQUENCE: 52
```

-continued ttagatagca gtaattt                                                17

<210> SEQ ID NO 53
<211> LENGTH: 23
<212> TYPE: DNA
<213> ORGANISM: Homo sapiens
<220> FEATURE:
<221> NAME/KEY: misc_feature
<222> LOCATION: (6)...(13)
<223> OTHER INFORMATION: These nucleotides may be absent

<400> SEQUENCE: 53
ggaagccggg aaggatctgt atc                                         23

<210> SEQ ID NO 54
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 54
gagaaagaga ggtaa                                                  15

<210> SEQ ID NO 55
<211> LENGTH: 19
<212> TYPE: DNA
<213> ORGANISM: Homo sapiens
<220> FEATURE:
<221> NAME/KEY: misc_feature
<222> LOCATION: 6, 7, 8, 10, 11, 12, 13, 14, 15, 16, 17, 18, 19
<223> OTHER INFORMATION: These nucleotides may be absent

<400> SEQUENCE: 55
aaagagaggt aactttttct                                             19

<210> SEQ ID NO 56
<211> LENGTH: 18
<212> TYPE: DNA
<213> ORGANISM: Homo sapiens
<220> FEATURE:
<221> NAME/KEY: misc_feature
<222> LOCATION: 5, 6, 7, 8
<223> OTHER INFORMATION: These nucleotides may be absent

<400> SEQUENCE: 56
aaagagaggt aacttttc                                               18

<210> SEQ ID NO 57
<211> LENGTH: 23
<212> TYPE: DNA
<213> ORGANISM: Homo sapiens
<220> FEATURE:
<221> NAME/KEY: misc_feature
<222> LOCATION: 11
<223> OTHER INFORMATION: This nucleotide may be absent

<400> SEQUENCE: 57
ttttaaaaaa aaaaaatagg tca                                         23

<210> SEQ ID NO 58
<211> LENGTH: 22
<212> TYPE: DNA
<213> ORGANISM: Homo sapiens
<220> FEATURE:
<221> NAME/KEY: misc_feature

```
<222> LOCATION: 11, 12
<223> OTHER INFORMATION: These nucleotides may be absent

<400> SEQUENCE: 58
aaaataggtc attgcttctt gc                                          22

<210> SEQ ID NO 59
<211> LENGTH: 16
<212> TYPE: DNA
<213> ORGANISM: Homo sapiens
<220> FEATURE:
<221> NAME/KEY: misc_feature
<222> LOCATION: 5, 6
<223> OTHER INFORMATION: These nucleotides may be absent

<400> SEQUENCE: 59
gacaaagaag aaaagg                                                 16

<210> SEQ ID NO 60
<211> LENGTH: 19
<212> TYPE: DNA
<213> ORGANISM: Homo sapiens
<220> FEATURE:
<221> NAME/KEY: misc_feature
<222> LOCATION: 6, 7, 8, 9
<223> OTHER INFORMATION: These nucleotides may be absent

<400> SEQUENCE: 60
gacaaagaag aaaaggaaa                                              19

<210> SEQ ID NO 61
<211> LENGTH: 25
<212> TYPE: DNA
<213> ORGANISM: Homo sapiens
<220> FEATURE:
<221> NAME/KEY: misc_feature
<222> LOCATION: 11, 12, 13, 14, 15
<223> OTHER INFORMATION: These nucleotides may be absent

<400> SEQUENCE: 61
aggaaaaaga ctggtattac gctca                                       25

<210> SEQ ID NO 62
<211> LENGTH: 24
<212> TYPE: DNA
<213> ORGANISM: Homo sapiens
<220> FEATURE:
<221> NAME/KEY: misc_feature
<222> LOCATION: 11, 12, 13, 14
<223> OTHER INFORMATION: These nucleotides may be absent

<400> SEQUENCE: 62
aaaagaatag atagtcttcc ttta                                        24

<210> SEQ ID NO 63
<211> LENGTH: 21
<212> TYPE: DNA
<213> ORGANISM: Homo sapiens
<220> FEATURE:
<221> NAME/KEY: misc_feature
<222> LOCATION: 11
<223> OTHER INFORMATION: This nucleotide may be absent

<400> SEQUENCE: 63
agatagtctt cctttaactg a                                           21

<210> SEQ ID NO 64
```

```
<211> LENGTH: 19
<212> TYPE: DNA
<213> ORGANISM: Homo sapiens
<220> FEATURE:
<221> NAME/KEY: misc_feature
<222> LOCATION: 6, 7, 8, 9
<223> OTHER INFORMATION: These nucleotides may be absent

<400> SEQUENCE: 64
tccttacaaa cagatatga                                              19

<210> SEQ ID NO 65
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 65
accagaaggc aatt                                                   14

<210> SEQ ID NO 66
<211> LENGTH: 17
<212> TYPE: DNA
<213> ORGANISM: Homo sapiens
<220> FEATURE:
<221> NAME/KEY: misc_feature
<222> LOCATION: 6, 7
<223> OTHER INFORMATION: These nucleotides may be absent

<400> SEQUENCE: 66
atcagagttg cgatgga                                                17

<210> SEQ ID NO 67
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 67
cgagcacagg taagtt                                                 16

<210> SEQ ID NO 68
<211> LENGTH: 15
<212> TYPE: DNA
<213> ORGANISM: Homo sapiens
<220> FEATURE:
<221> NAME/KEY: misc_feature
<222> LOCATION: 4, 5
<223> OTHER INFORMATION: These nucleotides may be absent

<400> SEQUENCE: 68
cactctgcac ctcga                                                  15

<210> SEQ ID NO 69
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 69
```
gatatgtcgc gaac 14

<210> SEQ ID NO 70
<211> LENGTH: 17
<212> TYPE: DNA
<213> ORGANISM: Homo sapiens
<220> FEATURE:
<221> NAME/KEY: misc_feature
<222> LOCATION: 6, 7
<223> OTHER INFORMATION: These nucleotides may be absent

<400> SEQUENCE: 70
aaagactctg tattgtt 17

<210> SEQ ID NO 71
<211> LENGTH: 15
<212> TYPE: DNA
<213> ORGANISM: Homo sapiens
<220> FEATURE:
<221> NAME/KEY: misc_feature
<222> LOCATION: 4, 5
<223> OTHER INFORMATION: These nucleotides may be absent

<400> SEQUENCE: 71
gacaagagag gcagg 15

<210> SEQ ID NO 72
<211> LENGTH: 17
<212> TYPE: DNA
<213> ORGANISM: Homo sapiens
<220> FEATURE:
<221> NAME/KEY: misc_feature
<222> LOCATION: 6, 7
<223> OTHER INFORMATION: These nucleotides may be absent

<400> SEQUENCE: 72
catgaaccag gcatgga 17

<210> SEQ ID NO 73
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 73
gaaccaggca tggacc 16

<210> SEQ ID NO 74
<211> LENGTH: 18
<212> TYPE: DNA
<213> ORGANISM: Homo sapiens
<220> FEATURE:
<221> NAME/KEY: misc_feature
<222> LOCATION: 6, 7, 8
<223> OTHER INFORMATION: These nucleotides may be absent

<400> SEQUENCE: 74
aatccaagta tgttctct 18

<210> SEQ ID NO 75
<211> LENGTH: 16
<212> TYPE: DNA
<213> ORGANISM: Homo sapiens
<220> FEATURE:

```
<221> NAME/KEY: misc_feature
<222> LOCATION: 6
<223> OTHER INFORMATION: This nucleotide may be absent

<400> SEQUENCE: 75
gctcctgttg aacatc                                                      16

<210> SEQ ID NO 76
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 76
aaactttcat ttgatg                                                      16

<210> SEQ ID NO 77
<211> LENGTH: 19
<212> TYPE: DNA
<213> ORGANISM: Homo sapiens
<220> FEATURE:
<221> NAME/KEY: misc_feature
<222> LOCATION: 5, 6, 7, 8, 9
<223> OTHER INFORMATION: These nucleotides may be absent

<400> SEQUENCE: 77
aaactttcat ttgatgaag                                                   19

<210> SEQ ID NO 78
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 78
ctacaggcca ttgc                                                        14

<210> SEQ ID NO 79
<211> LENGTH: 21
<212> TYPE: DNA
<213> ORGANISM: Homo sapiens
<220> FEATURE:
<221> NAME/KEY: misc_feature
<222> LOCATION: 11
<223> OTHER INFORMATION: This nucleotide may be absent

<400> SEQUENCE: 79
taaattaggg ggactacagg c                                                21

<210> SEQ ID NO 80
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 80
ttattgcaag tggac                                                       15
```

```
<210> SEQ ID NO 81
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 81
tacgggctta ctaat                                                15

<210> SEQ ID NO 82
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 82
agtattacac taagac                                               16

<210> SEQ ID NO 83
<211> LENGTH: 17
<212> TYPE: DNA
<213> ORGANISM: Homo sapiens
<220> FEATURE:
<221> NAME/KEY: misc_feature
<222> LOCATION: 6, 7
<223> OTHER INFORMATION: These nucleotides may be absent

<400> SEQUENCE: 83
attacactaa gacgata                                              17

<210> SEQ ID NO 84
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 84
ctaagacgat atgc                                                 14

<210> SEQ ID NO 85
<211> LENGTH: 17
<212> TYPE: DNA
<213> ORGANISM: Homo sapiens
<220> FEATURE:
<221> NAME/KEY: misc_feature
<222> LOCATION: 6, 7
<223> OTHER INFORMATION: These nucleotides may be absent

<400> SEQUENCE: 85
tgctctatga aaggctg                                              17

<210> SEQ ID NO 86
<211> LENGTH: 25
<212> TYPE: DNA
<213> ORGANISM: Homo sapiens
<220> FEATURE:
<221> NAME/KEY: misc_feature
<222> LOCATION: 6, 7, 8, 9, 10, 11, 12, 13, 14, 15
<223> OTHER INFORMATION: These nucleotides may be absent
```

```
<400> SEQUENCE: 86
atgagagcac ttgtggccca actaa                                    25

<210> SEQ ID NO 87
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 87
gacttacagc aggtac                                              16

<210> SEQ ID NO 88
<211> LENGTH: 17
<212> TYPE: DNA
<213> ORGANISM: Homo sapiens
<220> FEATURE:
<221> NAME/KEY: misc_feature
<222> LOCATION: 6, 7
<223> OTHER INFORMATION: These nucleotides may be absent

<400> SEQUENCE: 88
aaaaagacgt tgcgaga                                             17

<210> SEQ ID NO 89
<211> LENGTH: 19
<212> TYPE: DNA
<213> ORGANISM: Homo sapiens
<220> FEATURE:
<221> NAME/KEY: misc_feature
<222> LOCATION: 5, 6, 7, 8, 9
<223> OTHER INFORMATION: These nucleotides may be absent

<400> SEQUENCE: 89
gttggaagtg tgaaagcat                                           19

<210> SEQ ID NO 90
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 90
aaagcattga tggaat                                              16

<210> SEQ ID NO 91
<211> LENGTH: 18
<212> TYPE: DNA
<213> ORGANISM: Homo sapiens
<220> FEATURE:
<221> NAME/KEY: misc_feature
<222> LOCATION: 5, 6, 7, 8
<223> OTHER INFORMATION: These nucleotides may be absent

<400> SEQUENCE: 91
ttagaagtta aaaaggta                                            18

<210> SEQ ID NO 92
<211> LENGTH: 16
<212> TYPE: DNA
<213> ORGANISM: Homo sapiens
```

```
<220> FEATURE:
<221> NAME/KEY: misc_feature
<222> LOCATION: 6
<223> OTHER INFORMATION: This nucleotide may be absent

<400> SEQUENCE: 92
accctcaaaa gcgtat                                                     16

<210> SEQ ID NO 93
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 93
gccttatgga atttg                                                      15

<210> SEQ ID NO 94
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 94
gctgtagatg gtgc                                                       14

<210> SEQ ID NO 95
<211> LENGTH: 29
<212> TYPE: DNA
<213> ORGANISM: Homo sapiens
<220> FEATURE:
<221> NAME/KEY: misc_feature
<222> LOCATION: (4)...(19)
<223> OTHER INFORMATION: These nucleotides may be absent

<400> SEQUENCE: 95
gttggcactc ttacttaccg gagccagac                                       29

<210> SEQ ID NO 96
<211> LENGTH: 19
<212> TYPE: DNA
<213> ORGANISM: Homo sapiens
<220> FEATURE:
<221> NAME/KEY: misc_feature
<222> LOCATION: 6, 7, 8, 9
<223> OTHER INFORMATION: These nucleotides may be absent

<400> SEQUENCE: 96
cttacttacc ggagccaga                                                  19

<210> SEQ ID NO 97
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 97
acttaccgga gccag                                                      15
```

<210> SEQ ID NO 98
<211> LENGTH: 15
<212> TYPE: DNA
<213> ORGANISM: Homo sapiens
<220> FEATURE:
<221> NAME/KEY: misc_feature
<222> LOCATION: 4, 5
<223> OTHER INFORMATION: These nucleotides may be absent

<400> SEQUENCE: 98
agccagacaa acact                                                    15

<210> SEQ ID NO 99
<211> LENGTH: 18
<212> TYPE: DNA
<213> ORGANISM: Homo sapiens
<220> FEATURE:
<221> NAME/KEY: misc_feature
<222> LOCATION: 5, 6, 7, 8
<223> OTHER INFORMATION: These nucleotides may be
                        absent

<400> SEQUENCE: 99
agccagacaa acactta                                                  18

<210> SEQ ID NO 100
<211> LENGTH: 17
<212> TYPE: DNA
<213> ORGANISM: Homo sapiens
<220> FEATURE:
<221> NAME/KEY: misc_feature
<222> LOCATION: 4, 5, 6, 7
<223> OTHER INFORMATION: These nucleotides may be absent

<400> SEQUENCE: 100
acaaacactt tagccat                                                  17

<210> SEQ ID NO 101
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 101
ttagccatta ttgaaa                                                   16

<210> SEQ ID NO 102
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 102
ggaggtggga tatta                                                    15

<210> SEQ ID NO 103
<211> LENGTH: 15
<212> TYPE: DNA
<213> ORGANISM: Homo sapiens
<220> FEATURE:
<221> NAME/KEY: misc_feature
<222> LOCATION: 5

<223> OTHER INFORMATION: This nucleotide may be absent

<400> SEQUENCE: 103
atattacgga atgtg                                              15

<210> SEQ ID NO 104
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 104
ttacggaatg tgtcca                                             16

<210> SEQ ID NO 105
<211> LENGTH: 15
<212> TYPE: DNA
<213> ORGANISM: Homo sapiens
<220> FEATURE:
<221> NAME/KEY: misc_feature
<222> LOCATION: 4, 5
<223> OTHER INFORMATION: These nucleotides may be absent

<400> SEQUENCE: 105
agagagaaca actgt                                              15

<210> SEQ ID NO 106
<211> LENGTH: 34
<212> TYPE: DNA
<213> ORGANISM: Homo sapiens
<220> FEATURE:
<221> NAME/KEY: misc_feature
<222> LOCATION: (11)...(24)
<223> OTHER INFORMATION: These nucleotides may be absent

<400> SEQUENCE: 106
tatttcaggc aaatcctaag agagaacaac tgtc                         34

<210> SEQ ID NO 107
<211> LENGTH: 16
<212> TYPE: DNA
<213> ORGANISM: Homo sapiens
<220> FEATURE:
<221> NAME/KEY: misc_feature
<222> LOCATION: 5, 6
<223> OTHER INFORMATION: These nucleotides may be absent

<400> SEQUENCE: 107
aactgtctac aaactt                                             16

<210> SEQ ID NO 108
<211> LENGTH: 15
<212> TYPE: DNA
<213> ORGANISM: Homo sapiens
<220> FEATURE:
<221> NAME/KEY: misc_feature
<222> LOCATION: 4, 5
<223> OTHER INFORMATION: These nucleotides may be absent

<400> SEQUENCE: 108
ttattacaac actta                                              15

<210> SEQ ID NO 109
<211> LENGTH: 15

```
<212> TYPE: DNA
<213> ORGANISM: Homo sapiens
<220> FEATURE:
<221> NAME/KEY: misc_feature
<222> LOCATION: 4, 5
<223> OTHER INFORMATION: These nucleotides may be absent

<400> SEQUENCE: 109
cacttaaaat ctcat                                                    15

<210> SEQ ID NO 110
<211> LENGTH: 24
<212> TYPE: DNA
<213> ORGANISM: Homo sapiens
<220> FEATURE:
<221> NAME/KEY: misc_feature
<222> LOCATION: (4)...(14)
<223> OTHER INFORMATION: These nucleotides may be absent

<400> SEQUENCE: 110
agtttgacaa tagtcagtaa tgca                                          24

<210> SEQ ID NO 111
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 111
cacttatcag aaactt                                                   16

<210> SEQ ID NO 112
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 112
ttatcagaaa ctttt                                                    15

<210> SEQ ID NO 113
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 113
tcagaaactt ttgaca                                                   16

<210> SEQ ID NO 114
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 114
```
agtcccaagg catct					15

<210> SEQ ID NO 115
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 115
aagcaaagtc tctat					15

<210> SEQ ID NO 116
<211> LENGTH: 17
<212> TYPE: DNA
<213> ORGANISM: Homo sapiens
<220> FEATURE:
<221> NAME/KEY: misc_feature
<222> LOCATION: 6, 7
<223> OTHER INFORMATION: These nucleotides may be absent

<400> SEQUENCE: 116
aagcaaagtc tctatgg					17

<210> SEQ ID NO 117
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 117
caaagtctct atggt					15

<210> SEQ ID NO 118
<211> LENGTH: 16
<212> TYPE: DNA
<213> ORGANISM: Homo sapiens
<220> FEATURE:
<221> NAME/KEY: misc_feature
<222> LOCATION: 5, 6
<223> OTHER INFORMATION: These nucleotides may be absent

<400> SEQUENCE: 118
gattatgttt ttgaca					16

<210> SEQ ID NO 119
<211> LENGTH: 25
<212> TYPE: DNA
<213> ORGANISM: Homo sapiens
<220> FEATURE:
<221> NAME/KEY: misc_feature
<222> LOCATION: (6)...(15)
<223> OTHER INFORMATION: These nucleotides may be absent

<400> SEQUENCE: 119
gacaccaatc gacatgatga taata					25

<210> SEQ ID NO 120
<211> LENGTH: 16
<212> TYPE: DNA
<213> ORGANISM: Homo sapiens
<220> FEATURE:
<221> NAME/KEY: misc_feature

```
<222> LOCATION: 5, 6
<223> OTHER INFORMATION: These nucleotides may be absent

<400> SEQUENCE: 120
cgacatgatg ataata                                                    16

<210> SEQ ID NO 121
<211> LENGTH: 18
<212> TYPE: DNA
<213> ORGANISM: Homo sapiens
<220> FEATURE:
<221> NAME/KEY: misc_feature
<222> LOCATION: 5, 6, 7, 8
<223> OTHER INFORMATION: These nucleotides may be absent

<400> SEQUENCE: 121
tcagacaatt ttaatact                                                  18

<210> SEQ ID NO 122
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 122
tatttgaata ctac                                                      14

<210> SEQ ID NO 123
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 123
aatactacag tgtta                                                     15

<210> SEQ ID NO 124
<211> LENGTH: 28
<212> TYPE: DNA
<213> ORGANISM: Homo sapiens
<220> FEATURE:
<221> NAME/KEY: misc_feature
<222> LOCATION: (6)...(18)
<223> OTHER INFORMATION: These nucleotides may be absent

<400> SEQUENCE: 124
gtgttaccca gctcctcttc atcaagag                                       28

<210> SEQ ID NO 125
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 125
agctcctctt catcaa                                                    16

<210> SEQ ID NO 126
```

```
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 126
tcatcaagag gaagc                                                15

<210> SEQ ID NO 127
<211> LENGTH: 17
<212> TYPE: DNA
<213> ORGANISM: Homo sapiens
<220> FEATURE:
<221> NAME/KEY: misc_feature
<222> LOCATION: 6, 7
<223> OTHER INFORMATION: These nucleotides may be absent

<400> SEQUENCE: 127
aaagatagaa gtttgga                                              17

<210> SEQ ID NO 128
<211> LENGTH: 21
<212> TYPE: DNA
<213> ORGANISM: Homo sapiens
<220> FEATURE:
<221> NAME/KEY: misc_feature
<222> LOCATION: 5, 6, 7, 8, 9, 10, 11
<223> OTHER INFORMATION: These nucleotides may be absent

<400> SEQUENCE: 128
aaagatagaa gtttggagag a                                         21

<210> SEQ ID NO 129
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 129
gaacgcggaa ttggt                                                15

<210> SEQ ID NO 130
<211> LENGTH: 19
<212> TYPE: DNA
<213> ORGANISM: Homo sapiens
<220> FEATURE:
<221> NAME/KEY: misc_feature
<222> LOCATION: (5)...(9)
<223> OTHER INFORMATION: These nucleotides may be absent

<400> SEQUENCE: 130
cgcggaattg gtctaggca                                            19

<210> SEQ ID NO 131
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 131
```
cgcggaattg gtcta                                                15

<210> SEQ ID NO 132
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 132
cagatctcca ccac                                                 14

<210> SEQ ID NO 133
<211> LENGTH: 19
<212> TYPE: DNA
<213> ORGANISM: Homo sapiens
<220> FEATURE:
<221> NAME/KEY: misc_feature
<222> LOCATION: (6)...(9)
<223> OTHER INFORMATION: These nucleotides may be absent

<400> SEQUENCE: 133
gaagacagaa gttctgggt                                            19

<210> SEQ ID NO 134
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 134
gggtctacca ctgaa                                                15

<210> SEQ ID NO 135
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 135
gtgacagatg agagaa                                               16

<210> SEQ ID NO 136
<211> LENGTH: 19
<212> TYPE: DNA
<213> ORGANISM: Homo sapiens
<220> FEATURE:
<221> NAME/KEY: misc_feature
<222> LOCATION: (6)...(9)
<223> OTHER INFORMATION: These nucleotides may be absent

<400> SEQUENCE: 136
catacacatt caaacactt                                            19

<210> SEQ ID NO 137
<211> LENGTH: 19
<212> TYPE: DNA
<213> ORGANISM: Homo sapiens
<220> FEATURE:

```
<221> NAME/KEY: misc_feature
<222> LOCATION: (6)...(9)
<223> OTHER INFORMATION: These nucleotides may be absent

<400> SEQUENCE: 137
acacattcaa acacttaca                                                    19

<210> SEQ ID NO 138
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 138
cattcaaaca ctta                                                         14

<210> SEQ ID NO 139
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 139
cattcaaaca cttac                                                        15

<210> SEQ ID NO 140
<211> LENGTH: 17
<212> TYPE: DNA
<213> ORGANISM: Homo sapiens
<220> FEATURE:
<221> NAME/KEY: misc_feature
<222> LOCATION: (4)...(7)
<223> OTHER INFORMATION: These nucleotides may be absent

<400> SEQUENCE: 140
aacacttaca atttcac                                                      17

<210> SEQ ID NO 141
<211> LENGTH: 22
<212> TYPE: DNA
<213> ORGANISM: Homo sapiens
<220> FEATURE:
<221> NAME/KEY: misc_feature
<222> LOCATION: (5)...(12)
<223> OTHER INFORMATION: These nucleotides may be absent

<400> SEQUENCE: 141
tacaatttca ctaagtcgga aa                                                22

<210> SEQ ID NO 142
<211> LENGTH: 18
<212> TYPE: DNA
<213> ORGANISM: Homo sapiens
<220> FEATURE:
<221> NAME/KEY: misc_feature
<222> LOCATION: (5)...(8)
<223> OTHER INFORMATION: These nucleotides may be absent

<400> SEQUENCE: 142
ttcactaagt cggaaaat                                                     18
```

```
<210> SEQ ID NO 143
<211> LENGTH: 17
<212> TYPE: DNA
<213> ORGANISM: Homo sapiens
<220> FEATURE:
<221> NAME/KEY: misc_feature
<222> LOCATION: (4)...(7)
<223> OTHER INFORMATION: These nucleotides may be absent

<400> SEQUENCE: 143
aagtcggaaa attcaaa                                                17

<210> SEQ ID NO 144
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 144
acatgttcta tgcct                                                  15

<210> SEQ ID NO 145
<211> LENGTH: 16
<212> TYPE: DNA
<213> ORGANISM: Homo sapiens
<220> FEATURE:
<221> NAME/KEY: misc_feature
<222> LOCATION: 5, 6
<223> OTHER INFORMATION: These nucleotides may be absent

<400> SEQUENCE: 145
ttagaataca agagat                                                 16

<210> SEQ ID NO 146
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 146
aatgatagtt taaa                                                   14

<210> SEQ ID NO 147
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 147
agtttaaata gtgtca                                                 16

<210> SEQ ID NO 148
<211> LENGTH: 17
<212> TYPE: DNA
<213> ORGANISM: Homo sapiens
<220> FEATURE:
<221> NAME/KEY: misc_feature
<222> LOCATION: 4, 5, 6, 7
<223> OTHER INFORMATION: These nucleotides may be absent
```

<400> SEQUENCE: 148
ttaaatagtg tcagtag                                                17

<210> SEQ ID NO 149
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 149
tatggtaaaa gaggt                                                  15

<210> SEQ ID NO 150
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 150
ggtaaaagag gtcaaa                                                 16

<210> SEQ ID NO 151
<211> LENGTH: 16
<212> TYPE: DNA
<213> ORGANISM: Homo sapiens
<220> FEATURE:
<221> NAME/KEY: misc_feature
<222> LOCATION: 5, 6
<223> OTHER INFORMATION: These nucleotides may be absent

<400> SEQUENCE: 151
aaaagaggtc aaatga                                                 16

<210> SEQ ID NO 152
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 152
agtaagtttt gcagtt                                                 16

<210> SEQ ID NO 153
<211> LENGTH: 24
<212> TYPE: DNA
<213> ORGANISM: Homo sapiens
<220> FEATURE:
<221> NAME/KEY: misc_feature
<222> LOCATION: (4)...(14)
<223> OTHER INFORMATION: These nucleotides may be absent

<400> SEQUENCE: 153
aagttttgca gttatggtca atac                                        24

<210> SEQ ID NO 154
<211> LENGTH: 20
<212> TYPE: DNA
<213> ORGANISM: Homo sapiens

```
<220> FEATURE:
<221> NAME/KEY: misc_feature
<222> LOCATION: (4)...(10)
<223> OTHER INFORMATION: These nucleotides may be absent

<400> SEQUENCE: 154
caatacccag ccgacctagc                                               20

<210> SEQ ID NO 155
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 155
acaccaataa attat                                                    15

<210> SEQ ID NO 156
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 156
aaatattcag atga                                                     14

<210> SEQ ID NO 157
<211> LENGTH: 19
<212> TYPE: DNA
<213> ORGANISM: Homo sapiens
<220> FEATURE:
<221> NAME/KEY: misc_feature
<222> LOCATION: (5)...(9)
<223> OTHER INFORMATION: These nucleotides may be absent

<400> SEQUENCE: 157
tcagatgagc agttgaact                                                19

<210> SEQ ID NO 158
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 158
gatgagcagt tgaac                                                    15

<210> SEQ ID NO 159
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 159
tgggcaagac ccaaa                                                    15
```

<210> SEQ ID NO 160
<211> LENGTH: 19
<212> TYPE: DNA
<213> ORGANISM: Homo sapiens
<220> FEATURE:
<221> NAME/KEY: misc_feature
<222> LOCATION: (5)...(9)
<223> OTHER INFORMATION: These nucleotides may be absent

<400> SEQUENCE: 160
cacataatag aagatgaaa                                              19

<210> SEQ ID NO 161
<211> LENGTH: 19
<212> TYPE: DNA
<213> ORGANISM: Homo sapiens
<220> FEATURE:
<221> NAME/KEY: misc_feature
<222> LOCATION: (5)...(9)
<223> OTHER INFORMATION: These nucleotides may be absent

<400> SEQUENCE: 161
ataatagaag atgaaataa                                              19

<210> SEQ ID NO 162
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 162
atagaagatg aaataa                                                 16

<210> SEQ ID NO 163
<211> LENGTH: 20
<212> TYPE: DNA
<213> ORGANISM: Homo sapiens
<220> FEATURE:
<221> NAME/KEY: misc_feature
<222> LOCATION: (6)...(10)
<223> OTHER INFORMATION: These nucleotides may be absent

<400> SEQUENCE: 163
ataaaacaaa gtgagcaaag                                             20

<210> SEQ ID NO 164
<211> LENGTH: 17
<212> TYPE: DNA
<213> ORGANISM: Homo sapiens
<220> FEATURE:
<221> NAME/KEY: misc_feature
<222> LOCATION: (4)...(7)
<223> OTHER INFORMATION: These nucleotides may be absent

<400> SEQUENCE: 164
aaacaaagtg agcaaag                                                17

<210> SEQ ID NO 165
<211> LENGTH: 16
<212> TYPE: DNA
<213> ORGANISM: Homo sapiens
<220> FEATURE:
<221> NAME/KEY: misc_feature
<222> LOCATION: 5, 6
<223> OTHER INFORMATION: These nucleotides may be absent

<400> SEQUENCE: 165
aaacaaagtg agcaaa                                                                                           16

<210> SEQ ID NO 166
<211> LENGTH: 18
<212> TYPE: DNA
<213> ORGANISM: Homo sapiens
<220> FEATURE:
<221> NAME/KEY: misc_feature
<222> LOCATION: (5)...(8)
<223> OTHER INFORMATION: These nucleotides may be absent

<400> SEQUENCE: 166
caaagtgagc aaagacaa                                                                                         18

<210> SEQ ID NO 167
<211> LENGTH: 17
<212> TYPE: DNA
<213> ORGANISM: Homo sapiens
<220> FEATURE:
<221> NAME/KEY: misc_feature
<222> LOCATION: 6, 7
<223> OTHER INFORMATION: These nucleotides may be absent

<400> SEQUENCE: 167
caaagacaat caaggaa                                                                                          17

<210> SEQ ID NO 168
<211> LENGTH: 17
<212> TYPE: DNA
<213> ORGANISM: Homo sapiens
<220> FEATURE:
<221> NAME/KEY: misc_feature
<222> LOCATION: (4)...(7)
<223> OTHER INFORMATION: These nucleotides may be absent

<400> SEQUENCE: 168
caatcaagga atcaaag                                                                                          17

<210> SEQ ID NO 169
<211> LENGTH: 16
<212> TYPE: DNA
<213> ORGANISM: Homo sapiens
<220> FEATURE:
<221> NAME/KEY: misc_feature
<222> LOCATION: 5, 6
<223> OTHER INFORMATION: These nucleotides may be absent

<400> SEQUENCE: 169
caaagtacaa cttatc                                                                                           16

<210> SEQ ID NO 170
<211> LENGTH: 16
<212> TYPE: DNA
<213> ORGANISM: Homo sapiens
<220> FEATURE:
<221> NAME/KEY: misc_feature
<222> LOCATION: 5, 6
<223> OTHER INFORMATION: These nucleotides may be absent

<400> SEQUENCE: 170
actgagagca ctgatg                                                                                           16

<210> SEQ ID NO 171
<211> LENGTH: 17
<212> TYPE: DNA

```
<213> ORGANISM: Homo sapiens
<220> FEATURE:
<221> NAME/KEY: misc_feature
<222> LOCATION: 6, 7
<223> OTHER INFORMATION: These nucleotides may be absent

<400> SEQUENCE: 171
actgatgata aacacct                                                  17

<210> SEQ ID NO 172
<211> LENGTH: 17
<212> TYPE: DNA
<213> ORGANISM: Homo sapiens
<220> FEATURE:
<221> NAME/KEY: misc_feature
<222> LOCATION: (4)...(7)
<223> OTHER INFORMATION: These nucleotides may be absent

<400> SEQUENCE: 172
gataaacacc tcaagtt                                                  17

<210> SEQ ID NO 173
<211> LENGTH: 16
<212> TYPE: DNA
<213> ORGANISM: Homo sapiens
<220> FEATURE:
<221> NAME/KEY: misc_feature
<222> LOCATION: 5, 6
<223> OTHER INFORMATION: These nucleotides may be absent

<400> SEQUENCE: 173
cacctcaagt tccaac                                                   16

<210> SEQ ID NO 174
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 174
tttggacagc aggaa                                                    15

<210> SEQ ID NO 175
<211> LENGTH: 15
<212> TYPE: DNA
<213> ORGANISM: Homo sapiens
<220> FEATURE:
<221> NAME/KEY: misc_feature
<222> LOCATION: 4, 5
<223> OTHER INFORMATION: These nucleotides may be absent

<400> SEQUENCE: 175
tgtgtttctc catac                                                    15

<210> SEQ ID NO 176
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 176
cggggagcca atgg                                                     14
```

<210> SEQ ID NO 177
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 177
tcagaaacaa atcgag                                                       16

<210> SEQ ID NO 178
<211> LENGTH: 19
<212> TYPE: DNA
<213> ORGANISM: Homo sapiens
<220> FEATURE:
<221> NAME/KEY: misc_feature
<222> LOCATION: (6)...(9)
<223> OTHER INFORMATION: These nucleotides may be absent

<400> SEQUENCE: 178
attaatcaaa atgtaagcc                                                    19

<210> SEQ ID NO 179
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 179
caagaagatg acta                                                         14

<210> SEQ ID NO 180
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 180
gactatgaag atgata                                                       16

<210> SEQ ID NO 181
<211> LENGTH: 18
<212> TYPE: DNA
<213> ORGANISM: Homo sapiens
<220> FEATURE:
<221> NAME/KEY: misc_feature
<222> LOCATION: (4)...(8)
<223> OTHER INFORMATION: These nucleotides may be absent

<400> SEQUENCE: 181
gatgataagc ctaccaat                                                     18

<210> SEQ ID NO 182
<211> LENGTH: 16
<212> TYPE: DNA
<213> ORGANISM: Homo sapiens
<220> FEATURE:
<221> NAME/KEY: misc_feature
<222> LOCATION: 6

<223> OTHER INFORMATION: This nucleotide may be absent

<400> SEQUENCE: 182
cgttactctg aagaag                                                          16

<210> SEQ ID NO 183
<211> LENGTH: 19
<212> TYPE: DNA
<213> ORGANISM: Homo sapiens
<220> FEATURE:
<221> NAME/KEY: misc_feature
<222> LOCATION: (5)...(9)
<223> OTHER INFORMATION: These nucleotides may be absent

<400> SEQUENCE: 183
gaagaagaag agagaccaa                                                       19

<210> SEQ ID NO 184
<211> LENGTH: 18
<212> TYPE: DNA
<213> ORGANISM: Homo sapiens
<220> FEATURE:
<221> NAME/KEY: misc_feature
<222> LOCATION: 5, 6, 7, 8
<223> OTHER INFORMATION: These nucleotides may be absent

<400> SEQUENCE: 184
gaagaagaga gaccaaca                                                        18

<210> SEQ ID NO 185
<211> LENGTH: 17
<212> TYPE: DNA
<213> ORGANISM: Homo sapiens
<220> FEATURE:
<221> NAME/KEY: misc_feature
<222> LOCATION: 5, 6, 7, 8
<223> OTHER INFORMATION: These nucleotides may be absent

<400> SEQUENCE: 185
gaagagagac caacaaa                                                         17

<210> SEQ ID NO 186
<211> LENGTH: 18
<212> TYPE: DNA
<213> ORGANISM: Homo sapiens
<220> FEATURE:
<221> NAME/KEY: misc_feature
<222> LOCATION: (4)...(8)
<223> OTHER INFORMATION: These nucleotides may be absent

<400> SEQUENCE: 186
gaagagaaac gtcatgtg                                                        18

<210> SEQ ID NO 187
<211> LENGTH: 22
<212> TYPE: DNA
<213> ORGANISM: Homo sapiens
<220> FEATURE:
<221> NAME/KEY: misc_feature
<222> LOCATION: (6)...(12)
<223> OTHER INFORMATION: These nucleotides may be absent

<400> SEQUENCE: 187
gattatagtt taaaatatgc ca                                                   22

<210> SEQ ID NO 188
<211> LENGTH: 15

```
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 188
ttaaaatatg ccaca                                                    15

<210> SEQ ID NO 189
<211> LENGTH: 18
<212> TYPE: DNA
<213> ORGANISM: Homo sapiens
<220> FEATURE:
<221> NAME/KEY: misc_feature
<222> LOCATION: (4)...(8)
<223> OTHER INFORMATION: These nucleotides may be absent

<400> SEQUENCE: 189
gccacagata ttccttca                                                 18

<210> SEQ ID NO 190
<211> LENGTH: 15
<212> TYPE: DNA
<213> ORGANISM: Homo sapiens
<220> FEATURE:
<221> NAME/KEY: misc_feature
<222> LOCATION: 4, 5
<223> OTHER INFORMATION: These nucleotides may be absent

<400> SEQUENCE: 190
acagatattc cttca                                                    15

<210> SEQ ID NO 191
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 191
tcacagaaac agtcat                                                   16

<210> SEQ ID NO 192
<211> LENGTH: 15
<212> TYPE: DNA
<213> ORGANISM: Homo sapiens
<220> FEATURE:
<221> NAME/KEY: misc_feature
<222> LOCATION: 4, 5
<223> OTHER INFORMATION: These nucleotides may be absent

<400> SEQUENCE: 192
aaacagtcat tttca                                                    15

<210> SEQ ID NO 193
<211> LENGTH: 15
<212> TYPE: DNA
<213> ORGANISM: Homo sapiens
<220> FEATURE:
<221> NAME/KEY: misc_feature
<222> LOCATION: 4, 5
<223> OTHER INFORMATION: These nucleotides may be absent

<400> SEQUENCE: 193
```
tcaaagagtt catct                                    15

<210> SEQ ID NO 194
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 194
aaaaccgaac atatg                                    15

<210> SEQ ID NO 195
<211> LENGTH: 17
<212> TYPE: DNA
<213> ORGANISM: Homo sapiens
<220> FEATURE:
<221> NAME/KEY: misc_feature
<222> LOCATION: (4)...(7)
<223> OTHER INFORMATION: These nucleotides may be absent

<400> SEQUENCE: 195
accgaacata tgtcttc                                  17

<210> SEQ ID NO 196
<211> LENGTH: 15
<212> TYPE: DNA
<213> ORGANISM: Homo sapiens
<220> FEATURE:
<221> NAME/KEY: misc_feature
<222> LOCATION: 4, 5
<223> OTHER INFORMATION: These nucleotides may be absent

<400> SEQUENCE: 196
catatgtctt caagc                                    15

<210> SEQ ID NO 197
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 197
ccaagttctg cacaga                                   16

<210> SEQ ID NO 198
<211> LENGTH: 16
<212> TYPE: DNA
<213> ORGANISM: Homo sapiens
<220> FEATURE:
<221> NAME/KEY: misc_feature
<222> LOCATION: 5, 6
<223> OTHER INFORMATION: These nucleotides may be absent

<400> SEQUENCE: 198
tgcaaagttt cttcta                                   16

<210> SEQ ID NO 199
<211> LENGTH: 15
<212> TYPE: DNA
<213> ORGANISM: Homo sapiens
<220> FEATURE:
<221> NAME/KEY: misc_feature

```
<222> LOCATION: 4, 5
<223> OTHER INFORMATION: These nucleotides may be absent

<400> SEQUENCE: 199
atacagactt attgt                                                    15

<210> SEQ ID NO 200
<211> LENGTH: 17
<212> TYPE: DNA
<213> ORGANISM: Homo sapiens
<220> FEATURE:
<221> NAME/KEY: misc_feature
<222> LOCATION: 6, 7
<223> OTHER INFORMATION: These nucleotides may be absent

<400> SEQUENCE: 200
cagacttatt gtgtaga                                                  17

<210> SEQ ID NO 201
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 201
ccaatatgtt tttc                                                     14

<210> SEQ ID NO 202
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 202
agttcattat catc                                                     14

<210> SEQ ID NO 203
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 203
caggaagcag attctg                                                   16

<210> SEQ ID NO 204
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 204
accctgcaaa tagca                                                    15

<210> SEQ ID NO 205
```

```
<211> LENGTH: 18
<212> TYPE: DNA
<213> ORGANISM: Homo sapiens
<220> FEATURE:
<221> NAME/KEY: misc_feature
<222> LOCATION: (5)...(8)
<223> OTHER INFORMATION: These nucleotides may be absent

<400> SEQUENCE: 205
gaaataaaag aaaagatt                                                    18

<210> SEQ ID NO 206
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 206 ataaagaaa agat                                                         14

<210> SEQ ID NO 207
<211> LENGTH: 17
<212> TYPE: DNA
<213> ORGANISM: Homo sapiens
<220> FEATURE:
<221> NAME/KEY: misc_feature
<222> LOCATION: (4)...(7)
<223> OTHER INFORMATION: These nucleotides may be absent

<400> SEQUENCE: 207
aaagaaaaga ttggaac                                                     17

<210> SEQ ID NO 208
<211> LENGTH: 20
<212> TYPE: DNA
<213> ORGANISM: Homo sapiens
<220> FEATURE:
<221> NAME/KEY: misc_feature
<222> LOCATION: (6)...(10)
<223> OTHER INFORMATION: These nucleotides may be absent

<400> SEQUENCE: 208
aaagaaaaga ttggaactag                                                  20

<210> SEQ ID NO 209
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 209
gatcctgtga gcgaa                                                       15

<210> SEQ ID NO 210
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 210
```
gtgagcgaag ttccag                                                    16

<210> SEQ ID NO 211
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 211
gttccagcag tgtca                                                     15

<210> SEQ ID NO 212
<211> LENGTH: 22
<212> TYPE: DNA
<213> ORGANISM: Homo sapiens
<220> FEATURE:
<221> NAME/KEY: misc_feature
<222> LOCATION: (5)...(13)
<223> OTHER INFORMATION: These nucleotides may be absent

<400> SEQUENCE: 212
caccctagaa ccaaatccag ca                                             22

<210> SEQ ID NO 213
<211> LENGTH: 16
<212> TYPE: DNA
<213> ORGANISM: Homo sapiens
<220> FEATURE:
<221> NAME/KEY: misc_feature
<222> LOCATION: 5, 6
<223> OTHER INFORMATION: These nucleotides may be absent

<400> SEQUENCE: 213
agactgcagg gttcta                                                    16

<210> SEQ ID NO 214
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 214
cagggttcta gttt                                                      14

<210> SEQ ID NO 215
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 215
tctagtttat cttca                                                     15

<210> SEQ ID NO 216
<211> LENGTH: 15
<212> TYPE: DNA
<213> ORGANISM: Homo sapiens
<220> FEATURE:

```
<221> NAME/KEY: misc_feature
<222> LOCATION: 5
<223> OTHER INFORMATION: This nucleotide may be absent

<400> SEQUENCE: 216
ttatcttcag aatca                                                    15

<210> SEQ ID NO 217
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 217
gttgaatttt cttc                                                     14

<210> SEQ ID NO 218
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 218
ccctccaaaa gtggt                                                    15

<210> SEQ ID NO 219
<211> LENGTH: 17
<212> TYPE: DNA
<213> ORGANISM: Homo sapiens
<220> FEATURE:
<221> NAME/KEY: misc_feature
<222> LOCATION: (4)...(7)
<223> OTHER INFORMATION: These nucleotides may be absent

<400> SEQUENCE: 219
agtggtgctc agacacc                                                  17

<210> SEQ ID NO 220
<211> LENGTH: 17
<212> TYPE: DNA
<213> ORGANISM: Homo sapiens
<220> FEATURE:
<221> NAME/KEY: misc_feature
<222> LOCATION: 6, 7
<223> OTHER INFORMATION: These nucleotides may be absent

<400> SEQUENCE: 220
agtccacctg aacacta                                                  17

<210> SEQ ID NO 221
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 221
ccacctgaac actatg                                                   16
```

```
<210> SEQ ID NO 222
<211> LENGTH: 16
<212> TYPE: DNA
<213> ORGANISM: Homo sapiens
<220> FEATURE:
<221> NAME/KEY: misc_feature
<222> LOCATION: 5, 6
<223> OTHER INFORMATION: These nucleotides may be absent

<400> SEQUENCE: 222
tatgttcagg agaccc                                                      16

<210> SEQ ID NO 223
<211> LENGTH: 16
<212> TYPE: DNA
<213> ORGANISM: Homo sapiens
<220> FEATURE:
<221> NAME/KEY: misc_feature
<222> LOCATION: 5, 6
<223> OTHER INFORMATION: These nucleotides may be absent

<400> SEQUENCE: 223
gatagttttg agagtc                                                      16

<210> SEQ ID NO 224
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 224
attgccagct ccgttc                                                      16

<210> SEQ ID NO 225
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 225
agtggcatta taagcc                                                      16

<210> SEQ ID NO 226
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 226
agccctggac aaacc                                                       15

<210> SEQ ID NO 227
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent
```

```
<400> SEQUENCE: 227
cctggacaaa ccatgc                                                        16

<210> SEQ ID NO 228
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 228
atgccaccaa gcaga                                                         15

<210> SEQ ID NO 229
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 229
aaaaataaag caccta                                                        16

<210> SEQ ID NO 230
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 230
gaaaagagag agag                                                          14

<210> SEQ ID NO 231
<211> LENGTH: 17
<212> TYPE: DNA
<213> ORGANISM: Homo sapiens
<220> FEATURE:
<221> NAME/KEY: misc_feature
<222> LOCATION: (4)...(7)
<223> OTHER INFORMATION: These nucleotides may be absent

<400> SEQUENCE: 231
agagagagtg gacctaa                                                       17

<210> SEQ ID NO 232
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 232
gagagtggac ctaag                                                         15

<210> SEQ ID NO 233
<211> LENGTH: 16
<212> TYPE: DNA
<213> ORGANISM: Homo sapiens
```

```
<220> FEATURE:
<221> NAME/KEY: misc_feature
<222> LOCATION: 5, 6
<223> OTHER INFORMATION: These nucleotides may be absent

<400> SEQUENCE: 233
gagagtggac ctaagc                                                       16

<210> SEQ ID NO 234
<211> LENGTH: 15
<212> TYPE: DNA
<213> ORGANISM: Homo sapiens
<220> FEATURE:
<221> NAME/KEY: misc_feature
<222> LOCATION: 4, 5
<223> OTHER INFORMATION: These nucleotides may be absent

<400> SEQUENCE: 234
gagagtggac ctaag                                                        15

<210> SEQ ID NO 235
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 235
gccacggaaa gtac                                                         14

<210> SEQ ID NO 236
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 236
acggaaagta ctccag                                                       16

<210> SEQ ID NO 237
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 237
ccagatggat tttc                                                         14

<210> SEQ ID NO 238
<211> LENGTH: 17
<212> TYPE: DNA
<213> ORGANISM: Homo sapiens
<220> FEATURE:
<221> NAME/KEY: misc_feature
<222> LOCATION: (4)...(7)
<223> OTHER INFORMATION: These nucleotides may be absent

<400> SEQUENCE: 238
tcatccagcc tgagtgc                                                      17
```

<210> SEQ ID NO 239
<211> LENGTH: 20
<212> TYPE: DNA
<213> ORGANISM: Homo sapiens
<220> FEATURE:
<221> NAME/KEY: misc_feature
<222> LOCATION: (4)...(10)
<223> OTHER INFORMATION: These nucleotides may be absent

<400> SEQUENCE: 239
ttaagaataa tgcctccagt                                            20

<210> SEQ ID NO 240
<211> LENGTH: 17
<212> TYPE: DNA
<213> ORGANISM: Homo sapiens
<220> FEATURE:
<221> NAME/KEY: misc_feature
<222> LOCATION: 6, 7
<223> OTHER INFORMATION: These nucleotides may be absent

<400> SEQUENCE: 240
gaaacagaat cagagca                                               17

<210> SEQ ID NO 241
<211> LENGTH: 20
<212> TYPE: DNA
<213> ORGANISM: Homo sapiens
<220> FEATURE:
<221> NAME/KEY: misc_feature
<222> LOCATION: (6)...(10)
<223> OTHER INFORMATION: These nucleotides may be absent

<400> SEQUENCE: 241
tcaaatgaaa accaagagaa                                            20

<210> SEQ ID NO 242
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 242
gaaaaccaag agaa                                                  14

<210> SEQ ID NO 243
<211> LENGTH: 18
<212> TYPE: DNA
<213> ORGANISM: Homo sapiens
<220> FEATURE:
<221> NAME/KEY: misc_feature
<222> LOCATION: (5)...(8)
<223> OTHER INFORMATION: These nucleotides may be absent

<400> SEQUENCE: 243
gagaaagagg cagaaaaa                                              18

<210> SEQ ID NO 244
<211> LENGTH: 16
<212> TYPE: DNA
<213> ORGANISM: Homo sapiens
<220> FEATURE:
<221> NAME/KEY: misc_feature
<222> LOCATION: 5, 6
<223> OTHER INFORMATION: These nucleotides may be absent

```
<400> SEQUENCE: 244
gaatgtatta tttctg                                                16

<210> SEQ ID NO 245
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 245
ccagcccaga ctgctt                                                16

<210> SEQ ID NO 246
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 246
cagactgctt caaaat                                                16

<210> SEQ ID NO 247
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 247
ttcaatgata agctc                                                 15

<210> SEQ ID NO 248
<211> LENGTH: 19
<212> TYPE: DNA
<213> ORGANISM: Homo sapiens
<220> FEATURE:
<221> NAME/KEY: misc_feature
<222> LOCATION: (6)...(9)
<223> OTHER INFORMATION: These nucleotides may be absent

<400> SEQUENCE: 248
aatgattctt tgagttctc                                             19

<210> SEQ ID NO 249
<211> LENGTH: 19
<212> TYPE: DNA
<213> ORGANISM: Homo sapiens
<220> FEATURE:
<221> NAME/KEY: misc_feature
<222> LOCATION: (6)...(9)
<223> OTHER INFORMATION: These nucleotides may be absent

<400> SEQUENCE: 249
ccagacagag gggcagcaa                                             19

<210> SEQ ID NO 250
<211> LENGTH: 14
<212> TYPE: DNA
```

```
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 250
gaaaatactc cagt                                                      14

<210> SEQ ID NO 251
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 251
aacaataaag aaaa                                                      14

<210> SEQ ID NO 252
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 252
gaacctatca aagaga                                                    16

<210> SEQ ID NO 253
<211> LENGTH: 14
<212> TYPE: DNA
<213> ORGANISM: Homo sapiens
<220> FEATURE:
<221> NAME/KEY: misc_feature
<222> LOCATION: 4
<223> OTHER INFORMATION: This nucleotide may be absent

<400> SEQUENCE: 253
cctatcaaag agac                                                      14

<210> SEQ ID NO 254
<211> LENGTH: 15
<212> TYPE: DNA
<213> ORGANISM: Homo sapiens
<220> FEATURE:
<221> NAME/KEY: misc_feature
<222> LOCATION: 5
<223> OTHER INFORMATION: This nucleotide may be absent

<400> SEQUENCE: 254
gaaccaagta aacct                                                     15

<210> SEQ ID NO 255
<211> LENGTH: 16
<212> TYPE: DNA
<213> ORGANISM: Homo sapiens
<220> FEATURE:
<221> NAME/KEY: misc_feature
<222> LOCATION: 6
<223> OTHER INFORMATION: This nucleotide may be absent

<400> SEQUENCE: 255
agctccgcaa tgccaa                                                    16
```

<210> SEQ ID NO 256
<211> LENGTH: 23
<212> TYPE: DNA
<213> ORGANISM: Homo sapiens
<220> FEATURE:
<221> NAME/KEY: misc_feature
<222> LOCATION: (6)...(13)
<223> OTHER INFORMATION: These nucleotides may be absent

<400> SEQUENCE: 256
tcatcccttc ctcgagtaag cac                                    23

<210> SEQ ID NO 257
<211> LENGTH: 19
<212> TYPE: DNA
<213> ORGANISM: Homo sapiens
<220> FEATURE:
<221> NAME/KEY: misc_feature
<222> LOCATION: (6)...(9)
<223> OTHER INFORMATION: These nucleotides may be absent

<400> SEQUENCE: 257
ctaatttatc aaatggcac                                         19

<210> SEQ ID NO 258
<211> LENGTH: 18
<212> TYPE: DNA
<213> ORGANISM: Homo sapiens
<220> FEATURE:
<221> NAME/KEY: misc_feature
<222> LOCATION: 6
<223> OTHER INFORMATION: n = C or G
<220> FEATURE:
<221> NAME/KEY: misc_feature
<222> LOCATION: 7
<223> OTHER INFORMATION: n = A or n is absent
<220> FEATURE:
<221> NAME/KEY: misc_feature
<222> LOCATION: 8
<223> OTHER INFORMATION: n = A or n is absent

<400> SEQUENCE: 258 gaaganntt acagcagg                                           18

<210> SEQ ID NO 259
<211> LENGTH: 18
<212> TYPE: DNA
<213> ORGANISM: Homo sapiens
<220> FEATURE:
<221> NAME/KEY: misc_feature
<222> LOCATION: 6
<223> OTHER INFORMATION: n = T or C
<220> FEATURE:
<221> NAME/KEY: misc_feature
<222> LOCATION: 7
<223> OTHER INFORMATION: n = T
<220> FEATURE:
<221> NAME/KEY: misc_feature
<222> LOCATION: 8
<223> OTHER INFORMATION: n = A or n is absent

<400> SEQUENCE: 259
cttacnnncc ggagccag                                          18

<210> SEQ ID NO 260
<211> LENGTH: 25
<212> TYPE: DNA
<213> ORGANISM: Homo sapiens
<220> FEATURE:

```
<221> NAME/KEY: misc_feature
<222> LOCATION: 4
<223> OTHER INFORMATION: n = C or T
<220> FEATURE:
<221> NAME/KEY: misc_feature
<222> LOCATION: 5
<223> OTHER INFORMATION: n = T
<220> FEATURE:
<221> NAME/KEY: misc_feature
<222> LOCATION: 6
<223> OTHER INFORMATION: n = C or G
<220> FEATURE:
<221> NAME/KEY: misc_feature
<222> LOCATION: 7
<223> OTHER INFORMATION: n = A or C
<220> FEATURE:
<221> NAME/KEY: misc_feature
<222> LOCATION: 8
<223> OTHER INFORMATION: n = T or A
<220> FEATURE:
<221> NAME/KEY: misc_feature
<222> LOCATION: 9
<223> OTHER INFORMATION: n = G or n is absent
<220> FEATURE:
<221> NAME/KEY: misc_feature
<222> LOCATION: (10)...(10)
<223> OTHER INFORMATION: n = C or n is absent
<220> FEATURE:
<221> NAME/KEY: misc_feature
<222> LOCATION: (11)...(13)
<223> OTHER INFORMATION: n = T or n is absent
<220> FEATURE:
<221> NAME/KEY: misc_feature
<222> LOCATION: (14)...(15)
<223> OTHER INFORMATION: n = A or n is absent

<400> SEQUENCE: 260
aatnnnnnnn nnnnnggcaa atagg                                 25

<210> SEQ ID NO 261
<211> LENGTH: 12
<212> TYPE: DNA
<213> ORGANISM: Homo sapiens

<400> SEQUENCE: 261
ttgcagcttt aa                                               12

<210> SEQ ID NO 262
<211> LENGTH: 17
<212> TYPE: DNA
<213> ORGANISM: Homo sapiens
<220> FEATURE:
<221> NAME/KEY: misc_feature
<222> LOCATION: 5
<223> OTHER INFORMATION: n = G or T
<220> FEATURE:
<221> NAME/KEY: misc_feature
<222> LOCATION: 6
<223> OTHER INFORMATION: n = T or A
<220> FEATURE:
<221> NAME/KEY: misc_feature
<222> LOCATION: 7
<223> OTHER INFORMATION: n= A or n is absent

<400> SEQUENCE: 262
gatgnnntat ggtaaaa                                          17
```

RAPID ANALYSIS OF VARIATIONS IN A GENOME

CROSS-REFERENCE TO RELATED APPLICATIONS

This application is a continuation-in-part of U.S. patent application Ser. No. 10/093,618, filed Mar. 11, 2002, now U.S. Pat. No. 6,977,162, which claims benefit of provisional U.S. Patent Application No. 60/360,232, filed Mar. 1, 2002. This application also claims benefit of provisional U.S. Patent Application No. 60/378,354, filed May 8, 2002. The contents of these applications are hereby incorporated by reference in their entirety herein.

BACKGROUND OF THE INVENTION

1. Field of the Invention

The present invention is directed to a rapid method for determining the sequence of nucleic acid. The method is especially useful for genotyping, and for the detection of one to tens to hundreds to thousands of single nucleotide polymorphisms (SNPs) or mutations on single or on multiple chromosomes, and for the detection of chromosomal abnormalities, such as truncations, transversions, trisomies, and monosomies.

2. Background

Sequence variation among individuals comprises a continuum from deleterious disease mutations to neutral polymorphisms. There are more than three thousand genetic diseases currently known including Duchenne Muscular Dystrophy, Alzheimer's Disease, Cystic Fibrosis, and Huntington's Disease (D. N. Cooper and M. Krawczak, "Human Genome Mutations," BIOS Scientific Publishers, Oxford (1993)). Also, particular DNA sequences may predispose individuals to a variety of diseases such as obesity, arteriosclerosis, and various types of cancer, including breast, prostate, and colon. In addition, chromosomal abnormalities, such as trisomy 21, which results in Down's Syndrome, trisomy 18, which results in Edward's Syndrome, trisomy 13, which results in Patau Syndrome, monosomy X, which results in Turner's Syndrome, and other sex aneuploidies, account for a significant portion of the genetic defects in liveborn human beings. Knowledge of gene mutations, chromosomal abnormalities, and variations in gene sequences, such as single nucleotide polymorphisms (SNPs), will help to understand, diagnose, prevent, and treat diseases.

Most frequently, sequence variation is seen in differences in the lengths of repeated sequence elements, such as minisatellites and microsatellites, as small insertions or deletions, and as substitutions of the individual bases. Single nucleotide polymorphisms (SNPs) represent the most common form of sequence variation; three million common SNPs with a population frequency of over 5% have been estimated to be present in the human genome. Small deletions or insertions, which usually cause frameshift mutations, occur on average, once in every 12 kilobases of genomic DNA (Wang, D. G. et al., Science 280: 1077–1082 (1998)). A genetic map using these polymorphisms as a guide is being developed (http://research.marshfieldclinic.org/genetics/; internet address as of Jan. 10, 2002).

The nucleic acid sequence of the human genome was published in February, 2001, and provides a genetic map of unprecedented resolution, containing several hundred thousand SNP markers, and a potential wealth of information on human diseases (Venter et al., Science 291:1304–1351 (2001); International Human Genome Sequencing Consortium, Nature 409:860–921 (2001)). However, the length of DNA contained within the human chromosomes totals over 3 billion base pairs so sequencing the genome of every individual is impractical. Thus, it is imperative to develop high throughput methods for rapidly determining the presence of allelic variants of SNPs and point mutations, which predispose to or cause disease phenotypes. Efficient methods to characterize functional polymorphisms that affect an individual's physiology, psychology, audiology, opthamology, neurology, response to drugs, drug metabolism, and drug interactions also are needed.

Several techniques are widely used for analyzing and detecting genetic variations, such as DNA sequencing, restriction fragment length polymorphisms (RFLP), DNA hybridization assays, including DNA microarrays and peptide nucleic acid analysis, and the Protein Truncation Test (PTT), all of which have limitations. Although DNA sequencing is the most definitive method, it is also the most time consuming and expensive. Often, the entire coding sequence of a gene is analyzed even though only a small fraction of the coding sequence is of interest. In most instances, a limited number of mutations in any particular gene account for the majority of the disease phenotypes.

For example, the cystic fibrosis transmembrane conductance regulator (CFTR) gene is composed of 24 exons spanning over 250,000 base pairs (Rommens et al., Science 245:1059–1065 (1989); Riordan et al., Science 245:1066–73 (1989)). Currently, there are approximately 200 mutations in the CFTR gene that are associated with a disease state of Cystic Fibrosis. Therefore, only a very small percentage of the reading frame for the CFTR gene needs to be analyzed. Furthermore, a total of 10 mutations make up 75.1% of all known disease cases. The deletion of a single phenylalanine residue, F508, accounts for 66% of all Cystic Fibrosis cases in Caucasians.

Hybridization techniques, including Southern Blots, Slot Blots, Dot Blots, and DNA microarrays, are commonly used to detect genetic variations (Molecular Cloning, A Laboratory Manual, Cold Spring Harbor Laboratory Press, Third Edition (2001). In a typical hybridization assay, an unknown nucleotide sequence ("the target") is analyzed based on its affinity for another fragment with a known nucleotide sequence ("the probe"). If the two fragments hybridize under "stringent conditions," the sequences are thought to be complementary, and the sequence of the target fragment may be inferred from "the probe" sequence.

However, the results from a typical hybridization assay often are difficult to interpret. The absence or presence of a hybridization signal is dependent upon the definition of "stringent conditions." Any number of variables may be used to raise or lower stringency conditions such as salt concentration, the presence or absence of competitor nucleotide fragments, the number of washes performed to remove non-specific binding and the time and temperature at which the hybridizations are performed. Commonly, hybridization conditions must be optimized for each "target" nucleotide fragment, which is time-consuming, and inconsistent with a high throughput method. A high degree of variability is often seen in hybridization assays, as well as a high proportion of false positives. Typically, hybridization assays function as a screen for likely candidates but a positive confirmation requires DNA sequencing analysis.

Several techniques for the detection of mutations have evolved based on the principal of hybridization analysis. For example, in the primer extension assay, the DNA region spanning the nucleotide of interest is amplified by PCR, or any other suitable amplification technique. After amplification, a primer is hybridized to a target nucleic acid sequence, wherein the last nucleotide of the 3' end of the primer anneals immediately 5' to the nucleotide position on the target sequence that is to be analyzed. The annealed primer is extended by a single, labeled nucleotide triphosphate. The incorporated nucleotide is then detected.

There are several limitations to the primer extension assay. First, the region of interest must be amplified prior to primer extension, which increases the time and expense of the assay. Second, PCR primers and dNTPs must be completely removed before primer extension, and residual contaminants can interfere with the proper analysis of the results. Third, and the most restrictive aspect of the assay, is that the primer is hybridized to the DNA template, which requires optimization of conditions for each primer, and for each sequence that is analyzed. Hybridization assays have a low degree of reproducibility, and a high degree of non-specificity.

The Peptide Nucleic Acid (PNA) affinity assay is a derivative of traditional hybridization assays (Nielsen et al., Science 254:1497–1500 (1991); Egholm et al., J. Am. Chem. Soc. 114:1895–1897 (1992); James et al., Protein Science 3:1347–1350 (1994)). PNAs are structural DNA mimics that follow Watson-Crick base pairing rules, and are used in standard DNA hybridization assays. PNAs display greater specificity in hybridization assays because a PNA/DNA mismatch is more destabilizing than a DNA/DNA mismatch and complementary PNA/DNA strands form stronger bonds than complementary DNA/DNA strands. However, genetic analysis using PNAs still requires a laborious hybridization step, and as such, is subject to a high degree of non-specificity and difficulty with reproducibility.

Recently, DNA microarrays have been developed to detect genetic variations and polymorphisms (Taton et al., Science 289:1757–60, 2000; Lockhart et al., Nature 405: 827–836 (2000); Gerhold et al., Trends in Biochemical Sciences 24:168–73 (1999); Wallace, R. W., Molecular Medicine Today 3:384–89 (1997); Blanchard and Hood, Nature Biotechnology 149:1649 (1996)). DNA microarrays are fabricated by high-speed robotics, on glass or nylon substrates, and contain DNA fragments with known identities ("the probe"). The microarrays are used for matching known and unknown DNA fragments ("the target") based on traditional base-pairing rules. The advantage of DNA microarrays is that one DNA chip may provide information on thousands of genes simultaneously. However, DNA microarrays are still based on the principle of hybridization, and as such, are subject to the disadvantages discussed above.

The Protein Truncation Test (PTT) is also commonly used to detect genetic polymorphisms (Roest et al., Human Molecular Genetics 2:1719–1721, (1993); Van Der Luit et al., Genomics 20:1–4 (1994); Hogervorst et al., Nature Genetics 10: 208–212 (1995)). Typically, in the PTT, the gene of interest is PCR amplified, subjected to in vitro transcription/translation, purified, and analyzed by polyacrylamide gel electrophoresis. The PTT is useful for screening large portions of coding sequence and detecting mutations that produce stop codons, which significantly diminish the size of the expected protein. However, the PTT is not designed to detect mutations that do not significantly alter the size of the protein.

Thus, a need still exists for a rapid method of analyzing DNA, especially genomic DNA suspected of having one or more single nucleotide polymorphisms or mutations.

BRIEF SUMMARY OF THE INVENTION

The invention is directed to a method for determining a sequence of a locus of interest, the method comprising: (a) amplifying a locus of interest on a template DNA using a first and second primers, wherein the second primer contains a recognition site for a restriction enzyme such that digestion with the restriction enzyme generates a 5' overhang containing the locus of interest; (b) digesting the amplified DNA with the restriction enzyme that recognizes the recognition site on the second primer; (c) incorporating a nucleotide into the digested DNA of (b) by using the 5' overhang containing the locus of interest as a template; and (d) determining the sequence of the locus of interest by determining the sequence of the DNA of (c).

The invention is also directed to a method for determining a sequence of a locus of interest, said method comprising: (a) amplifying a locus of interest on a template DNA using a first and second primers, wherein the second primer contains a portion of a recognition site for a restriction enzyme, wherein a full recognition site for the restriction enzyme is generated upon amplification of the template DNA such that digestion with the restriction enzyme generates a 5' overhang containing the locus of interest; (b) digesting the amplified DNA with the restriction enzyme that recognizes the full recognition site generated by the second primer and the template DNA; (c) incorporating a nucleotide into the digested DNA of (b) by using the 5' overhang containing the locus of interest as a template; and determining the sequence of the locus of interest by determining the sequence of the DNA of (c).

The invention also is directed to a method for determining a sequence of a locus of interest, said method comprising (a) replicating a region of DNA comprising a locus of interest from a template polynucleotide by using a first and a second primer, wherein the second primer contains a sequence that generates a recognition site for a restriction enzyme such that digestion with the restriction enzyme generates a 5' overhang containing the locus of interest; (b) digesting the DNA with the restriction enzyme that recognizes the recognition site generated by the second primer to create a DNA fragment; (c) incorporating a nucleotide into the digested DNA of (b) by using the 5' overhang containing the locus of interest as a template; and (d) determining the sequence of the locus of interest by determining the sequence of the DNA of (c).

The invention also is directed to a DNA fragment containing a locus of interest to be sequenced and a recognition site for a restriction enzyme, wherein digestion with the restriction enzyme creates a 5' overhang on the DNA fragment, and wherein the locus of interest and the restriction enzyme recognition site are in relationship to each other such that digestion with the restriction enzyme generates a 5' overhang containing the locus of interest.

The template DNA can be obtained from any source including synthetic nucleic acid, preferably from a bacterium, fungus, virus, plant, protozoan, animal or human source. In one embodiment, the template DNA is obtained from a human source. In another embodiment, the template DNA is obtained from a cell, tissue, blood sample, serum sample, plasma sample, urine sample, spinal fluid, lymphatic fluid, semen, vaginal secretion, ascitic fluid, saliva, mucosa secretion, peritoneal fluid, fecal sample, or body exudates.

The 3' region of the first and/or second primer can contain a mismatch with the template DNA. The mismatch can occur at but is not limited to the last 1, 2, or 3 bases at the 3' end.

The restriction enzyme used in the invention can cut DNA at the recognition site. The restriction enzyme can be but is not limited to PflF I, Sau96 I, ScrF I, BsaJ I, Bssk I, Dde I, EcoN I, Fnu4H I, Hinf I, or Tth111 I. Alternatively, the restriction enzyme used in the invention can cut DNA at a distance from its recognition site.

In another embodiment, the first primer contains a recognition site for a restriction enzyme. In a preferred embodiment, the restriction enzyme recognition site is different from the restriction enzyme recognition site on the second primer. The invention includes digesting the amplified DNA with a restriction enzyme that recognizes the recognition site on the first primer.

Preferably, the recognition site on the second primer is for a restriction enzyme that cuts DNA at a distance from its recognition site and generates a 5' overhang, containing the locus of interest. In a preferred embodiment, the recognition site on the second primer is for a Type IIS restriction enzyme. The Type IIS restriction enzyme, e.g., is selected from the group consisting of: Alw I, Alw26 I, Bbs I, Bbv I, BceA I, Bmr I, Bsa I, Bst71 I, BsmA I, BsmB I, BsmF I, BspM I, Ear I, Fau I, Fok I, Hga I, Ple I, Sap I, SSfaN I, and Sthi32 I, and more preferably BceA I and BsmF I.

In one embodiment, the 5' region of the second primer does not anneal to the template DNA and/or the 5' region of the first primer does not anneal to the template DNA. The annealing length of the 3' region of the first or second primer can be 25–20, 20–15, 15, 14, 13, 12, 11, 10, 9, 8, 7, 6, 5, 4, or less than 4 bases.

In one embodiment, the amplification can comprise polymerase chain reaction (PCR). In a further embodiment, the annealing temperature for cycle 1 of PCR can be at about the melting temperature of the 3' region of the second primer that anneals to the template DNA. In another embodiment, the annealing temperature for cycle 2 of PCR can be about the melting temperature of the 3' region of the first primer that anneals to the template DNA. In another embodiment, the annealing temperature for the remaining cycles can be about the melting temperature of the entire sequence of the second primer.

In one embodiment, the 3' end of the second primer is adjacent to the locus of interest.

The first and/or second primer can contain a tag at the 5' terminus. Preferably, the first primer contains a tag at the 5' terminus. The tag can be used to separate the amplified DNA from the template DNA. The tag can be used to separate the amplified DNA containing the labeled nucleotide from the amplified DNA that does not contain the labeled nucleotide. The tag can be but is not limited to a radioisotope, fluorescent reporter molecule, chemiluminescent reporter molecule, antibody, antibody fragment, hapten, biotin, derivative of biotin, photobiotin, iminobiotin, digoxigenin, avidin, enzyme, acridinium, sugar, enzyme, apoenzyme, homopolymeric oligonucleotide, hormone, ferromagnetic moiety, paramagnetic moiety, diamagnetic moiety, phosphorescent moiety, luminescent moiety, electrochemiluminescent moiety, chromatic moiety, moiety having a detectable electron spin resonance, electrical capacitance, dielectric constant or electrical conductivity, or combinations thereof. Preferably, the tag is biotin. The biotin tag is used to separate amplified DNA from the template DNA using a streptavidin matrix. The streptavidin matrix is coated on wells of a microtiter plate.

The incorporation of a nucleotide in the method of the invention is by a DNA polymerase including but not limited to E. coli DNA polymerase, Klenow fragment of E. coli DNA polymerase I, T5 DNA polymerase, T7 DNA polymerase, T4 DNA polymerase, Taq polymerase, Pfu DNA polymerase, Vent DNA polymerase, bacteriophage 29, REDTaq™ Genomic DNA polymerase, and sequenase.

The incorporation of a nucleotide can further comprise using a mixture of labeled and unlabeled nucleotides. One nucleotide, two nucleotides, three nucleotides, four nucleotides, five nucleotides, or more than five nucleotides may be incorporated. A combination of labeled and unlabeled nucleotides can be incorporated. The labeled nucleotide can be but is not limited to a dideoxynucleotide triphosphate and deoxynucleotide triphosphate. The unlabeled nucleotide can be but is not limited to a dideoxynucleotide triphosphate and deoxynucleotide triphosphate. The labeled nucleotide is labeled with a molecule such as but not limited to a radioactive molecule, fluorescent molecule, antibody, antibody fragment, hapten, carbohydrate, biotin, and derivative of biotin, phosphorescent moiety, luminescent moiety, electrochemiluminescent moiety, chromatic moiety, or moiety having a detectable electron spin resonance, electrical capacitance, dielectric constant or electrical conductivity. Preferably, the labeled nucleotide is labeled with a fluorescent molecule. The incorporation of a fluorescent labeled nucleotide further includes using a mixture of fluorescent and unlabeled nucleotides.

In one embodiment, the determination of the sequence of the locus of interest comprises detecting the incorporated nucleotide. In one embodiment, the detection is by a method such as but not limited to gel electrophoresis, capillary electrophoresis, microchannel electrophoresis, polyacrylamide gel electrophoresis, fluorescence detection, sequencing, ELISA, mass spectrometry, time of flight mass spectrometry, quadrupole mass spectrometry, magnetic sector mass spectrometry, electric sector mass spectrometry, fluorometry, infrared spectrometry, ultraviolet spectrometry, palentiostatic amperometry, hybridization, such as Southern Blot, or microarray. In a preferred embodiment, the detection is by fluorescence detection.

In a preferred embodiment, the locus of interest is suspected of containing a single nucleotide polymorphism or mutation. The method can be used for determining sequences of multiple loci of interest concurrently. The template DNA can comprise multiple loci from a single chromosome. The template DNA can comprise multiple loci from different chromosomes. The loci of interest on template DNA can be amplified in one reaction. Alternatively, each of the loci of interest on template DNA can be amplified in a separate reaction. The amplified DNA can be pooled together prior to digestion of the amplified DNA. Each of the labeled DNA containing a locus of interest can be separated prior to determining the sequence of the locus of interest. In one embodiment, at least one of the loci of interest is suspected of containing a single nucleotide polymorphism or a mutation.

In another embodiment, the method of the invention can be used for determining the sequences of multiple loci of interest from a single individual or from multiple individuals. Also, the method of the invention can be used to determine the sequence of a single locus of interest from multiple individuals.

The first primer is shown modified with biotin at the 5' end to aid in purification. The sequence of the 3' end of the primers is such that the primers anneal at a desired distance upstream and downstream of the locus of interest. The second primer anneals close to the locus of interest; the annealing site, which is depicted as region "c," is designed such that the 3' end of the second primer anneals one base away from the locus of interest. The second primer can anneal any distance from the locus of interest provided that digestion with the restriction enzyme, which recognizes the region "d" on this primer, generates a 5' overhang that contains the locus of interest.

The first primer annealing site, which is depicted as region "b'," is about 20 bases.

FIG. 1B. A schematic diagram depicting the annealing and extension steps of the first cycle of amplification by PCR. The first cycle of amplification is performed at about the melting temperature of the 3' region, which anneals to the template DNA, of the second primer, depicted as region "c," and is 13 base pairs in this example. At this temperature, both the first and second primers anneal to their respective complementary strands and begin extension, depicted by dotted lines. In this first cycle, the second primer extends and copies the region b where the first primer can anneal in the next cycle.

FIG. 1C. A schematic diagram depicting the annealing and extension steps following denaturation in the second cycle of amplification of PCR. The second cycle of amplification is performed at a higher annealing temperature (TM2), which is about the melting temperature of the 20 bp of the 3' region of the first primer that anneals to the template DNA, depicted as region "b." Therefore at TM2, the first primer, which is complementary to region b, can bind to the DNA that was copied in the first cycle of the reaction. However, at TM2 the second primer cannot anneal to the original template DNA or to DNA that was copied in the first cycle of the reaction because the annealing temperature is too high. The second primer can anneal to 13 bases in the original template DNA but TM2 is calculated at about the melting temperature of 20 bases.

Figure 1A:
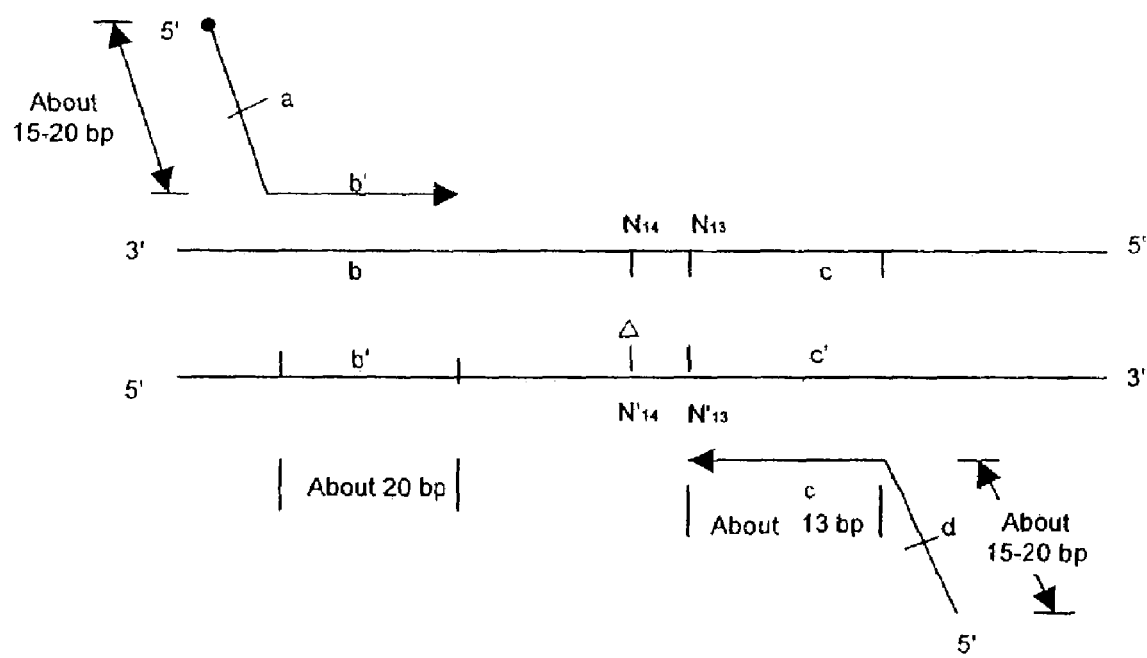
FIG. 1A. A Schematic diagram depicting a double stranded DNA molecule. A pair of primers, depicted as bent arrows, flank the locus of interest, depicted as a triangle symbol at base N14. The locus of interest can be a single nucleotide polymorphism, point mutation, insertion, deletion, translocation, etc. Each primer contains a restriction enzyme recognition site about 10 bp from the 5' terminus depicted as region "a" in the first primer and as region "d" in the second primer. Restriction recognition site "a" can be for any type of restriction enzyme but recognition site "d" is for a restriction enzyme, which cuts "n" nucleotides away from its recognition site and leaves a 5' overhang and a recessed 3' end. Examples of such enzymes include but are not limited to BceA I and BsmF I. The 5' overhang serves as a template for incorporation of a nucleotide into the 3' recessed end.
Figure 1D:
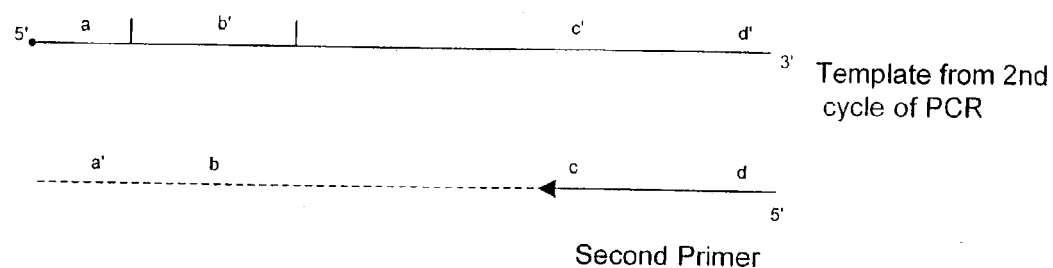

FIG. 1D. A schematic diagram depicting the annealing and extension reactions after denaturation during the third cycle of amplification. In this cycle, the annealing temperature, TM3, is about the melting temperature of the entire second primer, including regions "c" and "d." The length of regions "c"+"d" is about 27–33 bp long, and thus TM3 is significantly higher than TM1 and TM2. At this higher TM the second primer, which contain region c and d, anneals to the copied DNA generated in cycle 2.

Figure 1E:
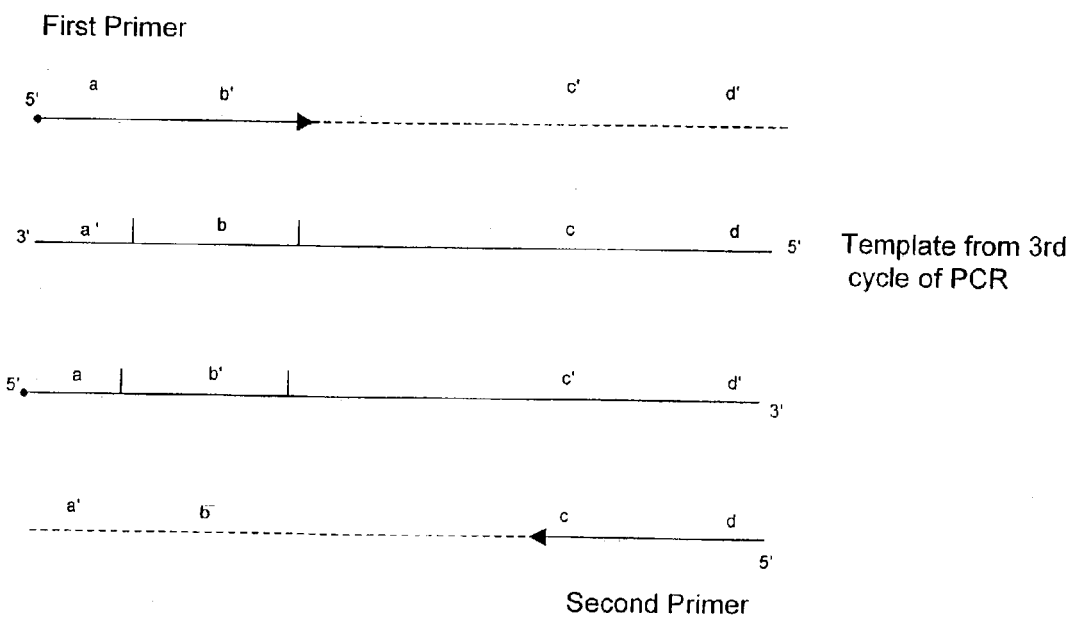

FIG. 1E. A schematic diagram depicting the annealing and extension reactions for the remaining cycles of amplification. The annealing temperature for the remaining cycles is TM3, which is about the melting temperature of the entire second primer. At TM3, the second primer binds to templates that contain regions c' and d' and the first primer binds to templates that contain regions a' and b. By raising the annealing temperature successively in each cycle for the first three cycles, from TM1 to TM2 to TM3, nonspecific amplification is significantly reduced.

Figure 1F:
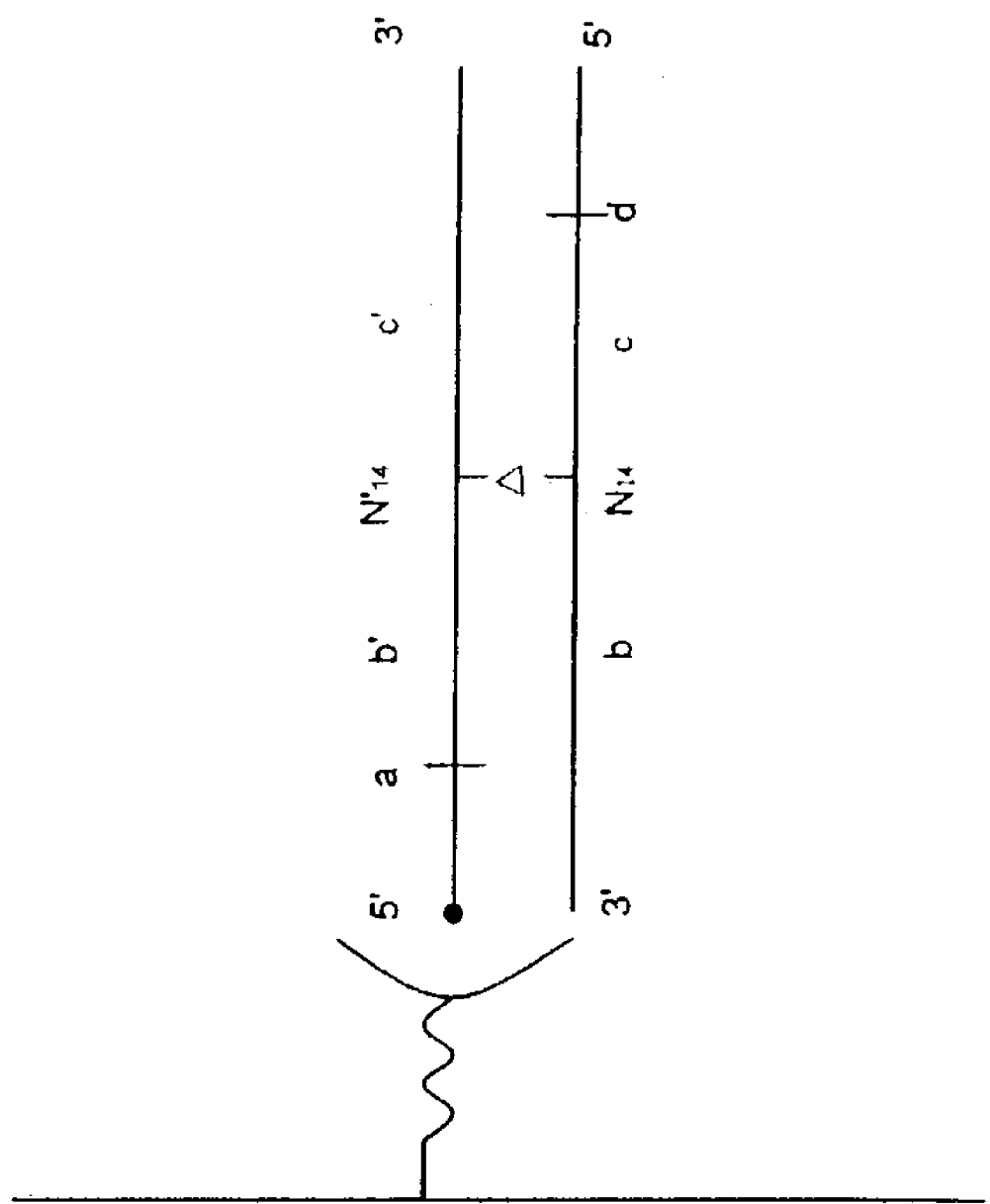

FIG. 1F. A schematic diagram depicting the amplified locus of interest bound to a solid matrix.

Figure 1G:
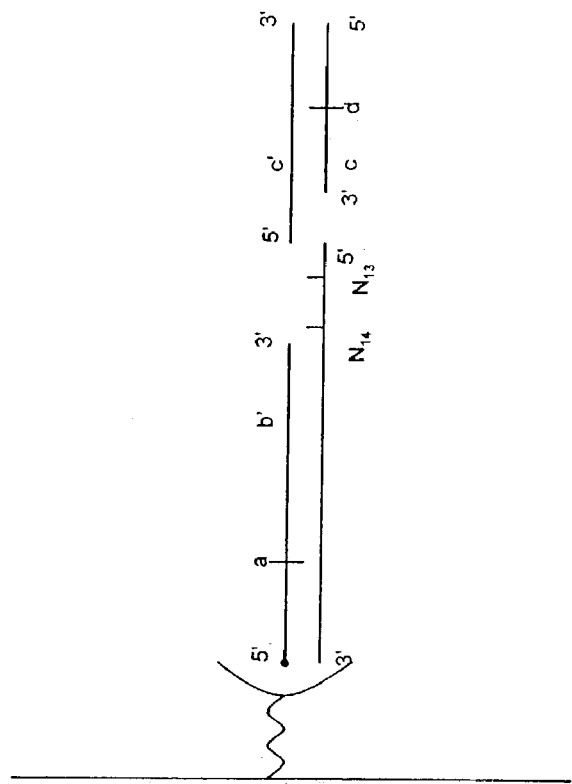

FIG. 1G. A schematic diagram depicting the bound, amplified DNA after digestion with a restriction enzyme that recognizes "d." The "downstream" end is released into the supernatant, and can be removed by washing with any suitable buffer. The upstream end containing the locus of interest remains bound to the solid matrix.

Figure 1H:
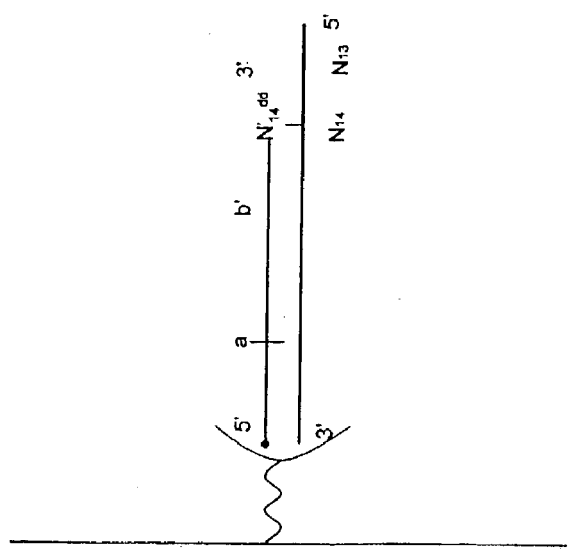

FIG. 1H. A schematic diagram depicting the bound amplified DNA, after "filling in" with a labeled ddNTP. A DNA polymerase is used to "fill in" the base ($N'_{14}$) that is complementary to the locus of interest ($N_{14}$). In this example, only ddNTPs are present in this reaction, such that only the locus of interest or SNP of interest is filled in.

Figure 1I:
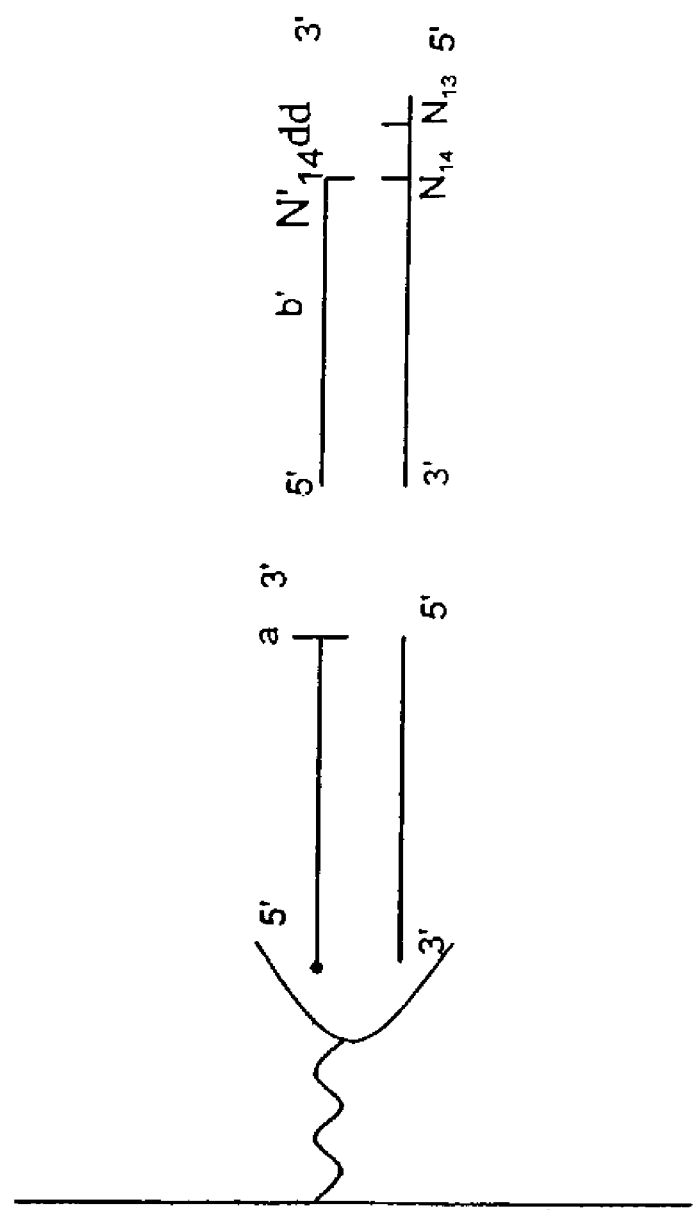

FIG. 1I. A schematic diagram depicting the labeled, bound DNA after digestion with restriction enzyme "a." The labeled DNA is released into the supernatant, which can be collected to identify the base that was incorporated.

Figure 2:
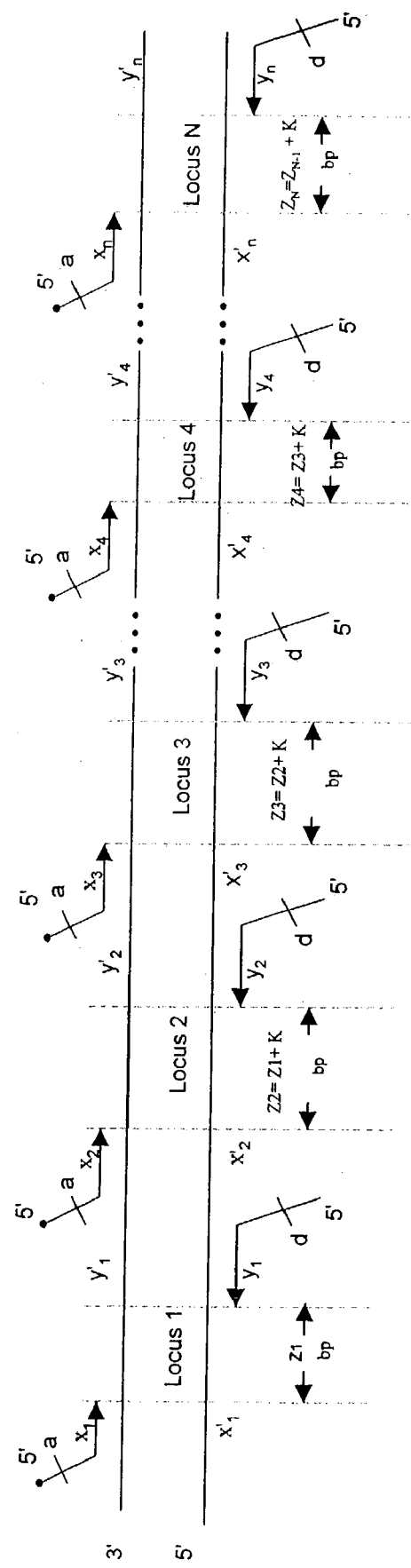
Figure 5C:
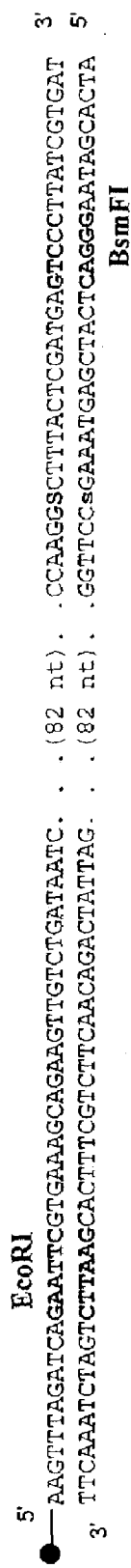
Figure 5D:
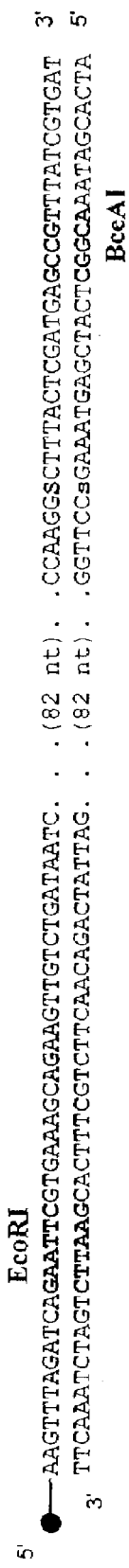

FIG. 2. A schematic diagram depicting double stranded DNA templates with "N" number of loci of interest and "n" number of primer pairs, $x_1$, $y_1$ to $X_n$, $y_n$, specifically annealed such that a primer flanks each locus of interest. The first primers are biotinylated at the 5' end, depicted by •, and contain a restriction enzyme recognition site, "a", which is recognized by any type of restriction enzyme. The second primers contain a restriction enzyme recognition site, "d," where "d" is a recognition site for a restriction enzyme that cuts DNA at a distance from its recognition site, and generates a 5' overhang containing the locus of interest and a recessed 3' end. The second primers anneal adjacent to the respective loci of interest. The exact position of the restriction enzyme site "d" in the second primers is designed such that digesting the PCR product of each locus of interest with restriction enzyme "d" generates a 5' overhang containing the locus of interest and a 3' recessed end. The annealing sites of the first primers are about 20 bases long and are selected such that each successive first primer is further away from its respective second primer. For example, if at locus 1 the 3' ends of the first and second primers are Z base pairs apart, then at locus 2, the 3' ends of the first and second primers are Z+K base pairs apart, where K=1, 2, 3 or more than three bases. Primers for locus N are $Z_{N-1}$+K base pairs apart. The purpose of making each successive first primer further apart from their respective second primers is such that the "filled in" restriction fragments (generated after amplification, purification, digestion and labeling as described in FIGS. 1B–1I) differ in size and can be resolved, for example by electrophoresis, to allow detection of each individual locus of interest.

FIG. 3A. Photograph of a gel demonstrating PCR amplification of the 4 DNA fragments containing different SNPs using the low stringency annealing temperature protocol.

FIG. 3B. Photograph of a gel demonstrating PCR amplification of the 4 DNA fragments containing different SNPs using the medium stringency annealing temperature protocol.

FIG. 3C. Photograph of a gel demonstrating PCR amplification of the 4 DNA fragments containing different SNPs using the high stringency annealing temperature protocol.

For FIGS. 3A–3C, the following conditions apply: A sample containing genomic DNA templates from thirty-six human volunteers was analyzed for the following four SNPs: SNP HC21S00340 (lane 1), identification number as assigned in the Human Chromosome 21 cSNP Database, located on chromosome 21; SNP TSC 0095512 (lane 2), located on chromosome 1; SNP TSC 0214366 (lane 3), located on chromosome 1; and SNP TSC 0087315 (lane 4), located on chromosome 1. Each DNA fragment containing a SNP was amplified by PCR using three different annealing temperature protocols, herein referred to as the low stringency annealing temperature; medium stringency annealing temperature; and high stringency annealing temperature. Regardless of the annealing temperature protocol, each DNA fragment containing a SNP was amplified for 40 cycles of PCR. The denaturation step for each PCR reaction was performed for 30 seconds at 95° C.

FIG. 4A. A depiction of the DNA sequence of SNP HC21S00027 (SEQ ID NOS:27 & 28), assigned by the Human Chromosome 21 cSNP database, located on chromosome 21. A first primer (SEQ ID NO:17) and a second primer (SEQ ID NO:18) are indicated above and below, respectively, the sequence of HC21S00027. The first primer is biotinylated and contains the restriction enzyme recognition site for EcoRI. The second primer contains the restriction enzyme recognition site for BsmF I and contains 13 bases that anneal to the DNA sequence. The SNP is indicated by R (A/G) and r (T/C; complementary to R).

FIG. 4B. A depiction of the DNA sequence of SNP HC21S00027 (SEQ ID NOS:27 & 28), as assigned by the Human Chromosome 21 cSNP database, located on chromosome 21. A first primer (SEQ ID NO:17) and a second primer (SEQ ID NO:19) are indicated above and below, respectively, the sequence of HC21S00027. The first primer is biotinylated and contains the restriction enzyme recognition site for EcoRI. The second primer contains the restriction enzyme recognition site for BceA I and has 13 bases that anneal to the DNA sequence. The SNP is indicated by R (A/G) and r (T/C; complementary to R).

FIG. 4C. A depiction of the DNA sequence of SNP TSC0095512 (SEQ ID NOS:29 & 30) from chromosome 1. The first primer (SEQ ID NO:11) and the second primer (SEQ ID NO:20) are indicated above and below, respectively, the sequence of TSC0095512. The first primer is biotinylated and contains the restriction enzyme recognition site for EcoRI. The second primer contains the restriction enzyme recognition site for BsmF I and has 13 bases that anneal to the DNA sequence. The SNP is indicated by S (G/C) and s (C/G; complementary to S).

FIG. 4D. A depiction of the DNA sequence of SNP TSC0095512 (SEQ ID NOS:29 & 30) from chromosome 1. The first primer (SEQ ID NO:11) and the second primer (SEQ ID NO:12) are indicated above and below, respectively, the sequence of TSC0095512. The first primer is biotinylated and contains the restriction enzyme recognition site for EcoRI. The second primer contains the restriction enzyme recognition site for BceA I and has 13 bases that anneal to the DNA sequence. The SNP is indicated by S (G/C) and s (C/G; complementary to S).

FIGS. 5A–5D. A schematic diagram depicting the nucleotide sequences of SNP HC21S00027 (FIG. 5A (SEQ ID NOS:31 & 32) and FIG. 5B (SEQ ID NOS:31 & 33)), and SNP TSC0095512 (FIG. 5C (SEQ ID NOS:34 & 35) and FIG. 5D (SEQ ID NOS:34 & 36)) after amplification with the primers described in FIGS. 4A–4D. Restriction sites in the primer sequence are indicated in bold.

Figure 6C:
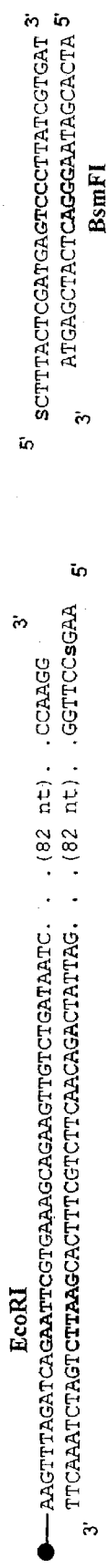
Figure 6D:
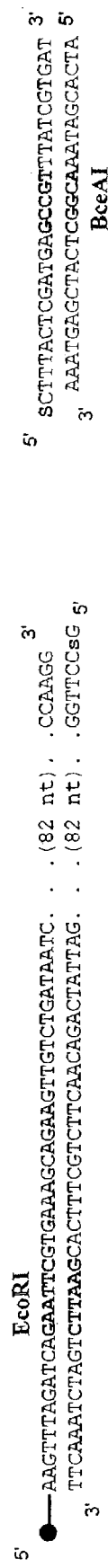

FIGS. 6A–6D. A schematic diagram depicting the nucleotide sequences of each amplified DNA fragment containing a SNP after digestion with the appropriate Type IIS restriction enzyme. FIG. 6A (SEQ ID NOS:31 & 32) and FIG. 6B (SEQ ID NOS:31 & 33) depict fragments of a DNA sequence containing SNP HC21S00027 digested with the Type IIS restriction enzymes BsmF I and BceA I, respectively. FIG. 6C (SEQ ID NOS:34 & 35) and FIG. 6D (SEQ ID NOS:34 & 36) depict fragments of a DNA sequence containing SNP TSC0095512 digested with the Type IIS restriction enzymes BsmF I and BceA I, respectively.

Figure 7C:
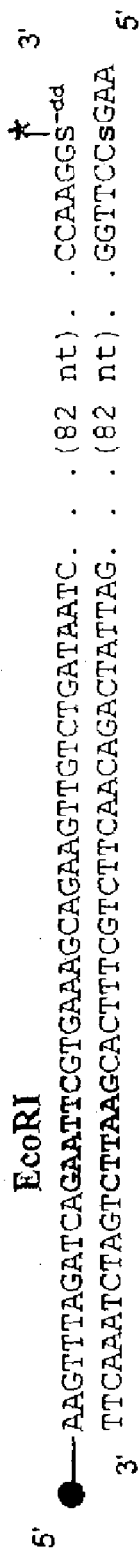
Figure 7D:
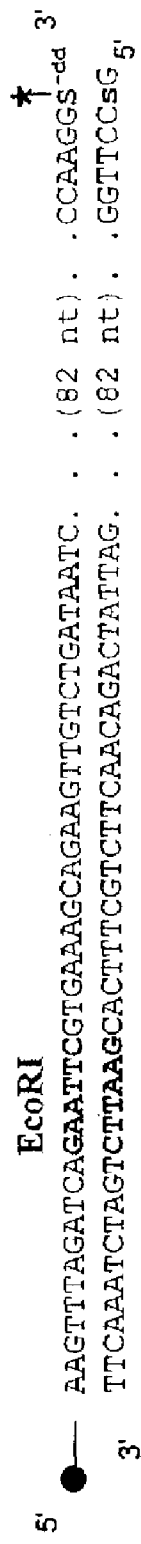

FIGS. 7A–7D. A schematic diagram depicting the incorporation of a fluorescently labeled nucleotide using the 5' overhang of the digested SNP site as a template to "fill in" the 3' recessed end. FIG. 7A (SEQ ID NOS:31, 37 & 41) and FIG. 7B (SEQ ID NOS:31, 37 & 39) depict the digested SNP HC21S00027 locus with an incorporated labeled ddNTP (*$R^{-dd}$=fluorescent dideoxy nucleotide). FIG. 7C (SEQ ID NOS:34 & 38) and FIG. 7D (SEQ ID NO:34) depict the digested SNP TSC0095512 locus with an incorporated labeled ddNTP (*$S^{-dd}$=fluorescent dideoxy nucleotide). The use of ddNTPs ensures that the 3' recessed end is extended by one nucleotide, which is complementary to the nucleotide of interest or SNP site present in the 5' overhang.

Figure 7E:
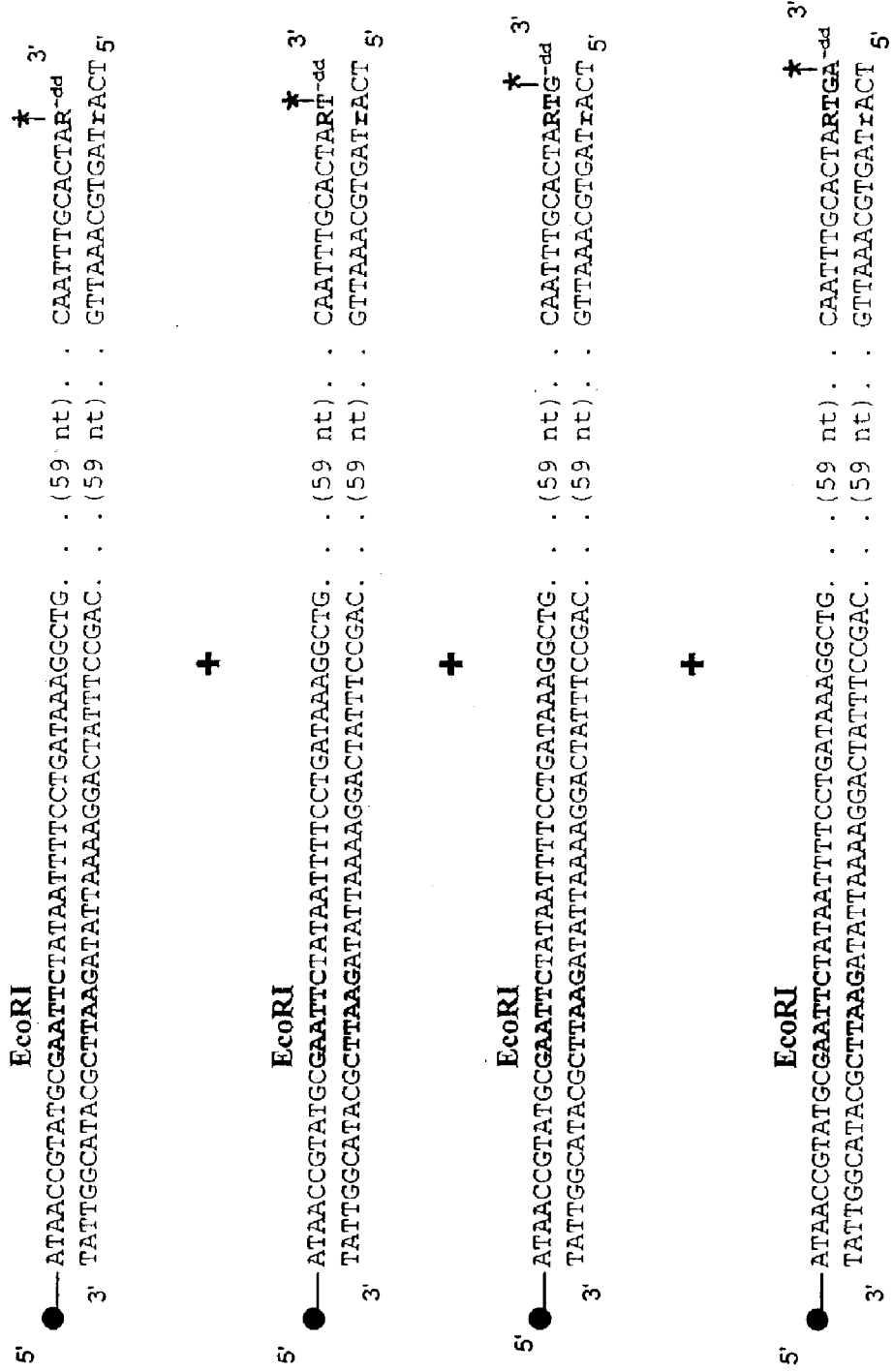

FIG. 7E. A schematic diagram depicting the incorporation of dNTPs and a ddNTP into the 5' overhang containing the SNP site. The DNA fragment containing SNP HC21S00007 was digested with BsmF I, which generates a four base 5' overhang. The use of a mixture of dNTPs and ddNTPs allows the 3' recessed end to be extended one nucleotide (a ddNTP is incorporated first) (SEQ ID NOS:31, 37 & 41); two nucleotides (a dNTP is incorporated followed by a ddNTP) (SEQ ID NOS:31, 39 & 41); three nucleotides (two dNTPs are incorporated, followed by a ddNTP) (SEQ ID NOS:31, 40 & 41); or four nucleotides (three dNTPs are incorporated, followed by a ddNTP) (SEQ ID NOS:31 & 41). All four products can be separated by size, and the incorporated nucleotide detected (*$R^{-dd}$=fluorescent dideoxy nucleotide). Detection of the first nucleotide, which corresponds to the SNP or locus site, and the next three nucleotides provides an additional level of quality assurance. The SNP is indicated by R (A/G) and r (T/C) (complementary to R).

Figure 8A:
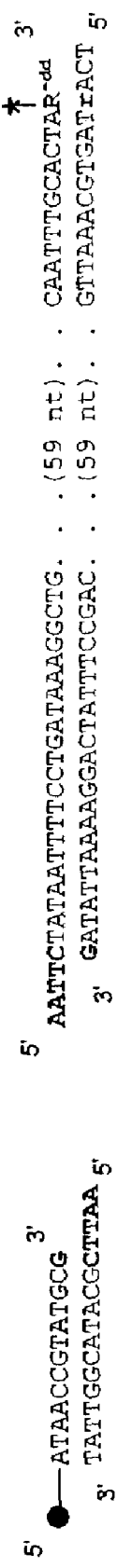
Figure 8B:
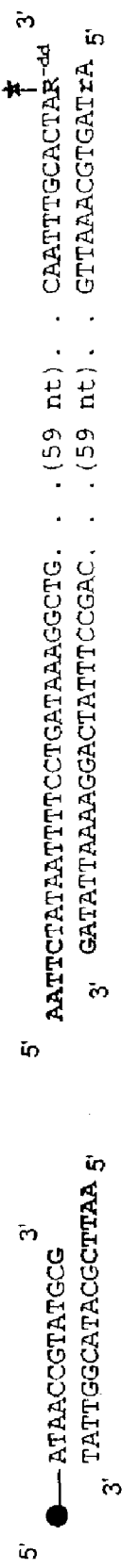
Figure 8C:
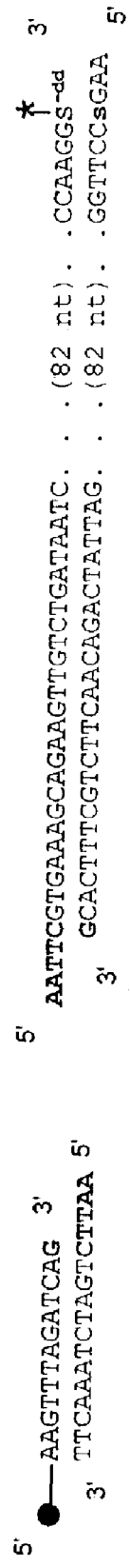
Figure 8D:
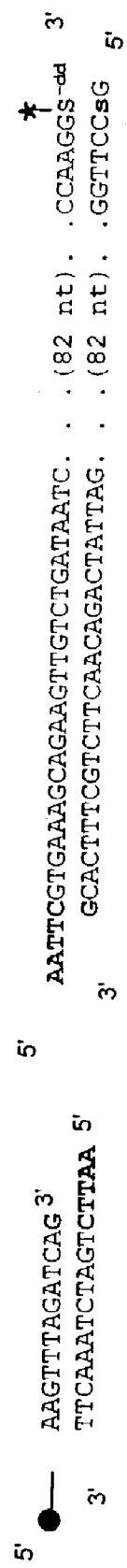

FIGS. 8A–8D. Release of the "filled in" SNP from the solid support matrix, i.e. streptavidin coated well. SNP HC21S00027 is shown in FIG. 8A (SEQ ID NOS:31, 37 & 41) and FIG. 8B (SEQ ID NOS:31, 37 & 39), while SNP TSC0095512 is shown in FIG. 8C (SEQ ID NOS:34 & 38) and FIG. 8D (SEQ ID NO:34). The "filled in" SNP is free in solution, and can be detected.

FIG. 9A. Sequence analysis of a DNA fragment containing SNP HC21S00027 digested with BceAI. Four "fill in" reactions are shown; each reaction contained one fluorescently labeled nucleotide, ddGTP, ddATP, ddTTP, or ddCTP, and unlabeled ddNTPs. The 5' overhang generated by digestion with BceA I and the expected nucleotides at this SNP site are indicated.

FIG. 9B. Sequence analysis of SNP TSC0095512. SNP TSC0095512 was amplified with a second primer that contained the recognition site for BceA I, and in a separate reaction, with a second primer that contained the recognition site for BsmF I. Four fill in reactions are shown for each PCR product; each reaction contained one fluorescently labeled nucleotide, ddGTP, ddATP, ddTTP, or ddCTP, and unlabeled ddNTPs. The 5' overhang generated by digestion with BceA I and with BsmF I and the expected nucleotides are indicated.

FIG. 9C. Sequence analysis of SNP TSC0264580 after amplification with a second primer that contained the recognition site for BsmF I. Four "fill in" reactions are shown; each reaction contained one fluorescently labeled nucleotide, which was ddGTP, ddATP, ddTTP, or ddCTP and unlabeled ddNTPs. Two different 5' overhangs are depicted:

one represents the DNA molecules that were cut 11 nucleotides away on the sense strand and 15 nucleotides away on the antisense strand and the other represents the DNA molecules that were cut 10 nucleotides away on the sense strand and 14 nucleotides away on the antisense strand. The expected nucleotides also are indicated.

FIG. 9D. Sequence analysis of SNP HC21S00027 amplified with a second primer that contained the recognition site for BsmF I. A mixture of labeled ddNTPs and unlabeled dNTPs was used to fill in the 5' overhang generated by digestion with BsmF I. Two different 5' overhangs are depicted: one represents the DNA molecules that were cut 11 nucleotides away on the sense strand and 15 nucleotides away on the antisense strand and the other represents the DNA molecules that were cut 10 nucleotides away on the sense strand and 14 nucleotides away on the antisense strand. The nucleotide upstream of the SNP, the nucleotide at the SNP site (the sample contained DNA templates from 36 individuals; both nucleotides would be expected to be represented in the sample), and the three nucleotides downstream of the SNP are indicated.

Figure 10:
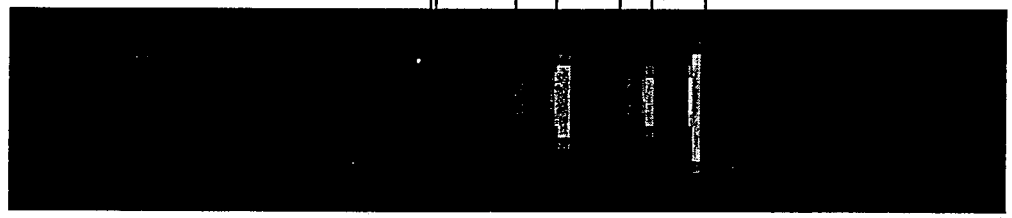

FIG. 10. Sequence analysis of multiple SNPs. SNPs HC21S00131, and HC21S00027, which are located on chromosome 21, and SNPs TSC0087315, SNP TSC0214366, SNP TSC0413944, and SNP TSC0095512, which are on chromosome 1, were amplified in separate PCR reactions with second primers that contained a recognition site for BsmF I. The primers were designed so that each amplified locus of interest was of a different size. After amplification, the reactions were pooled into a single sample, and all subsequent steps of the method performed (as described for FIGS. 1F–1I) on that sample. Each SNP and the nucleotide found at each SNP are indicated.

Figure 11:
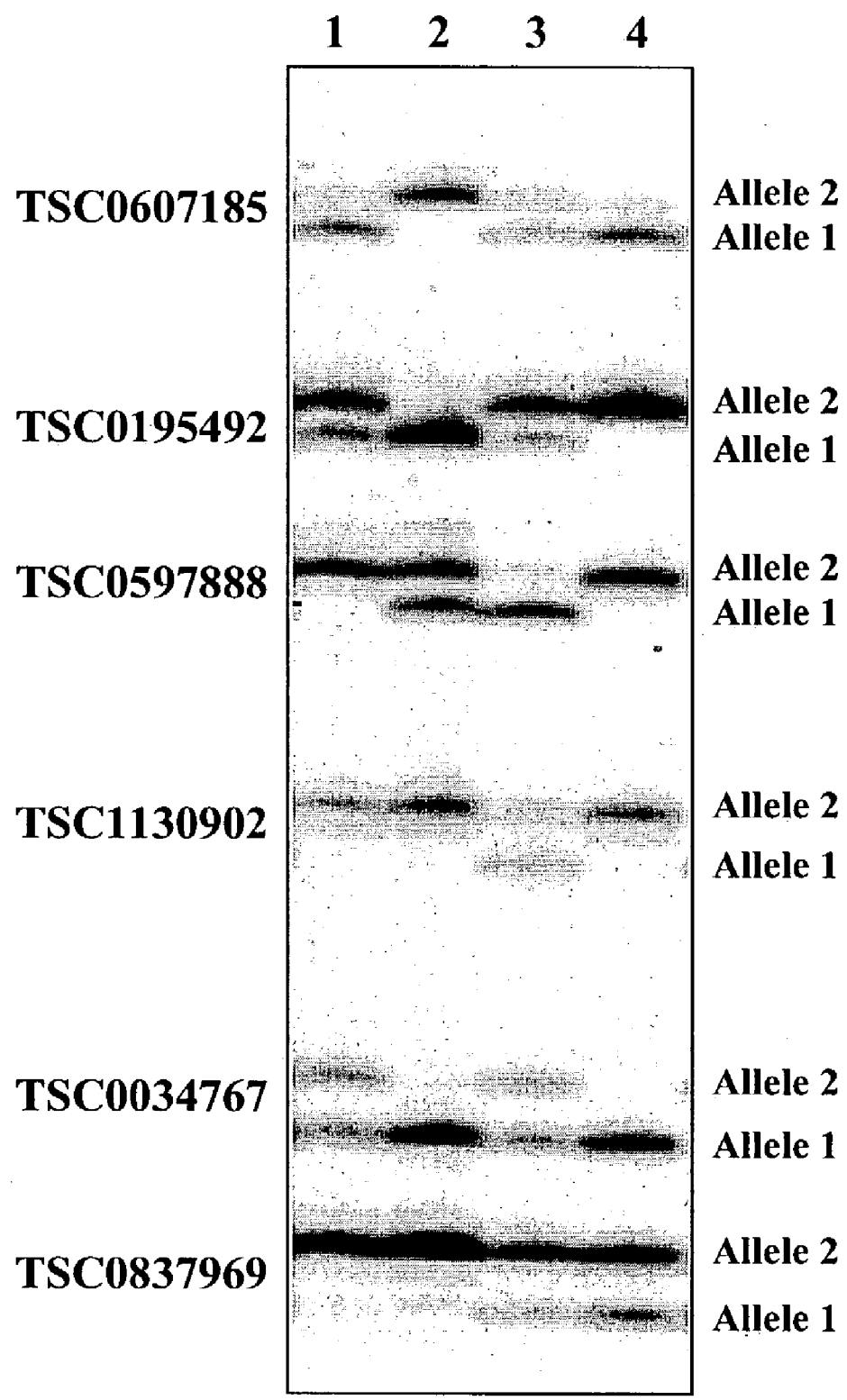

FIG. 11. Sequence determination of both alleles of SNPs TSC0837969, TSC0034767, TSC1130902, TSC0597888, TSC0195492, TSC0607185 using one fluorescently labeled nucleotide. Labeled ddGTP was used in the presence of unlabeled dATP, dCTP, dTTP to fill-in the overhang generated by digestion with BsmF I. The nucleotide preceding the variable site on the strand that was filled-in was not guanine, and the nucleotide after the variable site on the strand that was filled in was not guanine. The nucleotide two bases after the variable site on the strand that was filled-in was guanine. Alleles that contain guanine at variable site are filled in with labeled ddGTP. Alleles that do not contain guanine are filled in with unlabeled dATP, dCTP, or dTTP, and the polymerase continues to incorporate nucleotides until labeled ddGTP is filled in at position 3 complementary to the overhang.

DETAILED DESCRIPTION OF THE INVENTION

The present invention provides a novel method for rapidly determining the sequence of DNA, especially at a locus of interest or multiple loci of interest. The sequences of any number of DNA targets, from one to hundreds or thousands or more of loci of interest in any template DNA or sample of nucleic acid can be determined efficiently, accurately, and economically. The method is especially useful for the rapid sequencing of one to tens of thousands or more of genes, regions of genes, fragments of genes, single nucleotide polymorphisms, and mutations on a single chromosome or on multiple chromosomes.

The invention is directed to a method for determining a sequence of a locus of interest, the method comprising: (a) amplifying a locus of interest on a template DNA using a first and second primers, wherein the second primer contains a recognition site for a restriction enzyme such that digestion with the restriction enzyme generates a 5' overhang containing the locus of interest; (b) digesting the amplified DNA with the restriction enzyme that recognizes the recognition site on the second primer; (c) incorporating a nucleotide into the digested DNA of (b) by using the 5' overhang containing the locus of interest as a template; and (d) determining the sequence of the locus of interest by determining the sequence of the DNA of (c).

The invention is also directed to a method for determining a sequence of a locus of interest, said method comprising: (a) amplifying a locus of interest on a template DNA using a first and second primers, wherein the first and/or second primer contains a portion of a recognition site for a restriction enzyme, wherein a full recognition site for the restriction enzyme is generated upon amplification of the template DNA such that digestion with the restriction enzyme generates a 5' overhang containing the locus of interest; (b) digesting the amplified DNA with the restriction enzyme that recognizes the full recognition site generated by the second primer and the template DNA; (c) incorporating a nucleotide into the digested DNA of (b) by using the 5' overhang containing the locus of interest as a template; and determining the sequence of the locus of interest by determining the sequence of the DNA of (c).

DNA Template

By a "locus of interest" is intended a selected region of nucleic acid that is within a larger region of nucleic acid. A locus of interest can include but is not limited to 1–100, 1–50, 1–20, or 1–10 nucleotides, preferably 1–6, 1–5, 1–4, 1–3, 1–2, or 1 nucleotide(s).

As used herein, an "allele" is one of several alternate forms of a gene or non-coding regions of DNA that occupy the same position on a chromosome. The term allele can be used to describe DNA from any organism including but not limited to bacteria, viruses, fungi, protozoa, molds, yeasts, plants, humans, non-humans, animals, and archaebacteria.

As used herein with respect to individuals, "mutant alleles" refers to variant alleles that are associated with a disease state.

For example, bacteria typically have one large strand of DNA. The term allele with respect to bacterial DNA refers to the form of a gene found in one cell as compared to the form of the same gene in a different bacterial cell of the same species.

Alleles can have the identical sequence or can vary by a single nucleotide or more than one nucleotide. With regard to organisms that have two copies of each chromosome, if both chromosomes have the same allele, the condition is referred to as homozygous. If the alleles at the two chromosomes are different, the condition is referred to as heterozygous. For example, if the locus of interest is SNP X on chromosome 1, and the maternal chromosome contains an adenine at SNP X (A allele) and the paternal chromosome contains a guanine at SNP X (G allele), the individual is heterozygous at SNP X.

As used herein, "sequence" means the identity of, or to determine the identity of (depending on whether used as a noun or a verb, respectively), one nucleotide or more than one contiguous nucleotides in a polynucleotide. In the case of a single nucleotide, e.g., a SNP, "sequence" is used as a noun interchangeably with "identity" herein, and "sequence" is used interchangeably as a verb with "identify" herein.

The term "template" refers to any nucleic acid molecule that can be used for amplification in the invention. RNA or DNA that is not naturally double stranded can be made into double stranded DNA so as to be used as template DNA. Any double stranded DNA or preparation containing multiple, different double stranded DNA molecules can be used as template DNA to amplify a locus or loci of interest contained in the template DNA.

The source of the nucleic acid for obtaining the template DNA can be from any appropriate source including but not limited to nucleic acid from any organism, e.g., human or nonhuman, e.g., bacterium, virus, yeast, fungus, plant, protozoan, animal, nucleic acid-containing samples of tissues, bodily fluids (for example, blood, serum, plasma, saliva, urine, tears, semen, vaginal secretions, lymph fluid, cerebrospinal fluid or mucosa secretions), fecal matter, individual cells or extracts of the such sources that contain the nucleic acid of the same, and subcellular structures such as mitochondria or chloroplasts, using protocols well established within the art. Nucleic acid can also be obtained from forensic, food, archeological, or inorganic samples onto which nucleic acid has been deposited or extracted. In a preferred embodiment, the nucleic acid has been obtained from a human or animal to be screened for the presence of one or more genetic sequences that can be diagnostic for, or predispose the subject to, a medical condition or disease.

The nucleic acid that is to be analyzed can be any nucleic acid, e.g., genomic, plasmid, cosmid, yeast artificial chromosomes, artificial or man-made DNA, including unique DNA sequences, and also DNA that has been reverse transcribed from an RNA sample, such as cDNA. The sequence of RNA can be determined according to the invention if it is capable of being made into a double stranded DNA form to be used as template DNA.

The terms "primer" and "oligonucleotide primer" are interchangeable when used to discuss an oligonucleotide that anneals to a template and can be used to prime the synthesis of a copy of that template.

"Amplified" DNA is DNA that has been "copied" once or multiple times, e.g. by polymerase chain reaction. When a large amount of DNA is available to assay, such that a sufficient number of copies of the locus of interest are already present in the sample to be assayed, it may not be necessary to "amplify" the DNA of the locus of interest into an even larger number of replicate copies. Rather, simply "copying" the template DNA once using a set of appropriate primers, such as those containing hairpin structures that allow the restriction enzyme recognition sites to be double stranded, can suffice.

"Copy" as in "copied DNA" refers to DNA that has been copied once, or DNA that has been amplified into more than one copy.

In one embodiment, the nucleic acid is amplified directly in the original sample containing the source of nucleic acid. It is not essential that the nucleic acid be extracted, purified or isolated; it only needs to be provided in a form that is capable of being amplified. A hybridization step of the nucleic acid with the primers, prior to amplification, is not required. For example, amplification can be performed in a cell or sample lysate using standard protocols well known in the art. DNA that is on a solid support, in a fixed biological preparation, or otherwise in a composition that contains non-DNA substances and that can be amplified without first being extracted from the solid support or fixed preparation or non-DNA substances in the composition can be used directly, without further purification, as long as the DNA can anneal with appropriate primers, and be copied, especially amplified, and the copied or amplified products can be recovered and utilized as described herein.

In a preferred embodiment, the nucleic acid is extracted, purified or isolated from non-nucleic acid materials that are in the original sample using methods known in the art prior to amplification.

In another embodiment, the nucleic acid is extracted, purified or isolated from the original sample containing the source of nucleic acid and prior to amplification, the nucleic acid is fragmented using any number of methods well known in the art including but not limited to enzymatic digestion, manual shearing, and sonication. For example, the DNA can be digested with one or more restriction enzymes that have a recognition site, and especially an eight base or six base pair recognition site, which is not present in the loci of interest. Typically, DNA can be fragmented to any desired length, including 50, 100, 250, 500, 1,000, 5,000, 10,000, 50,000 and 100,000 base pairs long. In another embodiment, the DNA is fragmented to an average length of about 1000 to 2000 base pairs. However, it is not necessary that the DNA be fragmented.

Fragments of DNA that contain the loci of interest can be purified from the fragments of DNA that do not contain the loci of interest before amplification. The purification can be done by using primers that will be used in the amplification (see "Primer Design" section below) as hooks to retrieve the fragments containing the loci of interest, based on the ability of such primers to anneal to the loci of interest. In a preferred embodiment, tag-modified primers are used, such as e.g. biotinylated primers. See also the "Purification of Amplified DNA" section for additional tags.

By purifying the DNA fragments containing the loci of interest, the specificity of the amplification reaction can be improved. This will minimize amplification of nonspecific regions of the template DNA. Purification of the DNA fragments can also allow multiplex PCR (Polymerase Chain Reaction) or amplification of multiple loci of interest with improved specificity.

In one embodiment, the nucleic acid sample is obtained with a desired purpose in mind such as to determine the sequence at a predetermined locus or loci of interest using the method of the invention. For example, the nucleic acid is obtained for the purpose of identifying one or more conditions or diseases to which the subject can be predisposed or is in need of treatment for, or the presence of certain single nucleotide polymorphisms. In an alternative embodiment, the sample is obtained to screen for the presence or absence of one or more DNA sequence markers, the presence of which would identify that DNA as being from a specific bacterial or fungal microorganism, or individual.

The loci of interest that are to be sequenced can be selected based upon sequence alone. In humans, over 1.42 million single nucleotide polymorphisms (SNPs) have been described (Nature 409:928–933 (2001); The SNP Consortium LTD). On the average, there is one SNP every 1.9 kb of human genome. However, the distance between loci of interest need not be considered when selecting the loci of interest to be sequenced according to the invention. If more than one locus of interest on genomic DNA is being analyzed, the selected loci of interest can be on the same chromosome or on different chromosomes.

In a preferred embodiment, the length of sequence that is amplified is preferably different for each locus of interest so that the loci of interest can be separated by size.

In fact, it is an advantage of the invention that primers that copy an entire gene sequence need not be utilized. Rather, the copied locus of interest is preferably only a small part of the total gene. There is no advantage to sequencing the entire gene as this can increase cost and delay results. Sequencing only the desired bases or loci of interest within the gene maximizes the overall efficiency of the method because it allows for the maximum number of loci of interest to be determined in the fastest amount of time and with minimal cost.

Because a large number of sequences can be analyzed together, the method of the invention is especially amenable to the large-scale screening of a number of individual samples.

Any number of loci of interest can be analyzed and processed, especially concurrently, using the method of the invention. The sample(s) can be analyzed to determine the sequence at one locus of interest or at multiple loci of interest concurrently. For example, the 10 or 20 most frequently occurring mutation sites in a disease associated gene can be sequenced to detect the majority of the disease carriers.

Alternatively, 2, 3, 4, 5, 6, 7, 8, 9, 10–20, 20–25, 25–30, 30–35, 35–40, 40–45, 45–50, 50–100, 100–250, 250–500, 500–1,000, 1,000–2,000, 2,000–3,000, 3,000–5,000, 5,000–10,000, 10,000–50,000 or more than 50,000 loci of interest can be analyzed at the same time when a global genetic screening is desired. Such a global genetic screening might be desired when using the method of the invention to provide a genetic fingerprint to identify a certain microorganism or individual or for SNP genotyping.

The multiple loci of interest can be targets from different organisms. For example, a plant, animal or human subject in need of treatment can have symptoms of infection by one or more pathogens. A nucleic acid sample taken from such a plant, animal or human subject can be analyzed for the presence of multiple suspected or possible pathogens at the same time by determining the sequence of loci of interest which, if present, would be diagnostic for that pathogen. Not only would the finding of such a diagnostic sequence in the subject rapidly pinpoint the cause of the condition, but also it would rule out other pathogens that were not detected. Such screening can be used to assess the degree to which a pathogen has spread throughout an organism or environment. In a similar manner, nucleic acid from an individual suspected of having a disease that is the result of a genetic abnormality can be analyzed for some or all of the known mutations that result in the disease, or one or more of the more common mutations.

The method of the invention can be used to monitor the integrity of the genetic nature of an organism. For example, samples of yeast can be taken at various times and from various batches in the brewing process, and their presence or identity compared to that of a desired strain by the rapid analysis of their genomic sequences as provided herein.

The locus of interest that is to be copied can be within a coding sequence or outside of a coding sequence. Preferably, one or more loci of interest that are to be copied are within a gene. In a preferred embodiment, the template DNA that is copied is a locus or loci of interest that is within a genomic coding sequence, either intron or exon. In a highly preferred embodiment, exon DNA sequences are copied. The loci of interest can be sites where mutations are known to cause disease or predispose to a disease state. The loci of interest can be sites of single nucleotide polymorphisms. Alternatively, of the loci of interest that are to be copied can be outside of the coding sequence, for example, in a transcriptional regulatory region, and especially a promoter, enhancer, or repressor sequence.

Primer Design

Published sequences, including consensus sequences, can be used to design or select primers for use in amplification of template DNA. The selection of sequences to be used for the construction of primers that flank a locus of interest can be made by examination of the sequence of the loci of interest, or immediately thereto. The recently published sequence of the human genome provides a source of useful consensus sequence information from which to design primers to flank a desired human gene locus of interest.

By "flanking" a locus of interest is meant that the sequences of the primers are such that at least a portion of the 3' region of one primer is complementary to the antisense strand of the template DNA and upstream of the locus of interest (forward primer), and at least a portion of the 3' region of the other primer is complementary to the sense strand of the template DNA and downstream of the locus of interest (reverse primer). A "primer pair" is intended to specify a pair of forward and reverse primers. Both primers of a primer pair anneal in a manner that allows extension of the primers, such that the extension results in amplifying the template DNA in the region of the locus of interest.

Primers can be prepared by a variety of methods including but not limited to cloning of appropriate sequences and direct chemical synthesis using methods well known in the art (Narang et al., Methods Enzymol. 68:90 (1979); Brown et al., Methods Enzymol. 68:109 (1979)). Primers can also be obtained from commercial sources such as Operon Technologies, Amersham Pharmacia Biotech, Sigma, and Life Technologies. The primers of a primer pair can have the same length. Alternatively, one of the primers of the primer pair can be longer than the other primer of the primer pair. The primers can have an identical melting temperature. The lengths of the primers can be extended or shortened at the 5' end or the 3' end to produce primers with desired melting temperatures. In a preferred embodiment, the 3' annealing lengths of the primers, within a primer pair, differ. Also, the annealing position of each primer pair can be designed such that the sequence and length of the primer pairs yield the desired melting temperature. The simplest equation for determining the melting temperature of primers smaller than 25 base pairs is the Wallace Rule (Td=2(A+T)+4(G+C)). Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer is calculated using software programs such as Net Primer (free web based program at http://premierbiosoft.com/netprimer/netprlaunch/netprlaunch.html (internet address as of Feb. 13, 2002).

In another embodiment, the annealing temperature of the primers can be recalculated and increased after any cycle of amplification, including but not limited to cycle 1, 2, 3, 4, 5, cycles 6–10, cycles 10–15, cycles 15–20, cycles 20–25, cycles 25–30, cycles 30–35, or cycles 35–40. After the initial cycles of amplification, the 5' half of the primers is incorporated into the products from each loci of interest, thus the TM can be recalculated based on both the sequences of the 5' half and the 3' half of each primer.

For example, in FIG. 11B, the first cycle of amplification is performed at about the melting temperature of the 3' region of the second primer (region "c") that anneals to the template DNA, which is 13 bases. After the first cycle, the annealing temperature can be raised to TM2, which is about the melting temperature of the 3' region of the first primer (region "b'") that anneals to the template DNA. The second primer cannot bind to the original template DNA because it only anneals to 13 bases in the original DNA template, and TM2 is about the melting temperature of approximately 20 bases, which is the 3' annealing region of the first primer (FIG. 1C). However, the first primer can bind to the DNA that was copied in the first cycle of the reaction. In the third cycle, the annealing temperature is raised to TM3, which is about the melting temperature of the entire sequence of the second primer ("c" and "d"). The template DNA produced from the second cycle of PCR contains both regions c' and d', and therefore, the second primer can anneal and extend at TM3 (FIG. 1D). The remaining cycles are performed at TM3. The entire sequence of the first primer (a+b') can anneal to the template from the third cycle of PCR, and extend (FIG. 1E). Increasing the annealing temperature will decrease non-specific binding and increase the specificity of the reaction, which is especially useful if amplifying a locus of interest from human genomic DNA, which contains $3 \times 10^9$ base pairs.

As used herein, the term "about" with regard to annealing temperatures is used to encompass temperatures within 10 degrees Celsius of the stated temperatures.

In one embodiment, one primer pair is used for each locus of interest. However, multiple primer pairs can be used for each locus of interest.

In one embodiment, primers are designed such that one or both primers of the primer pair contain sequence in the 5' region for one or more restriction endonucleases (restriction enzyme).

As used herein, with regard to the position at which restriction enzymes digest DNA, the "sense" strand is the strand reading 5' to 3' in the direction in which the restriction enzyme cuts. For example, BsmF I recognizes the following sequence:

```
5'GGGAC(N)₁₀↓3'           (SEQ ID NO:1)
or

3'CCCTG(N)₁₄↑5'

5'↓(N)₁₄GTCCC3'           (SEQ ID NO:2)

3'↑(N)₁₀CAGGG5'
```

Thus, the sense strand is the strand containing the "GGGAC" sequence as it reads 5' to 3' in the direction that the restriction enzyme cuts.

As used herein, with regard to the position at which restriction enzymes digest DNA, the "antisense" strand is the strand reading 3' to 5' in the direction in which the restriction enzyme cuts. Thus, the antisense strand is the strand that contains the "ccctg" sequence as it reads 3' to 5'.

In the invention, one of the primers in a primer pair can be designed such that it contains a restriction enzyme recognition site for a restriction enzyme such that digestion with the restriction enzyme produces a recessed 3' end and a 5' overhang that contains the locus of interest (herein referred to as a "second primer"). For example, the second primer of a primer pair can contain a recognition site for a restriction enzyme that does not cut DNA at the recognition site but cuts "n" nucleotides away from the recognition site. "N" is a distance from the recognition site to the site of the cut by the restriction enzyme. If the recognition sequence is for the restriction enzyme BceA I, the enzyme will cut ten (10) nucleotides from the recognition site on the sense strand, and twelve (12) nucleotides away from the recognition site on the antisense strand.

The 3' region and preferably the 3' half of the primers is designed to anneal to a sequence that flanks the loci of interest (FIG. 1A). The second primer may anneal any distance from the locus of interest provided that digestion with the restriction enzyme that recognizes the restriction enzyme recognition site on this primer generates a 5' overhang that contains the locus of interest. The 5' overhang can be of any size, including but not limited to 1, 2, 3, 4, 5, 6, 7, 8, and more than 8 bases.

In a preferred embodiment, the 3' end of the second primer can anneal 1, 2, 3, 4, 5, 6, 7, 8, 9, 10, 11, 12, 13, 14, or more than 14 bases from the locus of interest or at the locus of interest.

In a preferred embodiment, the second primer is designed to anneal closer to the locus of interest than the other primer of a primer pair (the other primer is herein referred to as a "first primer"). The second primer can be a forward or reverse primer and the first primer can be a reverse or forward primer, respectively. Whether the first or second primer should be the forward or reverse primer can be determined by which design will provide better sequencing results.

For example, the primer that anneals closer to the locus of interest can contain a recognition site for the restriction enzyme BsmF I, which cuts ten (10) nucleotides from the recognition site on the sense strand, and fourteen (14) nucleotides from the recognition site on the antisense strand. In this case, the primer can be designed so that the restriction enzyme recognition site is 13 bases, 12 bases, 10 bases or 11 bases from the locus of interest. If the recognition site is 13 bases from the locus of interest, digestion with BsmF I will generate a 5' overhang (RXXX), wherein the locus of interest (R) is the first nucleotide in the overhang (reading 3' to 5'), and X is any nucleotide. If the recognition site is 12 bases from the locus of interest, digestion with BsmF I will generate a 5' overhang (XRXX), wherein the locus of interest (R) is the second nucleotide in the overhang (reading 3' to 5'). If the recognition site is 11 bases from the locus of interest, digestion with BsmF I will generate a 5' overhang (XXRX), wherein the locus of interest (R) is the third nucleotide in the overhang (reading 3' to 5'). The distance between the restriction enzyme recognition site and the locus of interest should be designed so that digestion with the restriction enzyme generates a 5' overhang, which contains the locus of interest. The effective distance between the recognition site and the locus of interest will vary depending on the choice of restriction enzyme.

In another embodiment, the second primer, which can anneal closer to the locus of interest relative to the first primer, can be designed so that the restriction enzyme that generates the 5' overhang, which contains the locus of interest, will see the same sequence at the cut site, independent of the nucleotide at the locus of interest. For example, if the primer that anneals closer to the locus of interest is designed so that the recognition site for the restriction enzyme BsmF I (5' GGGAC 3') is thirteen bases from the locus of interest, the restriction enzyme will cut the antisense strand one base upstream of the locus of interest. The nucleotide at the locus of interest is adjacent to the cut site, and may vary from DNA molecule to DNA molecule. If it is desired that the nucleotides adjacent to the cut site be identical, the primer can be designed so that the restriction enzyme recognition site for BsmF I is twelve bases away from the locus of interest. Digestion with BsmF I will generate a 5' overhang, wherein the locus of interest is in the second position of the overhang (reading 3' to 5') and is no longer adjacent to the cut site. Designing the primer so that the restriction enzyme recognition site is twelve (12) bases from the locus of interest allows the nucleotides adjacent to the cut site to be the same, independent of the nucleotide at the locus of interest. Also, primers that have been designed so that the restriction enzyme recognition site is eleven (11) or ten (10) bases from the locus of interest will allow the nucleotides adjacent to the cut site to be the same, independent of the nucleotide at the locus of interest.

The 3' end of the first primer (either the forward or the reverse) can be designed to anneal at a chosen distance from the locus of interest. Preferably, for example, this distance is between 10–25, 25–50, 50–75, 75–100, 100–150, 150–200, 200–250, 250–300, 300–350, 350–400, 400–450, 450–500, 500–550, 550–600, 600–650, 650–700, 700–750, 750–800, 800–850, 850–900, 900–950, 950–1000 and greater than 1000 bases away from the locus of interest. The annealing sites of the first primers are chosen such that each successive upstream primer is further and further away from its respective downstream primer.

For example, if at locus of interest 1 the 3' ends of the first and second primers are Z bases apart, then at locus of interest 2, the 3' ends of the upstream and downstream primers are Z+K bases apart, where K=1, 2, 3, 4, 5–10, 10–20, 20–30, 30–40, 40–50, 50–60, 60–70, 70–80, 80–90, 90–100, 100–200, 200–300, 300–400, 400–500, 500–600, 600–700, 700–800, 800–900, 900–1000, or greater than 1000 bases (FIG. 2). The purpose of making the upstream primers further and further apart from their respective downstream primers is so that the PCR products of all the loci of interest differ in size and can be separated, e.g., on a sequencing gel. This allows for multiplexing by pooling the PCR products in later steps.

In one embodiment, the 5' region of the first primer can have a recognition site for any type of restriction enzyme. In a preferred embodiment, the first primer has at least one restriction enzyme recognition site that is different from the restriction enzyme recognition site in the second primer. In another preferred embodiment, the first primer anneals further away from the locus of interest than the second primer.

In a preferred embodiment, the second primer contains a restriction enzyme recognition sequence for a Type IIS restriction enzyme including but not limited to BceA I and BsmF I, which produce a two base 5' overhang and a four base 5' overhang, respectively. Restriction enzymes that are Type IIS are preferred because they recognize asymmetric base sequences (not palindromic like the orthodox Type II enzymes). Type IIS restriction enzymes cleave DNA at a specified position that is outside of the recognition site, typically up to 20 base pairs outside of the recognition site. These properties make Type IIS restriction enzymes, and the recognition sites thereof, especially useful in the method of the invention. Preferably, the Type IIS restriction enzymes used in this method leave a 5' overhang and a recessed 3' end.

A wide variety of Type IIS restriction enzymes are known and such enzymes have been isolated from bacteria, phage, archaebacteria and viruses of eukaryotic algae and are commercially available (Promega, Madison Wis.; New England Biolabs, Beverly, Mass.; Szybalski W. et al., *Gene* 100:13–16, (1991)). Examples of Type IIS restriction enzymes that would be useful in the method of the invention include, but are not limited to enzymes such as those listed in Table I.

TABLE I

| Enzyme-Source | Recognition/ Cleavage Site | Supplier |
| --- | --- | --- |
| Alw I - *Acinetobacter lwoffii* | GGATC(4/5) | NE Biolabs |
| Alw26 I - *Acinetobacter lwoffi* | GTCTC(1/5) | Promega |
| Bbs I - *Bacillus laterosporus* | GAAGAC(2/6) | NE Biolabs |
| Bbv I - *Bacillus brevis* | GCAGC(8/12) | NE Biolabs |
| BceA I - *Bacillus cereus* 1315 | ACGGC(12/14) | NE Biolabs |
| Bmr I - *Bacillus megaterium* | ACTGGG(5/4) | NE Biolabs |
| Bsa I - *Bacillus stearothermophilus* 6-55 | GGTCTC(1/5) | NE Biolabs |
| Bst71 I - *Bacillus stearothermophilus* 71 | GCAGC(8/12) | Promega |
| BsmA I - *Bacillus stearothermophilus* A664 | GTCTC(1/5) | NE Biolabs |
| BsmB I - *Bacillus stearothermophilus* B61 | CGTCTC(1/5) | NE Biolabs |
| BsmF I - *Bacillus stearothermophilus* F | GGGAC(10/14) | NE Biolabs |
| BspM I - *Bacillus species* M | ACCTGC(4/8) | NE Biolabs |
| Ear I - *Enterobacter aerogenes* | CTCTTC(1/4) | NE Biolabs |
| Fau I - *Flavobacterium aquatile* | CCCGC(4/6) | NE Biolabs |
| Fok I - *Flavobacterium okeonokoites* | GGATG(9/13) | NE Biolabs |

TABLE I-continued

TYPE IIS RESTRICTION ENZYMES THAT GENERATE A 5' OVERHANG AND A RECESSED 3' END.

| Enzyme-Source | Recognition/ Cleavage Site | Supplier |
|---|---|---|
| Hga I - *Haemophilus gallinarum* | GACGC(5/10) | NE Biolabs |
| Ple I - *Pseudomonas lemoignei* | GAGTC(4/5) | NE Biolabs |
| Sap I - *Saccharopolyspora species* | GCTCTTC(1/4) | NE Biolabs |
| SfaN I - *Streptococcus faecalis* ND547 | GCATC(5/9) | NE Biolabs |
| Sth132 I - *Streptococcus thermophilus* ST132 | CCCG(4/8) | No commercial supplier (Gene 195:201–206 (1997)) |

In one embodiment, a primer pair has sequence at the 5' region of each of the primers that provides a restriction enzyme recognition site that is unique for one restriction enzyme.

In another embodiment, a primer pair has sequence at the 5' region of each of the primers that provide a restriction site that is recognized by more than one restriction enzyme, and especially for more than one Type IIS restriction enzyme. For example, certain consensus sequences can be recognized by more than one enzyme. For example, BsgI, Eco571 and BpmI all recognize the consensus 5' (G/C)TgnAG 3' and cleave 16 bp away on the antisense strand and 14 bp away on the sense strand. A primer that provides such a consensus sequence would result in a product that has a site that can be recognized by any of the restriction enzymes BsgI, Eco57I and BpmI.

Other restriction enzymes that cut DNA at a distance from the recognition site, and produce a recessed 3' end and a 5' overhang include Type III restriction enzymes. For example, the restriction enzyme EcoP15I recognizes the sequence 5'CAGCAG 3' and cleaves 25 bases downstream on the sense strand and 27 bases on the antisense strand. It will be further appreciated by a person of ordinary skill in the art that new restriction enzymes are continually being discovered and may readily be adopted for use in the subject invention.

In another embodiment, the second primer can contain a portion of the recognition sequence for a restriction enzyme, Second primer: 5'GGAAATTCCATGATGCGTGGG→ (SEQ ID NO:3)

Template DNA: 3'CCTTTAAGGTACTACGCAN$_1$·N$_2$·N$_3$·TG5'
5'GGAAATTCCATGATGCGTN$_1$N$_2$N$_3$AC3' (SEQ ID NO:4)

The second primer can be designed to anneal to the template DNA, wherein the next two bases of the template DNA are thymidine and guanine, such that an adenosine and cytosine are incorporated into the primer forming a recognition site for BsmF I, 5' GGGACN$_{10}$↓3' (SEQ ID NO: 1). The second primer can be designed to anneal in such a manner that digestion with BsmF I generates a 5' overhang containing the locus of interest.

In another embodiment, the second primer can contain an entire or full recognition site for a restriction enzyme or a portion of a recognition site, which generates a full recognition site upon amplification of the template DNA such that digestion with a restriction enzyme that cuts at the recognition site generates a 5' overhang that contains the locus of interest. For example, the restriction enzyme BsaJ I binds the following recognition site: 5' C↓CN$_1$N$_2$GG 3'. The second primer can be designed such that the 3' region of the primer ends with "CC." The SNP of interest is represented by "N$_1$,", and the template sequence downstream of the SNP is "N$_2$CC."

wherein the full recognition site for the restriction enzyme is generated upon amplification of the template DNA such that digestion with the restriction enzyme generates a 5' overhang containing the locus of interest. For example, the recognition site for BsmF I is 5' GGGACN$_{10}$↓3' (SEQ ID NO: 1). The 3' region, which anneals to the template DNA, of the second primer can end with the nucleotides "GGG," which do not have to be complementary with the template DNA. If the 3' annealing region is about 10–20 bases, even if the last three bases do not anneal, the primer will extend and, generate a BsmF I site.

Second primer 5' GGAAATTCCATGATGCGTACC→ (SEQ ID NO:5)
Template DNA 3' CCTTTAAGGTACTACTACGCATGGN$_1$,N$_2$,CC 5' (SEQ ID NO:28)
5' GGAAATTCCATGATGCGTACCN$_1$N$_2$GG 3' (SEQ ID NO:6)

After digestion with BsaJ I, a 5' overhang of the following sequence would be generated:

5' C      3'
3' GGN$_1$•N$_2$•C 5'

If the nucleotide guanine is not reported at the locus of interest, the 3' recessed end can be filled in with unlabeled cytosine, which is complementary to the first nucleotide in the overhang. After removing the excess cytosine, labeled ddNTPs can be used to fill in the next nucleotide, N$_1$, which represents the locus of interest. Alternatively if guanine is reported to be a potential nucleotide at the locus of interest, labeled nucleotides can be used to detect a nucleotide 3' of the locus of interest. Unlabeled dCTP can be used to "fill in" followed by a fill in with a labeled nucleotide other than cytosine. Cytosine will be incorporated until it reaches a base that is not complementary. If the locus of interest contained a guanine, it would be filled in with the dCTP, which would allow incorporation of the labeled nucleotide. However, if the locus of interest did not contain a guanine, the labeled nucleotide would not be incorporated. Other restriction enzymes can be used including but not limited to BssK I (5' ↓CCNGG 3'), Dde I (5' C↓TNAG 3'), EcoN I (5' CCTNN↓NNNAGG 3') (SEQ ID NO:7), Fnu4H I (5' GC↓NGC 3'), Hinf I (5' G↓ANTC 3'), PflF I (5' GACN↓NNGTC 3'), Sau96 I (5' G↓GNCC 3'), ScrF I (5' CC↓NGG 3'), and Tth111 I (5' GACN↓NNGTC 3').

It is not necessary that the 3' region, which anneals to the template DNA, of the second primer be 100% complementary to the template DNA. For example, the last 1, 2, or 3 nucleotides of the 3' end of the second primer can be mismatches with the template DNA. The region of the primer that anneals to the template DNA will target the primer, and allow the primer to extend. Even if, for example, the last two nucleotides are not complementary to the template DNA, the primer will extend and generate a restriction enzyme recognition site.

```
Second   5'GGAAATTCCATGATGCGTACC→           (SEQ
pri-                                         ID
mer:                                         NO:5)

Tem-     3'CCTTTAAGGTACTACGCATN_a·N_b·N_1·N_2·CC5'
plate
DNA:     5'GGAAATTCCATGATGCGTAN_aN_bN_1N_2GG3'  (SEQ
                                               ID
                                               NO:8)
```

After digestion with BsaJ I, a 5' overhang of the following sequence would be generated:

```
         5'C3'

3'GGN_1·N_2·C5'
```

If the nucleotide cytosine is not reported at the locus of interest, the 5' overhang can be filled in with unlabeled cytosine. The excess cytosine can be rinsed away, and filled in with labeled ddNTPs. The first nucleotide incorporated ($N_1$) corresponds to the locus of interest.

Alternatively, it is possible to create the full restriction enzyme recognition sequence using the first and second primers. The recognition site for any restriction enzyme can be generated, as long as the recognition site contains at least one variable nucleotide. Restriction enzymes that recognize sites that contain at least one variable nucleotide include but are not limited to BssK I (5'↓CCNGG 3'), Dde I (5'C↓TNAG 3'), Econ I (5'CCTNN↓NNNAGG 3') (SEQ ID NO:7), Fnu4H I (5'GC↓NGC 3'), Hinf I (5'G↓ANTC 3') PflF I (5' GACN↓NNGTC 3'), Sau96 I (5' G↓GNCC 3'), ScrF I (5' CC↓NGG 3'), and Tth111 I (5' GACN↓NNGTC 3'). In this embodiment, the first or second primer may anneal closer to the locus of interest or the first or second primer may anneal at an equal distance from the locus of interest. The first and second primers can be designed to contain mismatches in the template DNA at the 3' region; these mismatches create the restriction enzyme recognition site. The number of mismatches that can be tolerated at the 3' end depends on the length of the primer, and includes but is not limited to 1, 2, or more than 2 mismatches. For example, if the locus of interest is represented by $N_1$, a first primer can be designed to be complementary to the template DNA, depicted below as region "a." The 3' region of the first primer ends with "CC," which is not complementary to the template DNA. The second primer is designed to be complementary to the template DNA, which is depicted below as region "b"'. The 3' region of the second primer ends with "CC," which is not complementary to the template DNA.

```
First primer   5'_a_CC→

Template DNA   3'___a'___AAN_1·N_2·TT___b'___5'
               5'___a____TTN_1N_2AA____b____3'

←CC___b'___5' Second Primer
```

After one round of amplification the following products would be generated:

```
5'___a____CCN_1N_2AA____b____3'
and

5'___b'___CCN_2·N_1·AA___a'___3'.
```

In cycle two, the primers can anneal to the templates that were generated from the first cycle of PCR:

```
5'___a____CCN_1N_2AA____b____3'

←CC___b'___5'

←CC___a____5'

5'___b'___CCN_2·N_1·AA___a'___3'
```

After cycle two of PCR, the following products would be generated:

```
5'___a____CCN_1N_2GG____b____3'

3'___a'___GGN_1·N_2·CC___b'___5'
```

The restriction enzyme recognition site for BsaJ I is generated, and after digestion with BsaJ I, a 5' overhang containing the locus of interest is generated. The locus of interest can be detected as described in detail below. Alternatively, the 3' region of the first and second primers can contain 1, 2, 3, or more than 3 mismatches followed by a nucleotide that is complementary to the template DNA. For example, the first and second primers can be used to create a recognition site for the restriction enzyme EcoN I, which binds the following DNA sequence: 5' CCTNN↓NNNAGG 3' (SEQ ID NO: 7). The last nucleotides of each primer would be "CCTN_1 or CCTN_1N_2." The nucleotides "CCT" may or may not be complementary to the template DNA; however, $N_1$ and $N_2$ are nucleotides complementary to the template DNA. This allows the primers to anneal to the template DNA after the potential mismatches, which are used to create the restriction enzyme recognition site.

In another embodiment, a primer pair has sequence at the 5' region of each of the primers that provides two or more restriction sites that are recognized by two or more restriction enzymes.

In a most preferred embodiment, a primer pair has different restriction enzyme recognition sites at the 5' regions, especially 5' ends, such that a different restriction enzyme is required to cleave away any undesired sequences. For example, the first primer for locus of interest "A" can contain sequence recognized by a restriction enzyme, "X," which can be any type of restriction enzyme, and the second primer for locus of interest "A," which anneals closer to the locus of interest, can contain sequence for a restriction enzyme, "Y," which is a Type IIS restriction enzyme that cuts "n" nucleotides away and leaves a 5' overhang and a recessed 3' end. The 5' overhang contains the locus of interest. After binding the amplified DNA to streptavidin coated wells, one can digest with enzyme "Y," rinse, then fill in with labeled nucleotides and rinse, and then digest with restriction enzyme "X," which will release the DNA fragment containing the locus of interest from the solid matrix. The locus of interest can be analyzed by detecting the labeled nucleotide that was "filled in" at the locus of interest, e.g. SNP site.

In another embodiment, the second primers for the different loci of interest that are being amplified according to the invention contain recognition sequence in the 5' regions for the same restriction enzyme and likewise all the first primers also contain the same restriction enzyme recognition site, which is a different enzyme from the enzyme that recognizes the second primers. The primer (either the forward or reverse primer) that anneals closer to the locus of interest contains a recognition site for, e.g., a Type IIs restriction enzyme.

In another embodiment, the second primers for the multiple loci of interest that are being amplified according to the invention contain restriction enzyme recognition sequences in the 5' regions for different restriction enzymes.

In another embodiment, the first primers for the multiple loci of interest that are being amplified according to the invention contain restriction enzyme recognition sequences in the 5' regions for different restriction enzymes.

Multiple restriction enzyme sequences provide an opportunity to influence the order in which pooled loci of interest are released from the solid support. For example, if 50 loci of interest are amplified, the first primers can have a tag at the extreme 5' end to aid in purification and a restriction enzyme recognition site, and the second primers can contain a recognition site for a type IIS restriction enzyme. For example, several of the first primers can have a restriction enzyme recognition site for EcoR I, other first primers can have a recognition site for Pst I, and still other first primers can have a recognition site for BamH I. After amplification, the loci of interest can be bound to a solid support with the aid of the tag on the first primers. By performing the restriction digests one restriction enzyme at a time, one can serially release the amplified loci of interest. If the first digest is performed with EcoRI, the loci of interest amplified with the first primers containing the recognition site for EcoR I will be released, and collected while the other loci of interest remain bound to the solid support. The amplified loci of interest can be selectively released from the solid support by digesting with one restriction enzyme at a time. The use of different restriction enzyme recognition sites in the first primers allows a larger number of loci of interest to be amplified in a single reaction tube.

In a preferred embodiment, any region 5' of the restriction enzyme digestion site of each primer can be modified with a functional group that provides for fragment manipulation, processing, identification, and/or purification. Examples of such functional groups, or tags, include but are not limited to biotin, derivatives of biotin, carbohydrates, haptens, dyes, radioactive molecules, antibodies, and fragments of antibodies, peptides, and immunogenic molecules.

In another embodiment, the template DNA can be replicated once, without being amplified beyond a single round of replication. This is useful when there is a large amount of the DNA available for analysis such that a large number of copies of the loci of interest are already present in the sample, and further copies are not needed. In this embodiment, the primers are preferably designed to contain a "hairpin" structure in the 5' region, such that the sequence doubles back and anneals to a sequence internal to itself in a complementary manner. When the template DNA is replicated only once, the DNA sequence comprising the recognition site would be single-stranded if not for the "hairpin" structure. However, in the presence of the hairpin structure, that region is effectively double stranded, thus providing a double stranded substrate for activity by restriction enzymes.

To the extent that the reaction conditions are compatible, all the primer pairs to analyze a locus or loci of interest of DNA can be mixed together for use in the method of the invention. In a preferred embodiment, all primer pairs are mixed with the template DNA in a single reaction vessel. Such a reaction vessel can be, for example, a reaction tube, or a well of a microtiter plate.

Alternatively, to avoid competition for nucleotides and to minimize primer dimers and difficulties with annealing temperatures for primers, each locus of interest or small groups of loci of interest can be amplified in separate reaction tubes or wells, and the products later pooled if desired. For example, the separate reactions can be pooled into a single reaction vessel before digestion with the restriction enzyme that generates a 5' overhang, which contains the locus of interest or SNP site, and a 3' recessed end. Preferably, the primers of each primer pair are provided in equimolar amounts. Also, especially preferably, each of the different primer pairs is provided in equimolar amounts relative to the other pairs that are being used.

In another embodiment, combinations of primer pairs that allow efficient amplification of their respective loci of interest can be used (see e.g. FIG. 2). Such combinations can be determined prior to use in the method of the invention. Multi-well plates and PCR machines can be used to select primer pairs that work efficiently with one another. For example, gradient PCR machines, such as the Eppendorf Mastercycler® gradient PCR machine, can be used to select the optimal annealing temperature for each primer pair. Primer pairs that have similar properties can be used together in a single reaction tube.

In another embodiment, a multi-sample container including but not limited to a 96-well or more plate can be used to amplify a single locus of interest with the same primer pairs from multiple template DNA samples with optimal PCR conditions for that locus of interest. Alternatively, a separate multi-sample container can be used for amplification of each locus of interest and the products for each template DNA sample later pooled. For example, gene A from 96 different DNA samples can be amplified in microtiter plate 1, gene B from 96 different DNA samples can be amplified in microtiter plate 2, etc., and then the amplification products can be pooled.

The result of amplifying multiple loci of interest is a preparation that contains representative PCR products having the sequence of each locus of interest. For example, if DNA from only one individual is used as the template DNA and if hundreds of disease-related loci of interest were amplified from the template DNA, the amplified DNA would be a mixture of small, PCR products from each of the loci of interest. Such a preparation could be further analyzed at that time to determine the sequence at each locus of interest or at only some of loci of interest. Additionally, the preparation could be stored in a manner that preserves the DNA and can be analyzed at a later time. Information contained in the amplified DNA can be revealed by any suitable method including but not limited to fluorescence detection, sequencing, gel electrophoresis, and mass spectrometry (see "Detection of Incorporated Nucleotide" section below).

Amplification of Loci of Interest

The template DNA can be amplified using any suitable method known in the art including but not limited to PCR (polymerase chain reaction), 3SR (self-sustained sequence reaction), LCR (ligase chain reaction), RACE-PCR (rapid amplification of cDNA ends), PLCR (a combination of polymerase chain reaction and ligase chain reaction), Q-beta phage amplification (Shah et al., J. Medical Micro. 33: 1435–41 (1995)), SDA (strand displacement amplification), SOE-PCR (splice overlap extension PCR), and the like. These methods can be used to design variations of the releasable primer mediated cyclic amplification reaction explicitly described in this application. In the most preferred embodiment, the template DNA is amplified using PCR (PCR: A Practical Approach, M. J. McPherson, et al., IRL Press (1991); PCR Protocols: A Guide to Methods and Applications, Innis, et al., Academic Press (1990); and PCR Technology: Principals and Applications of DNA Amplification, H. A. Erlich, Stockton Press (1989)). PCR is also described in numerous U.S. patents, including U.S. Pat. Nos. 4,683,195; 4,683,202; 4,800,159; 4,965,188; 4,889,818; 5,075,216; 5,079,352; 5,104,792, 5,023,171; 5,091,310; and 5,066,584.

The components of a typical PCR reaction include but are not limited to a template DNA, primers, a reaction buffer (dependent on choice of polymerase), dNTPs (dATP, dTTP, dGTP, and dCTP) and a DNA polymerase. Suitable PCR primers can be designed and prepared as discussed above (see "Primer Design" section above). Briefly, the reaction is heated to 95° C. for 2 min. to separate the strands of the template DNA, the reaction is cooled to an appropriate temperature (determined by calculating the annealing temperature of designed primers) to allow primers to anneal to the template DNA, and heated to 72° C. for two minutes to allow extension.

In a preferred embodiment, the annealing temperature is increased in each of the first three cycles of amplification to reduce non-specific amplification. See also Example 1, below. The TM1 of the first cycle of PCR is about the melting temperature of the 3' region of the second primer that anneals to the template DNA. The annealing temperature can be raised in cycles 2–10, preferably in cycle 2, to TM2, which is about the melting temperature of the 3' region, which anneals to the template DNA, of the first primer. If the annealing temperature is raised in cycle 2, the annealing temperature remains about the same until the next increase in annealing temperature. Finally, in any cycle subsequent to the cycle in which the annealing temperature was increased to TM2, preferably cycle 3, the annealing temperature is raised to TM3, which is about the melting temperature of the entire second primer. After the third cycle, the annealing temperature for the remaining cycles may be at about TM3 or may be further increased. In this example, the annealing temperature is increased in cycles 2 and 3. However, the annealing temperature can be increased from a low annealing temperature in cycle 1 to a high annealing temperature in cycle 2 without any further increases in temperature or the annealing temperature can progressively change from a low annealing temperature to a high annealing temperature in any number of incremental steps. For example, the annealing temperature can be changed in cycles 2, 3, 4, 5, 6, etc.

After annealing, the temperature in each cycle is increased to an "extension" temperature to allow the primers to "extend" and then following extension the temperature in each cycle is increased to the denaturization temperature. For PCR products less than 500 base pairs in size, one can eliminate the extension step in each cycle and just have denaturization and annealing steps. A typical PCR reaction consists of 25–45 cycles of denaturation, annealing and extension as described above. However, as previously noted, even only one cycle of amplification (one copy) can be sufficient for practicing the invention.

Any DNA polymerase that catalyzes primer extension can be used including but not limited to E. coli DNA polymerase, Klenow fragment of E. coli DNA polymerase I, T7 DNA polymerase, T4 DNA polymerase, Taq polymerase, Pfu DNA polymerase, Vent DNA polymerase, bacteriophage 29, and REDTaq™ Genomic DNA polymerase, or sequenase. Preferably, a thermostable DNA polymerase is used. A "hot start" PCR can also be performed wherein the reaction is heated to 95° C. for two minutes prior to addition of the polymerase or the polymerase can be kept inactive until the first heating step in cycle 1. "Hot start" PCR can be used to minimize nonspecific amplification. Any number of PCR cycles can be used to amplify the DNA, including but not limited to 2, 5, 10, 15, 20, 25, 30, 35, 40, or 45 cycles. In a most preferred embodiment, the number of PCR cycles performed is such that equimolar amounts of each loci of interest are produced.

Purification of Amplified DNA

Purification of the amplified DNA is not necessary for practicing the invention. However, in one embodiment, if purification is preferred, the 5' end of the primer (first or second primer) can be modified with a tag that facilitates purification of the PCR products. In a preferred embodiment, the first primer is modified with a tag that facilitates purification of the PCR products. The modification is preferably the same for all primers, although different modifications can be used if it is desired to separate the PCR products into different groups.

The tag can be a radioisotope, fluorescent reporter molecule, chemiluminescent reporter molecule, antibody, antibody fragment, hapten, biotin, derivative of biotin, photobiotin, iminobiotin, digoxigenin, avidin, enzyme, acridinium, sugar, enzyme, apoenzyme, homopolymeric oligonucleotide, hormone, ferromagnetic moiety, paramagnetic moiety, diamagnetic moiety, phosphorescent moiety, luminescent moiety, electrochemiluminescent moiety, chromatic moiety, moiety having a detectable electron spin resonance, electrical capacitance, dielectric constant or electrical conductivity, or combinations thereof.

In a preferred embodiment, the 5' ends of the primers can be biotinylated (Kandpal et al., Nucleic Acids Res. 18:1789–1795 (1990); Kaneoka et al., Biotechniques 10:30–34 (1991); Green et al., Nucleic Acids Res. 18:6163–6164 (1990)). The biotin provides an affinity tag that can be used to purify the copied DNA from the genomic DNA or any other DNA molecules that are not of interest. Biotinylated molecules can be purified using a streptavidin coated matrix as shown in FIG. 1F, including but not limited to Streptawell, transparent, High-Bind plates from Roche Molecular Biochemicals (catalog number 1 645 692, as listed in Roche Molecular Biochemicals, 2001 Biochemicals Catalog).

The PCR product of each locus of interest is placed into separate wells of a Streptavidin coated plate. Alternatively, the PCR products of the loci of interest can be pooled and placed into a streptavidin coated matrix, including but not limited to the Streptawell, transparent, High-Bind plates from Roche Molecular Biochemicals (catalog number 1 645 692, as listed in Roche Molecular Biochemicals, 2001 Biochemicals Catalog).

The amplified DNA can also be separated from the template DNA using non-affinity methods known in the art, for example, by polyacrylamide gel electrophoresis using standard protocols.

Digestion of Amplified DNA

The amplified DNA can be digested with a restriction enzyme that recognizes a sequence that had been provided on the first or second primer using standard protocols known within the art (FIGS. 6A–6D). The enzyme used depends on the restriction recognition site generated with the first or second primer. See "Primer Design" section, above, for details on restriction recognition sites generated on primers.

Type IIS restriction enzymes are extremely useful in that they cut approximately 10–20 base pairs outside of the recognition site. Preferably, the Type IIS restriction enzymes used are those that generate a 5' overhang and a recessed 3' end, including but not limited to BceA I and BsmF I (see e.g. Table I). In a most preferred embodiment, the second primer (either forward or reverse), which anneals close to the locus of interest, contains a restriction enzyme recognition sequence for BsmF I or BceA I. The Type IIS restriction enzyme BsmF I recognizes the nucleic acid sequence GGGAC, and cuts 14 nucleotides from the recognition site on the antisense strand and 10 nucleotides from the recognition site on the sense strand. Digestion with BsmF I generates a 5' overhang of four (4) bases.

For example, if the second primer is designed so that after amplification the restriction enzyme recognition site is 13 bases from the locus of interest, then after digestion, the locus of interest is the first base in the 5' overhang (reading 3' to 5'), and the recessed 3' end is one base upstream of the locus of interest. The 3' recessed end can be filled in with a nucleotide that is complementary to the locus of interest. One base of the overhang can be filled in using dideoxynucleotides. However, 1, 2, 3, or all 4 bases of the overhang can be filled in using deoxynucleotides or a mixture of dideoxynucleotides and deoxynucleotides.

The restriction enzyme BsmF I cuts DNA ten (10) nucleotides from the recognition site on the sense strand and fourteen (14) nucleotides from the recognition site on the antisense strand. However, in a sequence dependent manner, the restriction enzyme BsmF I also cuts eleven (11) nucleotides from the recognition site on the sense strand and fifteen (15) nucleotides from the recognition site on the antisense strand. Thus, two populations of DNA molecules exist after digestion: DNA molecules cut at 10/14 and DNA molecules cut at 11/15. If the recognition site for BsmF I is 13 bases from the locus of interest in the amplified product, then DNA molecules cut at the 11/15 position will generate a 5' overhang that contains the locus of interest in the second position of the overhang (reading 3' to 5'). The 3' recessed end of the DNA molecules can be filled in with labeled nucleotides. For example, if labeled dideoxynucleotides are used, the 3' recessed end of the molecules cut at 11/15 would be filled in with one base, which corresponds to the base upstream of the locus of interest, and the 3' recessed end of molecules cut at 10/14 would be filled in with one base, which corresponds to the locus of interest. The DNA molecules that have been cut at the 10/14 position and the DNA molecules that have been cut at the 11/15 position can be separated by size, and the incorporated nucleotides detected. This allows detection of both the nucleotide before the locus of interest, detection of the locus of interest, and potentially the three bases pairs after the locus of interest.

Alternatively, if the base upstream of the locus of interest and the locus of interest are different nucleotides, then the 3' recessed end of the molecules cut at 11/15 can be filled in with deoxynucleotide that is complementary to the upstream base. The remaining deoxynucleotide is washed away, and the locus of interest site can be filled in with either labeled deoxynucleotides, unlabeled deoxynucleotides, labeled dideoxynucleotides, or unlabeled dideoxynucleotides. After the fill in reaction, the nucleotide can be detected by any suitable method. Thus, after the first fill in reaction with dNTP, the 3' recessed end of the molecules cut at 10/14 and 11/15 is upstream of the locus of interest. The 3' recessed end can now be filled in one base, which corresponds to the locus of interest, two bases, three bases or four bases.

Alternatively, if the base upstream of the locus of interest and the base downstream of the locus of interest are reported to be the same, the 3' recessed end of the molecules cut at 11/15 can be "filled in" with unlabeled deoxynucleotide, followed by a "fill in" with labeled dideoxynucleotide. For example, if the nucleotide upstream of the locus of interest is a cytosine, and a cytosine is a potential nucleotide at the locus of interest, and an adenosine is the first nucleotide 3' of the locus of interest, a "fill in" reaction can be performed with unlabeled deoxyguanine triphosphate (dGTP), followed by a fill in with labeled dideoxythymidine triphosphate. If the locus of interest contains a cytosine, the ddTTP will be incorporated and detected. However, if the locus of interest does not contain a cytosine, the dGTP will not be incorporated, which prevents incorporation of the ddTTP.

The restriction enzyme BceA I recognizes the nucleic acid sequence ACGGC and cuts 12 (twelve) nucleotides from the recognition site on the sense strand and 14 (fourteen) nucleotides from the recognition site on the antisense strand. If the distance from the recognition site for BceA I on the second primer is designed to be thirteen (13) bases from the locus of interest (see FIGS. 4A–4D), digestion with BceA I will generate a 5' overhang of two bases, which contains the locus of interest, and a recessed 3' end that is upstream of the locus of interest. The locus of interest is the first nucleotide in the 5' overhang (reading 3' to 5').

Alternative cutting is also seen with the restriction enzyme BceA I, although at a much lower frequency than is seen with BsmF I. The restriction enzyme BceA I can cut thirteen (13) nucleotides from the recognition site on the sense strand and fifteen (15) nucleotides from the recognition site on the antisense strand. Thus, two populations of DNA molecules exist: DNA molecules cut at 12/14 and DNA molecules cut at 13/15. If the restriction enzyme recognition site is 13 bases from the locus of interest in the amplified product, DNA molecules cut at the 13/15 position yield a 5' overhang, which contains the locus of interest in the second position of the overhang (reading 3' to 5'). Labeled dideoxynucleotides can be used to fill in the 3' recessed end of the DNA molecules. The DNA molecules cut at 13/15 will have the base upstream of the locus of interest filled in, and the DNA molecules cut at 12/14 will have the locus of interest site filled in. The DNA molecules cut at 13/15 and those cut at 12/14 can be separated by size, and the incorporated nucleotide detected. Thus, the alternative cutting can be used to obtain additional sequence information.

Alternatively, if the two bases in the 5' overhang are different, the 3' recessed end of the DNA molecules, which were cut at 13/15, can be filled in with the deoxynucleotide complementary to the first base in the overhang, and excess deoxynucleotide washed away. After filling in, the 3' recessed end of the DNA molecules that were cut at 12/14 and the DNA molecules that were cut at 13/15 are upstream of the locus of interest. The 3' recessed ends can be filled with either labeled dideoxynucleotides, unlabeled dideoxynucleotides, labeled deoxynucleotides, or unlabeled deoxynucleotides.

If the primers provide different restriction sites for certain of the loci of interest that were copied, all the necessary restriction enzymes can be added together to digest the copied DNA simultaneously. Alternatively, the different restriction digests can be made in sequence, for example, using one restriction enzyme at a time, so that only the product that is specific for that restriction enzyme is digested.

Incorporation of Labeled Nucleotides

Digestion with the restriction enzyme that recognizes the sequence on the second primer generates a recessed 3' end and a 5' overhang, which contains the locus of interest (FIG. 1G). The recessed 3' end can be filled in using the 5' overhang as a template in the presence of unlabeled or labeled nucleotides or a combination of both unlabeled and labeled nucleotides. The nucleotides can be labeled with any type of chemical group or moiety that allows for detection including but not limited to radioactive molecules, fluorescent molecules, antibodies, antibody fragments, haptens, carbohydrates, biotin, derivatives of biotin, phosphorescent moieties, luminescent moieties, electrochemiluminescent moieties, chromatic moieties, and moieties having a detectable electron spin resonance, electrical capacitance, dielectric constant or electrical conductivity. The nucleotides can be labeled with one or more than one type of chemical group or moiety. Each nucleotide can be labeled with the same chemical group or moiety. Alternatively, each different nucleotide can be labeled with a different chemical group or moiety. The labeled nucleotides can be dNTPs, ddNTPs, or a mixture of both dNTPs and ddNTPs. The unlabeled nucleotides can be dNTPs, ddNTPs or a mixture of both dNTPs and ddNTPs.

Any combination of nucleotides can be used to incorporate nucleotides including but not limited to unlabeled deoxynucleotides, labeled deoxynucleotides, unlabeled dideoxynucleotides, labeled dideoxynucleotides, a mixture of labeled and unlabeled deoxynucleotides, a mixture of labeled and unlabeled dideoxynucleotides, a mixture of labeled deoxynucleotides and labeled dideoxynucleotides, a mixture of labeled deoxynucleotides and unlabeled dideoxynucleotides, a mixture of unlabeled deoxynucleotides and unlabeled dideoxynucleotides, a mixture of unlabeled deoxynucleotides and labeled dideoxynucleotides, dideoxynucleotide analogues, deoxynucleotide analogues, a mixture of dideoxynucleotide analogues and deoxynucleotide analogues, phosphorylated nucleoside analogues, 2-deoxynucleoside-5' triphosphates and modified 2'-deoxynucleoside triphosphates.

For example, as shown in FIG. 1H, in the presence of a polymerase, the 3' recessed end can be filled in with fluorescent ddNTP using the 5' overhang as a template. The incorporated ddNTP can be detected using any suitable method including but not limited to fluorescence detection.

All four nucleotides can be labeled with different fluorescent groups, which will allow one reaction to be performed in the presence of all four labeled nucleotides. Alternatively, five separate "fill in" reactions can be performed for each locus of interest; each of the four reactions will contain a different labeled nucleotide (e.g. ddATP*, ddTTP*, ddUTP*, ddGTP*, or ddCTP*, where * indicates a labeled nucleotide). Each nucleotide can be labeled with different chemical groups or the same chemical groups. The labeled nucleotides can be dideoxynucleotides or deoxynucleotides.

In another embodiment, nucleotides can be labeled with fluorescent dyes including but not limited to fluorescein, pyrene, 7-methoxycoumarin, Cascade Blue™, Alexa Flur 350, Alexa Flur 430, Alexa Flur 488, Alexa Flur 532, Alexa Flur 546, Alexa Flur 568, Alexa Flur 594, Alexa Flur 633, Alexa Flur 647, Alexa Flur 660, Alexa Flur 680, AMCA-X, dialkylaminocoumarin, Pacific Blue, Marina Blue, BODIPY 493/503, BODIPY FI-X, DTAF, Oregon Green 500, Dansyl-X, 6-FAM, Oregon Green 488, Oregon Green 514, Rhodamine Green-X, Rhodol Green, Calcein, Eosin, ethidium bromide, NBD, TET, 2', 4', 5', 7' tetrabromosulfonefluorescien, BODIPY-R6G, BODIPY-FI BR2, BODIPY 530/550, HEX, BODIPY 558/568, BODIPY-TMR-X., PyMPO, BODIPY 564/570, TAMRA, BODIPY 576/589, Cy3, Rhodamine Red-x, BODIPY 581/591, carboxyXrhodamine, Texas Red-X, BODIPY-TR-X., Cy5, SpectrumAqua, SpectrumGreen #1, SpectrumGreen #2, SpectrumOrange, SpectrumRed, or naphthofluorescein.

In another embodiment, the "fill in" reaction can be performed with fluorescently labeled dNTPs, wherein the nucleotides are labeled with different fluorescent groups. The incorporated nucleotides can be detected by any suitable method including but not limited to Fluorescence Resonance Energy Transfer (FRET).

In another embodiment, a mixture of both labeled ddNTPs and unlabeled dNTPs can be used for filling in the recessed 3' end of the DNA sequence containing the SNP or locus of interest. Preferably, the 5' overhang consists of more than one base, including but not limited to 2, 3, 4, 5, 6 or more than 6 bases. For example, if the 5' overhang consists of the sequence "XGAA," wherein X is the locus of interest, e.g. SNP, then filling in with a mixture of labeled ddNTPs and unlabeled dNTPs will produce several different DNA fragments. If a labeled ddNTP is incorporated at position "X," the reaction will terminate and a single labeled base will be incorporated. If however, an unlabeled dNTP is incorporated, the polymerase continues to incorporate other bases until a labeled ddNTP is incorporated. If the first two nucleotides incorporated are dNTPs, and the third is a ddNTP, the 3' recessed end will be extended by three bases. This DNA fragment can be separated from the other DNA fragments that were extended by 1, 2, or 4 bases by size. A mixture of labeled ddNTPs and unlabeled dNTPs will allow all bases of the overhang to be filled in, and provides additional sequence information about the locus of interest, e.g. SNP (see FIGS. 7E and 9D).

After incorporation of the labeled nucleotide, the amplified DNA can be digested with a restriction enzyme that recognizes the sequence provided by the first primer. For example, in FIG. 1I, the amplified DNA is digested with a restriction enzyme that binds to region "a," which releases the DNA fragment containing the incorporated nucleotide from the streptavidin matrix.

Alternatively, one primer of each primer pair for each locus of interest can be attached to a solid support matrix including but not limited to a well of a microtiter plate. For example, streptavidin-coated microtiter plates can be used for the amplification reaction with a primer pair, wherein one primer is biotinylated. First, biotinylated primers are bound to the streptavidin-coated microtiter plates. Then, the plates are used as the reaction vessel for PCR amplification of the loci of interest. After the amplification reaction is complete, the excess primers, salts, and template DNA can be removed by washing. The amplified DNA remains attached to the microtiter plate. The amplified DNA can be digested with a restriction enzyme that recognizes a sequence on the second primer and generates a 5' overhang, which contains the locus of interest. The digested fragments can be removed by washing. After digestion, the SNP site or locus of interest is exposed in the 5' overhang. The recessed 3' end is filled in with a labeled nucleotide, including but not limited to, fluorescent ddNTP in the presence of a polymerase. The labeled DNA can be released into the supernatant in the microtiter plate by digesting with a restriction enzyme that recognizes a sequence in the 5' region of the first primer.

Analysis of the Locus of Interest

The labeled loci of interest can be analyzed by a variety of methods including but not limited to fluorescence detection, DNA sequencing gel, capillary electrophoresis on an automated DNA sequencing machine, microchannel electrophoresis, and other methods of sequencing, mass spectrometry, time of flight mass spectrometry, quadrupole mass spectrometry, magnetic sector mass spectrometry, electric sector mass spectrometry infrared spectrometry, ultraviolet spectrometry, palentiostatic amperometry or by DNA hybridization techniques including Southern Blots, Slot Blots, Dot Blots, and DNA microarrays, wherein DNA fragments would be useful as both "probes" and "targets," ELISA, fluorimetry, and Fluorescence Resonance Energy Transfer (FRET).

The loci of interest can be analyzed using gel electrophoresis followed by fluorescence detection of the incorporated nucleotide. Another method to analyze or read the loci of interest is to use a fluorescent plate reader or fluorimeter directly on the 96-well streptavidin coated plates. The plate can be placed onto a fluorescent plate reader or scanner such as the Pharmacia 9200 Typhoon to read each locus of interest.

Alternatively, the PCR products of the loci of interest can be pooled and after "filling in," (FIG. 10) the products can be separated by size, using any method appropriate for the same, and then analyzed using a variety of techniques including but not limited to fluorescence detection, DNA sequencing gel, capillary electrophoresis on an automated DNA sequencing machine, microchannel electrophoresis, other methods of sequencing, DNA hybridization techniques including Southern Blots, Slot Blots, Dot Blots, and DNA microarrays, mass spectrometry, time of flight mass spectrometry, quadrupole mass spectrometry, magnetic sector mass spectrometry, electric sector mass spectrometry infrared spectrometry, ultraviolet spectrometry, palentiostatic amperometry. For example, polyacrylamide gel electrophoresis can be used to separate DNA by size and the gel can be scanned to determine the color of fluorescence in each band (using e.g. ABI 377 DNA sequencing machine or a Pharmacia Typhoon 9200).

In another embodiment, one nucleotide can be used to determine the sequence of multiple alleles of a gene. A nucleotide that terminates the elongation reaction can be used to determine the sequence of multiple alleles of a gene. At one allele, the terminating nucleotide is complementary to the locus of interest in the 5' overhang of said allele. The nucleotide is incorporated and terminates the reaction. At a different allele, the terminating nucleotide is not complementary to the locus of interest, which allows a non-terminating nucleotide to be incorporated at the locus of interest of the different allele. However, the terminating nucleotide is complementary to a nucleotide downstream from the locus of interest in the 5' overhang of said different allele. The sequence of the alleles can be determined by analyzing the patterns of incorporation of the terminating nucleotide. The terminating nucleotide can be labeled or unlabeled.

In a another embodiment, the terminating nucleotide is a nucleotide that terminates or hinders the elongation reaction including but not limited to a dideoxynucleotide, a dideoxynucleotide derivative, a dideoxynucleotide analog, a dideoxynucleotide homolog, a dideoxynucleotide with a sulfur chemical group, a deoxynucleotide, a deoxynucleotide derivative, a deoxynucleotide homolog, a deoxynucleotide analog, and a deoxynucleotide with a sulfur chemical group, arabinoside triphosphate, an arabinoside triphosphate analog, a arabinoside triphosphate homolog, or an arabinoside derivative.

In another embodiment, a terminating nucleotide labeled with one signal generating moiety tag, including but not limited to a fluorescent dye, can be used to determine the sequence of the alleles of a locus of interest. The use of a single nucleotide labeled with one signal generating moiety tag eliminates any difficulties that can arise when using different fluorescent moieties. In addition, using one nucleotide labeled with one signal generating moiety tag to determine the sequence of alleles of a locus of interest reduces the number of reactions, and eliminates pipetting errors.

For example, if the second primer contains the restriction enzyme recognition site for BsmFI, digestion will generate a 5' overhang of 4 bases. The second primer can be designed such that the locus of interest is located in the first position of the overhang. A representative overhang is depicted below, where R represents the locus of interest:

```
5'CAC
3'GTG              R     T     G     G
Overhang position  1     2     3     4
```

One nucleotide with one signal generating moiety tag can be used to determine whether the variable site is homozygous or heterozygous. For example, if the variable site is adenine (A) or guanine (G), then either adenine or guanine can be used to determine the sequence of the alleles of the locus of interest, provided that there is an adenine or guanine in the overhang at position 2, 3, or 4.

For example, if the nucleotide in position 2 of the overhang is thymidine, which is complementary to adenine, then labeled ddATP, unlabeled dCTP, dGTP, and dTTP can be used to determine the sequence of the alleles of the locus of interest. The ddATP can be labeled with any signal generating moiety including but not limited to a fluorescent dye. If the template DNA is homozygous for adenine, then labeled ddATP* will be incorporated at position 1 complementary to the overhang at the alleles, and no nucleotide incorporation will be seen at position 2, 3 or 4 complementary to the overhang.

```
Allele 1              5'CCC    A*
                      3'GGG    T       T    G    G
Overhang position              1       2    3    4

Allele 2              5'CCC    A*
                      3'GGG    T       T    G    G
Overhang position              1       2    3    4
```

One signal will be seen corresponding to incorporation of labeled ddATP at position 1 complementary to the overhang, which indicates that the individual is homozygous for adenine at this position. This method of labeling eliminates any difficulties that may arise from using different dyes that have different quantum coefficients.

Homozygous Guanine:

If the template DNA is homozygous for guanine, then no ddATP will be incorporated at position 1 complementary to the overhang, but ddATP will be incorporated at the first available position, which in this case is position 2 complementary to the overhang. For example, if the second position in the overhang corresponds to a thymidine, then:

```
Allele 1              5'CCC    G       A*
                      3'GGG    C       T    G    G
Overhang position              1       2    3    4

Allele 2              5'CCC    G       A*
                      3'GGG    C       T    G    G
Overhang position              1       2    3    4
```

One signal will be seen corresponding to incorporation of ddATP at position 2 complementary to the overhang, which indicates that the individual is homozygous for guanine. The molecules that are filled in at position 2 complementary to the overhang will have a different molecular weight than the molecules filled in at position 1 complementary to the overhang.

Heterozygous Condition:

```
Allele 1              5'CCC    A*
                      3'GGG    T       T    G    G
Overhang position              1       2    3    4

Allele 2              5'CCC    G       A*
                      3'GGG    C       T    G    G
Overhang position              1       2    3    4
```

Two signals will be seen; the first signal corresponds to the ddATP filled in at position one complementary to the overhang and the second signal corresponds to the ddATP filled in at position 2 complementary to the overhang. The two signals can be separated based on molecular weight; allele 1 and allele 2 will be separated by a single base pair, which allows easy detection and quantitation of the signals. Molecules filled in at position one can be distinguished from molecules filled in at position two using any method that discriminates based on molecular weight including but not limited to gel electrophoresis, capillary gel electrophoresis, DNA sequencing, and mass spectrometry. It is not necessary that the nucleotide be labeled with a chemical moiety; the DNA molecules corresponding to the different alleles can be separated based on molecular weight.

If position 2 of the overhang is not complementary to adenine, it is possible that positions 3 or 4 may be complementary to adenine. For example, position 3 of the overhang may be complementary to the nucleotide adenine, in which case labeled ddATP may be used to determine the sequence of both alleles.

Homozygous for Adenine:

```
Allele 1              5'CCC    A*
                      3'GGG    T       G    T    G
Overhang position              1       2    3    4

Allele 2              5'CCC    A*
                      3'GGG    T       G    T    G
Overhang position              1       2    3    4
```

Homozygous for Guanine:

```
Allele 1              5'CCC    G       C    A*
                      3'GGG    C       G    T    G
Overhang position              1       2    3    4

Allele 2              5'CCC    G       C    A*
                      3'GGG    C       G    T    G
Overhang position              1       2    3    4
```

Heterozygous:

```
Allele 1              5'CCC    A*
                      3'GGG    T       G    T    G
Overhang position              1       2    3    4

Allele 2              5'CCC    G       C    A*
                      3'GGG    C       G    T    G
Overhang position              1       2    3    4
```

Two signals will be seen; the first signal corresponds to the ddATP filled in at position 1 complementary to the overhang and the second signal corresponds to the ddATP filled in at position 3 complementary to the overhang. The two signals can be separated based on molecular weight; allele 1 and allele 2 will be separated by two bases, which can be detected using any method that discriminates based on molecular weight.

Alternatively, if positions 2 and 3 are not complementary to adenine (i.e. positions 2 and 3 of the overhang correspond to guanine, cytosine, or adenine) but position 4 is complementary to adenine, labeled ddATP can be used to determine the sequence of both alleles.

Homozygous for Adenine:

```
Allele 1              5'CCC    A*
                      3'GGG    T       G    G    T
Overhang position              1       2    3    4

Allele 2              5'CCC    A*
                      3'GGG    T       G    G    T
Overhang position              1       2    3    4
```

One signal will be seen that corresponds to the molecular weight of molecules filled in with ddATP at position one complementary to the overhang, which indicates that the individual is homozygous for adenine at the variable site.

Homozygous for Guanine:

```
Allele 1              5'CCC    G       C    C    A*
                      3'GGG    C       G    G    T
Overhang position              1       2    3    4

Allele 2              5'CCC    G       C    C    A*
                      3'GGG    C       G    G    T
Overhang position              1       2    3    4
```

One signal will be seen that corresponds to the molecular weight of molecules filled in at position 4 complementary to the overhang, which indicates that the individual is homozygous for guanine.

Heterozygous:

```
Allele 1        5' CCC    A*
                3' GGG    T    G    G    T
Overhang position         1    2    3    4
Allele 2        5' CCC    G    C    C    A*
                3' GGG    C    G    G    T
Overhang position         1    2    3    4
```

Two signals will be seen; the first signal corresponds to the ddATP filled in at position one complementary to the overhang and the second signal corresponds to the ddATP filled in at position 4 complementary to the overhang. The two signals can be separated based on molecular weight; allele 1 and allele 2 will be separated by three bases, which allows detection and quantitation of the signals. The molecules filled in at position 1 and those filled in at position 4 can be distinguished based on molecular weight.

As discussed above, if the variable site contains either adenine or guanine, either labeled adenine or labeled guanine can be used to determine the sequence of both alleles. If positions 2, 3, or 4 of the overhang are not complementary to adenine but one of the positions is complementary to a guanine, then labeled ddGTP can be used to determine whether the template DNA is homozygous or heterozygous for adenine or guanine. For example, if position 3 in the overhang corresponds to a cytosine then the following signals will be expected if the template DNA is homozygous for guanine, homozygous for adenine, or heterozygous:

Homozygous for Guanine:

```
Allele 1        5' CCC    G*
                3' GGG    C    T    C    T
Overhang position         1    2    3    4
Allele 2        5' CCC    G*
                3' GGG    C    T    C    T
Overhang position         1    2    3    4
```

One signal will be seen that corresponds to the molecular weight of molecules filled in with ddGTP at position one complementary to the overhang, which indicates that the individual is homozygous for guanine.

Homozygous for Adenine:

```
Allele 1        5' CCC    A    A    G*
                3' GGG    T    T    C    T
Overhang position         1    2    3    4
Allele 2        5' CCC    A    A    G*
                3' GGG    T    T    C    T
Overhang position         1    2    3    4
```

One signal will be seen that corresponds to the molecular weight of molecules filled in at position 3 complementary to the overhang, which indicates that the individual is homozygous for adenine at the variable site.

Heterozygous:

```
Allele 1        5' CCC    G*
                3' GGG    C    T    C    T
Overhang position         1    2    3    4
Allele 2        5' CCC    A    A    G*
                3' GGG    T    T    C    T
Overhang position         1    2    3    4
```

Two signals will be seen; the first signal corresponds to the ddGTP filled in at position one complementary to the overhang and the second signal corresponds to the ddGTP filled in at position 3 complementary to the overhang. The two signals can be separated based on molecular weight; allele 1 and allele 2 will be separated by two bases, which allows easy detection and quantitation of the signals.

Some type IIS restriction enzymes also display alternative cutting as discussed above. For example, BsmFI will cut at 10/14 and 11/15 from the recognition site. However, the cutting patterns are not mutually exclusive; if the 11/15 cutting pattern is seen at a particular sequence, 10/14 cutting is also seen. If the restriction enzyme BsmF I cuts at 10/14 from the recognition site, the 5' overhang will be $X_1X_2X_3X_4$. If BsmF I cuts 11/15 from the recognition site, the 5' overhang will be $X_0X_1X_2X_3$. If position $X_0$ of the overhang is complementary to the labeled nucleotide, the labeled nucleotide will be incorporated at position $X_0$ and provides an additional level of quality assurance. It provides additional sequence information.

For example, if the variable site is adenine or guanine, and position 3 in the overhang is complementary to adenine, labeled ddATP can be used to determine the genotype at the variable site. If position 0 of the 11/15 overhang contains the nucleotide complementary to adenine, ddATP will be filled in and an additional signal will be seen.

Heterozygous:

```
10/14 Allele 1    5' CCA    A*
                  3' GGT    T    G    T    G
Overhang position            1    2    3    4
10/14 Allele 2    5' CCA    G    C    A*
                  3' GGT    C    G    T    G
Overhang position            1    2    3    4
11/15 Allele 1    5' CC     A*
                  3' GG     T    T    G    T
Overhang position           0    1    2    3
11/15 Allele 2    5' CC     A*
                  3' GG     T    C    G    T
Overhang position           0    1    2    3
```

Three signals are seen; one corresponding to the ddATP incorporated at position 0 complementary to the overhang, one corresponding to the ddATP incorporated at position 1 complementary to the overhang, and one corresponding to the ddATP incorporated at position 3 complementary to the overhang. The molecules filled in at position 0, 1, and 3 complementary to the overhang differ in molecular weight and can be separated using any technique that discriminates based on molecular weight including but not limited to gel electrophoresis, and mass spectrometry.

For quantitating the ratio of one allele to another allele or when determining the relative amount of a mutant DNA sequence in the presence of wild type DNA sequence, an accurate and highly sensitive method of detection must be used. The alternate cutting displayed by type IIS restriction enzymes may increase the difficulty of determining ratios of one allele to another allele because the restriction enzyme may not display the alternate cutting (11/15) pattern on the two alleles equally. For example, allele 1 may be cut at 10/14 80% of the time, and 11/15 20% of the time. However, because the two alleles may differ in sequence, allele 2 may be cut at 10/14 90% of the time, and 11/15 20% of the time.

For purposes of quantitation, the alternate cutting problem can be eliminated when the nucleotide at position 0 of the overhang is not complementary to the labeled nucleotide. For example, if the variable site corresponds to adenine or guanine, and position 3 of the overhang is complementary to adenine (i.e., a thymidine is located at position 3 of the overhang), labeled ddATP can be used to determine the genotype of the variable site. If position 0 of the overhang generated by the 11/15 cutting properties is not complementary to adenine, (i.e., position 0 of the overhang corresponds to guanine, cytosine, or adenine) no additional signal will be seen from the fragments that were cut 11/15 from the recognition site. Position 0 complementary to the overhang can be filled in with unlabeled nucleotide, eliminating any complexity seen from the alternate cutting pattern of restriction enzymes. This method provides a highly accurate method for quantitating the ratio of a variable site including but not limited to a mutation, or a single nucleotide polymorphism.

For instance, if SNP X can be adenine or guanine, this method of labeling allows quantitation of the alleles that correspond to adenine and the alleles that correspond to guanine, without determining if the restriction enzyme displays any differences between the alleles with regard to alternate cutting patterns.

Heterozygous:

| | | | | | |
|---|---|---|---|---|---|
| 10/14 Allele 1 | 5' CCG | A* | | | |
| | 3' GGC | T | G | T | G |
| Overhang position | | 1 | 2 | 3 | 4 |
| 10/14 Allele 2 | 5' CCG | G | C | A* | |
| | 3' GGC | C | G | T | G |
| Overhang position | | 1 | 2 | 3 | 4 |

The overhang generated by the alternate cutting properties of BsmF I is depicted below:

| | | | | | |
|---|---|---|---|---|---|
| 11/15 Allele 1 | 5' CC | | | | |
| | 3' GG | C | T | G | T |
| Overhang position | | 0 | 1 | 2 | 3 |
| 11/15 Allele 2 | 5' CC | | | | |
| | 3' GG | C | C | G | T |
| Overhang position | | 0 | 1 | 2 | 3 |

After filling in with labeled ddATP and unlabeled dGTP, dCTP, dTTP, the following molecules would be generated:

| | | | | | |
|---|---|---|---|---|---|
| 11/15 Allele 1 | 5' CC | G | A* | | |
| | 3' GG | C | T | G | T |
| Overhang position | | 0 | 1 | 2 | 3 |
| 11/15 Allele 2 | 5' CC | G | G | C | A* |
| | 3' GG | C | C | G | T |
| Overhang position | | 0 | 1 | 2 | 3 |

Two signals are seen; one corresponding to the molecules filled in with ddATP at position one complementary to the overhang and one corresponding to the molecules filled in with ddATP at position 3 complementary to the overhang. Position 0 of the 11/15 overhang is filled in with unlabeled nucleotide, which eliminates any difficulty in quantitating a ratio for the nucleotide at the variable site on allele 1 and the nucleotide at the variable site on allele 2.

Any nucleotide can be used including adenine, adenine derivatives, adenine homologues, guanine, guanine derivatives, guanine homologues, cytosine, cytosine derivatives, cytosine homologues, thymidine, thymidine derivatives, or thymidine homologues, or any combinations of adenine, adenine derivatives, adenine homologues, guanine, guanine derivatives, guanine homologues, cytosine, cytosine derivatives, cytosine homologues, thymidine, thymidine derivatives, or thymidine homologues.

The nucleotide can be labeled with any chemical group or moiety, including but not limited to radioactive molecules, fluorescent molecules, antibodies, antibody fragments, haptens, carbohydrates, biotin, derivatives of biotin, phosphorescent moieties, luminescent moieties, electrochemiluminescent moieties, chromatic moieties, and moieties having a detectable electron spin resonance, electrical capacitance, dielectric constant or electrical conductivity. The nucleotide can be labeled with one or more than one type of chemical group or moiety.

In another embodiment, labeled and unlabeled nucleotides can be used. Any combination of deoxynucleotides and dideoxynucleotides can be used including but not limited to labeled dideoxynucleotides and labeled deoxynucleotides; labeled dideoxynucleotides and unlabeled deoxynucleotides; unlabeled dideoxynucleotides and unlabeled deoxynucleotides; and unlabeled dideoxynucleotides and labeled deoxynucleotides.

In another embodiment, nucleotides labeled with a chemical moiety can be used in the PCR reaction. Unlabeled nucleotides then are used to fill-in the 5' overhangs generated after digestion with the restriction enzyme. An unlabeled terminating nucleotide can be used to in the presence of unlabeled nucleotides to determine the sequence of the alleles of a locus of interest.

For example, if labeled dTTP was used in the PCR reaction, the following 5' overhang would be generated after digestion with BsmF I:

| | | | | | |
|---|---|---|---|---|---|
| 10/14 Allele 1 | 5' CT*G | A | | | |
| | 3' GAC | T | G | T | G |
| Overhang position | | 1 | 2 | 3 | 4 |
| 10/14 Allele 2 | 5' CT*G | G | C | A | |
| | 3' GAC | C | G | T | G |
| Overhang position | | 1 | 2 | 3 | 4 |

Unlabeled ddATP, unlabeled dCTP, unlabeled dGTP, and unlabeled dTTP can be used to fill-in the 5' overhang. Two signals will be generated; one signal corresponds to the DNA molecules filled in with unlabeled ddATP at position 1 complementary to the overhang and the second signal corresponds to DNA molecules filled in with unlabeled ddATP at position 3 complementary to the overhang. The DNA molecules can be separated based on molecular weight and can be detected by the fluorescence of the dTTP, which was incorporated during the PCR reaction.

The labeled DNA loci of interest sites can be analyzed by a variety of methods including but not limited to fluorescence detection, DNA sequencing gel, capillary electrophoresis on an automated DNA sequencing machine, microchannel electrophoresis, and other methods of sequencing, mass spectrometry, time of flight mass spectrometry, quadrupole mass spectrometry, magnetic sector mass spectrometry, electric sector mass spectrometry infrared spectrometry, ultraviolet spectrometry, palentiostatic amperometry or by DNA hybridization techniques including Southern Blots, Slot Blots, Dot Blots, and DNA microarrays, wherein DNA fragments would be useful as both "probes" and "targets," ELISA, fluorimetry, and Fluorescence Resonance Energy Transfer (FRET).

This method of labeling is extremely sensitive and allows the detection of alleles of a locus of interest that are in various ratios including but not limited to 1:1, 1:2, 1:3, 1:4, 1:5, 1:6–1:10, 1:11–1:20, 1:21–1:30, 1:31–1:40, 1:41–1:50, 1:51–1:60, 1:61–1:70, 1:71–1:80, 1:81–1:90, 1:91:1:100, 1:101–1:200, 1:250, 1:251–1:300, 1:301–1:400, 1:401–1:500, 1:501–1:600, 1:601–1:700, 1:701–1:800, 1:801–1:900, 1:901–1:1000, 1:1001–1:2000, 1:2001–1:3000, 1:3001–1:4000, 1:4001–1:5000, 1:5001–1:6000, 1:6001–1:7000, 1:7001–1:8000, 1:8001–1:9000, 1:9001–1:10,000; 1:10,001–1:20,000, 1:20,001:1:30,000, 1:30,001–1:40,000, 1:40,001–1:50,000, and greater than 1:50,000.

For example, this method of labeling allows one nucleotide labeled with one signal generating moiety to be used to determine the sequence of alleles at a SNP locus, or detect a mutant allele amongst a population of normal alleles, or detect an allele encoding antibiotic resistance from a bacterial cell amongst alleles from antibiotic sensitive bacteria, or detect an allele from a drug resistant virus amongst alleles from drug-sensitive virus, or detect an allele from a non-pathogenic bacterial strain amongst alleles from a pathogenic bacterial strain.

As shown above, a single nucleotide can be used to determine the sequence of the alleles at a particular locus of interest. This method is especially useful for determining if an individual is homozygous or heterozygous for a particular mutation or to determine the sequence of the alleles at a particular SNP site. This method of labeling eliminates any errors caused by the quantum coefficients of various dyes. It also allows the reaction to proceed in a single reaction vessel including but not limited to a well of a microtiter plate, or a single eppendorf tube.

This method of labeling is especially useful for the detection of multiple genetic signals in the same sample. For example, this method is useful for the detection of fetal DNA in the blood, serum, or plasma of a pregnant female, which contains both maternal DNA and fetal DNA. The maternal DNA and fetal DNA may be present in the blood, serum or plasma at ratios such as 97:3; however, the above-described method can be used to detect the fetal DNA. This method of labeling can be used to detect two, three, or four different genetic signals in the sample population This method of labeling is especially useful for the detection of a mutant allele that is among a large population of wild type alleles. Furthermore, this method of labeling allows the detection of a single mutant cell in a large population of wild type cells. For example, this method of labeling can be used to detect a single cancerous cell among a large population of normal cells. Typically, cancerous cells have mutations in the DNA sequence. The mutant DNA sequence can be identified even if there is a large background of wild type DNA sequence. This method of labeling can be used to screen, detect, or diagnosis any type of cancer including but not limited to colon, renal, breast, bladder, liver, kidney, brain, lung, prostate, and cancers of the blood including leukemia.

This labeling method can also be used to detect pathogenic organisms, including but not limited to bacteria, fungi, viruses, protozoa, and mycobacteria. It can also be used to discriminate between pathogenic strains of microorganism and non-pathogenic strains of microorganisms including but not limited to bacteria, fungi, viruses, protozoa, and mycobacteria.

For example, there are several strains of *Escherichia coli* (*E. coli*), and most are non-pathogenic. However, several strains, such as *E. coli* 0157 are pathogenic. There are genetic differences between non-pathogenic *E. coli* strains and pathogenic *E. coli*. The above described method of labeling can be used to detect pathogenic microorganisms in a large population of non-pathogenic organisms, which are sometimes associated with the normal flora of an individual.

In another embodiment, the sequence of the locus of interest can be determined by detecting the incorporation of a nucleotide that is 3' to the locus of interest, wherein said nucleotide is a different nucleotide from the possible nucleotides at the locus of interest. This embodiment is especially useful for the sequencing and detection of SNPs. The efficiency and rate at which DNA polymerases incorporate nucleotides varies for each nucleotide.

According to the data from the Human Genome Project, 99% of all SNPs are binary. The sequence of the human genome can be used to determine the nucleotide that is 3' to the SNP of interest. When the nucleotide that is 3' to the SNP site differs from the possible nucleotides at the SNP site, a nucleotide that is one or more than one base 3' to the SNP can be used to determine the identity of the SNP.

For example, suppose the identity of SNP X on chromosome 13 is to be determined. The sequence of the human genome indicates that SNP X can either be adenosine or guanine and that a nucleotide 3' to the locus of interest is a thymidine. A primer that contains a restriction enzyme recognition site for BsmF I, which is designed to be 13 bases from the locus of interest after amplification, is used to amplify a DNA fragment containing SNP X. Digestion with the restriction enzyme BsmF I generates a 5' overhang that contains the locus of interest, which can either be adenosine or guanine. The digestion products can be split into two "fill in" reactions: one contains dTTP, and the other reaction contains dCTP. If the locus of interest is homozygous for guanine, only the DNA molecules that were mixed with dCTP will be filled in. If the locus of interest is homozygous for adenosine, only the DNA molecules that were mixed with dTTP will be filled in. If the locus of interest is heterozygous, the DNA molecules that were mixed with dCTP will be filled in as well as the DNA molecules that were mixed with dTTP. After washing to remove the excess dNTP, the samples are filled in with labeled ddATP, which is complementary to the nucleotide (thymidine) that is 3' to the locus of interest. The DNA molecules that were filled in by the previous reaction will be filled in with labeled ddATP. If the individual is homozygous for adenosine, the DNA molecules that were mixed with dTTP subsequently will be filled in with the labeled ddATP. However, the DNA molecules that were mixed with dCTP, would not have incorporated that nucleotide, and therefore, could not incorporate the ddATP. Detection of labeled ddATP only in the molecules that were mixed with dTTP indicates that the identity of the nucleotide at SNP X on chromosome 13 is adenosine.

In another embodiment, large scale screening for the presence or absence of single nucleotide mutations can be performed. One to tens to hundreds to thousands of loci of interest on a single chromosome or on multiple chromosomes can be amplified with primers as described above in the "Primer Design" section. The primers can be designed so that each amplified loci of interest is of a different size (FIG. 2). The amplified loci of interest that are predicted, based on the published wild type sequences, to have the same nucleotide at the locus of interest can be pooled together, bound to a solid support, including wells of a microtiter plate coated with streptavidin, and digested with the restriction enzyme that will bind the recognition site on the second primer. After digestion, the 3' recessed end can be filled in with a mixture of labeled ddATP, ddTTP, ddGTP, ddCTP, where each nucleotide is labeled with a different group. After washing to remove the excess nucleotide, the fluorescence spectra can be detected using a plate reader or fluorimeter directly on the streptavidin coated plates. If all 50 loci of interest contain the wild type nucleotide, only one fluorescence spectra will be seen. However, if one or more than one of the 50 loci of interest contain a mutation, a different nucleotide will be incorporated and other fluorescence pattern(s) will be seen. The nucleotides can be released from the solid matrix, and analyzed on a sequencing gel to determine the loci of interest that contained the mutations. As each of the 50 loci of interest are of different size, they will separate on a sequencing gel.

The multiple loci of interest can be of a DNA sample from one individual representing multiple loci of interest on a single chromosome, multiple chromosomes, multiple genes, a single gene, or any combination thereof. The multiple loci of interest also can represent the same locus of interest but from multiple individuals. For example, 50 DNA samples from 50 different individuals can be pooled and analyzed to determine a particular nucleotide of interest at gene "X."

When human data is being analyzed, the known sequence can be a specific sequence that has been determined from one individual (including e.g. the individual whose DNA is currently being analyzed), or it can be a consensus sequence such as that published as part of the human genome.

Kits

The methods of the invention are most conveniently practiced by providing the reagents used in the methods in the form of kits. A kit preferably contains one or more of the following components: written instructions for the use of the kit, appropriate buffers, salts, DNA extraction detergents, primers, nucleotides, labeled nucleotides, 5' end modification materials, and if desired, water of the appropriate purity, confined in separate containers or packages, such components allowing the user of the kit to extract the appropriate nucleic acid sample, and analyze the same according to the methods of the invention. The primers that are provided with the kit will vary, depending upon the purpose of the kit and the DNA that is desired to be tested using the kit. In preferred embodiments the kits contain a primer that allows the generation of a recognition site for a restriction enzyme such that digestion with the enzyme generates in the DNA fragment generated during the sequencing method, a 5' overhang containing the locus of interest.

A kit can also be designed to detect a desired or variety of single nucleotide polymorphisms, especially those associated with an undesired condition or disease. For example, one kit can comprise, among other components, a set or sets of primers to amplify one or more loci of interest associated with breast cancer. Another kit can comprise, among other components, a set or sets of primers for genes associated with a predisposition to develop type I or type II diabetes. Still, another kit can comprise, among other components, a set or sets of primers for genes associated with a predisposition to develop heart disease. Details of utilities for such kits are provided in the "Utilities" section below.

Utilities

The methods of the invention can be used whenever it is desired to know the sequence of a certain nucleic acid, locus of interest or loci of interest therein. The method of the invention is especially useful when applied to genomic DNA. When DNA from an organism-specific or species-specific locus or loci of interest is amplified, the method of the invention can be used in genotyping for identification of the source of the DNA, and thus confirm or provide the identity of the organism or species from which the DNA sample was derived. The organism can be any nucleic acid containing organism, for example, virus, bacterium, yeast, plant, animal or human.

Within any population of organisms, the method of the invention is useful to identify differences between the sequence of the sample nucleic acid and that of a known nucleic acid. Such differences can include, for example, allelic variations, mutations, polymorphisms and especially single nucleotide polymorphisms.

In a preferred embodiment, the method of the invention provides a method for identification of single nucleotide polymorphisms.

In a preferred embodiment, the method of the invention provides a method for identification of the presence of a disease, especially a genetic disease that arises as a result of the presence of a genomic sequence, or other biological condition that it is desired to identify in an individual for which it is desired to know the same. The identification of such sequence in the subject based on the presence of such genomic sequence can be used, for example, to determine if the subject is a carrier or to assess if the subject is predisposed to developing a certain genetic trait, condition or disease. The method of the invention is especially useful in prenatal genetic testing of parents and child. Examples of some of the diseases that can be diagnosed by this invention are listed in Table II.

TABLE II

Achondroplasia
Adrenoleukodystrophy, X-Linked
Agammaglobulinemia, X-Linked
Alagille Syndrome
Alpha-Thalassemia X-Linked Mental Retardation Syndrome
Alzheimer Disease
Alzheimer Disease, Early-Onset Familial
Amyotrophic Lateral Sclerosis Overview
Androgen Insensitivity Syndrome
Angelman Syndrome
Ataxia Overview, Hereditary
Ataxia-Telangiectasia
Becker Muscular Dystrophy (also The Dystrophinopathies)
Beckwith-Wiedemann Syndrome
Beta-Thalassemia
Biotinidase Deficiency
Branchiootorenal Syndrome
BRCA1 and BRCA2 Hereditary Breast/Ovarian Cancer TABLE II-continued Breast Cancer
CADASIL
Canavan Disease
Cancer
Charcot-Marie-Tooth Hereditary Neuropathy
Charcot-Marie-Tooth Neuropathy Type 1
Charcot-Marie-Tooth Neuropathy Type 2
Charcot-Marie-Tooth Neuropathy Type 4
Charcot-Marie-Tooth Neuropathy Type X
Cockayne Syndrome
Colon Cancer
Contractural Arachnodactyly, Congenital
Craniosynostosis Syndromes (FGFR-Related)
Cystic Fibrosis
Cystinosis
Deafness and Hereditary Hearing Loss
DRPLA (Dentatorubral-Pallidoluysian Atrophy)
DiGeorge Syndrome (also 22q11 Deletion Syndrome)
Dilated Cardiomyopathy, X-Linked
Down Syndrome (Trisomy 21)
Duchenne Muscular Dystrophy (also The Dystrophinopathies)
Dystonia, Early-Onset Primary (DYT1)
Dystrophinopathies, The
Ehlers-Danlos Syndrome, Kyphoscoliotic Form
Ehlers-Danlos Syndrome, Vascular Type
Epidermolysis Bullosa Simplex
Exostoses, Hereditary Multiple
Facioscapulohumeral Muscular Dystrophy
Factor V Leiden Thrombophilia
Familial Adenomatous Polyposis (FAP)
Familial Mediterranean Fever
Fragile X Syndrome
Friedreich Ataxia
Frontotemporal Dementia with Parkinsonism-17
Galactosemia
Gaucher Disease
Hemochromatosis, Hereditary
Hemophilia A
Hemophilia B
Hemorrhagic Telangiectasia, Hereditary
Hearing Loss and Deafness, Nonsyndromic, DFNA3 (Connexin 26)
Hearing Loss and Deafness, Nonsyndromic, DFNB1 (Connexin 26)
Hereditary Spastic Paraplegia
Hermansky-Pudlak Syndrome
Hexosaminidase A Deficiency (also Tay-Sachs)
Huntington Disease
Hypochondroplasia
Ichthyosis, Congenital, Autosomal Recessive
Incontinentia Pigmenti
Kennedy Disease (also Spinal and Bulbar Muscular Atrophy)
Krabbe Disease
Leber Hereditary Optic Neuropathy
Lesch-Nyhan Syndrome
Leukemias
Li-Fraumeni Syndrome
Limb-Girdle Muscular Dystrophy
Lipoprotein Lipase Deficiency, Familial
Lissencephaly
Marfan Syndrome
MELAS (Mitochondrial Encephalomyopathy, Lactic Acidosis, and Stroke-Like Episodes)
Monosomies
Multiple Endocrine Neoplasia Type 2
Multiple Exostoses, Hereditary
Muscular Dystrophy, Congenital
Myotonic Dystrophy
Nephrogenic Diabetes Insipidus
Neurofibromatosis 1
Neurofibromatosis 2
Neuropathy with Liability to Pressure Palsies, Hereditary
Niemann-Pick Disease Type C
Nijmegen Breakage Syndrome
Norrie Disease
Oculocutaneous Albinism Type 1
Oculopharyngeal Muscular Dystrophy
Ovarian Cancer
Pallister-Hall Syndrome
Parkin Type of Juvenile Parkinson Disease
Pelizaeus-Merzbacher Disease TABLE II-continued Pendred Syndrome
Peutz-Jeghers Syndrome
Phenylalanine Hydroxylase Deficiency
Prader-Willi Syndrome
PROP1-Related Combined Pituitary Hormone Deficiency (CPHD)
Prostate Cancer
Retinitis Pigmentosa
Retinoblastoma
Rothmund-Thomson Syndrome
Smith-Lemli-Opitz Syndrome
Spastic Paraplegia, Hereditary
Spinal and Bulbar Muscular Atrophy (also Kennedy Disease)
Spinal Muscular Atrophy
Spinocerebellar Ataxia Type 1
Spinocerebellar Ataxia Type 2
Spinocerebellar Ataxia Type 3
Spinocerebellar Ataxia Type 6
Spinocerebellar Ataxia Type 7
Stickler Syndrome (Hereditary Arthroophthalmopathy)
Tay-Sachs (also GM2 Gangliosidoses)
Trisomies
Tuberous Sclerosis Complex
Usher Syndrome Type I
Usher Syndrome Type II
Velocardiofacial Syndrome (also 22q11 Deletion Syndrome)
Von Hippel-Lindau Syndrome
Williams Syndrome
Wilson Disease
X-Linked Adrenoleukodystrophy
X-Linked Agammaglobulinemia
X-Linked Dilated Cardiomyopathy (also The Dystrophinopathies)
X-Linked Hypotonic Facies Mental Retardation Syndrome The method of the invention is useful for screening an individual at multiple loci of interest, such as tens, hundreds, or even thousands of loci of interest associated with a genetic trait or genetic disease by sequencing the loci of interest that are associated with the trait or disease state, especially those most frequently associated with such trait or condition. The invention is useful for analyzing a particular set of diseases including but not limited to heart disease, cancer, endocrine disorders, immune disorders, neurological disorders, musculoskeletal disorders, ophthalmologic disorders, genetic abnormalities, trisomies, monosomies, transversions, translocations, skin disorders, and familial diseases.

The method of the invention can be used to genotype microorganisms so as to rapidly identify the presence of a specific microorganism in a substance, for example, a food substance. In that regard, the method of the invention provides a rapid way to analyze food, liquids or air samples for the presence of an undesired biological contamination, for example, microbiological, fungal or animal waste material. The invention is useful for detecting a variety of organisms, including but not limited to bacteria, viruses, fungi, protozoa, molds, yeasts, plants, animals, and archaebacteria. The invention is useful for detecting organisms collected from a variety of sources including but not limited to water, air, hotels, conference rooms, swimming pools, bathrooms, aircraft, spacecraft, trains, buses, cars, offices, homes, businesses, churches, parks, beaches, athletic facilities, amusement parks, theaters, and any other facility that is a meeting place for the public.

The method of the invention can be used to test for the presence of many types of bacteria or viruses in blood cultures from human or animal blood samples.

The method of the invention can also be used to confirm or identify the presence of a desired or undesired yeast strain, or certain traits thereof, in fermentation products, e.g. wine, beer, and other alcohols or to identify the absence thereof.

The method of the invention can also be used to confirm or identify the relationship of a DNA of unknown sequence to a DNA of known origin or sequence, for example, for use in criminology, forensic science, maternity or paternity testing, archeological analysis, and the like.

The method the invention can also be used to determine the genotypes of plants, trees and bushes, and hybrid plants, trees and bushes, including plants, trees and bushes that produce fruits and vegetables and other crops, including but not limited to wheat, barley, corn, tobacco, alfalfa, apples, apricots, bananas, oranges, pears, nectarines, figs, dates, raisins, plums, peaches, apricots, blueberries, strawberries, cranberries, berries, cherries, kiwis, limes, lemons, melons, pineapples, plantains, guavas, prunes, passion fruit, tangerines, grapefruit, grapes, watermelon, cantaloupe, honeydew melons, pomegranates, persimmons, nuts, artichokes, bean sprouts, beets, cardoon, chayote, endive, leeks, okra, green onions, scallions, shallots, parsnips, sweet potatoes, yams, asparagus, avocados, kohlrabi, rutabaga, eggplant, squash, turnips, pumpkins, tomatoes, potatoes, cucumbers, carrots, cabbage, celery, broccoli, cauliflower, radishes, peppers, spinach, mushrooms, zucchini, onions, peas, beans, and other legumes.

Especially, the method of the invention is useful to screen a mixture of nucleic acid samples that contain many different loci of interest and/or a mixture of nucleic acid samples from different sources that are to be analyzed for a locus of interest. Examples of large scale screening include taking samples of nucleic acid from herds of farm animals, or crops of food plants such as, for example, corn or wheat, pooling the same, and then later analyzing the pooled samples for the presence of an undesired genetic marker, with individual samples only being analyzed at a later date if the pooled sample indicates the presence of such undesired genetic sequence. An example of an undesired genetic sequence would be the detection of viral or bacterial nucleic acid sequence in the nucleic acid samples taken from the farm animals, for example, mycobacterium or hoof and mouth disease virus sequences or fungal or bacterial pathogen of plants.

Another example where pools of nucleic acid can be used is to test for the presence of a pathogen or gene mutation in samples from one or more tissues from an animal or human subject, living or dead, especially a subject who can be in need of treatment if the pathogen or mutation is detected. For example, numerous samples can be taken from an animal or human subject to be screened for the presence of a pathogen or otherwise undesired genetic mutation, the loci of interest from each biological sample amplified individually, and then samples of the amplified DNA combined for the restriction digestion, "filling in," and detection. This would be useful as an initial screening for the assay of the presence or absence of nucleic acid sequences that would be diagnostic of the presence of a pathogen or mutation. Then, if the undesired nucleic acid sequence of the pathogen or mutation was detected, the individual samples could be separately analyzed to determine the distribution of the undesired sequence. Such an analysis is especially cost effective when there are large numbers of samples to be assayed. Samples of pathogens include the mycobacteria, especially those that cause tuberculosis or paratuberculosis, bacteria, especially bacterial pathogens used in biological warfare, including *Bacillus anthracis*, and virulent bacteria capable of causing food poisoning, viruses, especially the influenza and AIDS virus, and mutations known to be associated with malignant cells. Such an analysis would also be advantageous for the large scale screening of food products for pathogenic bacteria.

Conversely, the method of the invention can be used to detect the presence and distribution of a desired genetic sequence at various locations in a plant, animal or human subject, or in a population of subjects, e.g. by screening of a combined sample followed by screening of individual samples, as necessary.

The method of the invention is useful for analyzing genetic variations of an individual that have an effect on drug metabolism, drug interactions, and the responsiveness to a drug or to multiple drugs. The method of the invention is especially useful in pharmacogenomics.

Having now generally described the invention, the same will become better understood by reference to certain specific examples which are included herein for purposes of illustration only and are not intended to be limiting unless other wise specified.

EXAMPLES

The following examples are illustrative only and are not intended to limit the scope of the invention as defined by the claims.

Example 1

DNA sequences were amplified by PCR, wherein the annealing step in cycle 1 was performed at a specified temperature, and then increased in cycle 2, and further increased in cycle 3 for the purpose of reducing non-specific amplification. The TM1 of cycle 1 of PCR was determined by calculating the melting temperature of the 3' region, which anneals to the template DNA, of the second primer. For example, in FIG. 1B, the TM1 can be about the melting temperature of region "c." The annealing temperature was raised in cycle 2, to TM2, which was about the melting temperature of the 3' region, which anneals to the template DNA, of the first primer. For example, in FIG. 1C, the annealing temperature (TM2) corresponds to the melting temperature of region "b'". In cycle 3, the annealing temperature was raised to TM3, which was about the melting temperature of the entire sequence of the second primer For example, in FIG. 1D, the annealing temperature (TM3) corresponds to the melting temperature of region "c"+region "d". The remaining cycles of amplification were performed at TM3.

Preparation of Template DNA

The template DNA was prepared from a 5 ml sample of blood obtained by venipuncture from a human volunteer with informed consent. Blood was collected from 36 volunteers. Template DNA was isolated from each blood sample using QIAamp DNA Blood Midi Kit supplied by QIAGEN (Catalog number 51183). Following isolation, the template DNA from each of the 36 volunteers was pooled for further analysis.

Design of Primers

The following four single nucleotide polymorphisms were analyzed: SNP HC21S00340, identification number as assigned by Human Chromosome 21 cSNP Database, (FIG. 3, lane 1) located on chromosome 21; SNP TSC 0095512 (FIG. 3, lane 2) located on chromosome 1, SNP TSC 0214366 (FIG. 3, lane 3) located on chromosome 1; and SNP TSC 0087315 (FIG. 3, lane 4) located on chromosome 1. The SNP Consortium Ltd database can be accessed at http://snp.cshl.org/, website address effective as of Feb. 14, 2002.

SNP HC21S00340 was amplified using the following primers:
First primer:
5' TAGAATAGCACTGAATTCAGGAATACAATCATTGTCAC 3'                    (SEQ ID NO:9)

Second primer:
5' ATCACGATAAACGGCCAAACTCAGGTTA 3'                              (SEQ ID NO:10)

SNP T5C0095512 was amplified using the following primers:
First primer:
5' AAGTTTAGATCAGAATTCGTGAAAGCAGAAGTTGTCTG 3'                    (SEQ ID NO:11)

Second primer:
5' TCTCCAACTAACGGCTCATCGAGTAAAG 3'                              (SEQ ID NO:12)

SNP TSC0214366 was amplified using the following primers:
First primer:
5' ATGACTAGCTATGAATTCGTTCAAGGTAGAAAATGGAA 3'                    (SEQ ID NO:13)

Second primer:
5' GAGAATTAGAACGGCCCAAATCCCACTC 3'                              (SEQ ID NO:14)

SNP TSC 0087315 was amplified using the following primers:
First primer:
5' TTACAATGCATGAATTCATCTTGGTCTCTCAAAGTGC 3'                     (SEQ ID NO:15)

Second primer:
5' TGGACCATAAACGGCCAAAAACTGTAAG 3'                              (SEQ ID NO:16)

All primers were designed such that the 3' region was complementary to either the upstream or downstream sequence flanking each locus of interest and the 5' region contained a restriction enzyme recognition site. The first primer contained a biotin tag at the 5' end and a recognition site for the restriction enzyme EcoRI. The second primer contained the recognition site for the restriction enzyme BceA I.

PCR Reaction

All four loci of interest were amplified from the template genomic DNA using PCR (U.S. Pat. Nos. 4,683,195 and 4,683,202). The components of the PCR reaction were as follows: 40 ng of template DNA, 5 µM first primer, 5 µM second primer, 1× HotStarTaq Master Mix as obtained from QIAGEN (Catalog No. 203443). The HotStarTaq Master Mix contained DNA polymerase, PCR buffer, 200 µM of each dNTP, and 1.5 mM MgCl$_2$.

Amplification of each template DNA that contained the SNP of interest was performed using three different series of annealing temperatures, herein referred to as low stringency annealing temperature, medium stringency annealing temperature, and high stringency annealing temperature. Regardless of the annealing temperature protocol, each PCR reaction consisted of 40 cycles of amplification. PCR reactions were performed using the HotStarTaq Master Mix Kit supplied by QIAGEN. As instructed by the manufacturer, the reactions were incubated at 95° C. for 15 min. prior to the first cycle of PCR. The denaturation step after each extension step was performed at 95° C. for 30 sec. The annealing reaction was performed at a temperature that permitted efficient extension without any increase in temperature.

The low stringency annealing reaction comprised three different annealing temperatures in each of the first three cycles. The annealing temperature for the first cycle was 37° C. for 30 sec.; the annealing temperature for the second cycle was 57° C. for 30 sec.; the annealing temperature for the third cycle was 64° C. for 30 sec. Annealing was performed at 64° C. for subsequent cycles until completion. As shown in the photograph of the gel (FIG. 3A), multiple bands were observed after amplification of the DNA template containing SNP TSC 0087315 (lane 4). Amplification of the DNA templates containing SNP HC21S00340 (lane 1), SNP TSC0095512 (lane 2), and SNP TSC0214366 (lane 3) generated a single band of high intensity and one band of faint intensity, which was of higher molecular weight. When the low annealing temperature conditions were used, the correct size product was generated and this was the predominant product in each reaction.

The medium stringency annealing reaction comprised three different annealing temperatures in each of the first three cycles. The annealing temperature for the first cycle was 40° C. for 30 seconds; the annealing temperature for the second cycle was 60° C. for 30 seconds; and the annealing temperature for the third cycle was 67° C. for 30 seconds. Annealing was performed at 67° C. for subsequent cycles until completion. Similar to what was observed under low stringency annealing conditions, amplification of the DNA template containing SNP TSC0087315 (FIG. 3B, lane 4) generated multiple bands under conditions of medium stringency. Amplification of the other three DNA fragments containing SNPs (lanes 1–3) produced a single band. These results demonstrate that variable annealing temperatures can be used to cleanly amplify loci of interest from genomic DNA with a primer that has an annealing length of 13 bases.

The high stringency annealing reaction was comprised of three different annealing temperatures in each of the first three cycles. The annealing temperature of the first cycle was 46° C. for 30 seconds; the annealing temperature of the second cycle was 65° C. for 30 seconds; and the annealing temperature for the third cycle was 72° C. for 30 seconds. Annealing was performed at 72° C. for subsequent cycles until completion. As shown in the photograph of the gel (FIG. 3C), amplification of the DNA template containing SNP TSC0087315 (lane 4) using the high stringency annealing temperatures generated a single band of the correct molecular weight. By raising the annealing temperatures for each of the first three cycles, non-specific amplification was eliminated. Amplification of the DNA fragment containing SNP TSC0095512 (lane 2) generated a single band. DNA fragments containing SNPs HC21S00340 (lane 1), and TSC0214366 (lane 3) failed to amplify at the high stringency annealing temperatures, however, at the medium stringency annealing temperatures, these DNA fragments containing SNPs amplified as a single band. These results demonstrate that variable annealing temperatures can be used to reduce non-specific PCR products, as demonstrated for the DNA fragment containing SNP TSC0087315 (FIG. 3, lane 4).

Example 2

SNPs on chromosomes 1 (TSC0095512), 13 (TSC0264580), and 21 (HC21S00027) were analyzed. SNP TSC0095512 was analyzed using two different sets of primers, and SNP HC21S00027 was analyzed using two types of reactions for the incorporation of nucleotides.

Preparation of Template DNA

The template DNA was prepared from a 5 ml sample of blood obtained by venipuncture from a human volunteer with informed consent. Template DNA was isolated using the QIAmp DNA Blood Midi Kit supplied by QIAGEN (Catalog number 51183). The template DNA was isolated as per instructions included in the kit. Following isolation, template DNA from thirty-six human volunteers were pooled together and cut with the restriction enzyme EcoRI. The restriction enzyme digestion was performed as per manufacturer's instructions.

Design of Primers

SNP HC21S00027 was amplified by PCR using the following primer set:

```
First primer:  5' ATAACCGTATGCGAATTCTATAATTTTCCTGATAAAGG 3' (SEQ ID NO:17)

Second primer: 5' CTTAAATCAGGGGACTAGGTAAACTTCA 3'           (SEQ ID NO:18)
```

The first primer contained a biotin tag at the extreme 5' end, and the nucleotide sequence for the restriction enzyme EcoRI. The second primer contained the nucleotide sequence for the restriction enzyme BsmF I (FIG. 4A).

Also, SNP HC21S00027 was amplified by PCR using the same first primer but a different second primer with the following sequence:

Second primer:

5' CTTAAATCAGACGGCTAGGTAAACTTCA 3' (SEQ ID NO:19)

This second primer contained the recognition site for the restriction enzyme BceA I (FIG. 4B).

SNP TSC0095512 was amplified by PCR using the following primers:

First primer:

5' AAGTTTAGATCAGAATTCGTGAAAGCAGAAGTTGTCTG 3' (SEQ ID NO:11)

Second primer:

5' TCTCCAACTAGGGACTCATCGAGTAAAG 3' (SEQ ID NO:20)

The first primer had a biotin tag at the 5' end and contained a restriction enzyme recognition site for EcoRI. The second primer contained a restriction enzyme recognition site for BsmF I (FIG. 4C).

Also, SNP TSC0095512 was amplified using the same first primer and a different second primer with the following sequence:

Second primer:

5' TCTCCAACTAACGGCTCATCGAGTAAAG 3' (SEQ ID NO: 12)

This second primer contained the recognition site for the restriction enzyme BceA I (FIG. 4D).

SNP TSC0264580, which is located on chromosome 13, was amplified with the following primers:

First primer:

5' AACGCCGGGCGAGAATTCAGTTTTTCAACTTGCAAGG 3' (SEQ ID NO:21)

Second primer:

5' CTACACATATCTGGGACGTTGGCCATCC 3' (SEQ ID NO:22)

The first primer contained a biotin tag at the extreme 5' end and had a restriction enzyme recognition site for EcoRI. The second primer contained a restriction enzyme recognition site for BsmF I.

PCR Reaction

All loci of interest were amplified from the template genomic DNA using the polymerase chain reaction (PCR, U.S. Pat. Nos. 4,683,195 and 4,683,202, incorporated herein by reference). In this example, the loci of interest were amplified in separate reaction tubes but they could also be amplified together in a single PCR reaction. For increased specificity, a "hot-start" PCR was used. PCR reactions were performed using the HotStarTaq Master Mix Kit supplied by QIAGEN (catalog number 203443). The amount of template DNA and primer per reaction can be optimized for each locus of interest but in this example, 40 ng of template human genomic DNA and 5 μM of each primer were used. Forty cycles of PCR were performed. The following PCR conditions were used:

(1) 95° C. for 15 minutes and 15 seconds;
(2) 37° C. for 30 seconds;
(3) 95° C. for 30 seconds;
(4) 57° C. for 30 seconds;
(5) 95° C. for 30 seconds;
(6) 64° C. for 30 seconds;
(7) 95° C. for 30 seconds;
(8) Repeat steps 6 and 7 thirty nine (39) times;
(9) 72° C. for 5 minutes.

In the first cycle of PCR, the annealing temperature was about the melting temperature of the 3' annealing region of the second primers, which was 37° C. The annealing temperature in the second cycle of PCR was about the melting temperature of the 3' region, which anneals to the template DNA, of the first primer, which was 57° C. The annealing temperature in the third cycle of PCR was about the melting temperature of the entire sequence of the second primer, which was 64° C. The annealing temperature for the remaining cycles was 64° C. Escalating the annealing temperature from TM1 to TM2 to TM3 in the first three cycles of PCR greatly improves specificity. These annealing temperatures are representative, and the skilled artisan will understand the annealing temperatures for each cycle are dependent on the specific primers used.

The temperatures and times for denaturing, annealing, and extension, can be optimized by trying various settings and using the parameters that yield the best results. Schematics of the PCR products for SNP HC21S00027 and SNP TSC095512 are shown in FIGS. 5A–5D.

Purification of Fragment Containing Locus of Interest

The PCR products were separated from the genomic template DNA. Each PCR product was divided into four separate reaction wells of a Streptawell, transparent, High-Bind plate from Roche Diagnostics GmbH (catalog number 1 645 692, as listed in Roche Molecular Biochemicals, 2001 Biochemicals Catalog). The first primers contained a 5' biotin tag so the PCR products bound to the Streptavidin coated wells while the genomic template DNA did not. The streptavidin binding reaction was performed using a Thermomixer (Eppendorf) at 1000 rpm for 20 min. at 37° C. Each well was aspirated to remove unbound material, and washed three times with 1× PBS, with gentle mixing (Kandpal et al., Nucl. Acids Res. 18:1789–1795 (1990); Kaneoka et al., Biotechniques 10:30–34 (1991); Green et al., Nucl. Acids Res. 18:6163–6164 (1990)).

Restriction Enzyme Digestion of Isolated Fragments Containing Loci of Interest

The purified PCR products were digested with the restriction enzyme that bound the recognition site incorporated into the PCR products from the second primer. DNA templates containing SNP HC21S00027 (FIGS. 6A and 6B) and SNP TSC0095512 (FIGS. 6C and 6D) were amplified in separate reactions using two different second primers. FIG. 6A (SNP HC21S00027) and FIG. 6C (SNP TSC0095512) depict the PCR products after digestion with the restriction enzyme BsmF I (New England Biolabs catalog number R0572S). FIG. 6B (SNP HC21S00027) and FIG. 6D (SNP TSC0095512) depict the PCR products after digestion with the restriction enzyme BceA I (New England Biolabs, catalog number R0623S). The digests were performed in the Streptawells following the instructions supplied with the restriction enzyme. The DNA fragment containing SNP TSC0264580 was digested with BsmF I. After digestion with the appropriate restriction enzyme, the wells were washed three times with PBS to remove the cleaved fragments.

Incorporation of Labeled Nucleotide

The restriction enzyme digest described above yielded a DNA fragment with a 5' overhang, which contained the SNP site or locus of interest and a 3' recessed end. The 5' overhang functioned as a template allowing incorporation of a nucleotide or nucleotides in the presence of a DNA polymerase.

For each SNP, four separate fill in reactions were performed; each of the four reactions contained a different fluorescently labeled ddNTP (ddATP, ddTTP, ddGTP, or ddCTP). The following components were added to each fill in reaction: 1 µl of a fluorescently labeled ddNTP, 0.5 µl of unlabeled ddNTPs (40 µM), which contained all nucleotides except the nucleotide that was fluorescently labeled, 2 µl of 10× sequenase buffer, 0.25 µl of Sequenase, and water as needed for a 20 µl reaction. All of the fill in reactions were performed at 40° C. for 10 min. Non-fluorescently labeled ddNTP was purchased from Fermentas Inc. (Hanover, Md.). All other labeling reagents were obtained from Amersham (Thermo Sequenase Dye Terminator Cycle Sequencing Core Kit, US 79565). In the presence of fluorescently labeled ddNTPs, the 3' recessed end was extended by one base, which corresponds to the SNP or locus of interest (FIGS. 7A–7D).

A mixture of labeled ddNTPs and unlabeled dNTPs also was used for the "fill in" reaction for SNP HC21S00027. The "fill in" conditions were as described above except that a mixture containing 40 µM unlabeled dNTPs, 1 µl fluorescently labeled ddATP, 1 µl fluorescently labeled ddTTP, 1 µl fluorescently labeled ddCTP, and 1 µl ddGTP was used. The fluorescent ddNTPs were obtained from Amersham (Thermo Sequenase Dye Terminator Cycle Sequencing Core Kit, US 79565; Amersham did not publish the concentrations of the fluorescent nucleotides). The DNA fragment containing SNP HC21S00027 was digested with the restriction enzyme BsmF I, which generated a 5' overhang of four bases. As shown in FIG. 7E, if the first nucleotide incorporated is a labeled ddNTP, the 3' recessed end is filled in by one base, allowing detection of the SNP or locus of interest. However, if the first nucleotide incorporated is a dNTP, the polymerase continues to incorporate nucleotides until a ddNTP is filled in. For example, the first two nucleotides may be filled in with dNTPs, and the third nucleotide with a ddNTP, allowing detection of the third nucleotide in the overhang. Thus, the sequence of the entire 5' overhang may be determined, which increases the information obtained from each SNP or locus of interest.

After labeling, each Streptawell was rinsed with 1× PBS (100 µl) three times. The "filled in" DNA fragments were then released from the Streptawells by digestion with the restriction enzyme EcoRI, according to the manufacturer's instructions that were supplied with the enzyme (FIGS. 8A–8D). Digestion was performed for 1 hour at 37° C. with shaking at 120 rpm.

Detection of the Locus of Interest

After release from the streptavidin matrix, 2–3 µl of the 10 µl sample was loaded in a 48 well membrane tray (The Gel Company, catalog number TAM48-01). The sample in the tray was absorbed with a 48 Flow Membrane Comb (The Gel Company, catalog number AM48), and inserted into a 36 cm 5% acrylamide (urea) gel (BioWhittaker Molecular Applications, Long Ranger Run Gel Packs, catalog number 50691).

The sample was electrophoresed into the gel at 3000 volts for 3 min. The membrane comb was removed, and the gel was run for 3 hours on an ABI 377 Automated Sequencing Machine. The incorporated labeled nucleotide was detected by fluorescence.

As shown in FIG. 9A, from a sample of thirty six (36) individuals, one of two nucleotides, either adenosine or guanine, was detected at SNP HC21S00027. These are the two nucleotides reported to exist at SNP HC21S00027 (www.snp.schl.org/snpsearch.shtml). One of two nucleotides, either guanine or cytosine, was detected at SNP TSC0095512 (FIG. 9B). The same results were obtained whether the locus of interest was amplified with a second primer that contained a recognition site for BceA I or the second primer contained a recognition site for BsmF I.

As shown in FIG. 9C, one of two nucleotides was detected at SNP TSC0264580, which was either adenosine or cytosine. These are the two nucleotides reported for this SNP site (www.snp.schl.org/snpsearch.shtml). In addition, a thymidine was detected one base upstream of the locus of interest. In a sequence dependent manner, BsmF I cuts some DNA molecules at the 10/14 position and other DNA molecules, which have the same sequence, at the 11/15 position. When the restriction enzyme BsmF I cuts 11 nucleotides away on the sense strand and 15 nucleotides away on the antisense strand, the 3' recessed end is one base upstream of the SNP site. The sequence of SNP TSC0264580 indicated that the base immediately preceding the SNP site was a thymidine. The incorporation of a labeled ddNTP into this position generated a fragment one base smaller than the fragment that was cut at the 10/14 position. Thus, the DNA molecules cut at the 11/15 position provided identity information about the base immediately preceding the SNP site, and the DNA molecules cut at the 10/14 position provided identity information about the SNP site.

SNP HC21S00027 was amplified using a second primer that contained the recognition site for BsmF I. A mixture of labeled ddNTPs and unlabeled dNTPs was used to fill in the 5' overhang generated by digestion with BsmF I. If a dNTP was incorporated, the polymerase continued to incorporate nucleotides until a ddNTP was incorporated. A population of DNA fragments, each differing by one base, was generated, which allowed the full sequence of the overhang to be determined.

As seen in FIG. 9D, an adenosine was detected, which was complementary to the nucleotide (a thymidine) immediately preceding the SNP or locus of interest. This nucleotide was detected because of the 11/15 cutting property of BsmF I, which is described in detail above. A guanine and an adenosine were detected at the SNP site, which are the two nucleotides reported for this SNP site (FIG. 9A). The two nucleotides were detected at the SNP site because the molecular weights of the dyes differ, which allowed separation of the two nucleotides. The next nucleotide detected was a thymidine, which is complementary to the nucleotide immediately downstream of the SNP site. The next nucleotide detected was a guanine, which was complementary to the nucleotide two bases downstream of the SNP site. Finally, an adenosine was detected, which was complementary to the third nucleotide downstream of the SNP site. Sequence information was obtained not only for the SNP site but for the nucleotide immediately preceding the SNP site and the next three nucleotides.

including but not limited to a point mutation, insertion, deletion, translocation or any combination of said mutations, it could be identified by comparison to the consensus or published sequence. Comparison of the sequences attributed to each of the loci of interest to the native, non-disease related sequence of the gene at each locus of interest determines the presence or absence of a mutation in that sequence. The finding of a mutation in the sequence is then interpreted as the presence of the indicated disease, or a predisposition to develop the same, as appropriate, in that individual. The relative amounts of the mutated vs. normal or non-mutated sequence can be assessed to determine if the subject has one or two alleles of the mutated sequence, and thus whether the subject is a carrier, or whether the indicated mutation results in a dominant or recessive condition.

Example 3

Four loci of interest from chromosome 1 and two loci of interest from chromosome 21 were amplified in separate PCR reactions, pooled together, and analyzed. The primers were designed so that each amplified locus of interest was a different size, which allowed detection of the loci of interest.

Preparation of Template DNA

The template DNA was prepared from a 5 ml sample of blood obtained by venipuncture from a human volunteer with informed consent. Template DNA was isolated using the QIAmp DNA Blood Midi Kit supplied by QIAGEN (Catalog number 51183). The template DNA was isolated as per instructions included in the kit. Template DNA was isolated from thirty-six human volunteers, and then pooled into a single sample for further analysis.

Design of Primers

```
SNP TSC 0087315 was amplified using the following primers:
First primer:  5' TTACAATGCATGAATTCATCTTGGTCTCTCAAAGTGC 3'   (SEQ ID NO:15)

Second primer: 5' TGGACCATAAACGGCCAAAAACTGTAAG 3'            (SEQ ID NO:16)

SNP TSC0214366 was amplified using the following primers:
First primer:  5' ATGACTAGCTATGAATTCGTTCAAGGTAGAAAATGGAA 3'  (SEQ ID NO:13)

Second primer: 5' GAGAATTAGAACGGCCCAAATCCCACTC 3'            (SEQ ID NO:14)

SNP TSC 0413944 was amplified with the following primers:
First primer:  5' TACCTTTTGATCGAATTCAAGGCCAAAAATATTAAGTT 3'  (SEQ ID NO:23)

Second primer: 5' TCGAACTTTAACGGCCTTAGAGTAGAGA 3'            (SEQ ID NO:24)

SNP TSC0095512 was amplified using the following primers:
First primer:  5' AAGTTTAGATCAGAATTCGTGAAAGCAGAAGTTGTCTG 3' (SEQ ID NO:11)

Second primer: 5' TCTCCAACTAACGGCTCATCGAGTAAAG 3'            (SEQ ID NO:12)

SNP HC21S00131 was amplified with the following primers:
First primer:  5' CGATTTCGATAAGAATTCAAAAGCAGTTCTTAGTTCAG 3' (SEQ ID NO:25)

Second primer: 5' TGCGAATCTTACGGCTGCATCACATTCA 3'            (SEQ ID NO:26)
```

None of the loci of interest contained a mutation. However, if one of the loci of interest harbored a mutation SNP HC21S00027 was amplified with the following primers:

```
SNP HC21S00027 was amplified with the following primers:
First primer:  5' ATAACCGTATGCGAATTCTATAATTTTCCTGATAAAGG 3' (SEQ ID NO:17)

Second primer: 5' CTTAAATCAGACGGCTAGGTAAACTTCA 3'            (SEQ ID NO:19)
```

For each SNP, the first primer contained a recognition site for the restriction enzyme EcoRI and had a biotin tag at the extreme 5' end. The second primer used to amplify each SNP contained a recognition site for the restriction enzyme BceA I.

PCR Reaction

The PCR reactions were performed as described in Example 2 except that the following annealing temperatures were used: the annealing temperature for the first cycle of PCR was 37° C. for 30 seconds, the annealing temperature for the second cycle of PCR was 57° C. for 30 seconds, and the annealing temperature for the third cycle of PCR was 64° C. for 30 seconds. All subsequent cycles had an annealing temperature of 64° C. for 30 seconds. Thirty seven (37) cycles of PCR were performed. After PCR, ¼ of the volume was removed from each reaction, and combined into a single tube.

Purification of Fragment Containing Locus of Interest

The PCR products (now combined into one sample, and referred to as "the sample") were separated from the genomic template DNA as described in Example 2 except that the sample was bound to a single well of a Streptawell microtiter plate.

Restriction Enzyme Digestion of Isolated Fragments Containing Loci of Interest

The sample was digested with the restriction enzyme BceA I, which bound the recognition site in the second primer. The restriction enzyme digestions were performed following the instructions supplied with the enzyme. After the restriction enzyme digest, the wells were washed three times with 1× PBS.

Incorporation of Nucleotides

The restriction enzyme digest described above yielded DNA molecules with a 5' overhang, which contained the SNP site or locus of interest and a 3' recessed end. The 5' overhang functioned as a template allowing incorporation of a nucleotide in the presence of a DNA polymerase.

The following components were used for the fill in reaction: 1 μl of fluorescently labeled ddATP; 1 μl of fluorescently labeled ddTTP; 1 μl of fluorescently labeled ddGTP; 1 μl of fluorescently labeled ddCTP; 2 μl of 10× sequenase buffer, 0.25 μl of Sequenase, and water as needed for a 20 μl reaction. The fill in reaction was performed at 40° C. for 10 min. All labeling reagents were obtained from Amersham (Thermo Sequenase Dye Terminator Cycle Sequencing Core Kit (US 79565); the concentration of the ddNTPS provided in the kit is proprietary and not published by Amersham). In the presence of fluorescently labeled ddNTPs, the 3' recessed end was filled in by one base, which corresponds to the SNP or locus of interest.

After the incorporation of nucleotide, the Streptawell was rinsed with 1× PBS (100 μl) three times. The "filled in" DNA fragments were then released from the Streptawell by digestion with the restriction enzyme EcoRI following the manufacturer's instructions. Digestion was performed for 1 hour at 37° C. with shaking at 120 rpm.

Detection of the Locus of Interest

After release from the streptavidin matrix, 2–3 μl of the 10 μl sample was loaded in a 48 well membrane tray (The Gel Company, catalog number TAM48-01). The sample in the tray was absorbed with a 48 Flow Membrane Comb (The Gel Company, catalog number AM48), and inserted into a 36 cm 5% acrylamide (urea) gel (BioWhittaker Molecular Applications, Long Ranger Run Gel Packs, catalog number 50691).

The sample was electrophoresed into the gel at 3000 volts for 3 min. The membrane comb was removed, and the gel was run for 3 hours on an ABI 377 Automated Sequencing Machine. The incorporated nucleotide was detected by fluorescence.

The primers were designed so that each amplified locus of interest differed in size. As shown in FIG. 10, each amplified loci of interest differed by about 5–10 nucleotides, which allowed the loci of interest to be separated from one another by gel electrophoresis. Two nucleotides were detected for SNP TSC0087315, which were guanine and cytosine. These are the two nucleotides reported to exist at SNP TSC0087315 (www.snp.schl.org/snpsearch.shtml). The sample comprised template DNA from 36 individuals and because the DNA molecules that incorporated a guanine differed in molecular weight from those that incorporated a cytosine, distinct bands were seen for each nucleotide.

Two nucleotides were detected at SNP HC21S00027, which were guanine and adenosine (FIG. 10). The two nucleotides reported for this SNP site are guanine and adenosine (www.snp.schl.org/snpsearch.shtml). As discussed above, the sample contained template DNA from thirty-six individuals, and one would expect both nucleotides to be represented in the sample. The molecular weight of the DNA fragments that incorporated a guanine was distinct from the DNA fragments that incorporated an adenosine, which allowed both nucleotides to be detected.

The nucleotide cytosine was detected at SNP TSC0214366 (FIG. 10). The two nucleotides reported to exist at this SNP position are thymidine and cytosine.

The nucleotide guanine was detected at SNP TSC0413944 (FIG. 10). The two nucleotides reported for this SNP are guanine and cytosine (http://snp.cshl.org/snpsearch.shtml).

The nucleotide cytosine was detected at SNP TSC0095512 (FIG. 10). The two nucleotides reported for this SNP site are guanine and cytosine (www.snp.schl.org/snpsearch.shtml).

The nucleotide detected at SNP HC21S00131 was guanine. The two nucleotides reported for this SNP site are guanine and adenosine (www.snp.schl.org/snpsearch.shtml).

As discussed above, the sample was comprised of DNA templates from thirty-six individuals and one would expect both nucleotides at the SNP sites to be represented. For SNP TSC0413944, TSC0095512, TSC0214366 and HC21S00131, one of the two nucleotides was detected. It is likely that both nucleotides reported for these SNP sites are present in the sample but that one fluorescent dye overwhelms the other. The molecular weight of the DNA molecules that incorporated one nucleotide did not allow efficient separation of the DNA molecules that incorporated the other nucleotide. However, the SNPs were readily separated from one another, and for each SNP, a proper nucleotide was incorporated. The sequences of multiple loci of interest from multiple chromosomes, which were treated as a single sample after PCR, were determined.

A single reaction containing fluorescently labeled ddNTPs was performed with the sample that contained multiple loci of interest. Alternatively, four separate fill in reactions can be performed where each reaction contains one fluorescently labeled nucleotide (ddATP, ddTTP, ddGTP, or ddCTP) and unlabeled ddNTPs (see Example 2, FIGS. 7A–7D and FIGS. 9A–C). Four separate "fill in" reactions will allow detection of any nucleotide that is present at the loci of interest. For example, if analyzing a sample that contains multiple loci of interest from a single individual, and said individual is heterozygous at one or more than one loci of interest, four separate "fill in" reactions can be used to determine the nucleotides at the heterozygous loci of interest.

Also, when analyzing a sample that contains templates from multiple individuals, four separate "fill in" reactions will allow detection of nucleotides present in the sample, independent of how frequent the nucleotide is found at the locus of interest. For example, if a sample contains DNA templates from 50 individuals, and 49 of the individuals have a thymidine at the locus of interest, and one individual has a guanine, the performance of four separate "fill in" reactions, wherein each "fill in" reaction is run in a separate lane of a gel, such as in FIGS. 9A–9C, will allow detection of the guanine. When analyzing a sample comprised of multiple DNA templates, multiple "fill in" reactions will alleviate the need to distinguish multiple nucleotides at a single site of interest by differences in mass.

In this example, multiple single nucleotide polymorphisms were analyzed. It is also possible to determine the presence or absence of mutations, including point mutations, transitions, transversions, translocations, insertions, and deletions from multiple loci of interest. The multiple loci of interest can be from a single chromosome or from multiple chromosomes. The multiple loci of interest can be from a single gene or from multiple genes.

The sequence of multiple loci of interest that cause or predispose to a disease phenotype can be determined. For example, one could amplify one to tens to hundreds to thousands of genes implicated in cancer or any other disease. The primers can be designed so that each amplified loci of interest differs in size. After PCR, the amplified loci of interest can be combined and treated as a single sample. Alternatively, the multiple loci of interest can be amplified in one PCR reaction or the total number of loci of interest, for example 100, can be divided into samples, for example 10 loci of interest per PCR reaction, and then later pooled. As demonstrated herein, the sequence of multiple loci of interest can be determined. Thus, in one reaction, the sequence of one to ten to hundreds to thousands of genes that predispose or cause a disease phenotype can be determined.

Example 4

Genomic DNA was obtained from four individuals after informed consent was obtained. Six SNPs on chromosome 13 (TSC0837969, TSC0034767, TSC1130902, TSC0597888, TSC0195492, TSC0607185) were analyzed using the template DNA. Information regarding these SNPs can be found at the following website (www.snp.schl.org/snpsearch.shtml) website active as of Feb. 11, 2003).

A single nucleotide labeled with one fluorescent dye was used to genotype the individuals at the six selected SNP sites. The primers were designed to allow the six SNPs to be analyzed in a single reaction.

Preparation of Template DNA

The template DNA was prepared from a 9 ml sample of blood obtained by venipuncture from a human volunteer with informed consent. Template DNA was isolated using the QIAmp DNA Blood Midi Kit supplied by QIAGEN (Catalog number 51183). The template DNA was isolated as per instructions included in the kit.

Design of Primers

SNP TSC0837969 was amplified using the following primer set:
First primer: (SEQ ID NO: 30)
5' GGGCTAGTCTCCGAATTCCACCTATCCTACCAAATGTC 3'

Second primer: (SEQ ID NO: 31)
5' TAGCTGTAGTTAGGGACTGTTCTGAGCAC 3'

The first primer had a biotin tag at the 5' end and contained a restriction enzyme recognition site for EcoRI. The first primer was designed to anneal 44 bases from of the locus of interest. The second primer contained a restriction enzyme recognition site for BsmF I.

SNP TSC0034767 was amplified using the following primer set:
First primer: (SEQ ID NO: 32)
5' CGAATGCAAGGCGAATTCGTTAGTAATAACACAGTGCA 3'

Second primer: (SEQ ID NO: 33)
5' AAGACTGGATCCGGGACCATGTAGAATAC 3'

The first primer had a biotin tag at the 5' end and contained a restriction enzyme recognition site for EcoRI. The first primer was designed to anneal 50 bases from the locus of interest. The second primer contained a restriction enzyme recognition site for BsmF I.

SNP TSC1130902 was amplified using the following primer set:
First primer: (SEQ ID NO: 34)
5' TCTAACCATTGCGAATTCAGGGCAAGGGGGTGAGATC 3'

Second primer: (SEQ ID NO: 35)
5' TGACTTGGATCCGGGACAACGACTCATCC 3'

The first primer had a biotin tag at the 5' end and contained a restriction enzyme recognition site for EcoRI. The first primer was designed to anneal 60 bases from the locus of interest. The second primer contained a restriction enzyme recognition site for BsmF I.

SNP TSC0597888 was amplified using the following primer set:
First primer: (SEQ ID NO: 36)
5' ACCCAGGCGCCAGAATTCTTTAGATAAAGCTGAAGGGA 3'

Second primer: (SEQ ID NO: 37)
5' GTTACGGGATCCGGGACTCCATATTGATC 3'

The first primer had a biotin tag at the 5' end and contained a restriction enzyme recognition site for EcoRI. The first primer was designed to anneal 70 bases from the locus of interest. The second primer contained a restriction enzyme recognition site for BsmF I.

SNP TSC0195492 was amplified using the following primer set:
First primer: (SEQ ID NO: 38)
5' CGTTGGCTTGAGGAATTCGACCAAAAGAGCCAAGAGAA Second primer: (SEQ ID NO: 39)
5' AAAAAGGGATCCGGGACCTTGACTAGGAC 3'

The first primer had a biotin tag at the 5' end and contained a restriction enzyme recognition site for EcoRI.

The first primer was designed to anneal 80 bases from the locus of interest. The second primer contained a restriction enzyme recognition site for BsmF I.

```
SNP TSC0607185 was amplified using the following
primer set:
First                                    (SEQ ID NO: 40)
primer:
5' ACTTGATTCCGTGAATTCGTTATCAATAAATCTTACAT 3'

Second                                   (SEQ ID NO: 41)
primer:
5' CAAGTTGGATCCGGGACCCAGGGCTAACC 3'
```

The first primer had a biotin tag at the 5' end and contained a restriction enzyme recognition site for EcoRI. The first primer was designed to anneal 90 bases from the locus of interest. The second primer contained a restriction enzyme recognition site for BsmF I.

All loci of interest were amplified from the template genomic DNA using the polymerase chain reaction (PCR, U.S. Pat. Nos. 4,683,195 and 4,683,202, incorporated herein by reference). In this example, the loci of interest were amplified in separate reaction tubes but they could also be amplified together in a single PCR reaction. For increased specificity, a "hot-start" PCR was used. PCR reactions were performed using the HotStarTaq Master Mix Kit supplied by QIAGEN (catalog number 203443). The amount of template DNA and primer per reaction can be optimized for each locus of interest but in this example, 40 ng of template human genomic DNA and 5 μM of each primer were used. Forty cycles of PCR were performed. The following PCR conditions were used:

(1) 95° C. for 15 minutes and 15 seconds;
(2) 37° C. for 30 seconds;
(3) 95° C. for 30 seconds;
(4) 57° C. for 30 seconds;
(5) 95° C. for 30 seconds;
(6) 64° C. for 30 seconds;
(7) 95° C. for 30 seconds;
(8) Repeat steps 6 and 7 thirty nine (39) times;
(9) 72° C. for 5 minutes.

In the first cycle of PCR, the annealing temperature was about the melting temperature of the 3' annealing region of the second primers, which was 37° C. The annealing temperature in the second cycle of PCR was about the melting temperature of the 3' region, which anneals to the template DNA, of the first primer, which was 57° C. The annealing temperature in the third cycle of PCR was about the melting temperature of the entire sequence of the second primer, which was 64° C. The annealing temperature for the remaining cycles was 64° C. Escalating the annealing temperature from TM1 to TM2 to TM3 in the first three cycles of PCR greatly improves specificity. These annealing temperatures are representative, and the skilled artisan will understand the annealing temperatures for each cycle are dependent on the specific primers used.

The temperatures and times for denaturing, annealing, and extension, can be optimized by trying various settings and using the parameters that yield the best results. In this example, the first primer was designed to anneal at various distances from the locus of interest. The skilled artisan understands that the annealing location of the first primer can be 5–10, 11–15, 16–20, 21–25, 26–30, 31–35, 36–40, 41–45, 46–50, 51–55, 56–60, 61–65, 66–70, 71–75, 76–80, 81–85, 86–90, 91–95, 96–100, 101–105, 106–110, 111–115, 116–120, 121–125, 126–130, 131–140, 141–160, 161–180, 181–200, 201–220, 221–240, 241–260, 261–280, 281–300, 301–350, 351–400, 401–450, 451–500, or greater than 500 bases from the locus of interest.

Purification of Fragment Containing Locus of Interest

The PCR products were separated from the genomic template DNA. After the PCR reaction, ¼ of the volume of each PCR reaction from one individual was mixed together in a well of a Streptawell, transparent, High-Bind plate from Roche Diagnostics GmbH (catalog number 1 645 692, as listed in Roche Molecular Biochemicals, 2001 Biochemicals Catalog). The first primers contained a 5' biotin tag so the PCR products bound to the Streptavidin coated wells while the genomic template DNA did not. The streptavidin binding reaction was performed using a Thermomixer (Eppendorf) at 1000 rpm for 20 min. at 37° C. Each well was aspirated to remove unbound material, and washed three times with 1× PBS, with gentle mixing (Kandpal et al., Nucl. Acids Res. 18:1789–1795 (1990); Kaneoka et al., Biotechniques 10:30–34 (1991); Green et al., Nucl. Acids Res. 18:6163–6164 (1990)).

Restriction Enzyme Digestion of Isolated Fragments Containing Loci of Interest

The purified PCR products were digested with the restriction enzyme BsmF I, which binds to the recognition site incorporated into the PCR products from the second primer. The digests were performed in the Streptawells following the instructions supplied with the restriction enzyme. After digestion, the wells were washed three times with PBS to remove the cleaved fragments.

Incorporation of Labeled Nucleotide

The restriction enzyme digest with BsmF I yielded a DNA fragment with a 5' overhang, which contained the SNP site or locus of interest and a 3' recessed end. The 5' overhang functioned as a template allowing incorporation of a nucleotide or nucleotides in the presence of a DNA polymerase.

Below, a schematic of the 5' overhang for SNP TSC0837969 is shown. The entire DNA sequence is not reproduced, only the portion to demonstrate the overhang (where R indicates the variable site).

```
5' TTAA

3' AATT              R      A     C     A

Overhang position    1      2     3     4
```

The observed nucleotides for TSC0837969 on the 5' sense strand (here depicted as the top strand) are adenine and guanine. The third position in the overhang on the antisense strand corresponds to cytosine, which is complementary to guanine. As this variable site can be adenine or guanine, fluorescently labeled ddGTP in the presence of unlabeled dCTP, dTTP, and dATP was used to determine the sequence of both alleles. The fill-in reactions for an individual homozygous for guanine, homozygous for adenine or heterozygous are diagrammed below.

Homozygous for guanine at TSC 0837969:

| Allele 1 | 5'TTAA | G* | | | |
|---|---|---|---|---|---|
| | 3'AATT | C | A | C | A |
| Overhang position | | 1 | 2 | 3 | 4 |
| Allele 2 | 5'TTAA | G* | | | |
| | 3'AATT | C | A | C | A |
| Overhang position | | 1 | 2 | 3 | 4 |

Labeled ddGTP is incorporated into the first position of the overhang. Only one signal is seen, which corresponds to the molecules filled in with labeled ddGTP at the first position of the overhang.

Homozygous for adenine at TSC 0837969:

```
Allele 1              5'TTAA    A    T    G*
                      3'AATT    T    A    C    A
Overhang position               1    2    3    4

Allele 2              5'TTAA    A    T    G*
                      3'AATT    T    A    C    A
Overhang position               1    2    3    4
```

Unlabeled dATP is incorporated at position one of the overhang, and unlabeled dTTP is incorporated at position two of the overhang. Labeled ddGTP is incorporated at position three of the overhang. Only one signal will be seen; the molecules filled in with ddGTP at position 3 will have a different molecular weight from molecules filled in at position one, which allows easy identification of individuals homozygous for adenine or guanine.

Heterozygous at TSC0837969:

```
Allele 1              5'TTAA    G*
                      3'AATT    C    A    C    A
Overhang position               1    2    3    4

Allele 2              5'TTAA    A    T    G*
                      3'AATT    T    A    C    A
Overhang position               1    2    3    4
```

Two signals will be seen; one signal corresponds to the DNA molecules filled in with ddGTP at position 1, and a second signal corresponding to molecules filled in at position 3 of the overhang. The two signals can be separated using any technique that separates based on molecular weight including but not limited to gel electrophoresis.

Below, a schematic of the 5' overhang for SNP TSC0034767 is shown. The entire DNA sequence is not reproduced, only the portion to demonstrate the overhang (where R indicates the variable site).

```
    A    C    A    R    GTGT3'
                        CACA5'
    4    3    2    1    Overhang Position
```

The observed nucleotides for TSC0034767 on the 5' sense strand (here depicted as the top strand) are cytosine and guanine. The second position in the overhang corresponds to adenine, which is complementary to thymidine. The third position in the overhang corresponds to cytosine, which is complementary to guanine. Fluorescently labeled ddGTP in the presence of unlabeled dCTP, dTTP, and dATP is used to determine the sequence of both alleles.

In this case, the second primer anneals upstream of the locus of interest, and thus the fill-in reaction occurs on the anti-sense strand (here depicted as the bottom strand). Either the sense strand or the antisense strand can be filled in depending on whether the second primer, which contains the type IIS restriction enzyme recognition site, anneals upstream or downstream of the locus of interest.

Below, a schematic of the 5' overhang for SNP TSC1130902 is shown. The entire DNA sequence is not reproduced, only a portion to demonstrate the overhang (where R indicates the variable site).

```
5'TTCAT
3'AAGTA              R    T    C    C
Overhang position    1    2    3    4
```

The observed nucleotides for TSC1130902 on the 5' sense strand are adenine and guanine. The second position in the overhang corresponds to a thymidine, and the third position in the overhang corresponds to cytosine, which is complementary to guanine.

Fluorescently labeled ddGTP in the presence of unlabeled dCTP, dTTP, and dATP is used to determine the sequence of both alleles.

Below, a schematic of the 5' overhang for SNP TSC0597888 is shown. The entire DNA sequence is not reproduced, only the portion to demonstrate the overhang (where R indicates the variable site).

```
    T    C    T    R    ATTC3'
                        TAAG5'
    4    3    2    1    Overhang position
```

The observed nucleotides for TSC0597888 on the 5' sense strand (here depicted as the top strand) are cytosine and guanine. The third position in the overhang corresponds to cytosine, which is complementary to guanine. Fluorescently labeled ddGTP in the presence of unlabeled dCTP, dTTP, and dATP is used to determine the sequence of both alleles.

Below, a schematic of the 5' overhang for SNP TSC0607185 is shown. The entire DNA sequence is not reproduced, only the portion to demonstrate the overhang (where R indicates the variable site).

```
    C    C    T    R    TGTC3'
                        ACAG5'
    4    3    2    1    Overhang position
```

The observed nucleotides for TSC0607185 on the 5' sense strand (here depicted as the top strand) are cytosine and thymidine. In this case, the second primer anneals upstream of the locus of interest, which allows the anti-sense strand to be filled in. The anti-sense strand (here depicted as the bottom strand) will be filled in with guanine or adenine.

The second position in the 5' overhang is thymidine, which is complementary to adenine, and the third position in the overhang corresponds to cytosine, which is complementary to guanine. Fluorescently labeled ddGTP in the presence of unlabeled dCTP, dTTP, and dATP is used to determine the sequence of both alleles.

Below, a schematic of the 5' overhang for SNP TSC0195492 is shown. The entire DNA sequence is not reproduced, only the portion to demonstrate the overhang.

```
5'ATCT
3'TAGA               R    A    C    A
Overhang position    1    2    3    4
```

The observed nucleotides at this site are cytosine and guanine on the sense strand (here depicted as the top strand). The second position in the 5' overhang is adenine, which is complementary to thymidine, and the third position in the overhang corresponds to cytosine, which is complementary to guanine. Fluorescently labeled ddGTP in the presence of unlabeled dCTP, dTTP, and dATP was used to determine the sequence of both alleles.

As demonstrated above, the sequence of both alleles of the six SNPs can be determined by labeling with ddGTP in the presence of unlabeled dATP, dTTP, and dCTP. The following components were added to each fill in reaction: 1 µl of fluorescently labeled ddGTP, 0.5 µl of unlabeled ddNTPs (40 µM), which contained all nucleotides except guanine, 2 µl of 10× sequenase buffer, 0.25 µl of Sequenase, and water as needed for a 20 µl reaction. The fill in reaction was performed at 40° C. for 10 min. Non-fluorescently labeled ddNTP was purchased from Fermentas Inc. (Hanover, Md.). All other labeling reagents were obtained from Amersham (Thermo Sequenase Dye Terminator Cycle Sequencing Core Kit, US 79565).

After labeling, each Streptawell was rinsed with 1× PBS (100 µl) three times. The "filled in" DNA fragments were then released from the Streptawells by digestion with the restriction enzyme EcoRI, according to the manufacturer's instructions that were supplied with the enzyme. Digestion was performed for 1 hour at 37° C. with shaking at 120 rpm.

Detection of the Locus of Interest

After release from the streptavidin matrix, the sample was loaded into a lane of a 36 cm 5% acrylamide (urea) gel (BioWhittaker Molecular Applications, Long Ranger Run Gel Packs, catalog number 50691). The sample was electrophoresed into the gel at 3000 volts for 3 min. The gel was run for 3 hours on a sequencing apparatus (Hoefer SQ3 Sequencer). The gel was removed from the apparatus and scanned on the Typhoon 9400 Variable Mode Imager. The incorporated labeled nucleotide was detected by fluorescence.

As shown in FIG. 11, the template DNA in lanes 1 and 2 for SNP TSC0837969 is homozygous for adenine. The following fill-in reaction was expected to occur if the individual was homozygous for adenine:

Homozygous for adenine at TSC 0837969:

```
5'TTAA               A      T      G*
3'AATT               T      A      C      A
Overhang position    1      2      3      4
```

Unlabeled dATP was incorporated in the first position complementary to the overhang. Unlabeled dTTP was incorporated in the second position complementary to the overhang. Labeled ddGTP was incorporated in the third position complementary to the overhang. Only one band was seen, which migrated at about position 46 of the acrylamide gel. This indicated that adenine was the nucleotide filled in at position one. If the nucleotide guanine had been filled in, a band would be expected at position 44.

However, the template DNA in lanes 3 and 4 for SNP TSC0837969 was heterozygous. The following fill-in reactions were expected if the individual was heterozygous:

Heterozygous at TSC0837969:

```
Allele 1             5'TTAA    G*
                     3'AATT    C      A      C      A
Overhang position              1      2      3      4

Allele 2             5'TTAA    A      T      G*
                     3'AATT    T      A      C      A
Overhang position              1      2      3      4
```

Two distinct bands were seen; one band corresponds to the molecules filled in with ddGTP at position 1 complementary to the overhang (the G allele), and the second band corresponds to molecules filled in with ddGTP at position 3 complementary to the overhang (the A allele). The two bands were separated based on the differences in molecular weight using gel electrophoresis. One fluorescently labeled nucleotide ddGTP was used to determine that an individual was heterozygous at a SNP site. This is the first use of a single nucleotide to effectively detect the presence of two different alleles.

For SNP TSC0034767, the template DNA in lanes 1 and 3 is heterozygous for cytosine and guanine, as evidenced by the two distinct bands. The lower band corresponds to ddGTP filled in at position 1 complementary to the overhang. The second band of slightly higher molecular weight corresponds to ddGTP filled in at position 3, indicating that the first position in the overhang was filled in with unlabeled dCTP, which allowed the polymerase to continue to incorporate nucleotides until it incorporated ddGTP at position 3 complementary to the overhang. The template DNA in lanes 2 and 4 was homozygous for guanine, as evidenced by a single band of higher molecular weight than if ddGTP had been filled in at the first position complementary to the overhang.

For SNP TSC1130902, the template DNA in lanes 1, 2, and 4 is homozygous for adenine at the variable site, as evidenced by a single higher molecular weight band migrating at about position 62 on the gel. The template DNA in lane 3 is heterozygous at the variable site, as indicated by the presence of two distinct bands. The lower band corresponded to molecules filled in with ddGTP at position 1 complementary to the overhang (the guanine allele). The higher molecular weight band corresponded to molecules filled in with ddGTP at position 3 complementary to the overhang (the adenine allele).

For SNP TSC0597888, the template DNA in lanes 1 and 4 was homozygous for cytosine at the variable site; the template DNA in lane 2 was heterozygous at the variable site, and the template DNA in lane 3 was homozygous for guanine. The expected fill-in reactions are diagrammed below:

Homozygous for Cytosine:

```
Allele 1    T      C      T      G    ATTC 3'
                   G*     A      C    TAAG 5'
            4      3      2      1    Overhang position Allele 2    T      C      T      G    ATTC 3'
                   G*     A      C    TAAG 5'
            4      3      2      1    Overhang position
```

Homozygous for Guanine:

```
Allele 1    T      C      T      C    ATTC 3'
                                 G*   TAAG 5'
            4      3      2      1    Overhang position Allele 2    T      C      T      C    ATTC 3'
                                 G*   TAAG 5'
            4      3      2      1    Overhang position
```

Heterozygous for Guanine/Cytosine:

```
Allele 1    T      C      T      G    ATTC 3'
                   G*     A      C    TAAG 5'
            4      3      2      1    Overhang position
```

-continued

```
Allele 2   T      C      T      C      ATTC 3'

G*     TAAG 5'

4             3      2      1     Overhang position
```

Template DNA homozygous for guanine at the variable site displayed a single band, which corresponded to the DNA molecules filled in with ddGTP at position 1 complementary to the overhang. These DNA molecules were of lower molecular weight compared to the DNA molecules filled in with ddGTP at position 3 of the overhang (see lane 3 for SNP TSC0597888). The DNA molecules differed by two bases in molecular weight.

Template DNA homozygous for cytosine at the variable site displayed a single band, which corresponds to the DNA molecules filled in with ddGTP at position 3 complementary to the overhang. These DNA molecules migrated at a higher molecular weight than DNA molecules filled in with ddGTP at position 1 (see lanes 1 and 4 for SNP TSC0597888).

Template DNA heterozygous at the variable site displayed two bands; one band corresponded to the DNA molecules filled in with ddGTP at position 1 complementary to the overhang and was of lower molecular weight, and the second band corresponded to DNA molecules filled in with ddGTP at position 3 complementary to the overhang, and was of higher molecular weight (see lane 3 for SNP TSC0597888).

For SNP TSC0195492, the template DNA in lanes 1 and 3 was heterozygous at the variable site, which was demonstrated by the presence of two distinct bands. The template DNA in lane 2 was homozygous for guanine at the variable site. The template DNA in lane 4 was homozygous for cytosine. Only one band was seen in lane 4 for this SNP, and it had a higher molecular weight than the DNA molecules filled in with ddGTP at position 1 complementary to the overhang (compare lanes 2, 3 and 4).

The observed alleles for SNP TSC0607185 are reported as cytosine or thymidine. For consistency, the SNP consortium denotes the observed alleles as they appear in the sense strand (www.snp.schl.org/snpsearch.shtml); website active as of Feb. 11, 2003). For this SNP, the second primer annealed upstream of the locus of interest, which allowed the fill-in reaction to occur on the antisense strand after digestion with BsmF I.

The template DNA in lanes 1 and 3 was heterozygous; the template DNA in lane 2 was homozygous for thymidine, and the template DNA in lane 4 was homozygous for cytosine. The antisense strand was filled in with ddGTP, so the nucleotide on the sense strand corresponded to cytosine.

Molecular weight markers can be used to identify the positions of the expected bands. Alternatively, for each SNP analyzed, a known heterozygous sample can be used, which will identify precisely the position of the two expected bands.

As demonstrated in FIG. 11, one nucleotide labeled with one fluorescent dye can be used to determine the identity of a variable site including but not limited to SNPs and single nucleotide mutations. Typically, to determine if an individual is homozygous or heterozygous at a SNP site, multiple reactions are performed using one nucleotide labeled with one dye and a second nucleotide labeled with a second dye. However, this introduces problems in comparing results because the two dyes have different quantum coefficients. Even if different nucleotides are labeled with the same dye, the quantum coefficients are different. The use of a single nucleotide labeled with one dye eliminates any errors from the quantum coefficients of different dyes.

In this example, fluorescently labeled ddGTP was used. However, the method is applicable for a nucleotide tagged with any signal generating moiety including but not limited to radioactive molecule, fluorescent molecule, antibody, antibody fragment, hapten, carbohydrate, biotin, derivative of biotin, phosphorescent moiety, luminescent moiety, electrochemiluminescent moiety, chromatic moiety, and moiety having a detectable electron spin resonance, electrical capacitance, dielectric constant or electrical conductivity. In addition, labeled ddATP, ddTTP, or ddCTP can be used.

The above example used the third position complementary to the overhang as an indicator of the second allele. However, the second or fourth position of the overhang can be used as well (see Section on Incorporation of Nucleotides). Furthermore, the overhang was generated with the type IIS enzyme BsmF I; however any enzyme that cuts DNA at a distance from its binding site can be used including but not limited to the enzymes listed in Table I.

Also, in the above example, the nucleotide immediately preceding the SNP site was not a guanine on the strand that was filled in. This eliminated any effects of the alternative cutting properties of the type IIS restriction enzyme to be removed. For example, at SNP TSC0837969, the nucleotide upstream of the SNP site on the sense strand was an adenine. If BsmF I displayed alternate cutting properties, the following overhangs would be generated for the adenine allele and the guanine allele:

```
G allele - 11/15 Cut      5' TTA

3' AAT    T    C    A    C

Overhang position                   0    1    2    3

G allele after fill-in    5' TTA    A    G*

3' AAT    T    C    A    C
Overhang position                   0    1    2    3

A allele 11/15 Cut        5' TTA

3' AAT    T    T    A    C

Overhang position                   0    1    2    3

A allele after fill-in    5' TTA    A    A    T    G*

3' AAT    T    T    A    C

Overhang position                   0    1    2    3
```

For the guanine allele, the first position in the overhang would be filled in with dATP, which would allow the polymerase to incorporate ddGTP at position 2 complementary to the overhang. There would be no detectable difference between molecules cut at the 10/14 position or molecules cut at the 11/15 position.

For the adenine allele, the first position complementary to the overhang would be filled in with dATP, the second position would be filled in with dATP, the third position would be filled in with dTTP, and the fourth position would be filled in with ddGTP. There would be no difference in the molecular weights between molecules cut at 10/14 or molecules cut at 11/15. The only differences would correspond to whether the DNA molecules contained an adenine at the variable site or a guanine at the variable site.

As seen in FIG. 11, positioning the annealing region of the first primer allows multiple SNPs to be analyzed in a single lane of a gel. Also, when using the same nucleotide with the same dye, a single fill-in reaction can be performed. In this example, 6 SNPs were analyzed in one lane. However, any number of SNPs including but not limited to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 30–40, 41–50, 51–60, 61–70, 71–80, 81–100, 101–120, 121–140, 141–160, 161–180, 181–200, and greater than 200 can be analyzed in a single reaction.

Furthermore, one labeled nucleotide used to detect both alleles can be mixed with a second labeled nucleotide used to detect a different set of SNPs provided that neither of the nucleotides that are labeled occur immediately before the variable site (complementary to nucleotide at position 0 of the 11/15 cut). For example, suppose SNP X can be guanine or thymidine at the variable site and has the following 5' overhang generated after digestion with BsmF I:

| | | | | | |
|---|---|---|---|---|---|
| SNP X 10/14 | 5' TTGAC | | | | |
| G allele | 3' AACTG | C | A | C | T |
| Overhang position | | 1 | 2 | 3 | 4 |
| SNP X 11/15 | 5' TTGA | | | | |
| G allele | 3' AACT | G | C | A | C |
| Overhang position | | 0 | 1 | 2 | 3 |
| SNP X 10/14 | 5' TTGAC | | | | |
| T allele | 3' AACTG | A | A | C | T |
| Overhang position | | 1 | 2 | 3 | 4 |
| SNP X 11/15 | 5' TTGA | | | | |
| T allele | 3' AACT | G | A | A | C |
| Overhang position | | 0 | 1 | 2 | 3 |

After the fill-in reaction with labeled ddGTP, unlabeled dATP, dCTP, and dTTP, the following molecules would be generated:

| | | | | | |
|---|---|---|---|---|---|
| SNP X 10/14 | 5' TTGAC | G* | | | |
| G allele | 3' AACTG | C | A | C | T |
| Overhang position | | 1 | 2 | 3 | 4 |
| SNP X 11/15 | 5' TTGA | C | G* | | |
| G allele | 3' AACT | G | C | A | C |
| Overhang position | | 0 | 1 | 2 | 3 |
| SNP X 10/14 | 5' TTGAC | T | T | G* | |
| T allele | 3' AACTG | A | A | C | T |
| Overhang position | | 1 | 2 | 3 | 4 |
| SNP X 11/15 | 5' TTGA | C | T | T | G* |
| T allele | 3' AACT | G | A | A | C |
| Overhang position | | 0 | 1 | 2 | 3 |

Now suppose SNP Y can be adenine or thymidine and has the following 5' overhangs generated after digestion with BsmF I.

| | | | | | |
|---|---|---|---|---|---|
| SNP Y 10/14 | 5' GTTT | | | | |
| A allele | 3' CAAA | T | G | T | A |
| Overhang position | | 1 | 2 | 3 | 4 |
| SNP Y 11/15 | 5' GTT | | | | |
| A allele | 3' CAA | A | T | G | T |
| Overhang position | | 0 | 1 | 2 | 3 |
| SNP Y 10/14 | 5' GTTT | | | | |
| T allele | 3' CAAA | A | G | T | A |
| Overhang position | | 1 | 2 | 3 | 4 |
| SNP Y 11/15 | 5' GTT | | | | |
| T allele | 3' CAA | A | A | G | T |
| Overhang position | | 0 | 1 | 2 | 3 |

After fill-in with labeled ddATP and unlabeled dCTP, dGTP, and dTTP, the following molecules would be generated:

| | | | | | |
|---|---|---|---|---|---|
| SNP Y 10/14 | 5' GTTT | A* | | | |
| A allele | 3' CAAA | T | G | T | A |
| Overhang position | | 1 | 2 | 3 | 4 |
| SNP Y 11/15 | 5' GTT | T | A* | | |
| A allele | 3' CAA | A | T | G | T |
| Overhang position | | 0 | 1 | 2 | 3 |
| SNP Y 10/14 | 5' GTTT | T | C | A* | |
| T allele | 3' CAAA | A | G | T | A |
| Overhang position | | 1 | 2 | 3 | 4 |
| SNP Y 11/15 | 5' GTT | T | T | C | A* |
| T allele | 3' CAA | A | A | G | T |
| Overhang position | | 0 | 1 | 2 | 3 |

In this example, labeled ddGTP and labeled ddATP are used to determine the identity of both alleles of SNP X and SNP Y respectively. The nucleotide immediately preceding (the complementary nucleotide to position 0 of the overhang from the 11/15 cut SNP X is not guanine or adenine on the strand that is filled-in. Likewise, the nucleotide immediately preceding SNP Y is not guanine or adenine on the strand that is filled-in. This allows the fill-in reaction for both SNPs to occur in a single reaction with labeled ddGTP, labeled ddATP, and unlabeled dCTP and dTTP. This reduces the number of reactions that need to be performed and increases the number of SNPs that can be analyzed in one reaction.

The first primers for each SNP can be designed to anneal at different distances from the locus of interest, which allows the SNPs to migrate at different positions on the gel. For example, the first primer used to amplify SNP X can anneal at 30 bases from the locus of interest, and the first primer used to amplify SNP Y can anneal at 35 bases from the locus of interest. Also, the nucleotides can be labeled with fluorescent dyes that emit at spectrums that do not overlap. After running the gel, the gel can be scanned at one wavelength specific for one dye. Only those molecules labeled with that dye will emit a signal. The gel then can be scanned at the wavelength for the second dye. Only those molecules labeled with that dye will emit a signal. This method allows maximum compression for the number of SNPs that can be analyzed in a single reaction.

In this example, the nucleotide preceding the variable site on the strand that was filled-in is not be adenine or guanine. This method can work with any combination of labeled nucleotides, and the skilled artisan would understand which labeling reactions can be mixed and those that can not. For instance, if one SNP is labeled with thymidine and a second SNP is labeled with cytosine, the SNPs can be labeled in a single reaction if the nucleotide immediately preceding each variable site is not thymidine or cytosine on the sense strand and the nucleotide immediately after the variable site is not thymidine or cytosine on the sense strand.

This method allows the signals from one allele to be compared to the signal from a second allele without the added complexity of determining the degree of alternate cutting, or having to correct for the quantum coefficients of the dyes. This method is especially useful when trying to quantitate a ratio for one allele to another. For example, this method is useful for detecting chromosomal abnormalities. The ratio of alleles at a heterozygous site is expected to be about 1:1 (one A allele and one G allele). However, if an extra chromosome is present the ratio is expected to be about 1:2 (one A allele and 2 G alleles or 2 A alleles and 1 G allele). This method is especially useful when trying to detect fetal DNA in the presence of maternal DNA.

In addition, this method is useful for detecting two genetic signals in one sample. For example, this method can detect mutant cells in the presence of wild type cells (see Example 5). If a mutant cell contains a mutation in the DNA sequence of a particular gene, this method can be used to detect both the mutant signal and the wild type signal. This method can be used to detect the mutant DNA sequence in the presence of the wild type DNA sequence. The ratio of mutant DNA to wild type DNA can be quantitated because a single nucleotide labeled with one signal generating moiety is used.

Example 5

Non-invasive methods for the detection of various types of cancer have the potential to reduce morbidity and mortality from the disease. Several techniques for the early detection of colorectal tumors have been developed including colonoscopy, barium enemas, and sigmoidoscopy but are limited in use because the techniques are invasive, which causes a low rate of patient compliance. Non-invasive genetic tests may be useful in identifying early stage colorectal tumors.

In 1991, researchers identified the Adenomatous Polyposis Coli gene (APC), which plays a critical role in the formation of colorectal tumors (Kinzler et al., Science 253:661–665, 1991). The APC gene resides on chromosome 5q21-22 and a total of 15 exons code for an RNA molecule of 8529 nucleotides, which produces a 300 Kd APC protein. The protein is expressed in numerous cell types and is essential for cell adhesion.

Mutations in the APC gene generally initiate colorectal neoplasia (Tsao, J. et al., Am, J. Pathol. 145:531–534, 1994). Approximately 95% of the mutations in the APC gene result in nonsense/frameshift mutations. The most common mutations occur at codons 1061 and 1309; mutations at these codons account for ⅓ of all germline mutations. With regard to somatic mutations, 60% occur within codons 1286–1513, which is about 10% of the coding sequence. This region is termed the mutation Cluster Region (MCR). Numerous types of mutations have been identified in the APC gene including nucleotide substitutions (see Table III), splicing errors (see Table IV), small deletions (see Table V), small insertions (see Table VI), small insertions/deletions (see Table VII), gross deletions (see Table VIII), gross insertions (see Table IX), and complex rearrangements (see Table X).

Researchers have attempted to identify cells harboring mutations in the APC gene in stool samples (Traverso, G. et al., New England Journal of Medicine, Vol 346:311–320, 2002). While APC mutations are found in nearly all tumors, about 1 in 250 cells in the stool sample has a mutation in the APC gene; most of the cells are normal cells that have been shed into the feces. Furthermore, human DNA represents about one-billionth of the total DNA found in stool samples; the majority of DNA is bacterial. The technique employed by Traverso et al. only detects mutations that result in a truncated protein.

As discussed above, numerous mutations in the APC gene have been implicated in the formation of colorectal tumors. Thus, there still exists a need for a highly sensitive, non-invasive technique for the detection of colorectal tumors. Below, methods are described for detection of two mutations in the APC gene. However, any number of mutations can be analyzed using the methods described herein.

Preparation of Template DNA

The template DNA is purified from a sample containing colon cells including but not limited to a stool sample. The template DNA is purified using the procedures described by Ahlquist et al. (Gastroenterology, 119:1219–1227, 2000). If stool samples are frozen, the samples are thawed at room temperature, and homogenized with an Exactor stool shaker (Exact Laboratories, Maynard, Mass.) Following homogenization, a 4 gram stool equivalent of each sample is centrifuged at 2536×g for 5 minutes. The samples are centrifuged a second time at 16, 500×g for 10 minutes. Supernatants are incubated with 20 μl of RNase (0.5 mg per milliliter) for 1 hour at 37° C. DNA is precipitated with ⅒ volume of 3 mol of sodium acetate per liter and an equal volume of isopropanol. The DNA is dissolved in 5 ml of TRIS-EDTA (0.01 mol of Tris per liter (pH 7.4) and 0.001 mole of EDTA per liter.

Design of Primers

To determine if a mutation resides at codon 1370, the following primers are used:

```
First                                    (SEQ ID NO: 42)
primer:
5' GTGCAAAGGCCTGAATTCCCAGGCACAAAGCTGTTGAA 3'

Second                                   (SEQ ID NO: 43)
primer:
5' TGAAGCGAACTAGGGACTCAGGTGGACTT
```

The first primer contains a biotin tag at the extreme 5' end, and the nucleotide sequence for the restriction enzyme EcoRI. The second primer contains the nucleotide sequence for the restriction enzyme BsmF I.

To determine if a small deletion exists at codon 1302, the following primers are used:

```
First                                    (SEQ ID NO: 44)
primer:
5' GATTCCGTAAACGAATTCAGTTCATTATCATCTTTGTC 3'
```

```
-continued
Second                                    (SEQ ID NO: 45)
primer:
5' CCATTGTTAAGCGGGACTTCTGCTATTTG 3'
```

The first primer has a biotin tag at the 5' end and contains a restriction enzyme recognition site for EcoRI. The second primer contains a restriction enzyme recognition site for BsmF I.

PCR Reaction

The loci of interest are amplified from the template genomic DNA using the polymerase chain reaction (PCR, U.S. Pat. Nos. 4,683,195 and 4,683,202, incorporated herein by reference). The loci of interest are amplified in separate reaction tubes; they can also be amplified together in a single PCR reaction. For increased specificity, a "hot-start" PCR reaction is used, e.g. by using the HotStarTaq Master Mix Kit supplied by QIAGEN (catalog number 203443). The amount of template DNA and primer per reaction are optimized for each locus of interest but in this example, 40 ng of template human genomic DNA and 5 µM of each primer are used. Forty cycles of PCR are performed. The following PCR conditions are used:

(1) 95° C. for 15 minutes and 15 seconds;
(2) 37° C. for 30 seconds;
(3) 95° C. for 30 seconds;
(4) 57° C. for 30 seconds;
(5) 95° C. for 30 seconds;
(6) 64° C. for 30 seconds;
(7) 95° C. for 30 seconds;
(8) Repeat steps 6 and 7 thirty nine (39) times;
(9) 72° C. for 5 minutes.

In the first cycle of PCR, the annealing temperature is about the melting temperature of the 3' annealing region of the second primers, which is 37° C. The annealing temperature in the second cycle of PCR is about the melting temperature of the 3' region, which anneals to the template DNA, of the first primer, which is 57° C. The annealing temperature in the third cycle of PCR is about the melting temperature of the entire sequence of the second primer, which is 64° C. The annealing temperature for the remaining cycles is 64° C. Escalating the annealing temperature from TM1 to TM2 to TM3 in the first three cycles of PCR greatly improves specificity. These annealing temperatures are representative, and the skilled artisan understands that the annealing temperatures for each cycle are dependent on the specific primers used.

The temperatures and times for denaturing, annealing, and extension, are optimized by trying various settings and using the parameters that yield the best results.

Purification of Fragment Containing Locus of Interest

The PCR products are separated from the genomic template DNA. Each PCR product is divided into four separate reaction wells of a Streptawell, transparent, High-Bind plate from Roche Diagnostics GmbH (catalog number 1 645 692, as listed in Roche Molecular Biochemicals, 2001 Biochemicals Catalog). The first primers contain a 5' biotin tag so the PCR products bound to the Streptavidin coated wells while the genomic template DNA does not. The streptavidin binding reaction is performed using a Thermomixer (Eppendorf) at 1000 rpm for 20 min. at 37° C. Each well is aspirated to remove unbound material, and washed three times with 1× PBS, with gentle mixing (Kandpal et al., Nucl. Acids Res. 18:1789–1795 (1990); Kaneoka et al., Biotechniques 10:30–34 (1991); Green et al., Nucl. Acids Res. 18:6163–6164 (1990)).

Alternatively, the PCR products are placed into a single well of a streptavidin plate to perform the nucleotide incorporation reaction in a single well.

Restriction Enzyme Digestion of Isolated Fragments Containing Loci of Interest

The purified PCR products are digested with the restriction enzyme BsmF I (New England Biolabs catalog number R0572S), which binds to the recognition site incorporated into the PCR products from the second primer. The digests are performed in the Streptawells following the instructions supplied with the restriction enzyme. After digestion with the appropriate restriction enzyme, the wells are washed three times with PBS to remove the cleaved fragments.

Incorporation of Labeled Nucleotide

The restriction enzyme digest described above yields a DNA fragment with a 5' overhang, which contains the locus of interest and a 3' recessed end. The 5' overhang functions as a template allowing incorporation of a nucleotide or nucleotides in the presence of a DNA polymerase.

For each locus of interest, four separate fill in reactions are performed; each of the four reactions contains a different fluorescently labeled ddNTP (ddATP, ddTTP, ddGTP, or ddCTP). The following components are added to each fill in reaction: 1 µl of a fluorescently labeled ddNTP, 0.5 µl of unlabeled ddNTPs (40 EM), which contains all nucleotides except the nucleotide that is fluorescently labeled, 2 µl of 10× sequenase buffer, 0.25 µl of Sequenase, and water as needed for a 20 µl reaction. The fill are performed in reactions at 40° C. for 10 min. Non-fluorescently labeled ddNTP are purchased from Fermentas Inc. (Hanover, Md.). All other labeling reagents are obtained from Amersham (Thermo Sequenase Dye Terminator Cycle Sequencing Core Kit, US 79565). In the presence of fluorescently labeled ddNTPs, the 3' recessed end is extended by one base, which corresponds to the locus of interest.

A mixture of labeled ddNTPs and unlabeled dNTPs also can be used for the fill-in reaction. The "fill in" conditions are as described above except that a mixture containing 40 µM unlabeled dNTPs, 1 µl fluorescently labeled ddATP, 1 µl fluorescently labeled ddTTP, 1 µl fluorescently labeled ddCTP, and 1 µl ddGTP are used. The fluorescent ddNTPs are obtained from Amersham (Thermo Sequenase Dye Terminator Cycle Sequencing Core Kit, US 79565; Amersham does not publish the concentrations of the fluorescent nucleotides). The locus of interest is digested with the restriction enzyme BsmF I, which generates a 5' overhang of four bases. If the first nucleotide incorporated is a labeled ddNTP, the 3' recessed end is filled in by one base, allowing detection of the locus of interest. However, if the first nucleotide incorporated is a dNTP, the polymerase continues to incorporate nucleotides until a ddNTP is filled in. For example, the first two nucleotides may be filled in with dNTPs, and the third nucleotide with a ddNTP, allowing detection of the third nucleotide in the overhang. Thus, the sequence of the entire 5' overhang is determined, which increases the information obtained from each SNP or locus of interest. This type of fill in reaction is especially useful when detecting the presence of insertions, deletions, insertions and deletions, rearrangements, and translocations.

Alternatively, one nucleotide labeled with a single dye is used to determine the sequence of the locus of interest. See Example 4. This method eliminates any potential errors when using different dyes, which have different quantum coefficients.

After labeling, each Streptawell is rinsed with 1× PBS (100 µl) three times. The "filled in" DNA fragments are released from the Streptawells by digesting with the restriction enzyme EcoRI, according to the manufacturer's instructions that are supplied with the enzyme. The digestion is performed for 1 hour at 37° C. with shaking at 120 rpm.

Detection of the Locus of Interest

After release from the streptavidin matrix, the sample is loaded into a lane of a 36 cm 5% acrylamide (urea) gel (BioWhittaker Molecular Applications, Long Ranger Run Gel Packs, catalog number 50691). The sample is electrophoresed into the gel at 3000 volts for 3 min. The gel is run for 3 hours using a sequencing apparatus (Hoefer SQ3 Sequencer). The incorporated labeled nucleotide is detected by fluorescence.

To determine if any cells contain mutations at codon 1370 of the APC gene when separate fill-in reactions are performed, the lanes of the gel that correspond to the fill-in reaction for ddATP and ddTTP are analyzed. If only normal cells are present, the lane corresponding to the fill in reaction with ddATP is a bright signal. No signal is detected for the "fill-in" reaction with ddTTP. However, if the patient sample contains cells with mutations at codon 1370 of the APC gene, the lane corresponding to the fill in reaction with ddATP is a bright signal, and a signal is detected from the lane corresponding to the fill in reaction with ddTTP. The intensity of the signal from the lane corresponding to the fill in reaction with ddTTP is indicative of the number of mutant cells in the sample.

Alternatively, one labeled nucleotide is used to determine the sequence of the alleles at codon 1370 of the APC gene. At codon 1370, the normal sequence is AAA, which codes for the amino acid lysine. However, a nucleotide substitution has been identified at codon 1370, which is associated with colorectal tumors. Specifically, a change from A to T (AAA-TAA) typically is found at codon 1370, which results in a stop codon. A single fill-in reaction is performed using labeled ddATP, and unlabeled dTTP, dCTP, and dGTP. A single nucleotide labeled with one fluorescent dye is used to determine the presence of both the normal and mutant DNA sequence that codes for codon 1370. The relevant DNA sequence is depicted below with the sequence corresponding to codon 1370 in bold:

```
5' CCCAAAAGTCCACCTGA (SEQ ID NO: 46)

3' GGGTTTTCAGGTGGACT (SEQ ID NO: 47)
```

After digest with BsmF I, the following overhang is produced:

```
                  5' CCC

3' GGG      T  T  T  T

Overhang position             1  2  3  4
```

If the patient sample has no cells harboring a mutation at codon 1370, one signal is seen corresponding to incorporation of labeled ddATP.

```
                  5' CCC      A*

3' GGG      T  T  T  T

Overhang position             1  2  3  4
```

However, if the patient sample has cells with mutations at codon 1370 of the APC gene, one signal is seen, which corresponds to the normal sequence at codon 1370, and a second signal is seen, which corresponds to the mutant sequence at codon 1370. The signals clearly are identified as they differ in molecular weight.

```
Overhang of normal DNA sequence:    CCC
                                    GGG    T  T  T  T
Overhang position                          1  2  3  4

Normal DNA sequence after fill-in:  CCC    A*
                                    GGG    T  T  T  T
Overhang position                          1  2  3  4

Overhang of mutant DNA sequence:    CCC
                                    GGG    A  T  T  T
Overhang position                          1  2  3  4

Mutant DNA sequence after fill-in:  CCC    T  A*
                                    GGG    A  T  T  T
Overhang position                          1  2  3  4
```

Two signals are seen when the mutant allele is present. The mutant DNA molecules are filled in one base after the wild type DNA molecules. The two signals are separated using any method that discriminates based on molecular weight. One labeled nucleotide (ddATP) is used to detect the presence of both the wild type DNA sequence and the mutant DNA sequence. This method of labeling reduces the number of reactions that need to be performed and allows accurate quantitation for the number of mutant cells in the patient sample. The number of mutant cells in the sample is used to determine patient prognosis, the degree and the severity of the disease. This method of labeling eliminates the complications associated with using different dyes, which have distinct quantum coefficients. This method of labeling also eliminates errors associated with pipetting reactions.

To determine if any cells contain mutations at codon 1302 of the APC gene when separate fill-in reactions are performed, the lanes of the gel that correspond to the fill-in reaction for ddTTP and ddCTP are analyzed. The normal DNA sequence is depicted below with sequence coding for codon 1302 in bold type-face.

```
Normal Sequence:   5' ACCCTGCAAATAGCAGAA
                      (SEQ ID NO: 48)

3' TGGGACGTTTATCGTCTT
                      (SEQ ID NO: 49)
```

After digest, the following 5' overhang is produced:

```
                  5' ACCC

3' TGGG      A  C  G  T

Overhang position               1  2  3  4
```

After the fill-in reaction, labeled ddTTP is incorporated.

```
                  5' ACCC      T*

3' TGGG      A  C  G  T

Overhang position               1  2  3  4
```

A deletion of a single base of the APC sequence, which typically codes for codon 1302, has been associated with colorectal tumors. The mutant DNA sequence is depicted below with the relevant sequence in bold:

```
Mutant Sequence:    5' ACCCGCAAATAGCAGAA
                    (SEQ ID NO: 50)

3' TGGGCGTTTATCGTCTT
                    (SEQ ID NO: 51)

After digest:
                    5' ACC

3' TGG    G  C  G  T

Overhang position             1  2  3  4

After fill-in:
                    5' ACC    C*

3' TGG    G  C  G  T

Overhang position             1  2  3  4
```

If there are no mutations in the APC gene, signal is not detected for the fill in reaction with ddCTP*, but a bright signal is detected for the fill-in reaction with ddTTP*. However, if there are cells in the patient sample that have mutations in the APC gene, signals are seen for the fill-in reactions with ddCTP* and ddTTP*.

Alternatively, a single fill-in reaction is performed using a mixture containing unlabeled dNTPs, fluorescently labeled ddATP, fluorescently labeled ddTTP, fluorescently labeled ddCTP, and fluorescently labeled ddGTP. If there is no deletion, labeled ddTTP is incorporated.

```
                    5' ACCC   T*
                    3' TGGG   A  C  G  T
Overhang position             1  2  3  4
```

However, if the T has been deleted, labeled ddCTP* is incorporated.

```
                    5' ACC    C*
                    3' TGG    G  C  G  T
Overhang position             1  2  3  4
```

The two signals are separated by molecular weight because of the deletion of the thymidine nucleotide. If mutant cells are present, two signals are generated in the same lane but are separated by a single base pair (this principle is demonstrated in FIG. 9D). The deletion causes a change in the molecular weight of the DNA fragments, which allows a single fill in reaction to be used to detect the presence of both normal and mutant cells.

In the above example, methods for the detection of a nucleotide substitution and a small deletion are described. However, the methods are used for the detection of any type of mutation including but not limited to nucleotide substitutions (see Table III), splicing errors (see Table IV), small deletions (see Table V), small insertions (see Table VI), small insertions/deletions (see Table VII), gross deletions (see Table VIII), gross insertions (see Table IX), and complex rearrangements (see Table X).

In addition, the above-described methods are used for the detection of any type of disease including but not limited to those listed in Table II. Furthermore, any type of mutant gene is detected using the inventions described herein including but not limited to the genes associated with the diseases listed in Table II, BRCA1, BRCA2, MSH6, MSH2, MLH1, RET, PTEN, ATM, H-RAS, p53, ELAC2, CDH1, APC, AR, PMS2, MLH3, CYP1A1, GSTP1, GSTM1, AXIN2, CYP19, MET, NAT1, CDKN2A, NQ01, trc8, RAD51, PMS1, TGFBR2, VHL, MC4R, POMC, NROB2, UCP2, PCSK1, PPARG, ADRB2, UCP3, glur1, cart, SORBS1, LEP, LEPR, SIM1, TNF, IL-6, IL-1, IL-2, IL-3, IL1A, TAP2, THPO, THRB, NBS1, RBM15, LIF, MPL, RUNX1, Her-2, glucocorticoid receptor, estrogen receptor, thyroid receptor, p21, p27, K-RAS, N-RAS, retinoblastoma protein, Wiskott-Aldrich (WAS) gene, Factor V Leiden, Factor II (prothrombin), methylene tetrahydrofolate reductase, cystic fibrosis, LDL receptor, HDL receptor, superoxide dismutase gene, SHOX gene, genes involved in nitric oxide regulation, genes involved in cell cycle regulation, tumor suppressor genes, oncogenes, genes associated with neurodegeneration, genes associated with obesity. Abbreviations correspond to the proteins as listed on the Human Gene Mutation Database, which is incorporated herein by reference (www.archive.uwcm.ac.uk/uwcm) website address active as of Feb. 12, 2003).

The above-example demonstrates the detection of mutant cells and mutant alleles from a fecal sample. However, the methods described herein are used for detection of mutant cells from any biological sample including but not limited to blood sample, serum sample, plasma sample, urine sample, spinal fluid, lymphatic fluid, semen, vaginal secretion, ascitic fluid, saliva, mucosa secretion, peritoneal fluid, fecal sample, body exudates, breast fluid, lung aspirates, cells, tissues, individual cells or extracts of the such sources that contain the nucleic acid of the same, and subcellular structures such as mitochondria or chloroplasts. In addition, the methods described herein are used for the detection of mutant cells and mutated DNA from any number of nucleic acid containing sources including but not limited to forensic, food, archeological, agricultural or inorganic samples.

The above example is directed to detection of mutations in the APC gene. However, the inventions described herein are used for the detection of mutations in any gene that is associated with or predisposes to disease (see Table XI).

For example, hypermethylation of the glutathione S-transferase P1 (GSTP1) promoter is the most common DNA alteration in prostrate cancer. The methylation state of the promoter is determined using sodium bisulfite and the methods described herein.

Treatment with sodium bisulfite converts unmethylated cytosine residues into uracil, and leaving the methylated cytosines unchanged. Using the methods described herein, a first and second primer are designed to amplify the regions of the GSTP1 promoter that are often methylated. Below, a region of the GSTP1 promoter is shown prior to sodium bisulfite treatment:

Before Sodium Bisulfite treatment:
5' ACCGCTACA
3' TGGCGATCA

Below, a region of the GSTP1 promoter is shown after sodium bisulfite treatment, PCR amplification, and digestion with the type IIS restriction enzyme BsmF I:

```
Unmethylated
            5' ACC

3' TGG    U  G  A  T

Overhang position     1  2  3  4

Methylated
            5' ACC

3' TGG    C  G  A  T

Overhang position     1  2  3  4
```

Labeled ddATP, unlabeled dCTP, dGTP, and dTTP are used to fill-in the 5' overhangs. The following molecules are generated:

```
Unmethylated
          5'ACC      A*
          3'TGG      U   G   A   T
Overhang position    1   2   3   4
Methylated
          5'ACC      G   C   T   A*
          3'TGG      C   G   A   T
Overhang position    1   2   3   4
```

Two signals are seen; one corresponds to DNA molecules filled in with ddATP at position one complementary to the overhang (unmethylated), and the other corresponds to the DNA molecules filled in with ddATP at position 4 complementary to the overhang (methylated). The two signals are separated based on molecular weight. Alternatively, the fill-in reactions are performed in separate reactions using labeled ddGTP in one reaction and labeled ddATP in another reaction.

The methods described herein are used to screen for prostate cancer and also to monitor the progression and severity of the disease. The use of a single nucleotide to detect both the methylated and unmethylated sequences allows accurate quantitation and provides a high level of sensitivity for the methylated sequences, which is a useful tool for earlier detection of the disease.

The information contained in Tables III–X was obtained from the Human Gene Mutation Database. With the information provided herein, the skilled artisan will understand how to apply these methods for determining the sequence of the alleles for any gene. A large number of genes and their associated mutations can be found at the following website: www.archive.uwcm.ac.uk./uwcm.

TABLE III

NUCLEOTLDE SUBSTITUTIONS

| Codon | Nucleotide | Amino acid | Phenotype |
|---|---|---|---|
| 99 | CGG-TGG | Arg-Trp | Adenomatous polyposis coli |
| 121 | AGA-TGA | Arg-Term | Adenomatous polyposis coli |
| 157 | TGG-TAG | Trp-Term | Adenomatous polyposis coli |
| 159 | TAC-TAG | Tyr-Term | Adenomatous polyposis coli |
| 163 | CAG-TAG | Gln-Term | Adenomatous polyposis coli |
| 168 | AGA-TGA | Arg-Term | Adenomatous polyposis coli |
| 171 | AGT-ATT | Ser-Ile | Adenomatous polyposis coli |
| 181 | CAA-TAA | Gln-Term | Adenomatous polyposis coli |
| 190 | GAA-TAA | Glu-Term | Adenomatous polyposis coli |
| 202 | GAA-TAA | Glu-Term | Adenomatous polyposis coli |
| 208 | CAG-CGG | Gln-Arg | Adenomatous polyposis coli |
| 208 | CAG-TAG | Gln-Term | Adenomatous polyposis coli |
| 213 | CGA-TGA | Arg-Term | Adenomatous polyposis coli |
| 215 | CAG-TAG | Gln-Term | Adenomatous polyposis coli |
| 216 | CGA-TGA | Arg-Term | Adenomatous polyposis coli |
| 232 | CGA-TGA | Arg-Term | Adenomatous polyposis coli |
| 233 | CAG-TAG | Gln-Term | Adenomatous polyposis coli |
| 247 | CAG-TAG | Gln-Term | Adenomatous polyposis coli |
| 267 | GGA-TGA | Gly-Term | Adenomatous polyposis coli |
| 278 | CAG-TAG | Gln-Term | Adenomatous polyposis coli |
| 280 | TCA-TGA | Ser-Term | Adenomatous polyposis coli |
| 280 | TCA-TAA | Ser-Term | Adenomatous polyposis coli |
| 283 | CGA-TGA | Arg-Term | Adenomatous polyposis coli |
| 302 | CGA-TGA | Arg-Term | Adenomatous polyposis coli |
| 332 | CGA-TGA | Arg-Term | Adenomatous polyposis coli |
| 358 | CAG-TAG | Gln-Term | Adenomatous polyposis coli |
| 405 | CGA-TGA | Arg-Term | Adenomatous polyposis coli |
| 414 | CGC-TGC | Arg-Cys | Adenomatous polyposis coli |
| 422 | GAG-TAG | Glu-Term | Adenomatous polyposis coli |
| 423 | TGG-TAG | Trp-Term | Adenomatous polyposis coli |
| 424 | CAG-TAG | Gln-Term | Adenomatous polyposis coli |
| 433 | CAG-TAG | Gln-Term | Adenomatous polyposis coli |
| 443 | GAA-TAA | Glu-Term | Adenomatous polyposis coli |
| 457 | TCA-TAA | Ser-Term | Adenomatous polyposis coli |
| 473 | CAG-TAG | Gln-Term | Adenomatous polyposis coli |
| 486 | TAC-TAG | Tyr-Term | Adenomatous polyposis coli |
| 499 | CGA-TGA | Arg-Term | Adenomatous polyposis coli |
| 500 | TAT-TAG | Tyr-Term | Adenomatous polyposis coli |
| 541 | CAG-TAG | Gln-Term | Adenomatous polyposis coli |
| 553 | TGG-TAG | Trp-Term | Adenomatous polyposis coli |
| 554 | CGA-TGA | Arg-Term | Adenomatous polyposis coli |
| 564 | CGA-TGA | Arg-Term | Adenomatous polyposis coli |
| 577 | TTA-TAA | Leu-Term | Adenomatous polyposis coli |
| 586 | AAA-TAA | Lys-Term | Adenomatous polyposis coli |
| 592 | TTA-TGA | Leu-Term | Adenomatous polyposis coli |
| 593 | TGG-TAG | Trp-Term | Adenomatous polyposis coli |
| 593 | TGG-TGA | Trp-Term | Adenomatous polyposis coli |
| 622 | TAC-TAA | Tyr-Term | Adenomatous polyposis coli |
| 625 | CAG-TAG | Gln-Term | Adenomatous polyposis coli |
| 629 | TTA-TAA | Leu-Term | Adenomatous polyposis coli |
| 650 | GAG-TAG | Glu-Term | Adenomatous polyposis coli |
| 684 | TTG-TAG | Leu-Term | Adenomatous polyposis coli |
| 685 | TGG-TGA | Trp-Term | Adenomatous polyposis coli |

TABLE III-continued

NUCLEOTIDE SUBSTITUTIONS

| Codon | Nucleotide | Amino acid | Phenotype |
|---|---|---|---|
| 695 | CAG-TAG | Gln-Term | Adenomatous polyposis coli |
| 699 | TGG-TGA | Trp-Term | Adenomatous polyposis coli |
| 699 | TGG-TAG | Trp-Term | Adenomatous polyposis coli |
| 713 | TCA-TGA | Ser-Term | Adenomatous polyposis coli |
| 722 | AGT-GGT | Ser-Gly | Adenomatous polyposis coli |
| 747 | TCA-TGA | Ser-Term | Adenomatous polyposis coli |
| 764 | TTA-TAA | Leu-Term | Adenomatous polyposis coli |
| 784 | TCT-ACT | Ser-Thr | Adenomatous polyposis coli |
| 805 | CGA-TGA | Arg-Term | Adenomatous polyposis coli |
| 811 | TCA-TGA | Ser-Term | Adenomatous polyposis coli |
| 848 | AAA-TAA | Lys-Term | Adenomatous polyposis coli |
| 876 | CGA-TGA | Arg-Term | Adenomatous polyposis coli |
| 879 | CAG-TAG | Gln-Term | Adenomatous polyposis coli |
| 893 | GAA-TAA | Glu-Term | Adenomatous polyposis coli |
| 932 | TCA-TAA | Ser-Term | Adenomatous polyposis coli |
| 932 | TCA-TGA | Ser-Term | Adenomatous polyposis coli |
| 935 | TAC-TAG | Tyr-Term | Adenomatous polyposis coli |
| 935 | TAC-TAA | Tyr-Term | Adenomatous polyposis coli |
| 995 | TGC-TGA | Gys-Term | Adenomatous polyposis coli |
| 997 | TAT-TAG | Tyr-Term | Adenomatous polyposis coli |
| 999 | CAA-TAA | Gln-Term | Adenomatous polyposis coli |
| 1000 | TAC-TAA | Tyr-Term | Adenomatous polyposis coli |
| 1020 | GAA-TAA | Glu-Term | Adenomatous polyposis coli |
| 1032 | TCA-TAA | Ser-Term | Adenomatous polyposis coli |
| 1041 | CAA-TAA | Gln-Term | Adenomatous polyposis coli |
| 1044 | TCA-TAA | Ser-Term | Adenomatous polyposis coli |
| 1045 | CAG-TAG | Gln-Term | Adenomatous polyposis coli |
| 1049 | TGG-TGA | Trp-Term | Adenomatous polyposis coli |
| 1067 | CAA-TAA | Gln-Term | Adenomatous polyposis coli |
| 1071 | CAA-TAA | Gln-Term | Adenomatous polyposis coli |
| 1075 | TAT-TAA | Tyr-Term | Adenomatous polyposis coli |
| 1075 | TAT-TAG | Tyr-Term | Adenomatous polyposis coli |
| 1102 | TAC-TAG | Tyr-Term | Adenomatous polyposis coli |
| 1110 | TCA-TGA | Ser-Term | Adenomatous polyposis coli |
| 1114 | CGA-TGA | Arg-Term | Adenomatous polyposis coli |
| 1123 | CAA-TAA | Gln-Term | Adenomatous polyposis coli |
| 1135 | TAT-TAG | Tyr-Term | Adenomatous polyposis coli |
| 1152 | CAG-TAG | Gln-Term | Adenomatous polyposis coli |
| 1155 | GAA-TAA | Glu-Term | Adenomatous polyposis coli |
| 1168 | GAA-TAA | Glu-Term | Adenomatous polyposis coli |
| 1175 | CAG-TAG | Gln-Term | Adenomatous polyposis coli |
| 1176 | CCT-CTT | Pro-Leu | Adenomatous polyposis coli |
| 1184 | GCC-CCC | Ala-Pro | Adenomatous polyposis coli |
| 1193 | CAG-TAG | Gln-Term | Adenomatous polyposis coli |
| 1194 | TCA-TGA | Ser-Term | Adenomatous polyposis coli |
| 1198 | TCA-TGA | Ser-Term | Adenomatous polyposis coli |
| 1201 | TCA-TGA | Ser-Term | Adenomatous polyposis coli |
| 1228 | CAG-TAG | Gln-Term | Adenomatous polyposis coli |
| 1230 | CAG-TAG | Gln-Term | Adenomatous polyposis coli |
| 1244 | CAA-TAA | Gln-Term | Adenomatous polyposis coli |
| 1249 | TGC-TGA | Cys-Term | Adenomatous polyposis coli |
| 1256 | CAA-TAA | Gln-Term | Adenomatous polyposis coli |
| 1262 | TAT-TAA | Tyr-Term | Adenomatous polyposis coli |
| 1270 | TGT-TGA | Cys-Term | Adenomatous polyposis coli |
| 1276 | TCA-TGA | Ser-Term | Adenomatous polyposis coli |
| 1278 | TCA-TAA | Ser-Term | Adenomatous polyposis coli |
| 1286 | GAA-TAA | Glu-Term | Adenomatous polyposis coli |
| 1289 | TGT-TGA | Cys-Term | Adenomatous polyposis coli |
| 1294 | CAG-TAG | Gln-Term | Adenomatous polyposis coli |
| 1307 | ATA-AAA | Ile-Lys | Colorectal cancer, predisposition to, association |
| 1309 | GAA-TAA | Glu-Term | Adenomatous polyposis coli |
| 1317 | GAA-CAA | Glu-Gln | Colorectal cancer, predisposition to |
| 1328 | CAG-TAG | Gln-Term | Adenomatous polyposis coli |
| 1338 | CAG-TAG | Gln-Term | Adenomatous polyposis coli |
| 1342 | TTA-TAA | Leu-Term | Adenomatous polyposis coli |
| 1342 | TTA-TGA | Leu-Term | Adenomatous polyposis coli |
| 1348 | AGG-TGG | Arg-Trp | Adenomatous polyposis coli |
| 1357 | GGA-TGA | Gly-Term | Adenomatous polyposis coli |
| 1367 | CAG-TAG | Gln-Term | Adenomatous polyposis coli |
| 1370 | AAA-TAA | Lys-Term | Adenomatous polyposis coli |
| 1392 | TCA-TAA | Ser-Term | Adenomatous polyposis coli |
| 1392 | TCA-TGA | Ser-Term | Adenomatous polyposis coli |
| 1397 | GAG-TAG | Glu-Term | Adenomatous polyposis coli |

TABLE III-continued

NUCLEOTLDE SUBSTITUTIONS

| Codon | Nucleotide | Amino acid | Phenotype |
|---|---|---|---|
| 1449 | AAG-TAG | Lys-Term | Adenomatous polyposis coli |
| 1450 | CGA-TGA | Arg-Term | Adenomatous polyposis coli |
| 1451 | GAA-TAA | Glu-Term | Adenomatous polyposis coli |
| 1503 | TCA-TAA | Ser-Term | Adenomatous polyposis coli |
| 1517 | CAG-TAG | Gln-Term | Adenomatous polyposis coli |
| 1529 | CAG-TAG | Gln-Term | Adenomatous polyposis coli |
| 1539 | TCA-TAA | Ser-Term | Adenomatous polyposis coli |
| 1541 | CAG-TAG | Gln-Term | Adenomatous polyposis coli |
| 1564 | TTA-TAA | Leu-Term | Adenomatous polyposis coli |
| 1567 | TCA-TGA | Ser-Term | Adenomatous polyposis coli |
| 1640 | CGG-TGG | Arg-Trp | Adenomatous polyposis coli |
| 1693 | GAA-TAA | Glu-Term | Adenomatous polyposis coli |
| 1822 | GAC-GTC | Asp-Val | Adenomatous polyposis coli association with ? |
| 2038 | CTG-GTG | Leu-Val | Adenomatous polyposis coli |
| 2040 | CAG-TAG | Gln-Term | Adenomatous polyposis coli |
| 2566 | AGA-AAA | Arg-Lys | Adenomatous polyposis coli |
| 2621 | TCT-TGT | Ser-Cys | Adenomatous polyposis coli |
| 2839 | CTT-TTT | Leu-Phe | Adenomatous polyposis coli |

TABLE IV

NUCLEOTIDE SUBSTITUTIONS

| Donor/Acceptor | Relative location | Substitution | Phenotype |
|---|---|---|---|
| ds | -1 | G-C | Adenomatous polyposis coli |
| as | -1 | G-A | Adenomatous polyposis coli |
| as | -1 | G-C | Adenomatous polyposis coli |
| ds | +2 | T-A | Adenomatous polyposis coli |
| as | -1 | G-C | Adenomatous polyposis coli |
| as | -1 | G-T | Adenomatous polyposis coli |
| as | -1 | G-A | Adenomatous polyposis coli |
| as | -2 | A-C | Adenomatous polyposis coli |
| as | -5 | A-G | Adenomatous polyposis coli |
| ds | +3 | A-C | Adenomatous polyposis coli |
| as | -1 | G-A | Adenomatous polyposis coli |
| ds | +1 | G-A | Adenomatous polyposis coli |
| as | -1 | G-T | Adenomatous polyposis coli |
| ds | +1 | G-A | Adenomatous polyposis coli |
| as | -1 | G-A | Adenomatous polyposis coli |
| ds | +1 | G-A | Adenomatous polyposis coli |
| ds | +3 | A-G | Adenomatous polyposis coli |
| ds | +5 | G-T | Adenomatous polyposis coli |
| as | -1 | G-A | Adenomatous polyposis coli |
| as | -6 | A-G | Adenomatous polyposis coli |
| as | -5 | A-G | Adenomatous polyposis coli |
| as | -2 | A-G | Adenomatous polyposis coli |
| ds | +2 | T-C | Adenomatous polyposis coli |
| as | -2 | A-G | Adenomatous polyposis coli |
| ds | +1 | G-A | Adenomatous polyposis coli |
| ds | +1 | G-T | Adenomatous polyposis coli |
| ds | +2 | T-G | Adenomatous polyposis coli |

TABLE V

APC SMALL DELETIONS

| Location/codon | Deletion | Phenotype |
|---|---|---|
| 77 | TTAgataGCAGTAATTT | Adenomatous polyposis coli |
| 97 | GGAGccgggaagGATCTGTATC | Adenomatous polyposis coli |
| 138 | GAGAaAGAGAG_E3I3_GTAA | Adenomatous polyposis coli |

TABLE V-continued

APC SMALL DELETIONS

| Location/codon | Deletion | Phenotype |
|---|---|---|
| 139 | AAAGAgag_E3I3_Gtaacttttct | Thyroid cancer |
| 139 | AAAGAgag_E3I3_GTAACTTTTC | *Adenomatous polyposis coli* |
| 142 | TTTTAAAAAAaAAAAATAG_I3E4_GTCA | *Adenomatous polyposis coli* |
| 144 | AAAATAG_I3E4_GTCatTGCTTCTTGC | *Adenomatous polyposis coli* |
| 149 | GACAaaGAAGAAAAGG | *Adenomatous polyposis coli* |
| 149 | GACAAagaaGAAAAGGAAA | *Adenomatous polyposis coli* |
| 155 | AGGAA^AAAGActggtATTACGCTCA | *Adenomatous polyposis coli* |
| 169 | AAAAGA^ATAGatagTCTTCCTTTA | *Adenomatous polyposis coli* |
| 172 | AGATAGT^CTTcCTTTAAGTGA | *Adenomatous polyposis coli* |
| 179 | TCCTTacaaACAGATATGA | *Adenomatous polyposis coli* |
| 185 | ACCaGAAGGCAATT | *Adenomatous polyposis coli* |
| 196 | ATCAGagTTGCGATGGA | *Adenomatous polyposis coli* |
| 213 | CGAGCaCAG_E5I5_GTAAGTT | *Adenomatous polyposis coli* |
| 298 | CACtcTGCACCTCGA | *Adenomatous polyposis coli* |
| 329 | GATaTGTCGCGAAC | *Adenomatous polyposis coli* |
| 365 | AAAGActCTGTATTGTT | *Adenomatous polyposis coli* |
| 397 | GACaaGAGAGGCAGG | *Adenomatous polyposis coli* |
| 427 | CATGAacCAGGCATGGA | *Adenomatous polyposis coli* |
| 428 | GAACCaGGCATGGACC | *Adenomatous polyposis coli* |
| 436 | AATCCaa_E9I9_gTATGTTCTCT | *Adenomatous polyposis coli* |
| 440 | GCTCCtGTTGAACATC | *Adenomatous polyposis coli* |
| 455 | AAACTtTCATTTGATG | *Adenomatous polyposis coli* |
| 455 | AAACtttcaTTTGATGAAG | *Adenomatous polyposis coli* |
| 472 | CTAcAGGCCATTGC | *Adenomatous polyposis coli* |
| 472 | TAAATTAG_I10E11_GGgGACTACAGGC | *Adenomatous polyposis coli* |
| 478 | TTATtGCAAGTGGAC | *Adenomatous polyposis coli* |
| 486 | TACGgGCTTACTAAT | *Adenomatous polyposis coli* |
| 494 | AGTAtTACACTAAGAC | *Adenomatous polyposis coli* |
| 495 | ATTACacTAAGACGATA | *Adenomatous polyposis coli* |
| 497 | CTAaGACGATATGC | *Adenomatous polyposis coli* |
| 520 | TGCTCtaTGAAAGGCTG | *Adenomatous polyposis coli* |
| 526 | ATGAgcacttgtgGCCCAACTAA | *Adenomatous polyposis coli* |
| 539 | GACTTaCAGCAG_E12I12_GTAC | *Adenomatous polyposis coli* |
| 560 | AAAAgaCGTTGCGAGA | *Adenomatous polyposis coli* |
| 566 | GTTGgaagtGTGAAAGCAT | *Adenomatous polyposis coli* |
| 570 | AAAGCaTTGATGGAAT | *Adenomatous polyposis coli* |
| 577 | TTAGaagtTAAAAAG_E13I13_GTA | *Adenomatous polyposis coli* |

TABLE V-continued

APC SMALL DELETIONS

| Location/codon | Deletion | Phenotype |
| --- | --- | --- |
| 584 | ACCCTcAAAAGCGTAT | *Adenomatous polyposis coli* |
| 591 | GCCTtATGGAATTTG | *Adenomatous polyposis coli* |
| 608 | GCTgTAGATGGTGC | *Adenomatous polyposis coli* |
| 617 | GTTggcactcttacttaccGGAGCCAGAC | *Adenomatous polyposis coli* |
| 620 | CTTACttacCGGAGCCAGA | *Adenomatous polyposis coli* |
| 621 | ACTTaCCGGAGCCAG | *Adenomatous polyposis coli* |
| 624 | AGCcaGACAAACACT | *Adenomatous polyposis coli* |
| 624 | AGCCagacAAACACTTTA | *Adenomatous polyposis coli* |
| 626 | ACAaacaCTTTAGCCAT | *Adenomatous polyposis coli* |
| 629 | TTAGCcATTATTGAAA | *Adenomatous polyposis coli* |
| 635 | GGAGgTGGGATATTA | *Adenomatous polyposis coli* |
| 638 | ATATtACGGAATGTG | *Adenomatous polyposis coli* |
| 639 | TTACggAATGTGTCCA | *Adenomatous polyposis coli* |
| 657 | AGAgaGAACAACTGT | *Adenomatous polyposis coli* |
| 659 | TATTTCAG_I14E15_GCaaatcctaagagagAACAACTGTC | *Adenomatous polyposis coli* |
| 660 | AACTgtCTACAAACTT | *Adenomatous polyposis coli* |
| 665 | TTAttACAACACTTA | *Adenomatous polyposis coli* |
| 668 | CACttAAAATCTCAT | *Adenomatous polyposis coli* |
| 673 | AGTttgacaatagtCAGTAATGCA | *Adenomatous polyposis coli* |
| 768 | CACTTaTCAGAAACTT | *Adenomatous polyposis coli* |
| 769 | TTATcAGAAACTTTT | *Adenomatous polyposis coli* |
| 770 | TCAGaaACTTTTGACA | *Adenomatous polyposis coli* |
| 780 | AGTGcCAAGGCATCT | *Adenomatous polyposis coli* |
| 792 | AAGcaAAGTCTCTAT | *Adenomatous polyposis coli* |
| 792 | AAGCAaaGTCTCTATGG | *Adenomatous polyposis coli* |
| 793 | CAAAgTGTCTATGGT | *Adenomatous polyposis coli* |
| 798 | GATTatGTTTTTGACA | *Adenomatous polyposis coli* |
| 802 | GACACcaatcgacatGATGATAATA | *Adenomatous polyposis coli* |
| 805 | CGACatGATGATAATA | *Adenomatous polyposis coli* |
| 811 | TCAGacaaTTTTAATACT | *Adenomatous polyposis coli* |
| 825 | TATtTGAATACTAC | *Adenomatous polyposis coli* |
| 827 | AATAcTACAGTGTTA | *Adenomatous polyposis coli* |
| 830 | GTGTTacccagctcctctTCATCAAGAG | *Adenomatous polyposis coli* |
| 833 | AGCTCcTCTTCATCAA | *Adenomatous polyposis coli* |
| 836 | TCATcAAGAGGAAGC | *Adenomatous polyposis coli* |
| 848 | AAAGtaGAAGTTTGGA | *Adenomatous polyposis coli* |
| 848 | AAAGatagaagTTTGGAGAGA | *Adenomatous polyposis coli* |

TABLE V-continued

APC SMALL DELETIONS

| Location/codon | Deletion | Phenotype |
|---|---|---|
| 855 | GAACgCGGAATTGGT | Adenomatous polyposis coli |
| 856 | CGCGgaattGGTCTAGGCA | Adenomatous polyposis coli |
| 856 | CGCGgAATTGGTCTA | Adenomatous polyposis coli |
| 879 | CAGa**TCTCCACCAC | Adenomatous polyposis coli |
| 902 | GAAGAcagaa**GTTCTGGGT | Adenomatous polyposis coli |
| 907 | GGGTcTACCACTGAA | Adenomatous polyposis coli |
| 915 | GTGACa**GATGAGAGAA | Adenomatous polyposis coli |
| 929 | CATACacatTCAAACACTT | Adenomatous polyposis coli |
| 930 | ACACAttcaAACACTTACA | Adenomatous polyposis coli |
| 931 | CATt**CAAACACTTA | Adenomatous polyposis coli |
| 931 | CATTc**CAAACACTTAC | Adenomatous polyposis coli |
| 933 | AACacttACAATTTCAC | Adenomatous polyposis coli |
| 935 | TACAatttcactAAGTCGGAAA | Adenomatous polyposis coli |
| 937 | TTCActaaGTCGGAAAAT | Adenomatous polyposis coli |
| 939 | AAGtcggAAAATTGAAA | Adenomatous polyposis coli |
| 946 | ACATg**TTCTATGCCT | Adenomatous polyposis coli |
| 954 | TTAGaaTACAAGAGAT | Adenomatous polyposis coli |
| 961 | AATg**ATAGTTTAAA | Adenomatous polyposis coli |
| 963 | AGTTTa**AATAGTGTCA | Adenomatous polyposis coli |
| 964 | TTAaataGTGTCAGTAG | Adenomatous polyposis coli |
| 973 | TATGgTAAAAGAGGT | Adenomatous polyposis coli |
| 974 | GGTAAaAGAGGTCAAA | Adenomatous polyposis coli |
| 975 | AAAAgaGGTGAAATGA | Thyroid cancer |
| 992 | AGTAAgTTTTGCAGTT | Thyroid cancer |
| 993 | AAGttttgcagtta**TGGTCAATAC | Adenomatous polyposis coli |
| 999 | CAAtacccag**CCGACCTAGC | Adenomatous polyposis coli |
| 1023 | ACACc**AATAAATTAT | Adenomatous polyposis coli |
| 1030 | AAAt**aTTCAGATGA | Adenomatous polyposis coli |
| 1032 | TCAGatgag**CAGTTGAACT | Adenomatous polyposis coli |
| 1033 | GATGaGCAGTTGAAC | Adenomatous polyposis coli |
| 1049 | TGGGcAAGACCCAAA | Adenomatous polyposis coli |
| 1054 | CACAtaataGAAGATGAAA | Adenomatous polyposis coli |
| 1055 | ATAAtagaaGATGAAATAA | Adenomatous polyposis coli |
| 1056 | ATAGAaGATGAAATAA | Adenomatous polyposis coli |
| 1060 | ATAAAacaaaGTGAGCAAAG | Adenomatous polyposis coli |
| 1061 | AAAcaaa**GTGAGCAAAG | Adenomatous polyposis coli |
| 1061 | AAACaaAGTGAGCAAA | Adenomatous polyposis coli |

TABLE V-continued

APC SMALL DELETIONS

| Location/codon | Deletion | Phenotype |
| --- | --- | --- |
| 1062 | CAAAgtgaGCAAAGACAA | Adenomatous polyposis coli |
| 1065 | CAAAGacAATCAAGGAA | Adenomatous polyposis coli |
| 1067 | CAAtcaaGGAATCAAAG | Adenomatous polyposis coli |
| 1071 | CAAAgtACAACTTATC | Adenomatous polyposis coli |
| 1079 | ACTGagAGCACTGATG | Adenomatous polyposis coli |
| 1082 | ACTGAtgATAAACACCT | Adenomatous polyposis coli |
| 1084 | GATaaacACCTCAAGTT | Adenomatous polyposis coli |
| 1086 | CACCtcAAGTTCCAAC | Adenomatous polyposis coli |
| 1093 | TTTGgACAGCAGGAA | Adenomatous polyposis coli |
| 1098 | TGTgtTTCTCCATAC | Adenomatous polyposis coli |
| 1105 | CGGgGAGCCAATGG | Thyroid cancer |
| 1110 | TCAGAaACAAATCGAG | Adenomatous polyposis coli |
| 1121 | ATTAAtcaaAATGTAAGCC | Adenomatous polyposis coli |
| 1131 | CAAgAAGATGACTA | Adenomatous polyposis coli |
| 1134 | GACTAtGAAGATGATA | Adenomatous polyposis coli |
| 1137 | GATgataaGCCTACCAAT | Adenomatous polyposis coli |
| 1146 | CGTTAcTCTGAAGAAG | Adenomatous polyposis coli |
| 1154 | GAAGaagaaGAGAGACCAA | Adenomatous polyposis coli |
| 1155 | GAAGaagaGAGACCAACA | Adenomatous polyposis coli |
| 1156 | GAAgagaGACCAACAAA | Adenomatous polyposis coli |
| 1168 | GAAgagaaACGTCATGTG | Adenomatous polyposis coli |
| 1178 | GATTAtagtttaAAATATGCCA | Adenomatous polyposis coli |
| 1181 | TTAAaATATGCCACA | Adenomatous polyposis coli |
| 1184 | GCCacagaTATTCCTTCA | Adenomatous polyposis coli |
| 1185 | ACAgaTATTCCTTCA | Adenomatous polyposis coli |
| 1190 | TCACAgAAACAGTCAT | Adenomatous polyposis coli |
| 1192 | AAAcaGTCATTTTCA | Adenomatous polyposis coli |
| 1198 | TCAaaGAGTTCATCT | Adenomatous polyposis coli |
| 1207 | AAAAcCGAACATATG | Adenomatous polyposis coli |
| 1208 | ACCgaacATATGTCTTC | Adenomatous polyposis coli |
| 1210 | CATatGTCTTCAAGC | Adenomatous polyposis coli |
| 1233 | CCAAGtTCTGCACAGA | Adenomatous polyposis coli |
| 1249 | TGCAaaGTTTCTTCTA | Adenomatous polyposis coli |
| 1259 | ATAcaGACTTATTGT | Adenomatous polyposis coli |
| 1260 | CAGACttATTGTGTAGA | Adenomatous polyposis coli |
| 1268 | CCAaTATGTTTTTC | Adenomatous polyposis coli |
| 1275 | AGTtCATTATCATC | Adenomatous polyposis coli |

TABLE V-continued

APC SMALL DELETIONS

| Location/codon | Deletion | Phenotype |
| --- | --- | --- |
| 1294 | CAGGAaGCAGATTCTG | *Adenomatous polyposis coli* |
| 1301 | ACCCtGCAAATAGCA | *Adenomatous polyposis coli* |
| 1306 | GAAAtaaaAGAAAAGATT | *Adenomatous polyposis coli* |
| 1307 | ATAaAAGAAAAGAT | *Adenomatous polyposis coli* |
| 1308 | AAAgaaaAGATTGGAAC | *Adenomatous polyposis coli* |
| 1308 | AAAGAaaagaTTGGAACTAG | *Adenomatous polyposis coli* |
| 1318 | GATCcTGTGAGCGAA | *Adenomatous polyposis coli* |
| 1320 | GTGAGcGAAGTTCCAG | *Adenomatous polyposis coli* |
| 1323 | GTTCcAGCAGTGTCA | *Adenomatous polyposis coli* |
| 1329 | CACCctagaaccAAATCCAGCA | *Adenomatous polyposis coli* |
| 1336 | AGACtgCAGGGTTCTA | *Adenomatous polyposis coli* |
| 1338 | CAGgGTTCTAGTTT | *Adenomatous polyposis coli* |
| 1340 | TCTAgTTTATCTTCA | *Adenomatous polyposis coli* |
| 1342 | TTATcTTCAGAATCA | *Adenomatous polyposis coli* |
| 1352 | TTTgAATTTTCTTC | *Adenomatous polyposis coli* |
| 1361 | CCCTcCAAAAGTGGT | *Adenomatous polyposis coli* |
| 1364 | AGTggtgCTCAGACACC | *Adenomatous polyposis coli* |
| 1371 | AGTCCacCTGAACACTA | *Adenomatous polyposis coli* |
| 1372 | CCACCtGAACACTATG | *Adenomatous polyposis coli* |
| 1376 | TATGttCAGGAGACCC | *Adenomatous polyposis coli* |
| 1394 | GATAgtTTTGAGAGTC | *Adenomatous polyposis coli* |
| 1401 | ATTGCcAGCTCCGTTC | *Adenomatous polyposis coli* |
| 1415 | AGTGGcATTATAAGCC | *Adenomatous polyposis coli* |
| 1426 | AGCCcTGGACAAACC | *Adenomatous polyposis coli* |
| 1427 | CCTGGaCAAACCATGC | *Adenomatous polyposis coli* |
| 1431 | ATGCcACCAAGCAGA | *Adenomatous polyposis coli* |
| 1454 | AAAAAtAAAGCACCTA | *Adenomatous polyposis coli* |
| 1461 | GAAaAGAGAGAGAG | *Adenomatous polyposis coli* |
| 1463 | AGAgagaGTGGACCTAA | *Adenomatous polyposis coli* |
| 1464 | GAGAgTGGACCTAAG | *Adenomatous polyposis coli* |
| 1464 | GAGAgtGGACCTAAGC | *Adenomatous polyposis coli* |
| 1464 | GAGagTGGACCTAAG | *Adenomatous polyposis coli* |
| 1492 | GCCaCGGAAAGTAC | *Adenomatous polyposis coli* |
| 1493 | ACGGAaAGTACTCCAG | *Adenomatous polyposis coli* |
| 1497 | CCAgATGGATTTTC | *Adenomatous polyposis coli* |
| 1503 | TCAtccaGCCTGAGTGC | *Adenomatous polyposis coli* |
| 1522 | TTAagaataaTGCCTCCAGT | *Adenomatous polyposis coli* |

TABLE V-continued

APC SMALL DELETIONS

| Location/codon | Deletion | Phenotype |
|---|---|---|
| 1536 | GAAACagAATCAGAGCA | Adenomatous polyposis coli |
| 1545 | TCAAAtgaaaACCAAGAGAA | Adenomatous polyposis coli |
| 1547 | GAAaACCAAGAGAA | Adenomatous polyposis coli |
| 1550 | GAGAaagaGGCAGAAAAA | Adenomatous polyposis coli |
| 1577 | GAATgtATTATTTCTG | Adenomatous polyposis coli |
| 1594 | CCAGCcCAGACTGCTT | Adenomatous polyposis coli |
| 1596 | CAGACtGCTTCAAAAT | Adenomatous polyposis coli |
| 1823 | TTCAaTGATAAGCTC | Adenomatous polyposis coli |
| 1859 | AATGAttctTTGAGTTCTC | Adenomatous polyposis coli |
| 1941 | CCAGAcagaGGGGCAGCAA | Desmoid tumours |
| 1957 | GAAaATACTCCAGT | Adenomatous polyposis coli |
| 1980 | AACaATAAAGAAAA | Adenomatous polyposis coli |
| 1985 | GAACCtATCAAAGAGA | Adenomatous polyposis coli |
| 1986 | CCTaTCAAAGAGAC | Adenomatous polyposis coli |
| 1998 | GAACcAAGTAAACCT | Adenomatous polyposis coli |
| 2044 | AGCTCcGCAATGCCAA | Adenomatous polyposis coli |
| 2556 | TCATCccttcctcGAGTAAGCAC | Adenomatous polyposis coli |
| 2643 | CTAATttatCAAATGGCAC | Adenomatous polyposis coli |

Bold letters indicate the codon.
Undercase letters represent the deletion.
Where deletions extend beyond the coding region, other positional information is provided. For example, the abbreviation 5'UTR represents 5' untranslated region, and the abbreviation E6I6 denotes exon 6/intron 6 boundary.

TABLE VI

SMALL INSERTIONS

| Codon | Insertion | Phenotype |
|---|---|---|
| 157 | T | Adenomatous polyposis coli |
| 170 | AGAT | Adenomatous polyposis coli |
| 172 | T | Adenomatous polyposis coli |
| 199 | G | Adenomatous polyposis coli |
| 243 | AG | Adenomatous polyposis coli |
| 266 | T | Adenomatous polyposis coli |
| 357 | A | Adenomatous polyposis coli |
| 405 | C | Adenomatous polyposis coli |
| 413 | T | Adenomatous polyposis coli |
| 416 | A | Adenomatous polyposis coli |
| 457 | G | Adenomatous polyposis coli |
| 473 | A | Adenomatous polyposis coli |
| 503 | ATTC | Adenomatous polyposis coli |
| 519 | C | Adenomatous polyposis coli |
| 528 | A | Adenomatous polyposis coli |
| 561 | A | Adenomatous polyposis coli |
| 608 | A | Adenomatous polyposis coli |
| 620 | CT | Adenomatous polyposis coli |
| 621 | A | Adenomatous polyposis coli |
| 623 | TTAC | Adenomatous polyposis coli |
| 627 | A | Adenomatous polyposis coli |
| 629 | A | Adenomatous polyposis coli |
| 636 | GT | Adenomatous polyposis coli |

TABLE VI-continued

SMALL INSERTIONS

| Codon | Insertion | Phenotype |
|---|---|---|
| 639 | A | Adenomatous polyposis coli |
| 704 | T | Adenomatous polyposis coli |
| 740 | ATGC | Adenomatous polyposis coli |
| 764 | T | Adenomatous polyposis coli |
| 779 | TT | Adenomatous polyposis coli |
| 807 | AT | Adenomatous polyposis coli |
| 827 | AT | Adenomatous polyposis coli |
| 831 | A | Adenomatous polyposis coli |
| 841 | CTTA | Adenomatous polyposis coli |
| 865 | CT | Adenomatous polyposis coli |
| 865 | AT | Adenomatous polyposis coli |
| 900 | TG | Adenomatous polyposis coli |
| 921 | G | Adenomatous polyposis coli |
| 927 | A | Adenomatous polyposis coli |
| 935 | A | Adenomatous polyposis coli |
| 936 | C | Adenomatous polyposis coli |
| 975 | A | Adenomatous polyposis coli |
| 985 | T | Adenomatous polyposis coli |
| 997 | A | Adenomatous polyposis coil |
| 1010 | TA | Adenomatous polyposis coli |
| 1085 | C | Adenomatous polyposis coli |
| 1085 | AT | Adenomatous polyposis coli |
| 1095 | A | Adenomatous polyposis coli |
| 1100 | GTTT | Adenomatous polyposis coli |
| 1107 | GGAG | Adenomatous polyposis coli |
| 1120 | G | Adenomatous polyposis coli |
| 1166 | A | Adenomatous polyposis coli |
| 1179 | T | Adenomatous polyposis coli |
| 1187 | A | Adenomatous polyposis coli |
| 1211 | T | Adenomatous polyposis coli |
| 1256 | A | Adenomatous polyposis coli |
| 1265 | T | Adenomatous polyposis coli |
| 1267 | GATA | Adenomatous polyposis coli |
| 1268 | T | Adenomatous polyposis coli |
| 1301 | A | Adenomatous polyposis coli |
| 1301 | C | Adenomatous polyposis coli |
| 1323 | A | Adenomatous polyposis coli |
| 1342 | T | Adenomatous polyposis coli |
| 1382 | T | Adenomatous polyposis coli |
| 1458 | GTAG | Adenomatous polyposis coli |
| 1463 | AG | Adenomatous polyposis coli |
| 1488 | T | Adenomatous polyposis coli |
| 1531 | A | Adenomatous polyposis coli |
| 1533 | T | Adenomatous polyposis coli |
| 1554 | A | Adenomatous polyposis coli |
| 1555 | A | Adenomatous polyposis coli |
| 1556 | T | Adenomatous polyposis coli |
| 1563 | GACCT | Adenomatous polyposis coli |
| 1924 | AA | Desmoid tumours |

TABLE VII

SMALL INSERTIONS/DELETIONS

| Location/codon | Deletion | Insertion | Phenotype |
|---|---|---|---|
| 538 | GAAGAcTTACAGCAGG | gaa | Adenomatous polyposis coli |
| 620 | CTTACttaCCGGAGCCAG | ct | Adenomatous polyposis coli |
| 728 | AATctcatGGCAAATAGG Ttgcagctttaa | Adenomatous polyposis coli |
| 971 | GATGgtTATGGTAAAA | taa | Adenomatous polyposis coli |

TABLE VIII

GROSS DELETIONS

| | |
|---|---|
| 2 kb including ex. 11 | *Adenomatous polyposis coli* |
| 3 kb I10E11–1.5 kb to I12E13–170 bp | *Adenomatous polyposis coil* |
| 335 bp nt. 1409–1743 ex. 11–13 | *Adenomatous polyposis coli* |
| 6 kb incl. ex. 14 | *Adenomatous polyposis coil* |
| 817 bp I13E14–679 to I13E14+138 | *Adenomatous polyposis coli* |
| ex. 11–15M | *Adenomatous polyposis coli* |
| ex. 11-3'UTR | *Adenomatous polyposis coil* |
| ex. 15A–ex. 15F | *Adenomatous polyposis coli* |
| ex. 4 | *Adenomatous polyposis coli* |
| ex. 7, 8 and 9 | *Adenomatous polyposis coli* |
| ex. 8 to beyond ex. 15F | *Adenomatous polyposis coil* |
| ex. 8–ex. 15F | *Adenomatous polyposis coli* |
| ex. 9 | *Adenomatous polyposis coil* |
| >10 mb (del 5q22) | *Adenomatous polyposis coil* |

TABLE IX

ROSS INSERTIONS AND DUPLICATIONS

| Description | Phenotype |
|---|---|
| Insertion of 14 bp nt. 3816 | *Adenomatous polyposis coli* |
| Insertion of 22 bp nt. 4022 | *Adenomatous polyposis coli* |
| Duplication of 43 bp cd. 1295 | *Adenomatous polyposis coli* |

TABLE IX-continued

ROSS INSERTIONS AND DUPLICATIONS

| Description | Phenotype |
|---|---|
| Insertion of 337 bp of Alu I sequence cd. 1526 | Desmoid tumours |

TABLE X

COMPLEX REARRANGEMENTS (INCLUDING INVERSIONS)

| | |
|---|---|
| A-T nt. 4893 Q1625H, Del C nt. 4897 cd. 1627 | *Adenomatous polyposis coli* |
| Del 1099 bp I13E14 − 728 to E14I14 + 156, ins 126 bp | *Adenomatous polyposis coli* |
| Del 1601 bp E14I14 + 27 to E14I14 + 1627, ins 180 bp | *Adenomatous polyposis coli* |
| Del 310 bp, ins. 15 bp nt. 4394, cd 1464 | *Adenomatous polyposis coli* |
| Del A and T cd. 1395 | *Adenomatous polyposis coli* |
| Del TC nt. 4145, Del TGT nt. 4148 | *Adenomatous polyposis coli* |
| Del. T, nt. 983, Del. 70 bp, nt. 985 | *Adenomatous polyposis coli* |
| Del. nt. 3892–3903, ins ATTT | *Adenomatous polyposis coli* |

TABLE XI

| Cancer Type | Marker | Application | Reference |
|---|---|---|---|
| DIAGNOSTIC APPLICATIONS | | | |
| Breast | Her2/Neu Detection - polymorphism at codon 655 (GTC/valine to ATC/isoleucine [Val(655)Ile]) | Using methods described herein, design second primer such that after PCR, and digestion with restriction enzyme, a 5' overhang containing DNA sequence for codon 655 of Her2/Neu is generated. Her2/Neu can be detected and quantified as a possible marker for breast cancer. Methods described herein can detect both mutant allele and normal allele, even when mutant allele is small fraction of total DNA. Herceptin therapy for breast cancer is based upon screening for Her2. The earlier the mutant allele can be detected, the faster therapy can be provided. | D. Xie et al., J. Natl. Cancer Institute, 92, 412 (2000) K. S. Wilson et al., Am. J. Pathol., 161, 1171 (2002) L. Newman, Cancer Control, 9, 473 (2002) |
| Breast/Ovarian | Hypermethylation of BRCA1 | Methods described herein can be used to differentiate between tumors resulting from inherited BRCA1 mutations and those from non-inherited abnormal methylation of the gene | M. Esteller et al., New England Jnl Med., 344, 539 (2001) |
| Bladder | Microsatellite analysis of free tumor DNA in Urine, Serum and Plasma | Methods described herein can be applied to microsatellite analysis and FGFR3 mutation analysis for detection of bladder cancer. Methods described herein provide a non-invasive method for detection of bladder cancer. | W. G. Bas et al., Clinical Cancer Res., 9,257 (2003) M. Utting et al., Clincal Cancer Res., 8,35 (2002) L. Mao, D. Sidransky et al., Science, 271, 669 (1996) |

TABLE XI-continued

| Cancer Type | Marker | Application | Reference |
|---|---|---|---|
| Lung | Microsatellite analysis of DNA from sputum | Methods described herein can be used to detect mutations in sputum samples, and can markedly boost the accuracy of preclinical lung cancer screening | T. Liloglou et al., Cancer Research, 61, 1624, (2001) M. Tockman et al., Cancer Control, 7, 19 (2000) Field et al., Cancer Research, 59, 2690 (1999) |
| Cervical | Analysis of HPV genotype | Methods described herein can be used to detect HPV genotype from a cervical smear preparation. | N. Munoz et al., New England Jnl Med., 348, 518 (2003) |
| Head and Neck | Tumor specific alterations in exfoliated oral mucosal cells (microsatellite markers) | Methods described herein can be used to detect any of 23 microsatellite markers, which are associated with Head and Neck Squamous Cell Carcinoma (HNSCC). | M. Spafford et al. Clinical Cancer Research, 17, 607 (2001) A. El-Naggar et al., J. Mol. Diag., 3,164 (2001) |
| Colorectal | Screening for mutation in K-ras2 and APC genes. | Methods described herein can be used to detect K-ras 2 mutations, which can be used as a prognostic indicator for colorectal cancer. APC (see Example 5). | B. Ryan et al. Gut, 52, 101 (2003) |
| Prostate | GSTP1 Hypermethylation | Methods described herein can be used to detect GSTP1 hypermethylation in urine from patients with prostate cancer; this can be a more accurate indicator than PSA. | P. Cairns et al. Clin. Can. Res., 7,2727 (2001) |
| HIV | | | |
| Antiretroviral resistance | Screening individuals for mutations in HIV virus - e.g. 154V mutation or CCR5 Δ 32 allele. | Methods described herein can be used for detection of mutations in the HIV virus. Treatment outcomes are improved in individuals receiving anti retroviral therapy based upon resistance screening. | J. Durant et al. The Lancet, 353, 2195 (1999) |
| CARDIOLOGY | | | |
| Congestive Heart Failure | Synergistic polymorphisms of beta1 and alpha2c adrenergic receptors | Methods described herein can be used to genotype these loci and may help identify people who are at a higher risk of heart failure. | K. Small et al. New Eng. Jnl. Med., 347,1135 (2002) |

Having now fully described the invention, it will be understood by those of skill in the art that the invention can be performed with a wide and equivalent range of conditions, parameters, and the like, without affecting the spirit or scope of the invention or any embodiment thereof.

All documents, e.g., scientific publications, patents and patent publications recited herein are hereby incorporated by reference in their entirety to the same extent as if each individual document was specifically and individually indicated to be incorporated by reference in its entirety. Where the document cited only provides the first page of the document, the entire document is intended, including the remaining pages of the document.

What is claimed is:

1. A method for determining a sequence of alleles of a locus of interest, said method comprising:
(a) amplifying a locus of interest on a template DNA using a first and second primers, wherein the second primer contains a recognition site for a restriction enzyme that cuts DNA at a distance from the recognition site and digestion with the restriction enzyme generates a 5' overhang containing the locus of interest, and wherein the first primer contains a recognition site for a restriction enzyme that is different from the recognition site for the restriction enzyme on the second primer and contains a tag at the 5' end;
(b) digesting the amplified DNA with the restriction enzyme that recognizes the recognition site on the second primer;
(c) incorporating nucleotides into the digested DNA of (b), wherein;
  (i) a labeled nucleotide that terminates elongation, and is complementary to the locus of interest of an allele, is incorporated into the 5' overhang of said allele, and
  (ii) a nucleotide complementary to the locus of interest of a different allele is incorporated into the 5' overhang of said different allele, and said terminating nucleotide, which is complementary to a nucleotide in the 5' overhang of said different allele, is incorporated into the 5' overhang of said different allele;
(d) digesting the DNA of (c) with the restriction enzyme that recognizes the recognition site on the first primer; and
(e) determining the sequence of the alleles of the locus of interest by determining the sequence of the digested DNA of (d) containing the labeled nucleotide.

2. The method of claim 1, wherein the template DNA is obtained from a source selected from the group consisting of a bacterium, fungus, virus, protozoan, plant, animal and human.

3. The method of claim 1, wherein the template DNA is obtained from a human source.

4. The method of claim 1, wherein the template DNA is obtained from a sample selected from the group consisting of a cell, tissue, blood, serum, plasma, urine, spinal fluid, lymphatic fluid, semen, vaginal secretion, ascitic fluid, saliva, mucosa secretion, peritoneal fluid, fecal matter, and body exudates.

5. The method of claim 1, wherein the amplification in (a) comprises polymerase chain reaction (PCR).

6. The method of claim 1, wherein a 5' region of the second primer does not anneal to the template DNA.

7. The method of claim 1, wherein a 5' region of the first primer does not anneal to the template DNA.

8. The method of claim 6, wherein an annealing length of the 3' region of the second primer is selected from the group consisting of 25–20, 20–15, 15, 14, 13, 12, 11, 10, 9, 8, 7, 6, 5, 4, and less than 4 bases.

9. The method of claim 1, wherein an annealing temperature for cycle 1 of PCR is about the melting temperature of the portion of the 3' region of the second primer that anneals to the template DNA.

10. The method of claim 9, wherein an annealing temperature for cycle 2 of PCR is about the melting temperature of the portion of the 3' region of the first primer that anneals to the template DNA.

11. The method of claim 10, wherein an annealing temperature for the remaining cycles of PCR is at about the melting temperature of the entire second primer.

12. The method of claim 1, wherein the 3' end of the second primer is adjacent to the locus of interest.

13. The method of claim 1, wherein the recognition site on the second primer is for a Type IIS restriction enzyme.

14. The method of claim 13, wherein the Type IIS restriction enzyme is selected from the group consisting of: Alw I, Alw26 I, Bbs I, Bbv I, BceA I, Bmr I, Bsa I, Bst71 I, BsmA I, BsmB I, BsmF I, BspM I, Ear I, Fau I, Fok I, Hga I, Ple I, Sap I, SSfaN I, and Sthi32 I.

15. The method of claim 13, wherein the Type IIS restriction enzyme is BceA I.

16. The method of claim 13, wherein the Type IIS restriction enzyme is BsmF I.

17. The method of claim 1, wherein the tag is used to separate the amplified DNA from the template DNA.

18. The method of claim 17, wherein the tag is used to separate the amplified DNA containing the incorporated nucleotide from the amplified DNA that does not contain the incorporated nucleotide.

19. The method of claim 1, wherein the tag is selected from the group consisting of: radioisotope, fluorescent reporter molecule, chemiluminescent reporter molecule, antibody, antibody fragment, hapten, biotin, derivative of biotin, photobiotin, iminobiotin, digoxigenin, avidin, enzyme, acridinium, sugar, enzyme, apoenzyme, homopolymeric oligonucleotide, hormone, ferromagnetic moiety, paramagnetic moiety, diamagnetic moiety, phosphorescent moiety, luminescent moiety, electrochemiluminescent moiety, chromatic moiety, moiety having a detectable electron spin resonance, electrical capacitance, dielectric constant or electrical conductivity, and combinations thereof.

20. The method of claim 1, wherein the tag is biotin.

21. The method of claim 20, wherein the biotin tag is used to separate amplified DNA from the template DNA using a streptavidin matrix.

22. The method of claim 21, wherein the streptavidin matrix is coated on wells of a microtiter plate.

23. The method of claim 1, wherein the incorporation of a nucleotide in (c) is by a DNA polymerase selected from the group consisting of E. coli DNA polymerase, Klenow fragment of E. coli DNA polymerase I, T7 DNA polymerase, T4 DNA polymerase, Taq polymerase, Pfu DNA polymerase, Vent DNA polymerase and sequenase.

24. The method of claim 1, wherein the incorporation of a nucleotide in (c)(i) comprises incorporation of a labeled nucleotide.

25. The method of claim 1, wherein the incorporation of a nucleotide in (c)(i) comprises incorporation of a dideoxynucleotide.

26. The method of claim 1, wherein the incorporation of a nucleotide in (c)(i) further comprises incorporation of a deoxynucleotide and a dideoxynucleotide.

27. The method of claim 1, wherein the incorporation of a nucleotide in (c)(i) further comprises using a mixture of labeled and unlabeled nucleotides.

28. The method of claim 1, wherein the incorporation of a nucleotide in (c)(ii) comprises incorporation of a labeled nucleotide.

29. The method of claim 1, wherein the incorporation of a nucleotide in (c)(ii) comprises incorporation of a deoxynucleotide.

30. The method of claim 1, wherein the incorporation of a nucleotide in (c)(ii) further comprises incorporation of a deoxynucleotide and a dideoxynucleotide.

31. The method of claim 1, wherein the incorporation of a nucleotide in (c)(ii) further comprises using a mixture of labeled and unlabeled nucleotides.

32. The method of claim 24, wherein the labeled nucleotide is a dideoxynucleotide.

33. The method of claim 24, wherein the labeled nucleotide is labeled with a molecule selected from the group consisting of radioactive molecule, fluorescent molecule, antibody, antibody fragment, hapten, carbohydrate, biotin, derivative of biotin, phosphorescent moiety, luminescent moiety, electrochemiluminescent moiety, chromatic moiety, and moiety having a detectable electron spin resonance, electrical capacitance, dielectric constant and electrical conductivity.

34. The method of claim 24, wherein the labeled nucleotide is labeled with a fluorescent molecule.

35. The method of claim 34, wherein the incorporation of a nucleotide in (c)(i) further comprises incorporation of an unlabeled nucleotide.

36. The method of claim 1, wherein the determination of the sequence of the locus of interest in (e) comprises detecting a nucleotide.

37. The method of claim 24, wherein the determination of the sequence of the locus of interest in (e) comprises detecting a labeled nucleotide.

38. The method of claim 37, wherein the detection is by a method selected from the group consisting of gel electrophoresis, polyacrylamide gel electrophoresis, fluorescence detection system, sequencing, ELISA, mass spectrometry, fluorometry, hybridization, microarray, and Southern Blot.

39. The method of claim 37, wherein the detection method is DNA sequencing.

40. The method of claim 37, wherein the detection method is fluorescence detection.

41. The method of claim 1, wherein the alleles of a locus of interest are suspected of containing a single nucleotide polymorphism or mutation.

42. The method of claim 1, wherein the method is used for determining sequences of multiple loci of interest concurrently.

43. The method of claim 42, wherein the template DNA comprises multiple loci from a single chromosome.

44. The method of claim 42, wherein the template DNA comprises multiple loci from different chromosomes.

45. The method of claim 42, wherein the loci of interest on template DNA are amplified in one reaction.

46. The method of claim 42, wherein each of the loci of interest on template DNA is amplified in a separate reaction.

47. The method of claim 46, wherein the amplified DNA are pooled together prior to digestion of the amplified DNA.

48. The method of claim 42, wherein each of the labeled DNA in (c) containing a locus of interest is separated prior to (e).

49. The method of claim 42, wherein at least one of the loci of interest is suspected of containing a single nucleotide polymorphism or a mutation.

50. A method for determining a sequence of alleles of a locus of interest, said method comprising:

(a) amplifying a locus of interest on a template DNA using a first and second primers, wherein the second primer contains a recognition site for a restriction enzyme that cuts DNA at a distance from the recognition site and digestion with the restriction enzyme generates a 5' overhang containing the locus of interest, wherein the first primer contains a recognition site for a restriction enzyme that is different from the recognition site for the restriction enzyme on the second primer, and contains a tag at the 5' end, and wherein the annealing temperature for cycle 1 of PCR is at about the melting temperature of the portion of 3' region of the second primer that anneals to the template DNA, the annealing temperature for cycle 2 of PCR is at about the melting temperature of the portion of the 3' region of the first primer that anneals to the template DNA, and the annealing temperature for the remaining cycles is at about the melting temperature of the entire second primer;

(b) digesting the amplified DNA with the restriction enzyme that recognizes the recognition site on the second primer;

(c) incorporating nucleotides into the digested DNA of (b), wherein;

(i) a labeled nucleotide that terminates elongation, and is complementary to the locus of interest of an allele, is incorporated into the 5' overhang of said allele, and (ii) a nucleotide complementary to the locus of interest of a different allele is incorporated into the 5' overhang of said different allele, and said terminating nucleotide, which is complementary to a nucleotide in the 5' overhang of said different allele, is incorporated into the 5' overhang of said different allele;

(d) digesting the DNA of (c) with the restriction enzyme that recognizes the recognition site on the first primer; and (e) determining the sequence of the alleles of the locus of interest by determining the sequence of the digested DNA of (d) containing the labeled nucleotide.

51. The method of claim 50, wherein the tag is used to separate the amplified DNA from the template DNA.

* * * * *